US012162881B2

(12) United States Patent
Masse et al.

(10) Patent No.: US 12,162,881 B2
(45) Date of Patent: Dec. 10, 2024

(54) FORMS AND COMPOSITIONS OF INHIBITORS OF JAK2

(71) Applicant: Ajax Therapeutics, Inc., New York, NY (US)

(72) Inventors: Craig E. Masse, Cambridge, MA (US); Jeremy R. Greenwood, Brooklyn, NY (US); Jiayi Xu, Marlboro, NJ (US); Sayan Mondal, New York, NY (US); Phani Ghanakota, Edison, NJ (US)

(73) Assignee: Ajax Therapeutics, Inc., New York, NY (US)

( * ) Notice: Subject to any disclaimer, the term of this patent is extended or adjusted under 35 U.S.C. 154(b) by 3 days.

(21) Appl. No.: 17/982,664

(22) Filed: Nov. 8, 2022

(65) Prior Publication Data

US 2023/0146125 A1 May 11, 2023

Related U.S. Application Data

(60) Provisional application No. 63/277,419, filed on Nov. 9, 2021.

(51) Int. Cl.
C07D 471/04 (2006.01)

(52) U.S. Cl.
CPC .................. C07D 471/04 (2013.01)

(58) Field of Classification Search
None
See application file for complete search history.

(56) References Cited

U.S. PATENT DOCUMENTS

| | | |
|---|---|---|
| 5,270,148 A | 12/1993 | Morigaki et al. |
| 5,512,590 A | 4/1996 | George et al. |
| 5,616,537 A | 4/1997 | Yokota et al. |
| 5,702,877 A | 12/1997 | Odenwalder et al. |
| 5,814,633 A | 9/1998 | Muller et al. |
| 5,852,046 A | 12/1998 | Lang et al. |
| 5,994,629 A | 11/1999 | Bojsen et al. |
| 6,329,383 B1 | 12/2001 | Hedgecock et al. |
| 6,346,531 B1 | 2/2002 | Luengo et al. |
| 6,444,816 B1 | 9/2002 | Das et al. |
| 6,552,192 B1 | 4/2003 | Hanus et al. |
| 6,566,372 B1 | 5/2003 | Zhi et al. |
| 6,630,470 B1 | 10/2003 | Luengo et al. |
| 6,743,800 B1 | 6/2004 | Peyman et al. |
| 6,747,016 B1 | 6/2004 | Peyman et al. |
| 7,256,196 B1 | 8/2007 | Sabat et al. |
| 7,531,553 B2 | 5/2009 | Di Pietro et al. |
| 8,114,874 B2 | 2/2012 | Zou et al. |
| 8,293,923 B2 | 10/2012 | Guckian et al. |
| 8,614,330 B2 | 12/2013 | Amiri et al. |
| 8,846,697 B2 | 9/2014 | Carson et al. |
| 9,145,438 B2 | 9/2015 | Chesworth et al. |
| 9,200,020 B2 | 12/2015 | De Jersey et al. |
| 9,284,299 B2 | 3/2016 | Ji et al. |
| 10,766,888 B1 | 9/2020 | Biddle et al. |
| 11,691,963 B2 | 7/2023 | Masse et al. |
| 2001/0056090 A1 | 12/2001 | Aquila et al. |
| 2002/0010159 A1 | 1/2002 | Weigele et al. |
| 2002/0052368 A1 | 5/2002 | Marlowe et al. |
| 2002/0058677 A1 | 5/2002 | Marlowe et al. |
| 2002/0068721 A1 | 6/2002 | Weigele et al. |
| 2002/0094994 A1 | 7/2002 | Bourzat et al. |
| 2002/0120144 A1 | 8/2002 | Akama et al. |
| 2002/0165261 A1 | 11/2002 | Borisy et al. |
| 2002/0173506 A1 | 11/2002 | Clark et al. |
| 2003/0109714 A1 | 6/2003 | Wishart et al. |
| 2003/0187261 A1 | 10/2003 | Havlicek et al. |
| 2003/0199564 A1 | 10/2003 | Fenton et al. |
| 2004/0006117 A1 | 1/2004 | Blume et al. |
| 2004/0034224 A1 | 2/2004 | Hammarstrom et al. |
| 2004/0077633 A1 | 4/2004 | Watson et al. |
| 2004/0082583 A1 | 4/2004 | Cheung et al. |
| 2004/0122237 A1 | 6/2004 | Amiri et al. |
| 2004/0171630 A1 | 9/2004 | Kim et al. |
| 2004/0198725 A1 | 10/2004 | Sun et al. |
| 2005/0049263 A1 | 3/2005 | Kasibhatla et al. |
| 2005/0101647 A1 | 5/2005 | Oda et al. |
| 2005/0137234 A1 | 6/2005 | Bressi et al. |
| 2005/0192287 A1 | 9/2005 | Costales et al. |
| 2005/0209176 A1 | 9/2005 | Meutermans et al. |
| 2005/0239821 A1 | 10/2005 | Neyts et al. |
| 2005/0272765 A1 | 12/2005 | Feng et al. |
| 2005/0282802 A1 | 12/2005 | Kostik et al. |
| 2006/0042026 A1 | 3/2006 | Glenn et al. |
| 2006/0052331 A1 | 3/2006 | Koch et al. |
| 2006/0111362 A1 | 5/2006 | Kira et al. |

(Continued)

FOREIGN PATENT DOCUMENTS

| | | |
|---|---|---|
| CN | 1148043 A | 4/1997 |
| CN | 101239980 A | 8/2008 |

(Continued)

OTHER PUBLICATIONS

Aitipamula et al., Polymorphs, Salts, and Cocrystals: What's in a Name? Crystal Growth & Design, 2012, 12, 2147-2152.*
Berge et al., Pharmaceutical Salts. Journal of Pharmaceutical Sciences, 1977, 66, 1-19.*
U.S. Appl. No. 17/559,051, Ajax Therapeutics, Inc.
U.S. Appl. No. 17/982,663, Masse et al.
Aaronson, D. S. and Horvath, C. M., A Road Map for Those Who Don't Know JAK-STAT, Science, 296(5573):1653-1655 (2002).
Akhtar, W. et al., Therapeutic evolution of benzimidazole derivatives in the last quinquennial period, European Journal of Medicinal Chemistry, 126:705-753 (2017).
Andraos, R. et al., Modulation of activation-loop phosphorylation by JAK inhibitors is binding mode dependent, Cancer Discovery, 2(6):512-523 (2012).
Bundgard, Design of Prodrugs, Amsterdam, New York, Oxford, Elsevier, pp. 7-9, 21-24 (1985).

(Continued)

*Primary Examiner* — Po-Chih Chen
(74) *Attorney, Agent, or Firm* — Choate, Hall & Stewart LLP; Charles E. Lyon; Michael A. Shinall

(57) ABSTRACT

The present disclosure provides compounds and compositions thereof which are useful as inhibitors of JAK2 and which exhibit desirable characteristics for the same.

20 Claims, 46 Drawing Sheets

(56) References Cited

U.S. PATENT DOCUMENTS

| | | |
|---|---|---|
| 2006/0116383 A1 | 6/2006 | Bloxham et al. |
| 2006/0148830 A1 | 7/2006 | Terakado et al. |
| 2006/0154977 A1 | 7/2006 | Morand et al. |
| 2006/0160872 A1 | 7/2006 | Norman et al. |
| 2007/0032493 A1 | 2/2007 | Foley et al. |
| 2007/0043043 A1 | 2/2007 | Chen et al. |
| 2007/0049622 A1 | 3/2007 | Dimitroff et al. |
| 2007/0093544 A1 | 4/2007 | Parmee et al. |
| 2007/0105930 A1 | 5/2007 | Parmee et al. |
| 2007/0112048 A1 | 5/2007 | Bavari et al. |
| 2007/0173527 A1 | 7/2007 | Bressi et al. |
| 2007/0197450 A1 | 8/2007 | Fushimi et al. |
| 2007/0219235 A1 | 9/2007 | Mjalli et al. |
| 2007/0249637 A1 | 10/2007 | Collins et al. |
| 2007/0275984 A1 | 11/2007 | Imogai et al. |
| 2008/0008682 A1 | 1/2008 | Chong et al. |
| 2008/0009488 A1 | 1/2008 | Anand et al. |
| 2008/0032936 A1 | 2/2008 | Gai et al. |
| 2008/0058297 A1 | 3/2008 | Ono et al. |
| 2008/0096903 A1 | 4/2008 | Chen et al. |
| 2008/0132501 A1 | 6/2008 | Sun et al. |
| 2008/0161254 A1 | 7/2008 | Green et al. |
| 2008/0194803 A1 | 8/2008 | Sinclair et al. |
| 2008/0221148 A1 | 9/2008 | Ibrahim et al. |
| 2008/0284322 A1 | 11/2008 | Hosokawa et al. |
| 2009/0047249 A1 | 2/2009 | Graupe et al. |
| 2009/0118200 A1 | 5/2009 | Bergman et al. |
| 2009/0140637 A1 | 6/2009 | Hosokawa et al. |
| 2009/0176778 A1 | 7/2009 | Schmitz et al. |
| 2009/0232844 A1 | 9/2009 | Sutton et al. |
| 2009/0233946 A1 | 9/2009 | Krasinski et al. |
| 2009/0278115 A1 | 11/2009 | Hosokawa et al. |
| 2010/0010217 A1 | 1/2010 | Valiante et al. |
| 2010/0029709 A1 | 2/2010 | Menet et al. |
| 2010/0093747 A1 | 4/2010 | Goodhew |
| 2010/0197688 A1 | 8/2010 | Nantermet et al. |
| 2010/0204265 A1 | 8/2010 | Baskaran et al. |
| 2010/0210598 A1 | 8/2010 | Carson et al. |
| 2010/0216810 A1 | 8/2010 | Okaniwa et al. |
| 2010/0249119 A1 | 9/2010 | Hirose et al. |
| 2010/0256188 A1 | 10/2010 | Pfau et al. |
| 2010/0261679 A1 | 10/2010 | Sutton et al. |
| 2010/0267714 A1 | 10/2010 | Jorgensen et al. |
| 2011/0021518 A1 | 1/2011 | Magnuson et al. |
| 2011/0039895 A1 | 2/2011 | Chai et al. |
| 2011/0059962 A1 | 3/2011 | Alekshun et al. |
| 2011/0105498 A1 | 5/2011 | Pettus et al. |
| 2011/0117073 A1 | 5/2011 | Singh et al. |
| 2011/0172186 A1 | 7/2011 | Behnke et al. |
| 2011/0201605 A1 | 8/2011 | Baumann et al. |
| 2011/0237620 A1 | 9/2011 | Okaniwa |
| 2011/0263598 A1 | 10/2011 | Sampson et al. |
| 2011/0281865 A1 | 11/2011 | Muthuppalaniappan et al. |
| 2011/0312935 A1 | 12/2011 | Pfau et al. |
| 2012/0028969 A1 | 2/2012 | Barnes et al. |
| 2012/0115902 A1 | 5/2012 | Pfau et al. |
| 2012/0122930 A1 | 5/2012 | Pfau et al. |
| 2012/0172351 A1 | 7/2012 | Negoro et al. |
| 2012/0202287 A1 | 8/2012 | Adams et al. |
| 2012/0208839 A1 | 8/2012 | Priepke et al. |
| 2012/0214786 A1 | 8/2012 | Priepke et al. |
| 2012/0258967 A1 | 10/2012 | Qiao et al. |
| 2013/0059851 A1 | 3/2013 | Garraway et al. |
| 2013/0079342 A1 | 3/2013 | Dransfield et al. |
| 2013/0084346 A1 | 4/2013 | Wolkenberg et al. |
| 2013/0090327 A1 | 4/2013 | Hata et al. |
| 2013/0096136 A1 | 4/2013 | Hata et al. |
| 2013/0136782 A1 | 5/2013 | Blackwell et al. |
| 2013/0149717 A1 | 6/2013 | Krause et al. |
| 2013/0165446 A1 | 6/2013 | Fujita et al. |
| 2013/0184240 A1 | 7/2013 | Tonogaki et al. |
| 2013/0184248 A1 | 7/2013 | Grauert et al. |
| 2013/0190320 A1 | 7/2013 | Xu et al. |
| 2013/0224195 A1 | 8/2013 | Costales et al. |
| 2013/0225596 A1 | 8/2013 | Kai et al. |
| 2013/0261125 A1 | 10/2013 | Shipps, Jr. et al. |
| 2013/0310333 A1 | 11/2013 | Chesworth et al. |
| 2013/0345261 A1 | 12/2013 | Waters et al. |
| 2014/0011763 A1 | 1/2014 | Lakshman |
| 2014/0031339 A1 | 1/2014 | Abeywardane et al. |
| 2014/0155379 A1 | 6/2014 | Ho et al. |
| 2014/0194420 A1 | 7/2014 | Kojima et al. |
| 2014/0303102 A1 | 10/2014 | Choe et al. |
| 2014/0303360 A1 | 10/2014 | Schroeder et al. |
| 2014/0364386 A1 | 12/2014 | Choe et al. |
| 2015/0018291 A1 | 1/2015 | Choe et al. |
| 2015/0057309 A1 | 2/2015 | Vakkalanka et al. |
| 2015/0126436 A1 | 5/2015 | Phillips et al. |
| 2015/0133490 A1 | 5/2015 | Burkholder et al. |
| 2015/0133500 A1 | 5/2015 | Tafesse et al. |
| 2015/0152065 A1 | 6/2015 | Brookings et al. |
| 2015/0197497 A1 | 7/2015 | Abeywickrama et al. |
| 2015/0216168 A1 | 8/2015 | Frackenpohl et al. |
| 2015/0243903 A1 | 8/2015 | Zeng et al. |
| 2015/0249221 A1 | 9/2015 | Zeng et al. |
| 2016/0024072 A1 | 1/2016 | Kai et al. |
| 2016/0046619 A1 | 2/2016 | Flynn et al. |
| 2016/0052922 A1 | 2/2016 | Chesworth et al. |
| 2016/0096804 A1 | 4/2016 | Shuttleworth et al. |
| 2016/0168165 A1 | 6/2016 | Koehler et al. |
| 2016/0176825 A1 | 6/2016 | Gray et al. |
| 2016/0229837 A1 | 8/2016 | Xi et al. |
| 2016/0257641 A1 | 9/2016 | Kobayashi et al. |
| 2016/0297795 A1 | 10/2016 | Heer et al. |
| 2016/0304511 A1 | 10/2016 | Jackson et al. |
| 2016/0304513 A1 | 10/2016 | Deligny et al. |
| 2017/0114078 A1 | 4/2017 | McGowan et al. |
| 2017/0121349 A1 | 5/2017 | Kim et al. |
| 2017/0129883 A1 | 5/2017 | Jackson et al. |
| 2017/0158688 A1 | 6/2017 | Jackson et al. |
| 2017/0222157 A1 | 8/2017 | Jatsch et al. |
| 2017/0333398 A1 | 11/2017 | Kojima et al. |
| 2018/0030453 A1 | 2/2018 | Zakharenko et al. |
| 2018/0072688 A1 | 3/2018 | Qian et al. |
| 2018/0079727 A1 | 3/2018 | Ohyabu et al. |
| 2018/0086725 A1 | 3/2018 | Kumar et al. |
| 2018/0153877 A1 | 6/2018 | Azam |
| 2018/0273511 A1 | 9/2018 | Long |
| 2019/0002442 A1 | 1/2019 | Zhao et al. |
| 2019/0022074 A1 | 1/2019 | Hadari et al. |
| 2019/0038603 A1 | 2/2019 | Jakobsson |
| 2019/0119217 A1 | 4/2019 | Long et al. |
| 2019/0134042 A1 | 5/2019 | Miao et al. |
| 2019/0135834 A1 | 5/2019 | Tamura et al. |
| 2019/0183866 A1 | 6/2019 | Tamura et al. |
| 2019/0382377 A1 | 12/2019 | Li et al. |
| 2019/0388426 A1 | 12/2019 | Nguyen et al. |
| 2020/0039933 A1 | 2/2020 | Gaisina et al. |
| 2020/0039961 A1 | 2/2020 | Campbell et al. |
| 2020/0039998 A1 | 2/2020 | Campbell et al. |
| 2020/0054635 A1 | 2/2020 | Campbell et al. |
| 2020/0062758 A1 | 2/2020 | Liu et al. |
| 2020/0101091 A1 | 4/2020 | Peyrottes et al. |
| 2020/0113901 A1 | 4/2020 | Campbell et al. |
| 2020/0113907 A1 | 4/2020 | Hagiwara et al. |
| 2020/0237717 A1 | 7/2020 | Jensen et al. |
| 2020/0268753 A1 | 8/2020 | Nguyen et al. |
| 2020/0274072 A1 | 8/2020 | Kugler |
| 2020/0317642 A1 | 10/2020 | Campbell et al. |
| 2021/0008046 A1 | 1/2021 | Bravo et al. |
| 2022/0127260 A1 | 4/2022 | Gray et al. |
| 2022/0127284 A1 | 4/2022 | Gray et al. |
| 2022/0411403 A1 | 12/2022 | Masse et al. |
| 2023/0099203 A1 | 3/2023 | Masse et al. |
| 2023/0167110 A1 | 6/2023 | Masse et al. |
| 2023/0265075 A1* | 8/2023 | Masse .................. C07D 401/12 514/210.21 |

FOREIGN PATENT DOCUMENTS

| | | |
|---|---|---|
| CN | 107383014 A | 11/2017 |
| CN | 108689942 A | 10/2018 |
| CN | 110092798 A | 8/2019 |
| EP | 639573 A1 | 2/1995 |

(56) References Cited

FOREIGN PATENT DOCUMENTS

| | | |
|---|---|---|
| EP | 3059225 A1 | 8/2016 |
| EP | 3279187 A1 | 2/2018 |
| EP | 3450435 A1 | 3/2019 |
| JP | H11-283746 A | 10/1999 |
| JP | 2000299186 A | 10/2000 |
| JP | 2004067629 A | 3/2004 |
| JP | 2005289921 A | 10/2005 |
| JP | 2009149589 A | 7/2009 |
| JP | 2016132649 A | 7/2016 |
| KR | 10-2019-0064508 A | 6/2019 |
| WO | WO-93/05163 A1 | 3/1993 |
| WO | WO-97/11065 A1 | 3/1997 |
| WO | WO-99/26932 A1 | 6/1999 |
| WO | WO-2001/044259 A1 | 6/2001 |
| WO | WO-2002/076960 A1 | 10/2002 |
| WO | WO-2003/082272 A1 | 10/2003 |
| WO | WO-2004/006849 A2 | 1/2004 |
| WO | WO-2004/085425 A1 | 10/2004 |
| WO | WO-2005/032548 A1 | 4/2005 |
| WO | WO-2005/035526 A1 | 4/2005 |
| WO | WO-2005/037273 A1 | 4/2005 |
| WO | WO-2006/027365 A1 | 3/2006 |
| WO | WO-2006/128129 A2 | 11/2006 |
| WO | WO-2006/130469 A1 | 12/2006 |
| WO | WO-2007/091950 A1 | 8/2007 |
| WO | WO-2007/121484 A2 | 10/2007 |
| WO | WO-2008/016666 A2 | 2/2008 |
| WO | WO-2008/124145 A1 | 10/2008 |
| WO | WO-2008/144062 A1 | 11/2008 |
| WO | WO-2008/150015 A1 | 12/2008 |
| WO | WO-2009/011775 A1 | 1/2009 |
| WO | WO-2009/017954 A1 | 2/2009 |
| WO | WO-2009/034386 A1 | 3/2009 |
| WO | WO-2009/050228 A2 | 4/2009 |
| WO | WO-2009/155565 A1 | 12/2009 |
| WO | WO-2010/002492 A1 | 1/2010 |
| WO | WO-2010/141796 A2 | 12/2010 |
| WO | WO-2010/144909 A1 | 12/2010 |
| WO | WO-2011/063908 A1 | 6/2011 |
| WO | WO-2011/127833 A1 | 10/2011 |
| WO | WO-2012/016133 A2 | 2/2012 |
| WO | WO-2013/024078 A1 | 2/2013 |
| WO | WO-2014/069426 A1 | 5/2014 |
| WO | WO-2014/072435 A1 | 5/2014 |
| WO | WO-2014/175330 A1 | 10/2014 |
| WO | WO-2015/008861 A1 | 1/2015 |
| WO | WO-2016/014576 A1 | 1/2016 |
| WO | WO-2016/119700 A1 | 8/2016 |
| WO | WO-2017/143014 A1 | 8/2017 |
| WO | WO-2017/175068 A1 | 10/2017 |
| WO | WO-2018/039557 A1 | 3/2018 |
| WO | WO-2018/064498 A1 | 4/2018 |
| WO | WO-2018/066545 A1 | 4/2018 |
| WO | WO-2018/191146 A1 | 10/2018 |
| WO | WO-2018/200786 A1 | 11/2018 |
| WO | WO-2018/203099 A1 | 11/2018 |
| WO | WO-2018/204765 A1 | 11/2018 |
| WO | WO-2019/000683 A1 | 1/2019 |
| WO | WO-2019/018119 A1 | 1/2019 |
| WO | WO-2019/038683 A1 | 2/2019 |
| WO | WO-2019/079596 A1 | 4/2019 |
| WO | WO-2019/079607 A1 | 4/2019 |
| WO | WO-2019/088159 A1 | 5/2019 |
| WO | WO-2019/217838 A1 | 11/2019 |
| WO | WO-2020/014599 A1 | 1/2020 |
| WO | WO-2020/081450 A1 | 4/2020 |
| WO | WO-2020/089455 A1 | 5/2020 |
| WO | WO-2020/093905 A1 | 5/2020 |
| WO | WO-2020/097396 A1 | 5/2020 |
| WO | WO-2020/097398 A1 | 5/2020 |
| WO | WO-2020/097400 A1 | 5/2020 |
| WO | WO-2020/118045 A1 | 6/2020 |
| WO | WO-2020/165907 A1 | 8/2020 |
| WO | WO-2020/176597 A1 | 9/2020 |
| WO | WO-2020/180768 A1 | 9/2020 |
| WO | WO-2020/181050 A1 | 9/2020 |
| WO | WO-2020/210481 A1 | 10/2020 |
| WO | WO-2020/243457 A1 | 12/2020 |
| WO | WO-2021/067682 A1 | 4/2021 |
| WO | WO-2021/091575 A1 | 5/2021 |
| WO | WO-2021/113557 A1 | 6/2021 |
| WO | WO-2021/226261 A1 | 11/2021 |
| WO | WO-2022/140527 A1 | 6/2022 |
| WO | WO-2023/086319 A1 | 5/2023 |
| WO | WO-2023/086320 A1 | 5/2023 |

OTHER PUBLICATIONS

Choi, H.G. et al., Development of 'DFG-out' inhibitors of gatekeeper mutant kinases, Bioorganic & Medicinal Chemistry Letters, 22:5297-5302 (2012).

Clark, J. et al., Discovery and Development of Janus Kinase (JAK) Inhibitors for Inflammatory Diseases, Journal of Medicinal Chemistry, J. Med. Chem., 57:5023-5038 (2014).

Dymock et al., Inhibitors of JAK2 and JAK3: an update on the patent literature 2010-2012, Expert Opin Ther Pat., 23(4):449-501 (2013).

Elf, S. et al., Mutant calreticulin requires both its mutant C-terminus and the thrombopoietin receptor for oncogenic transformation, Science Discovery, 6(4):368-381 (2016).

Extended European Search Report for Application No. EP19882411.2, mailed Jun. 21, 2022.

Extended European Search Report for EP 19882880.8 mailed Jul. 11, 2022.

Extended European Search Report for EP19881035.0 mailed Jun. 29, 2022.

Harrison, C. et al., JAK Inhibition with Ruxolitinib versus Best Available Therapy for Myelofibrosis, The New England Journal of Medicine, 366(9):787-798 (2012).

International Search Report for PCT/US2019/060358, mailed on Mar. 3, 2020.

International Search Report for PCT/US2019/060360, mailed on Mar. 3, 2020.

International Search Report for PCT/US2019/060363, mailed on Mar. 9, 2020.

International Search Report for PCT/US2020/053922, mailed on Mar. 8, 2021.

International Search Report for PCT/US2021/030926, 7 pages (Sep. 8, 2021).

International Search Report for PCT/US2021/064830, 4 pages (Mar. 25, 2022).

Jaffer, T. and Ma, D., The emerging role of chemokine receptor CXCR2 in cancer progression, Transl. Cancer Res., 5(Suppl 4):S616-S628 (2016).

Jutzi, J. et al., LSD1 Inhibition Prolongs Survival in Mouse Models of MPN by Selectivity Targeting the Disease Clone, HemaSphere, 2:3, 13 pages (2018).

Koppikar, P. et al., Heterodimeric JAK-STAT Activation as a Mechanism of Persistence to JAK2 Inhibitor Therapy, Nature, 489(7414):155-159 (2012).

Leroy, E. et al., Rethinking JAK2 inhibition: towards novel strategies of more specific and versatile janus kinase inhibition, Leukemia, 31(5):1023-1038 (2017).

Levine, R. L., JAK-mutant Myeloproliferative Neoplasms, Current Topics in Microbiology and Immunology, 355:119-133 (2011).

Li, et al., AutoT&T v.2: An Efficient and Versatile Tool for Lead Structure Generation and Optimization, J. Chem. Inf. Model, 56(2):435-453 (2016).

Meyer, S. and Levine, R., Molecular Pathways: Molecular Basis for Sensitivity and Resistance to JAK Kinase Inhibitors, Clin. Cancer Res., 20(8):2051-2059 (2014).

O'Hare, T. et al., AP24534, a Pan-BCR-ABL Inhibitor for Chronic Myeloid Leukemia, Potently Inhibits the T315I Mutant and Overcomes Mutation-Based Resistance, Cancer Cell, 16(5):401-412 (2009).

(56) References Cited

OTHER PUBLICATIONS

Okaniwa, et al., Design and synthesis of novel DFG-out RAF/vascular endothelial growth factor receptor 2 (VEGF2) inhibitors. 1. Exploration of [5,6]-fused bicyclic scaffolds, J Med Chem., 55(7):3452-78 (2012).
O'Shea, J. et al., Janus kinase Inhibitors in autoimmune diseases, Ann Rheum. Dis., 72, 11 pages (2013).
Pandey, A. et al., Cloning of a receptor subunit required for signaling by thymic stromal lymphopoietin, Nature Immunology, 1(1):59-64 (2000).
Ramurthy, S. et al., Design and Synthesis of Orally Bioavailable Benzimidazoles as Raf Kinase Inhibitors, J. Med. Chem., 51:7049-7052 (2008).
Ramurthy, S. et al., Supporting Information Design and Synthesis of Benzimidazoles Amides as Raf Kinase Inibitors, Novartis Institutes of Biomedical Research, 38 pages (2018).
Roberts, K. G. et al., Targetable Kinase-Activating Lesions in Ph-like Acute Lymphoblastic Leukemia, New England Journal of Medicine, 371(11):1005-1015 (2014).
Rodrigues, M.A. and Torres, T., JAK/STAT inhibitors for the treatment of atopic dermatitis, Journal of Dermatological Treatment, 31(1):33-40 (2020).
Rui, L. et al., Cooperative Epigenetic Modulation by Cancer Amplicon Genes, Cancer Cell., 18(6):590-605 (2010).
Rzymski, T. et al., SEL120-34A is a novel CDK8 inhibitor active in AML cells with high levels of serine phosphorylation of STAT1 and STAT5 transactivation domains, Oncotarget, 8(20):33779-33795 (2017).
Shiels, M. S. et al., Cancer Burden in the HIV-Infected Population in the United States, J Natl Cancer Inst., 103(9):753-762 (2011).
Smith, A. et al., Imidazo[1,2-a]pyridin-6-yl-benzamide analogs as potent RAF inhibitors, Bioorg Med Chem Lett., 27(23):5221-5224 (2017).
Subramanian, S. et al., Design and Synthesis of Orally Bioavailable Benzimidazole Reverse Amides as Pan RAF Kinase Inhibitors, ACS Med. Chem. Lett., 5:989-992 (2014).
Vainchenker, W. et al., JAK inhibitors for the treatment of myeloproliferative neoplasms and other disorders, F1000 Research, 7(F1000 Faculty Rev), 19 pages (last updated Jan. 17, 2018).
Verstovsek, S. et al., A Double-Blind Placebo-Controlled Trial of Ruxolitinib for Myelofibrosis, N Engl J Med., 366(9):799-807 (2012).
Williams et al., Discovery of RAF265: A Potent mut-B-RAF Inhibitor for the Treatment of Metastatic Melanoma, ACS Med. Chem Lett., 6(9):961-965 (2015).
Wu, S. et al., Activity of the Type II JAK2 Inhibitor CHZ868 in B Cell Acute Lymphoblastic Leukemia, Cancer Cell, 28:29-41 (2015).
Yuanyuan, W. et al., Design, synthesis, biological evaluation and molecular modeling of novel 1H-pyrazolo [3,4-d] pyrimidine derivatives as BRAFV600Eand VEGFR-2 dual inhibitors, European Journal of Medicinal Chemistry, 155:210-228 (2018).
Yumeen, S. et al., JAK inhibition synergistically potentiates BCL2, BET, HDAC, and proteasome inhibition in advanced CTCL, Blood Advances, 4(10):2213-2226 (2020).
Zhao, et al., Exploration of type II binding mode: A privileged approach for kinase inhibitor focused drug discovery?, ACS Chem Biol., 9(6):1230-41 (2014).
International Search Report for PCT/US2022/049223, 3 pages (mailed Feb. 9, 2023).

* cited by examiner

FORMS AND COMPOSITIONS OF INHIBITORS OF JAK2

RELATED APPLICATIONS

This application claims priority to and benefit of U.S. Application No. 63/277,419, filed Nov. 9, 2021, the entire contents of which are hereby incorporated by reference.

BACKGROUND OF THE INVENTION

Janus kinase 2 (JAK2) is a non-receptor tyrosine kinase involved in the JAK-STAT signaling pathway, which plays a role in cell processes such as immunity, cell division, and cell death. Dysfunction of the JAK-STAT pathway is implicated in various diseases, including cancer and other proliferative diseases, as well as diseases of the immune system. For example, essentially all BCR-ABL1-negative myeloproliferative neoplasms are associated with mutations that activate JAK2. In particular, JAK2V617F is the most prevalent mutation in myeloproliferative neoplasms, occurring in approx. 70% of all patients, and in up to 95% of patients with polycythemia vera. (Vainchenker, W., Kralovics, R. Blood 2017, 129(6):667-79). Even less common mutations, such as in MPL and CALR, have been shown to effect activation of JAK2, thereby initiating and/or driving disease progression. (Vainchenker, W. et al., F1000Research 2018, 7 (F1000 Faculty Rev): 82). Furthermore, polymorphisms in JAK2 have been linked to various autoimmune diseases and inflammatory conditions, such as psoriasis and inflammatory bowel disease. (O'Shea, J. J. et al., Ann. Rheum. Dis. 2013 April, 72:ii111-ii115). Increased signaling through JAK2, as well as other members of the JAK family, is also associated with atopic dermatitis. (Rodrigues, M. A. and Torres, T. J. Derm. Treat. 2019, 31(1):33-40).

Inhibitors of JAKs (e.g., JAK2) are classified based on their binding mode. All currently approved JAK inhibitors are Type I inhibitors, which are those that bind the ATP-binding site in the active conformation of the kinase domain, thereby blocking catalysis (Vainchenker, W. et al.). However, increased phosphorylation of the JAK2 activation loop is observed with Type I inhibitors and may lead to acquired resistance in certain patients (Meyer S. C., Levine, R. L. Clin. Cancer Res. 2014, 20(8):2051-9). Type II inhibitors, on the other hand, bind the ATP-binding site of the kinase domain in the inactive conformation and, therefore, may avoid hyperphosphorylation observed with Type I inhibitors (Wu, S. C. et al. Cancer Cell 2015 Jul. 13, 28(1):29-41).

Chemical compounds can form one or more different pharmaceutically acceptable salts and/or solid forms, including amorphous and polymorphic crystal forms. Individual salts and solid forms of bioactive chemical compounds can have different properties. There is a need for the identification and selection of appropriate salts and/or solid forms of bioactive chemical compounds (including appropriate crystalline forms, where applicable) for the development of pharmaceutically acceptable dosage forms for the treatment of various diseases or conditions associated with JAK2.

SUMMARY OF THE INVENTION

The present disclosure provides novel salts and solid forms useful as inhibitors of JAK2. In general, salt forms or free base forms, and pharmaceutically acceptable compositions thereof, are useful for treating or lessening the severity of a variety of diseases or disorders as described in detail herein.

DETAILED DESCRIPTION OF CERTAIN EMBODIMENTS

Figure 1:
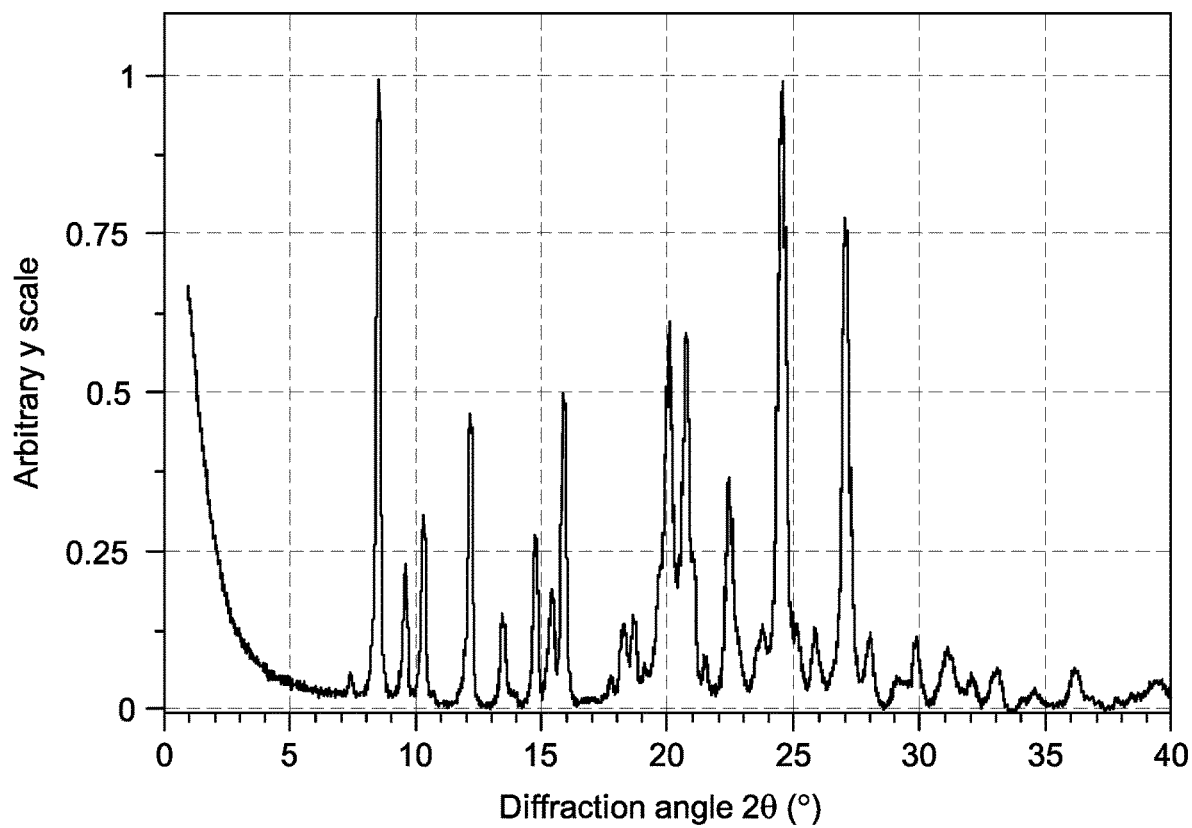
FIG. 1 provides a X-ray powder diffraction (XRPD) pattern of Compound 1 Form 1 (free base).

The compound N-(4-((7-cyano-1-methyl-2-((1-methyl-2-oxo-5-(trifluoromethyl)-1,2-dihydropyridin-3-yl)amino)-1H-imidazo[4,5-h]pyridin-6-yl)oxy)pyridin-2-yl)acetamide:

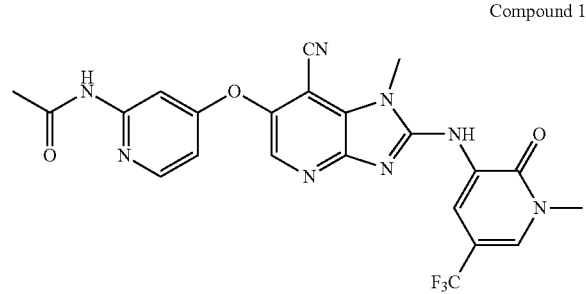 [SMILES: CC(=O)Nc1cc(Oc2cnc3nc(Nc4cc(C(F)(F)F)cn(C)c4=O)n(C)c3c2C#N)ccn1]

Compound 1 is a small molecule inhibitor of JAK2. The present disclosure provides various free base and salt forms of Compound 1, solid forms thereof, pharmaceutical compositions thereof, and methods of preparing those novel free base and salt forms of Compound 1 and solid forms thereof.

Compound 1 has shown potency against JAK2 in an in vitro assay. Accordingly, Compound 1 is useful for treating diseases, disorders, or conditions associated with JAK2.

The present disclosure provides various free base solid forms of Compound 1, salt forms of Compound 1 and solid forms thereof, pharmaceutical compositions thereof, and methods of preparing solid forms of Compound 1 and salts and solid forms thereof. Salt forms and solid forms (e.g., crystalline solid forms) impart or may impart characteristics such as improved aqueous solubility, stability, hygroscopicity (e.g., provided forms may be less hygroscopic than another form), absorption, bioavailability, and ease of formulation.

As used herein, unless otherwise indicated the term "salt" refers to a salt or co-crystal of two or more (e.g., two) component molecules (e.g., Compound 1 and a co-former). In the combination of an acid and a base compound for the preparation of a solid form, a $\Delta pK_a$ ($pK_a$(base)–$pK_a$(acid)) ≥1 generally will permit the formation of a salt compound where the two compounds are ionized. Where this threshold is not met, non-ionic interactions (e.g., hydrogen bonds) can still occur between neutral acid and the base compounds to form, e.g., a co-crystal. In some embodiments, a provided solid form is a salt. In other embodiments, a provided solid form is a co-crystal.

It will be appreciated that a crystalline solid form of Compound 1 or a salt thereof may exist in a neat (i.e., unsolvated) form, a hydrated form, a solvated form, and/or a heterosolvated form. In some embodiments, a crystalline solid form of Compound 1 or a salt thereof does not have any water or other solvent incorporated into the crystal lattice (i.e., is "unsolvated" or an "anhydrate"). In some embodiments, a crystalline solid form of Compound 1 or a salt thereof comprises water and/or other solvent in the crystal lattice (i.e., are hydrates and/or solvates, respectively). It will be appreciated that solvates comprising only certain solvents (most notably, water) are suitable for development as a drug. Solvates comprising other solvents may be useful for manufacturing and/or testing, inter alia, even if they may not be acceptable for use in an approved therapeutic product.

Without wishing to be bound by any particular theory, it was initially believed that salt forms of Compound 1 (e.g., Compounds 2-5) would be advantageous (e.g., improved aqueous solubility, stability, hygroscopicity, absorption, bioavailability, ease of formulation) as compared to free base solid forms of Compound 1. It will be appreciated that, in some embodiments, it is desirable for compound salt forms to not be prone to disproportionation, e.g., upon storage, in the presence of excipients, and/or when stirred in a solvent (e.g., water) for a period of time, particularly if such salt forms are to be used in a pharmaceutical product. The present disclosure encompasses the recognition that i) certain salt forms of Compound 1 possess properties (e.g., lower solubility and/or propensity for disproportionation) that may render them less favorable for use as pharmaceutical product, and ii) that certain crystalline free base solid forms of Compound 1 unexpectedly possess properties (e.g., stability, solubility, ease of formulation, and/or hygroscopicity) that render them more favorable for use as a pharmaceutical product as compared with other free base solid forms of Compound 1 or salts thereof. As described herein, in some embodiments, certain provided free base forms of Compound 1 are preferred over certain provided salt forms, because certain salt forms are prone to disproportionation. For example, as described in Example 11 herein, Compound 1 Form A can be prepared via a disproportionation reaction of Compound 2, demonstrating a superior stability of Compound 1 Form A over Compound 2.

Without wishing to be bound by any particular theory, the present disclosure recognizes certain challenges in obtaining free base solid forms of Compound 1 in a consistent manner, as well as provides a solution to this problem. As described in Example 9, despite using similar methods of synthesis and purification, different lots of Compound 1 comprised different free base forms and mixtures thereof. The present disclosure provides methods of preparing Compound 1 free base forms that are substantially free of impurities and/or other free base forms, and that reproducibly provide the same polymorphic form. For example, a process for preparing Compound 1 Form A is described in Example 11, and a process for preparing Compound 1 Form N is described in Example 21.

I. Free Base Forms of Compound 1

1. Compound 1

It is contemplated that Compound 1 can exist in a variety of physical forms. For example, Compound 1 can be in solution, suspension, or in solid form. In certain embodiments, Compound 1 is in solid form. When Compound 1 is in solid form, said compound may be amorphous, crystalline, or a mixture thereof. Exemplary solid forms are described in more detail below.

In some embodiments, the present disclosure provides a form of Compound 1 substantially free of impurities. As used herein, the term "substantially free of impurities" means that the compound contains no significant amount of extraneous matter. Such extraneous matter may include different forms of Compound 1, residual solvents, or any other impurities that may result from the preparation of, and/or isolation of, Compound 1. In certain embodiments, at least about 95% by weight of a form of Compound 1 is present. In certain embodiments, at least about 95%, about 96%, about 97%, about 98%, or about 99% by weight of a form of Compound 1 is present. In still other embodiments of the disclosure, at least about 99% by weight of a form of Compound 1 is present.

The terms "about" and "approximately", unless otherwise stated and when used herein in reference to a value, refers to a value that is similar, in context to the referenced value. In general, those skilled in the art, familiar with the context, will appreciate the relevant degree of variance encompassed by about/approximately in that context. Unless otherwise stated, in some embodiments the term "about" or "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would be less than 0%, or would exceed 100% of a possible value).

According to one embodiment, a form of Compound 1 is present in an amount of at least about 97.0, 97.5, 98.0, 98.5, 99.0, 99.5, or 99.8 weight percent where the percentages are based on the total weight of the composition. According to another embodiment, a form of Compound 1 contains no more than about 3.0 area percent HPLC of total organic impurities and, in certain embodiments, no more than about 1.5 area percent HPLC total organic impurities relative to the total area of the HPLC chromatogram. In other embodiments, a form of Compound 1 contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for a form of Compound 1 is also meant to include all tautomeric forms of Compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this disclosure.

It has been found that Compound 1 can exist in a variety of solid forms.

In some embodiments, Compound 1 is amorphous. In some embodiments, Compound 1 is amorphous, and is substantially free of crystalline Compound 1. As used herein, the term "substantially free of crystalline Compound 1" means that the compound contains no significant amount of crystalline Compound 1. In some embodiments, at least about 95%, about 96%, about 97%, about 98%, or about 99% by weight of amorphous Compound 1 is present. In some embodiments, at least about 99% by weight of amorphous Compound 1 is present.

In certain embodiments, Compound 1 is a crystalline solid. In some embodiments, Compound 1 is a crystalline solid substantially free of amorphous Compound 1. As used herein, the term "substantially free of amorphous Compound 1" means that the compound contains no significant amount of amorphous Compound 1. In certain embodiments, at least about 95% by weight of crystalline Compound 1 is present. In certain embodiments, at least about 95%, about 96%, about 97%, about 98%, or about 99% by weight of crystalline Compound 1 is present. In still other embodiments of the disclosure, at least about 99% by weight of crystalline Compound 1 is present.

In some embodiments, Compound 1 is provided as a particular crystalline form that is substantially free of other crystalline forms of Compound 1. For example, in some embodiments, a composition comprises Compound 1 Form A substantially free of other crystalline forms of Compound 1 (e.g., Form B, Form C, Form D, Form E, Form F, Form G, Form H, Form J, Form K, Form L, Form M, Form N, Form O, and/or Form P). As used herein, the term "substantially free of other crystalline forms of Compound 1" means that the compound contains no significant amount of other crystalline forms of Compound 1. In some embodiments, at least about 95%, about 96%, about 97%, about 98%, or about 99% by weight of a particular crystalline form (e.g., Form A) of Compound 1 is present. In some embodiments, at least about 99% by weight of a particular crystalline form (e.g., Form A) of Compound 1 is present.

Compound 1 Form 1

In certain embodiments, the present disclosure provides a solid form of Compound 1 referred to herein as Form 1. In some embodiments, Compound 1 is in Form 1, substantially free from other free base forms of Compound 1. It will be appreciated that, in some embodiments, "Compound 1 Form 1" describes a mixture of one or more forms of Compound 1 (e.g., Compound 1 Form A and Compound 1 Form B, as described herein).

In some embodiments, Compound 1 Form 1 has at least 1, 2, 3, 4 or 5 X-ray Powder Diffraction (XRPD) peaks selected from the angles (degrees 2 theta±0.20) listed in Table 1 below.

TABLE 1

XRPD Peak Positions for Compound 1 Form 1
Angle/° 2θ

| Angle/° 2θ |
| --- |
| 6.18 |
| 6.70 |
| 7.33 |
| 8.04 |
| 8.77 |
| 9.10 |
| 9.59 |
| 9.78 |
| 10.31 |
| 11.22 |
| 11.46 |
| 12.07 |
| 12.32 |
| 12.98 |
| 14.01 |
| 15.34 |
| 15.62 |
| 15.85 |
| 16.62 |
| 16.89 |
| 17.59 |
| 18.04 |
| 18.19 |
| 18.94 |
| 19.70 |
| 20.08 |
| 20.62 |
| 21.36 |
| 21.71 |
| 22.22 |
| 22.87 |
| 23.31 |
| 23.56 |
| 24.09 |
| 25.22 |
| 26.20 |
| 26.58 |
| 27.29 |

In some embodiments, Compound 1 Form 1 is characterized by an X-ray powder diffraction (XRPD) pattern having diffractions at angles (degrees 2 theta±0.20) and corresponding d-spacing of:

TABLE 2

XRPD Peak Positions and d-Spacing for Compound 1 Form 1

| Angle/° 2θ | d-spacing/Angstrom |
| --- | --- |
| 6.18 | 14.301 ± 0.463 |
| 6.70 | 13.174 ± 0.393 |
| 7.33 | 12.045 ± 0.328 |
| 8.04 | 10.985 ± 0.273 |
| 8.77 | 10.080 ± 0.230 |
| 9.10 | 9.708 ± 0.213 |
| 9.59 | 9.212 ± 0.192 |
| 9.78 | 9.035 ± 0.184 |
| 10.31 | 8.570 ± 0.166 |
| 11.22 | 7.880 ± 0.140 |
| 11.46 | 7.715 ± 0.134 |
| 12.07 | 7.324 ± 0.121 |
| 12.32 | 7.181 ± 0.116 |
| 12.98 | 6.814 ± 0.105 |
| 14.01 | 6.317 ± 0.090 |
| 15.34 | 5.770 ± 0.075 |
| 15.62 | 5.670 ± 0.072 |
| 15.85 | 5.586 ± 0.070 |
| 16.62 | 5.330 ± 0.064 |
| 16.89 | 5.246 ± 0.062 |
| 17.59 | 5.037 ± 0.057 |
| 18.04 | 4.914 ± 0.054 |
| 18.19 | 4.874 ± 0.053 |
| 18.94 | 4.683 ± 0.049 |
| 19.70 | 4.503 ± 0.045 |
| 20.08 | 4.418 ± 0.044 |
| 20.62 | 4.303 ± 0.041 |
| 21.36 | 4.156 ± 0.038 |
| 21.71 | 4.091 ± 0.037 |
| 22.22 | 3.998 ± 0.036 |
| 22.87 | 3.886 ± 0.034 |
| 23.31 | 3.814 ± 0.032 |
| 23.56 | 3.774 ± 0.032 |
| 24.09 | 3.691 ± 0.030 |
| 25.22 | 3.529 ± 0.028 |
| 26.20 | 3.398 ± 0.025 |
| 26.58 | 3.351 ± 0.025 |
| 27.29 | 3.265 ± 0.023 |

In some embodiments, Compound 1 Form 1 s characterized in that it has one or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has two or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has three or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has four or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has five or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has six or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has seven or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has eight or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has nine or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has ten or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has eleven or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has twelve or more peaks in its X-ray powder diffraction pattern selected from those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has peaks in its X-ray powder diffraction pattern comprising those at about 7.33, 11.22, 11.46, 14.01, 16.89, 18.94, 19.70, 21.71, 23.31, 23.56, 25.22, 26.20, and 26.58 degrees 2-theta. In some embodiments, Compound 1 Form 1 is characterized in that it has peaks in its X-ray powder diffraction pattern comprising those at about 7.33, 11.22, 11.46, 14.01, 16.89, 18.94, 19.70, 21.71, 23.31, 23.56, 25.22, 26.20, and 26.58 degrees 2-theta, corresponding to d-spacing shown in Table 2 above. As used herein, the term "about", when used in reference to a degree 2-theta value refers to the stated value±0.2 degree 2-theta.

In certain embodiments, the X-ray powder diffraction pattern of Compound 1 Form 1 is substantially similar to the XRPD provided in FIG. 1.

Methods for preparing Compound 1 Form 1 are described infra.

Compound 1 Form A

In certain embodiments, the present disclosure provides a solid form of Compound 1 referred to herein as Form A. In some embodiments, Compound 1 Form A is a hydrate. In some embodiments, Compound 1 is provided as Form A, substantially free from other free base forms of Compound 1 (e.g., Compound 1 Form B).

In some embodiments, Compound 1 Form A has at least 1, 2, 3, 4 or 5 X-ray Powder Diffraction (XRPD) peaks selected from the angles (degrees 2 theta±0.20) listed in Table A-1 below.

TABLE A-1

| XRPD Peak Positions for Compound 1 Form A Angle/° 2θ |
|---|
| 7.32 |
| 9.57 |
| 9.77 |
| 11.15 |
| 11.45 |
| 12.90 |
| 13.20 |
| 13.99 |
| 14.41 |
| 14.69 |
| 16.39 |
| 16.58 |
| 16.85 |
| 17.24 |
| 17.98 |
| 18.60 |
| 18.95 |
| 19.23 |
| 19.68 |
| 20.23 |
| 20.75 |
| 21.29 |
| 21.68 |
| 22.19 |
| 22.40 |
| 22.93 |
| 23.56 |
| 23.98 |
| 24.51 |
| 25.23 |
| 25.97 |
| 26.60 |
| 27.25 |

TABLE A-1-continued

| XRPD Peak Positions for Compound 1 Form A Angle/° 2θ |
|---|
| 27.80 |
| 28.78 |
| 29.07 |
| 29.78 |
| 30.70 |

In some embodiments, Compound 1 Form A is characterized by an X-ray powder diffraction (XRPD) pattern having diffractions at angles (degrees 2 theta±0.20) and corresponding d-spacing of:

TABLE A-2

| XRPD Peak Positions and d-Spacing for Compound 1 Form A | |
|---|---|
| Angle/° 2θ | d-spacing/Angstrom |
| 7.32 | 12.074 ± 0.330 |
| 9.57 | 9.238 ± 0.193 |
| 9.77 | 9.048 ± 0.185 |
| 11.15 | 7.929 ± 0.142 |
| 11.45 | 7.723 ± 0.134 |
| 12.90 | 6.856 ± 0.106 |
| 13.20 | 6.702 ± 0.101 |
| 13.99 | 6.325 ± 0.090 |
| 14.41 | 6.141 ± 0.085 |
| 14.69 | 6.026 ± 0.082 |
| 16.39 | 5.404 ± 0.066 |
| 16.58 | 5.342 ± 0.064 |
| 16.85 | 5.259 ± 0.062 |
| 17.24 | 5.138 ± 0.059 |
| 17.98 | 4.930 ± 0.054 |
| 18.60 | 4.768 ± 0.051 |
| 18.95 | 4.678 ± 0.049 |
| 19.23 | 4.613 ± 0.048 |
| 19.68 | 4.508 ± 0.045 |
| 20.23 | 4.385 ± 0.043 |
| 20.75 | 4.277 ± 0.041 |
| 21.29 | 4.171 ± 0.039 |
| 21.68 | 4.096 ± 0.037 |
| 22.19 | 4.002 ± 0.036 |
| 22.40 | 3.966 ± 0.035 |
| 22.93 | 3.875 ± 0.033 |
| 23.56 | 3.773 ± 0.032 |
| 23.98 | 3.708 ± 0.030 |
| 24.51 | 3.628 ± 0.029 |
| 25.23 | 3.526 ± 0.027 |
| 25.97 | 3.428 ± 0.026 |
| 26.60 | 3.348 ± 0.025 |
| 27.25 | 3.270 ± 0.024 |
| 27.80 | 3.206 ± 0.023 |
| 28.78 | 3.099 ± 0.021 |
| 29.07 | 3.069 ± 0.021 |
| 29.78 | 2.998 ± 0.020 |
| 30.70 | 2.910 ± 0.018 |

In some embodiments, Compound 1 Form A is characterized in that it has one or more peaks in its X-ray powder diffraction pattern selected from those at about 7.32, 11.15, 13.99, 16.58, 18.95, 21.68, 23.56, 25.23, and 26.60 degrees 2-theta. In some embodiments, Compound 1 Form A is characterized in that it has two or more peaks in its X-ray powder diffraction pattern selected from those at about 7.32, 11.15, 13.99, 16.58, 18.95, 21.68, 23.56, 25.23, and 26.60 degrees 2-theta. In some embodiments, Compound 1 Form A is characterized in that it has three or more peaks in its X-ray powder diffraction pattern selected from those at about 7.32, 11.15, 13.99, 16.58, 18.95, 21.68, 23.56, 25.23, and 26.60 degrees 2-theta. In some embodiments, Compound 1 Form A is characterized in that it has four or more peaks in its X-ray powder diffraction pattern selected from those at about 7.32, 11.15, 13.99, 16.58, 18.95, 21.68, 23.56, 25.23, and 26.60 degrees 2-theta. In some embodiments, Compound 1 Form A is characterized in that it has five or more peaks in its X-ray powder diffraction pattern selected from those at about 7.32, 11.15, 13.99, 16.58, 18.95, 21.68, 23.56, 25.23, and 26.60 degrees 2-theta. In some embodiments, Compound 1 Form A is characterized in that it has six or more peaks in its X-ray powder diffraction pattern selected from those at about 7.32, 11.15, 13.99, 16.58, 18.95, 21.68, 23.56, 25.23, and 26.60 degrees 2-theta. In some embodiments, Compound 1 Form A is characterized in that it has seven or more peaks in its X-ray powder diffraction pattern selected from those at about 7.32, 11.15, 13.99, 16.58, 18.95, 21.68, 23.56, 25.23, and 26.60 degrees 2-theta. In some embodiments, Compound 1 Form A is characterized in that it has eight or more peaks in its X-ray powder diffraction pattern selected from those at about 7.32, 11.15, 13.99, 16.58, 18.95, 21.68, 23.56, 25.23, and 26.60 degrees 2-theta. In some embodiments, Compound 1 Form A is characterized in that it has peaks in its X-ray powder diffraction pattern selected from those at about 7.32, 11.15, 13.99, 16.58, 18.95, 21.68, 23.56, 25.23, and 26.60 degrees 2-theta. In some embodiments, Compound 1 Form A is characterized in that it has peaks in its X-ray powder diffraction pattern selected from those at about 7.32, 11.15, 13.99, 16.58, 18.95, 21.68, 23.56, 25.23, and 26.60 degrees 2-theta, corresponding to d-spacing shown in Table A-2 above. As used herein, the term "about", when used in reference to a degree 2-theta value refers to the stated value±0.2 degree 2-theta.

Figure 19:
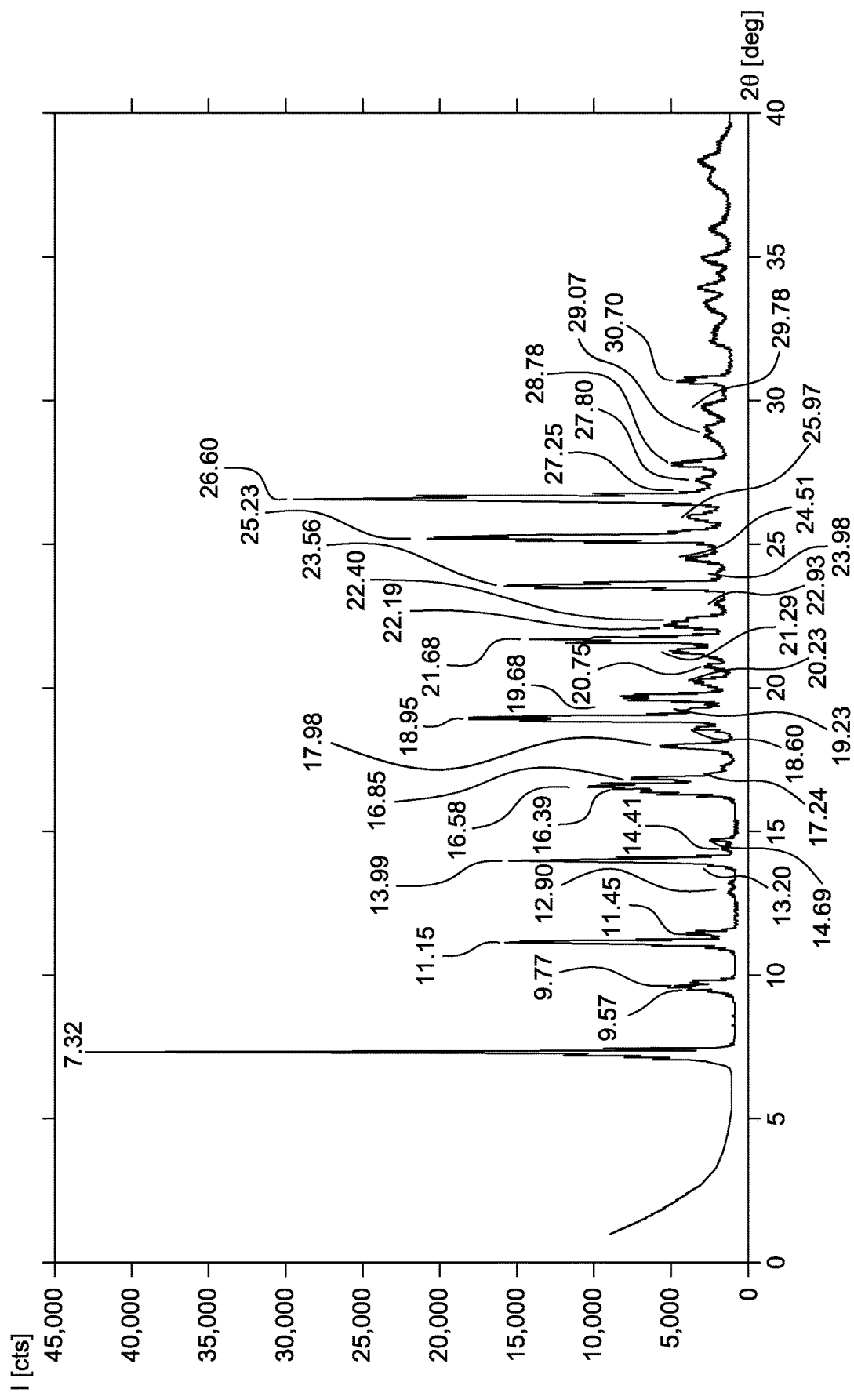
FIG. 19 provides a XRPD pattern of Compound 1 Form A.

In certain embodiments, the X-ray powder diffraction pattern of Compound 1 Form A is substantially similar to the XRPD provided in FIG. 19.

Methods for preparing Compound 1 Form A are described infra.

Compound 1 Form B

In certain embodiments, the present disclosure provides a solid form of Compound 1 referred to herein as Form B. In some embodiments, Compound 1 Form B is anhydrous. In some embodiments, Compound 1 is provided as Form B, substantially free from other free base forms of Compound 1.

Figure 22:
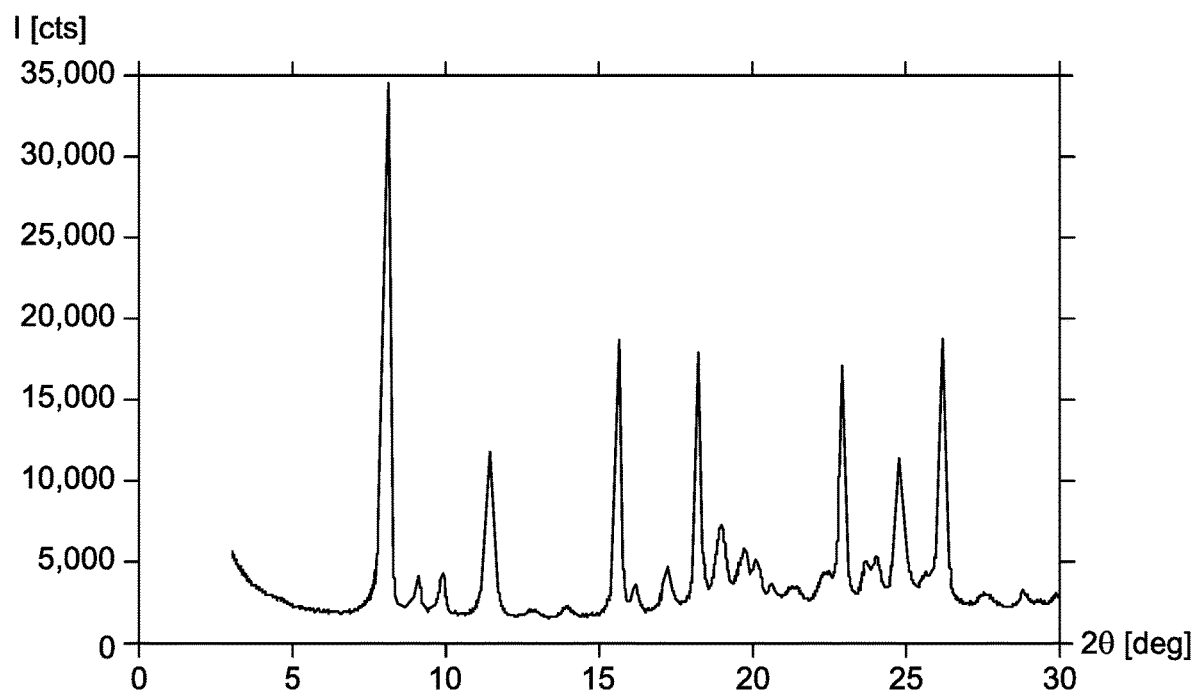
FIG. 22 provides a XRPD pattern of Compound 1 Form B.

In certain embodiments, the X-ray powder diffraction pattern of Compound 1 Form B is substantially similar to the XRPD provided in FIG. 22.

Methods for preparing Compound 1 Form B are described infra.

Compound 1 Form C

In certain embodiments, the present disclosure provides a solid form of Compound 1 referred to herein as Form C. In some embodiments, Compound 1 Form C is a tri-acetic acid cocrystal. In some embodiments, Compound 1 is provided as Form C, substantially free from other free base forms of Compound 1.

Figure 23:
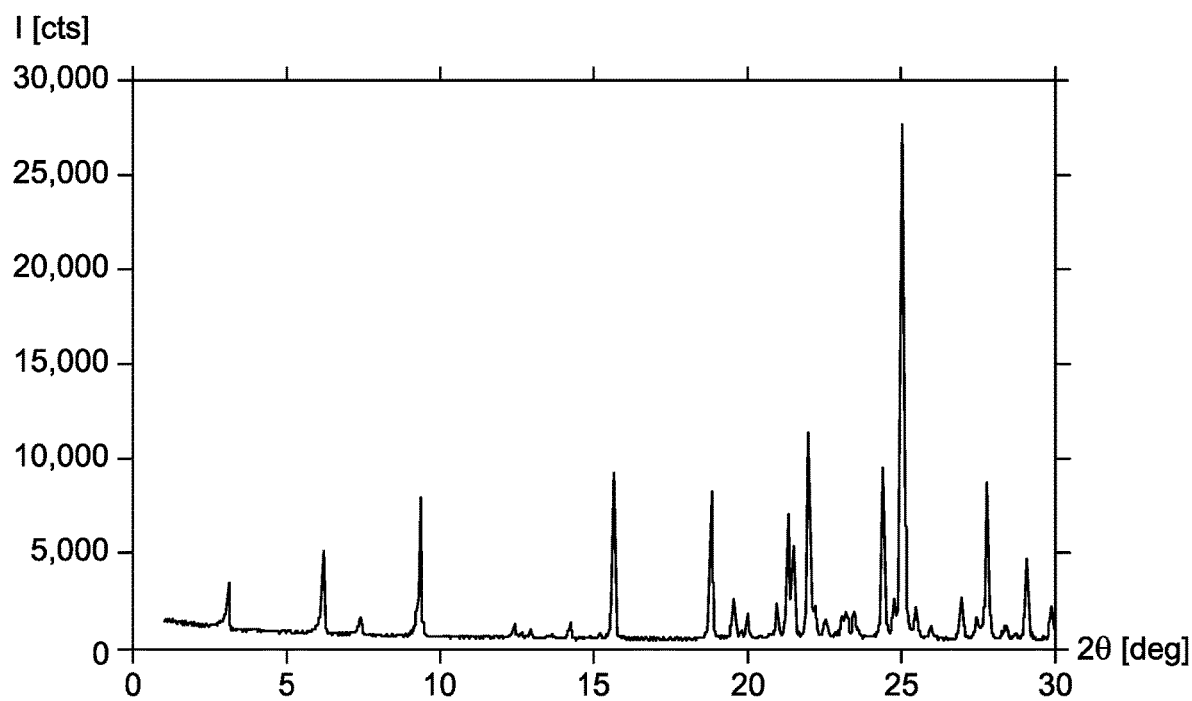
FIG. 23 provides a XRPD pattern of Compound 1 Form C.

In certain embodiments, the X-ray powder diffraction pattern of Compound 1 Form C is substantially similar to the XRPD provided in FIG. 23.

Methods for preparing Compound 1 Form C are described infra.

Compound 1 Form D

In certain embodiments, the present disclosure provides a solid form of Compound 1 referred to herein as Form D. In some embodiments, Compound 1 Form D is a bis-dimethylacetamide (DMA) solvate. In some embodiments, Compound 1 is provided as Form D, substantially free from other free base forms of Compound 1.

Figure 25:
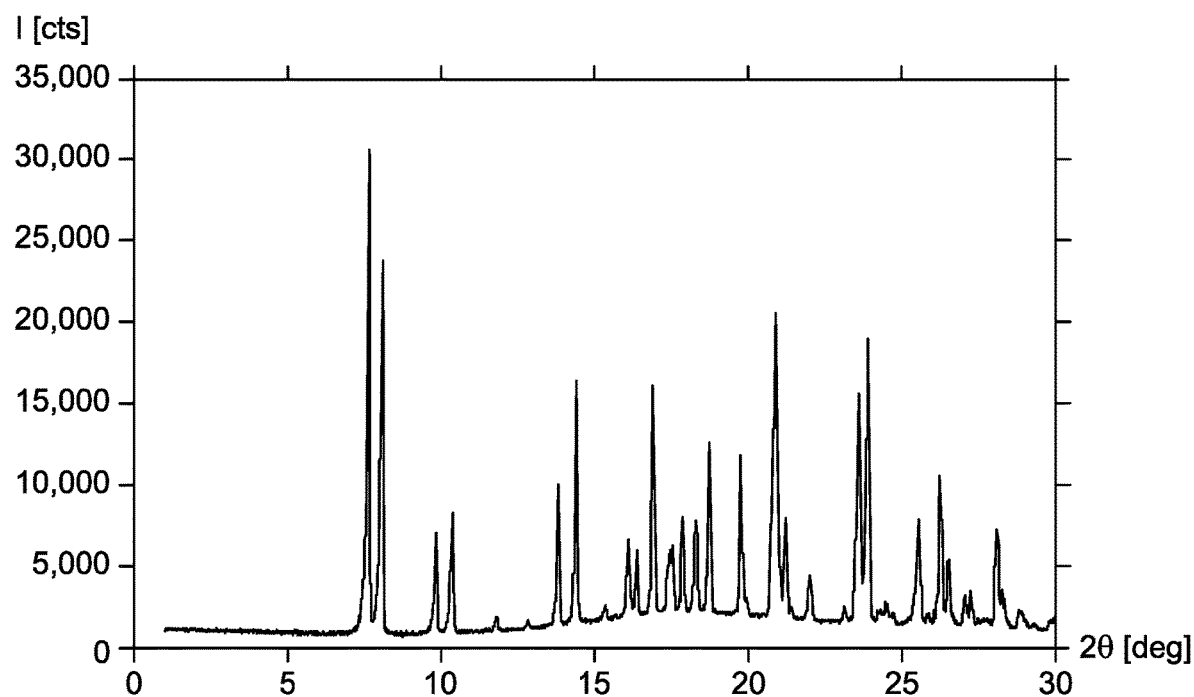
FIG. 25 provides a XRPD pattern of Compound 1 Form D.

In certain embodiments, the X-ray powder diffraction pattern of Compound 1 Form D is substantially similar to the XRPD provided in FIG. 25.

Methods for preparing Compound 1 Form D are described infra.

Compound 1 Form E

In certain embodiments, the present disclosure provides a solid form of Compound 1 referred to herein as Form E. In some embodiments, Compound 1 Form E is a tris-dimethylsulfoxide (DMSO) solvate. In some embodiments, Compound 1 is provided as Form E, substantially free from other free base forms of Compound 1.

Figure 27:
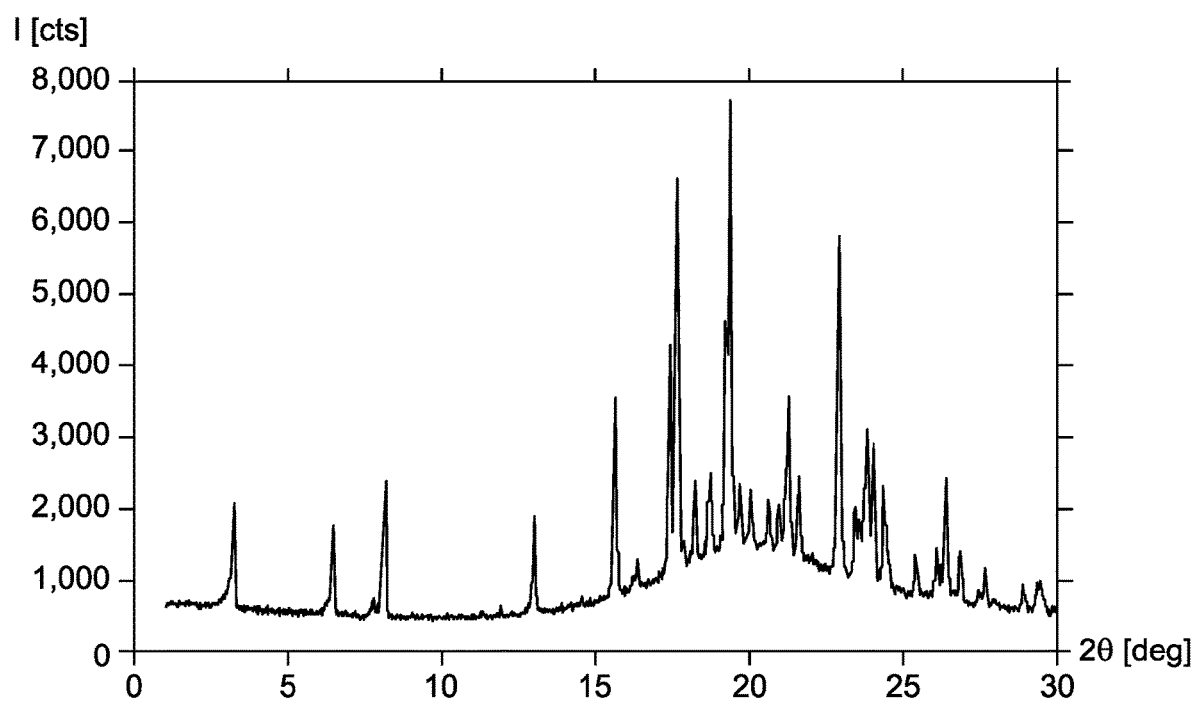
FIG. 27 provides a XRPD pattern of Compound 1 Form E.

In certain embodiments, the X-ray powder diffraction pattern of Compound 1 Form E is substantially similar to the XRPD provided in FIG. 27.

Methods for preparing Compound 1 Form E are described infra.

Compound 1 Form F

In certain embodiments, the present disclosure provides a solid form of Compound 1 referred to herein as Form F. In some embodiments, Compound 1 Form F is a bis-N-methyl-2-pyrrolidone (NMP) solvate. In some embodiments, Compound 1 is provided as Form F, substantially free from other free base forms of Compound 1.

Figure 29:
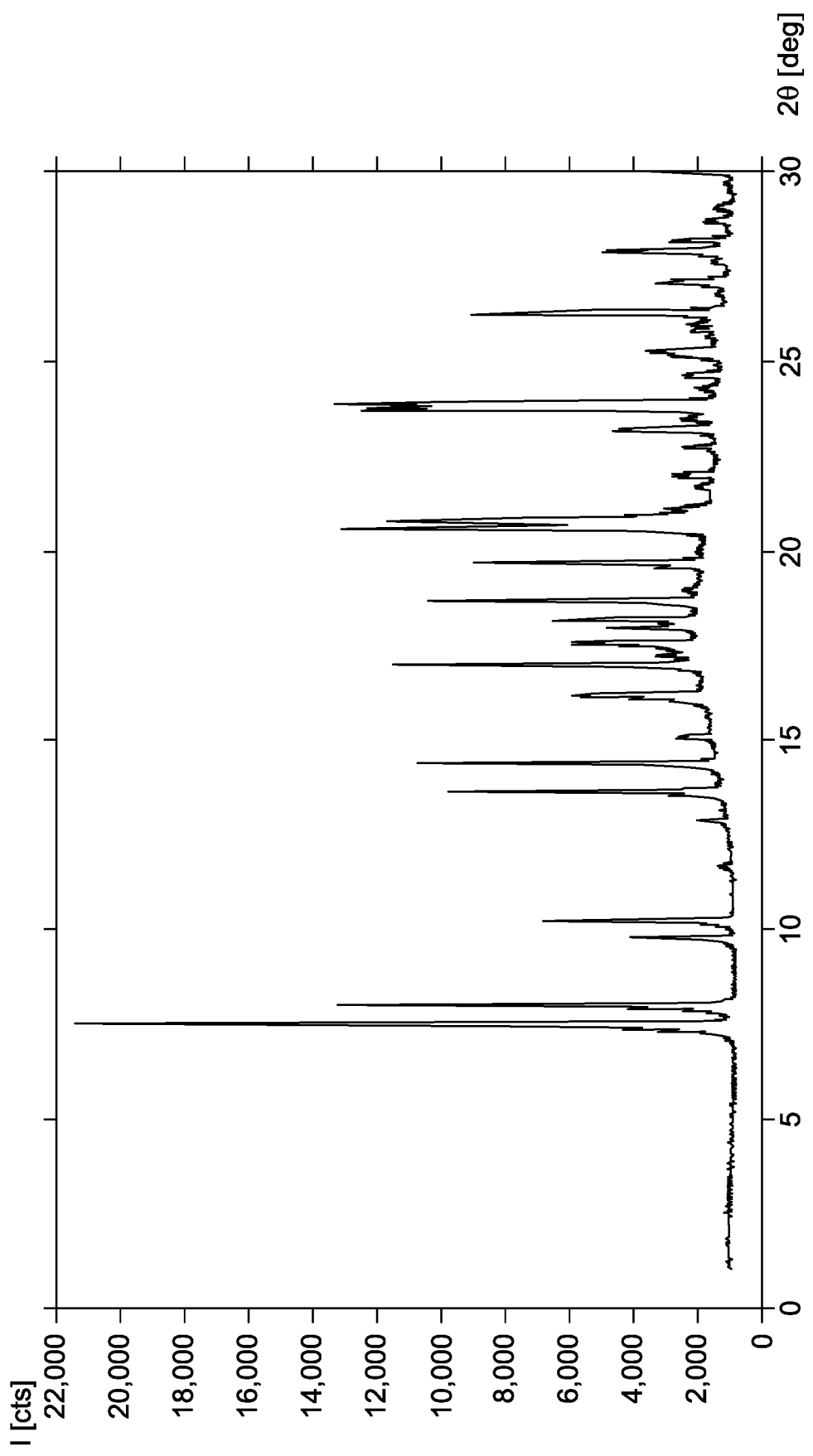
FIG. 29 provides a XRPD pattern of Compound 1 Form F.

In certain embodiments, the X-ray powder diffraction pattern of Compound 1 Form F is substantially similar to the XRPD provided in FIG. 29.

Methods for preparing Compound 1 Form F are described infra.

Compound 1 Form G

In certain embodiments, the present disclosure provides a solid form of Compound 1 referred to herein as Form G. In some embodiments, Compound 1 Form G is a bis-dimethylformamide (DMF) solvate. In some embodiments, Compound 1 is provided as Form G, substantially free from other free base forms of Compound 1.

Figure 31:
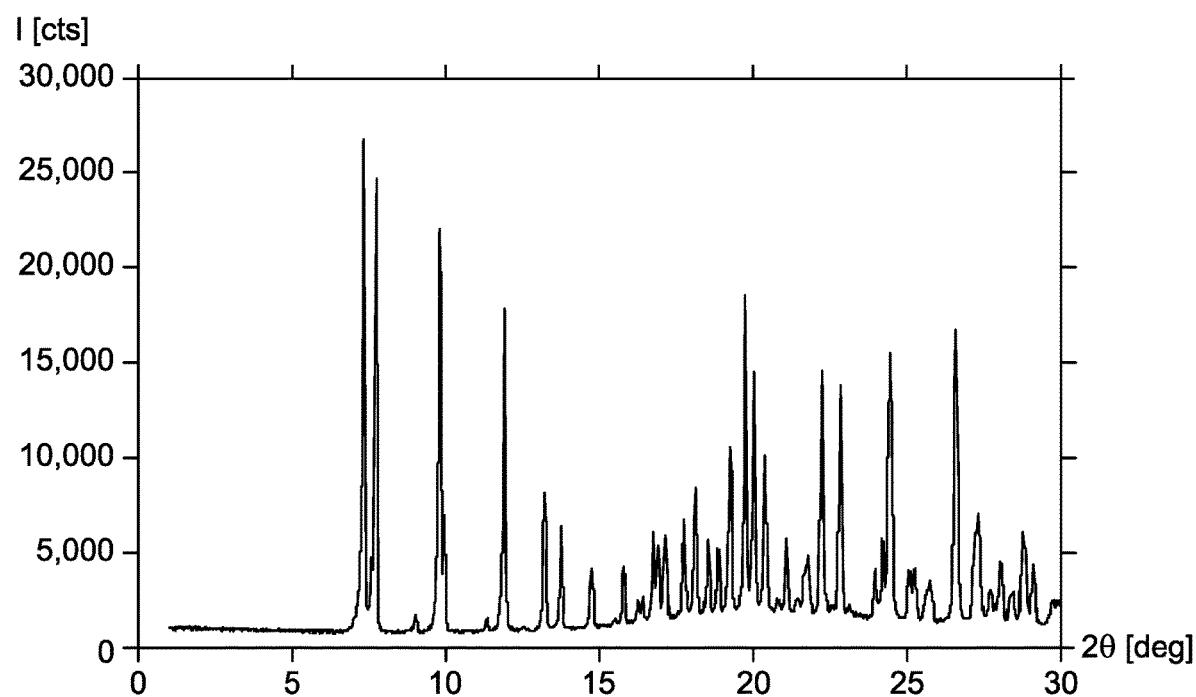
FIG. 31 provides a XRPD pattern of Compound 1 Form G.

In certain embodiments, the X-ray powder diffraction pattern of Compound 1 Form G is substantially similar to the XRPD provided in FIG. 31.

Methods for preparing Compound 1 Form G are described infra.

Compound 1 Form H

In certain embodiments, the present disclosure provides a solid form of Compound 1 referred to herein as Form H. In some embodiments, Compound 1 is provided as Form H, substantially free from other free base forms of Compound 1.

Figure 28:
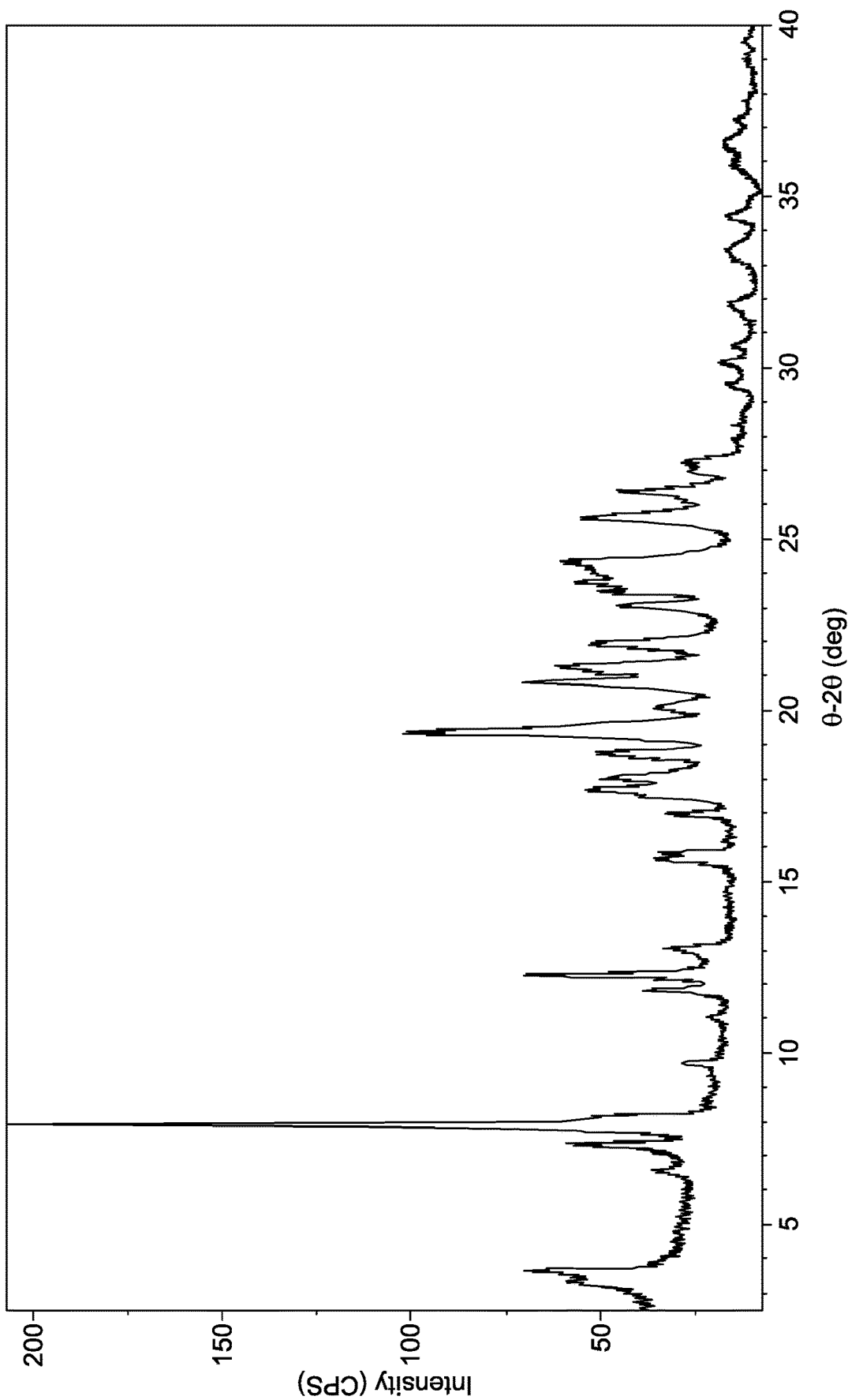
FIG. 28 provides a XRPD pattern of Compound 1 Form H.

In certain embodiments, the X-ray powder diffraction pattern of Compound 1 Form H is substantially similar to the XRPD provided in FIG. 28.

Methods for preparing Compound 1 Form H are described infra.

Compound 1 Form J

In certain embodiments, the present disclosure provides a solid form of Compound 1 referred to herein as Form J. In some embodiments, Compound 1 is provided as Form J, substantially free from other free base forms of Compound 1.

Figure 32:
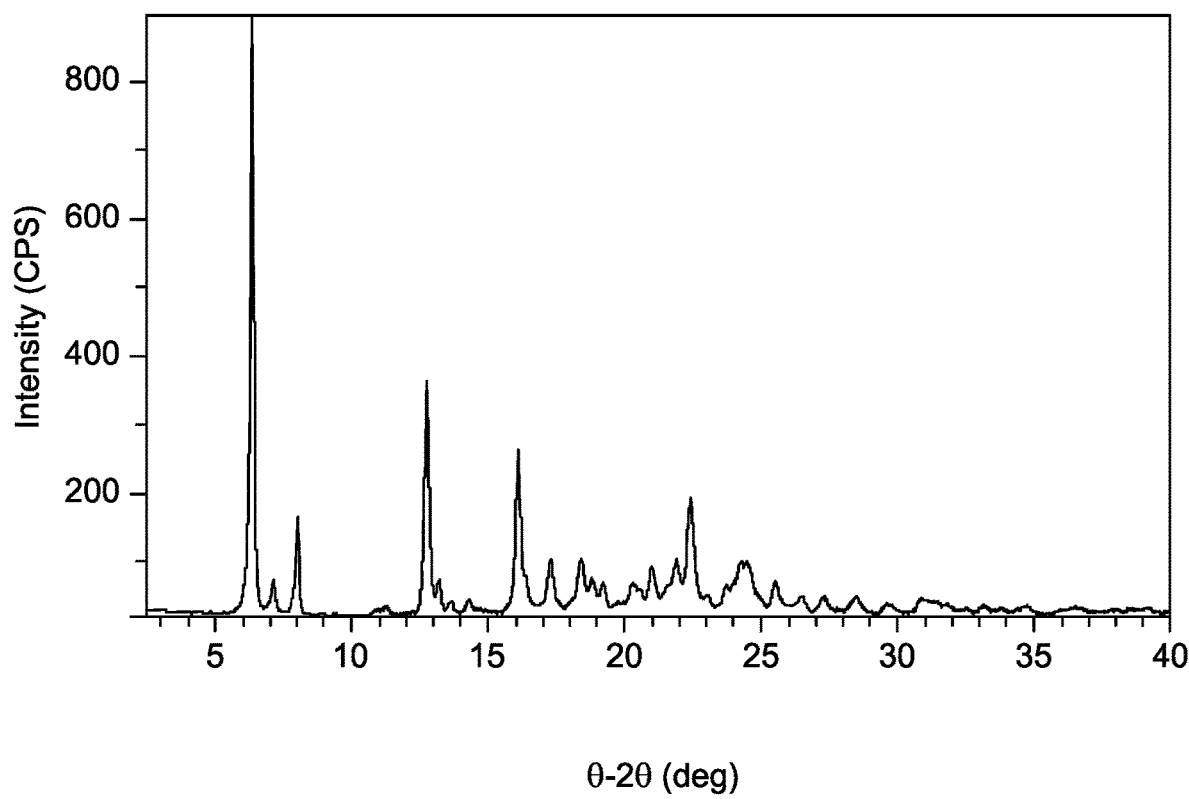
FIG. 32 provides a XRPD pattern of Compound 1 Form J.

In certain embodiments, the X-ray powder diffraction pattern of Compound 1 Form J is substantially similar to the XRPD provided in FIG. 32.

Methods for preparing Compound 1 Form J are described infra.

Compound 1 Form K

In certain embodiments, the present disclosure provides a solid form of Compound 1 referred to herein as Form K. In some embodiments, Compound 1 is provided as Form K, substantially free from other free base forms of Compound 1.

Figure 33:
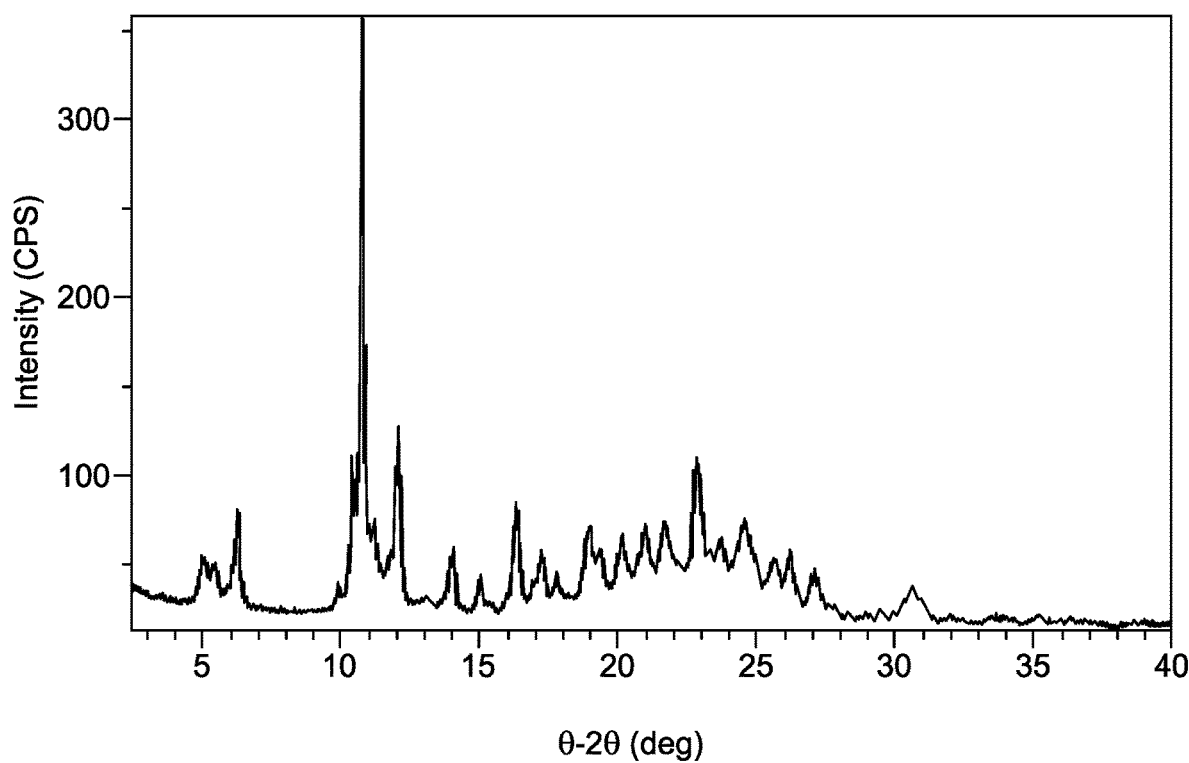
FIG. 33 provides a XRPD pattern of Compound 1 Form K.

In certain embodiments, the X-ray powder diffraction pattern of Compound 1 Form K is substantially similar to the XRPD provided in FIG. 33.

Methods for preparing Compound 1 Form K are described infra.

Compound 1 Form L

In certain embodiments, the present disclosure provides a solid form of Compound 1 referred to herein as Form L. In some embodiments, Compound 1 Form L is a bis-tetrahydrofuran (THF) solvate. In some embodiments, Compound 1 is provided as Form L, substantially free from other free base forms of Compound 1.

Figure 34:
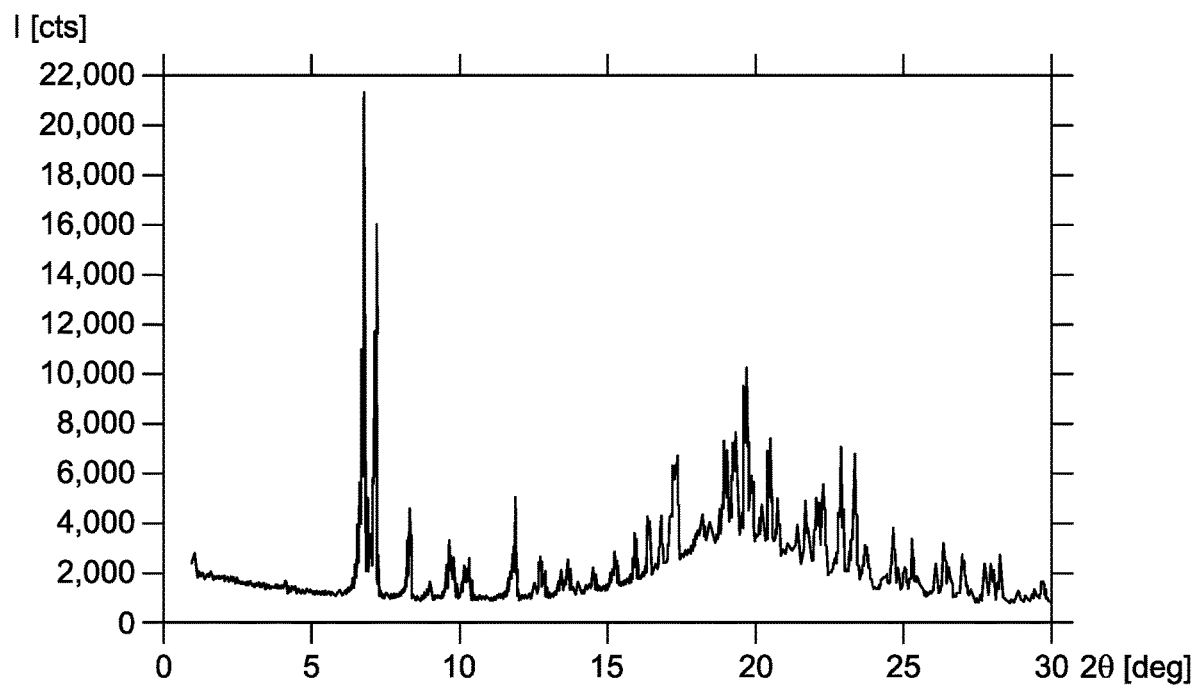
FIG. 34 provides a XRPD pattern of Compound 1 Form L.

In certain embodiments, the X-ray powder diffraction pattern of Compound 1 Form L is substantially similar to the XRPD provided in FIG. 34.

Methods for preparing Compound 1 Form L are described infra.

Compound 1 Form M

In certain embodiments, the present disclosure provides a solid form of Compound 1 referred to herein as Form M. In some embodiments, Compound 1 Form M is a bis- or tris-dimethylformamide (DMF) solvate. In some embodiments, Compound 1 is provided as Form M, substantially free from other free base forms of Compound 1.

Figure 36:
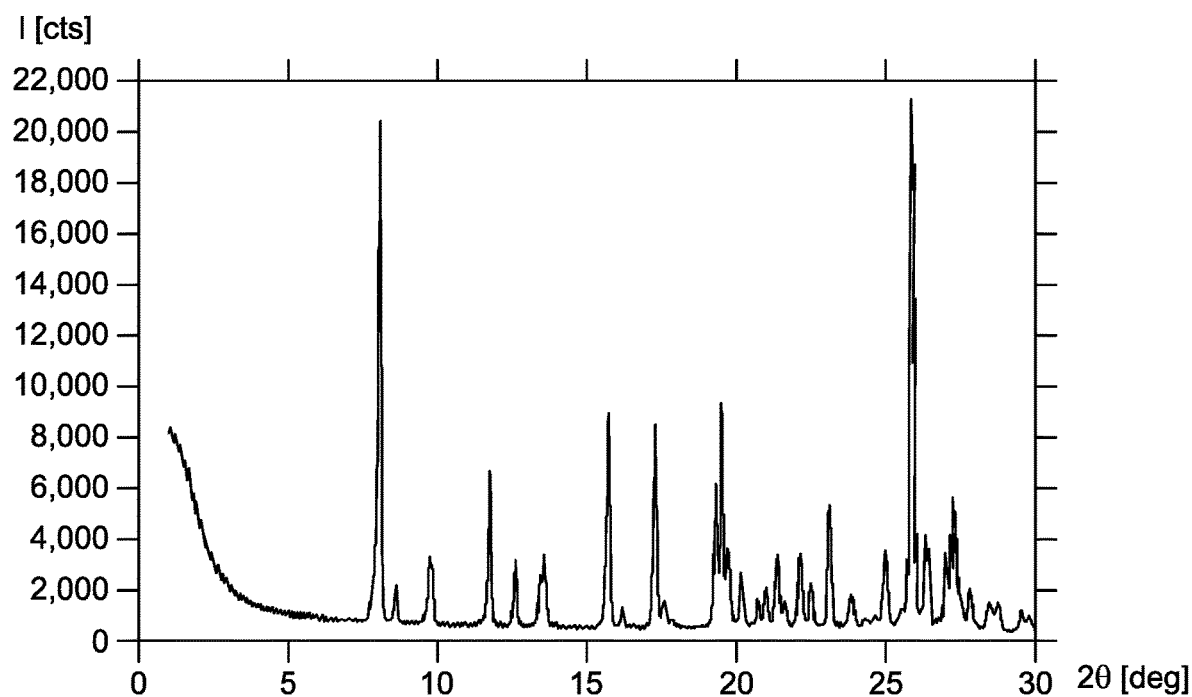
FIG. 36 provides a XRPD pattern of Compound 1 Form N.

In certain embodiments, the X-ray powder diffraction pattern of Compound 1 Form M is substantially similar to the XRPD provided in FIG. 36.

Methods for preparing Compound 1 Form M are described infra.

Compound 1 Form N

In certain embodiments, the present disclosure provides a solid form of Compound 1 referred to herein as Form N. In some embodiments, Compound 1 Form N is anhydrous. In some embodiments, Compound 1 is provided as Form N, substantially free from other free base forms of Compound 1.

In some embodiments, Compound 1 Form N has at least 1, 2, 3, 4 or 5 X-ray Powder Diffraction (XRPD) peaks selected from the angles (degrees 2 theta±0.20) listed in Table N-1

TABLE N-1

| XRPD Peak Positions for Compound 1 Form N Angle/° 2θ |
|---|
| 8.08 |
| 8.62 |
| 9.75 |
| 9.81 |
| 11.76 |
| 12.62 |
| 13.44 |
| 13.56 |
| 15.73 |
| 16.21 |
| 17.31 |
| 17.59 |
| 17.87 |
| 19.32 |
| 19.54 |
| 19.74 |
| 20.21 |
| 20.74 |
| 21.00 |
| 21.39 |
| 21.62 |
| 22.15 |

TABLE N-1-continued

| XRPD Peak Positions for Compound 1 Form N Angle/° 2θ |
|---|
| 22.52 |
| 23.13 |
| 23.86 |
| 24.34 |
| 24.66 |
| 25.02 |
| 25.57 |
| 25.90 |
| 26.38 |
| 27.06 |
| 27.31 |
| 27.85 |
| 28.49 |
| 28.77 |
| 29.55 |
| 29.81 |
| 30.47 |
| 31.04 |
| 31.79 |
| 32.46 |
| 33.27 |
| 34.45 |
| 34.83 |

In some embodiments, Compound 1 Form N is characterized by an X-ray powder diffraction (XRPD) pattern having diffractions at angles (degrees 2 theta±0.20) and corresponding d-spacing of:

TABLE N-2

| XRPD Peak Positions and d-Spacing for Compound 1 Form N | |
|---|---|
| Angle/° 2θ | d-spacing/Angstrom |
| 8.08 | 10.933 ± 0.270 |
| 8.62 | 10.250 ± 0.237 |
| 9.75 | 9.064 ± 0.185 |
| 9.81 | 9.009 ± 0.183 |
| 11.76 | 7.519 ± 0.127 |
| 12.62 | 7.009 ± 0.111 |
| 13.44 | 6.583 ± 0.098 |
| 13.56 | 6.525 ± 0.096 |
| 15.73 | 5.629 ± 0.071 |
| 16.21 | 5.464 ± 0.067 |
| 17.31 | 5.119 ± 0 059 |
| 17.59 | 5.038 ± 0.057 |
| 17.87 | 4.960 ± 0.055 |
| 19.32 | 4.591 ± 0.047 |
| 19.54 | 4.539 ± 0.046 |
| 19.74 | 4.494 ± 0.045 |
| 20.21 | 4.390 ± 0.043 |
| 20.74 | 4.279 ± 0.041 |
| 21.00 | 4.227 ± 0.040 |
| 21.39 | 4.151 ± 0.038 |
| 21.62 | 4.107 ± 0.038 |
| 22.15 | 4.010 ± 0.036 |
| 22.52 | 3.945 ± 0.035 |
| 23.13 | 3.842 ± 0.033 |
| 23.86 | 3.726 ± 0.031 |
| 24.34 | 3.654 ± 0.030 |
| 24.66 | 3.607 ± 0.029 |
| 25.02 | 3.556 ± 0.028 |
| 25.57 | 3.481 ± 0.027 |
| 25.90 | 3.437 ± 0.026 |
| 26.38 | 3.376 ± 0.025 |
| 27.06 | 3.293 ± 0.024 |
| 27.31 | 3.263 ± 0.023 |
| 27.85 | 3.201 ± 0.023 |
| 28.49 | 3.130 ± 0.022 |
| 28.77 | 3.101 ± 0.021 |
| 29.55 | 3.020 ± 0.020 |
| 29.81 | 2.995 ± 0.020 |
| 30.47 | 2.931 ± 0.019 |
| 31.04 | 2.879 ± 0.018 |

TABLE N-2-continued

XRPD Peak Positions and d-Spacing for Compound 1 Form N

| Angle/° 2θ | d-spacing/Angstrom |
|---|---|
| 31.79 | 2.813 ± 0.017 |
| 32.46 | 2.756 ± 0.017 |
| 33.27 | 2.691 ± 0.016 |
| 34.45 | 2.601 ± 0.015 |
| 34.83 | 2.574 ± 0.014 |

In some embodiments, Compound 1 Form N is characterized in that it has one or more peaks in its X-ray powder diffraction pattern selected from those at about 8.08, 11.76, 15.73, 17.31, 19.32, 19.54, 23.13, 25.90, and 27.31 degrees 2-theta. In some embodiments, Compound 1 Form N is characterized in that it has two or more peaks in its X-ray powder diffraction pattern selected from those at about 8.08, 11.76, 15.73, 17.31, 19.32, 19.54, 23.13, 25.90, and 27.31 degrees 2-theta. In some embodiments, Compound 1 Form N is characterized in that it has three or more peaks in its X-ray powder diffraction pattern selected from those at about 8.08, 11.76, 15.73, 17.31, 19.32, 19.54, 23.13, 25.90, and 27.31 degrees 2-theta. In some embodiments, Compound 1 Form N is characterized in that it has four or more peaks in its X-ray powder diffraction pattern selected from those at about 8.08, 11.76, 15.73, 17.31, 19.32, 19.54, 23.13, 25.90, and 27.31 degrees 2-theta. In some embodiments, Compound 1 Form N is characterized in that it has five or more peaks in its X-ray powder diffraction pattern selected from those at about 8.08, 11.76, 15.73, 17.31, 19.32, 19.54, 23.13, 25.90, and 27.31 degrees 2-theta. In some embodiments, Compound 1 Form N is characterized in that it has six or more peaks in its X-ray powder diffraction pattern selected from those at about 8.08, 11.76, 15.73, 17.31, 19.32, 19.54, 23.13, 25.90, and 27.31 degrees 2-theta. In some embodiments, Compound 1 Form N is characterized in that it has seven or more peaks in its X-ray powder diffraction pattern selected from those at about 8.08, 11.76, 15.73, 17.31, 19.32, 19.54, 23.13, 25.90, and 27.31 degrees 2-theta. In some embodiments, Compound 1 Form N is characterized in that it has eight or more peaks in its X-ray powder diffraction pattern selected from those at about 8.08, 11.76, 15.73, 17.31, 19.32, 19.54, 23.13, 25.90, and 27.31 degrees 2-theta. In some embodiments, Compound 1 Form N is characterized in that it has peaks in its X-ray powder diffraction pattern selected from those at about 8.08, 11.76, 15.73, 17.31, 19.32, 19.54, 23.13, 25.90, and 27.31 degrees 2-theta. In some embodiments, Compound 1 Form N is characterized in that it has peaks in its X-ray powder diffraction pattern selected from those at about 8.08, 11.76, 15.73, 17.31, 19.32, 19.54, 23.13, 25.90, and 27.31 degrees 2-theta, corresponding to d-spacing shown in Table N-2 above. As used herein, the term "about", when used in reference to a degree 2-theta value refers to the stated value±0.2 degree 2-theta.

In certain embodiments, the X-ray powder diffraction pattern of Compound 1 Form N is substantially similar to the XRPD provided in FIG. 36.

Methods for preparing Compound 1 Form N are described infra.

Compound 1 Form O

In certain embodiments, the present disclosure provides a solid form of Compound 1 referred to herein as Form O. In some embodiments, Compound 1 is provided as Form O, substantially free from other free base forms of Compound 1.

Figure 14A:
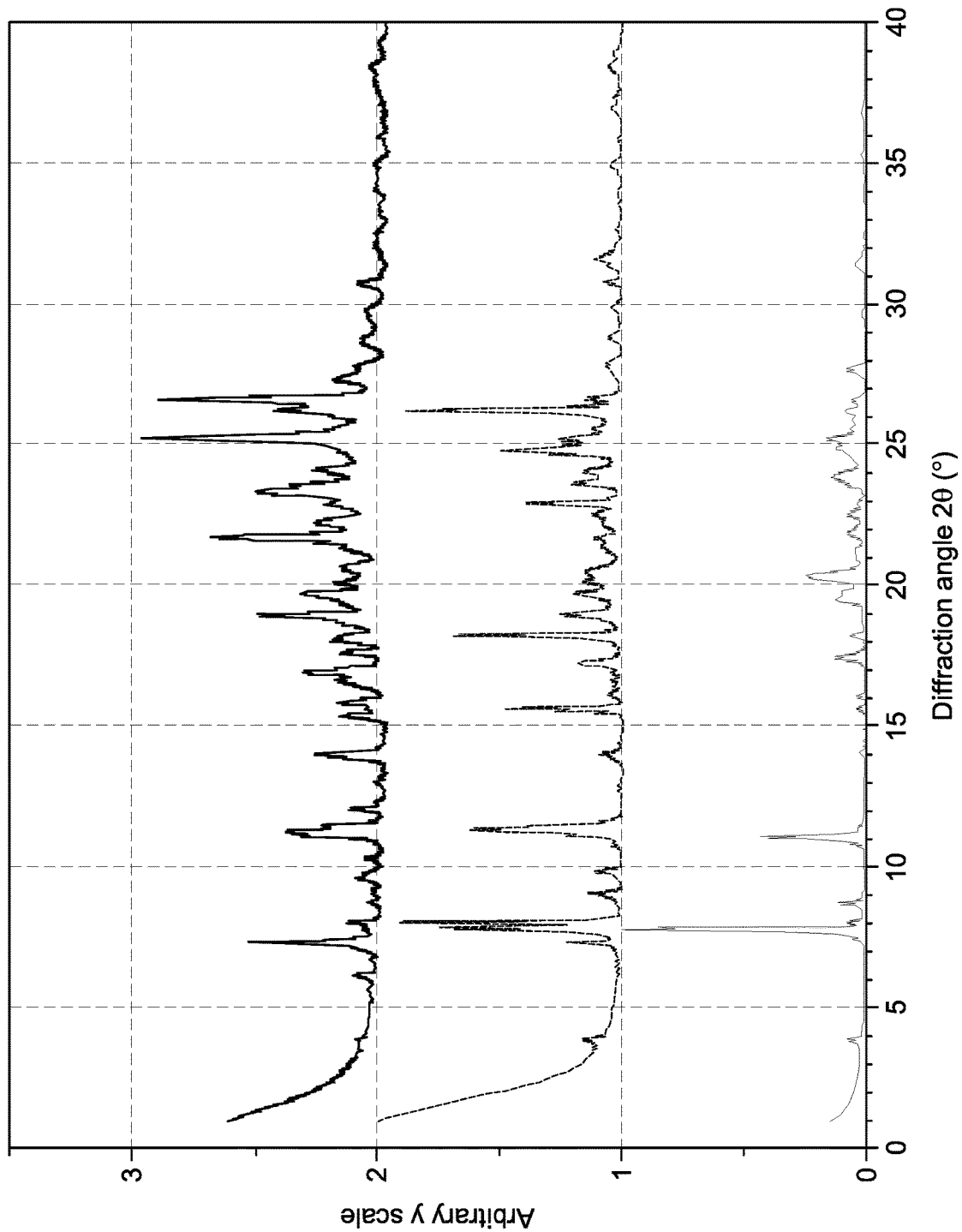
FIG. 14A provides XRPD spectra of three lots of Compound 1. From top to bottom: Compound 1 Lot I, Compound 1 Lot 11, and Compound 1 Lot III.
Figure 14B:
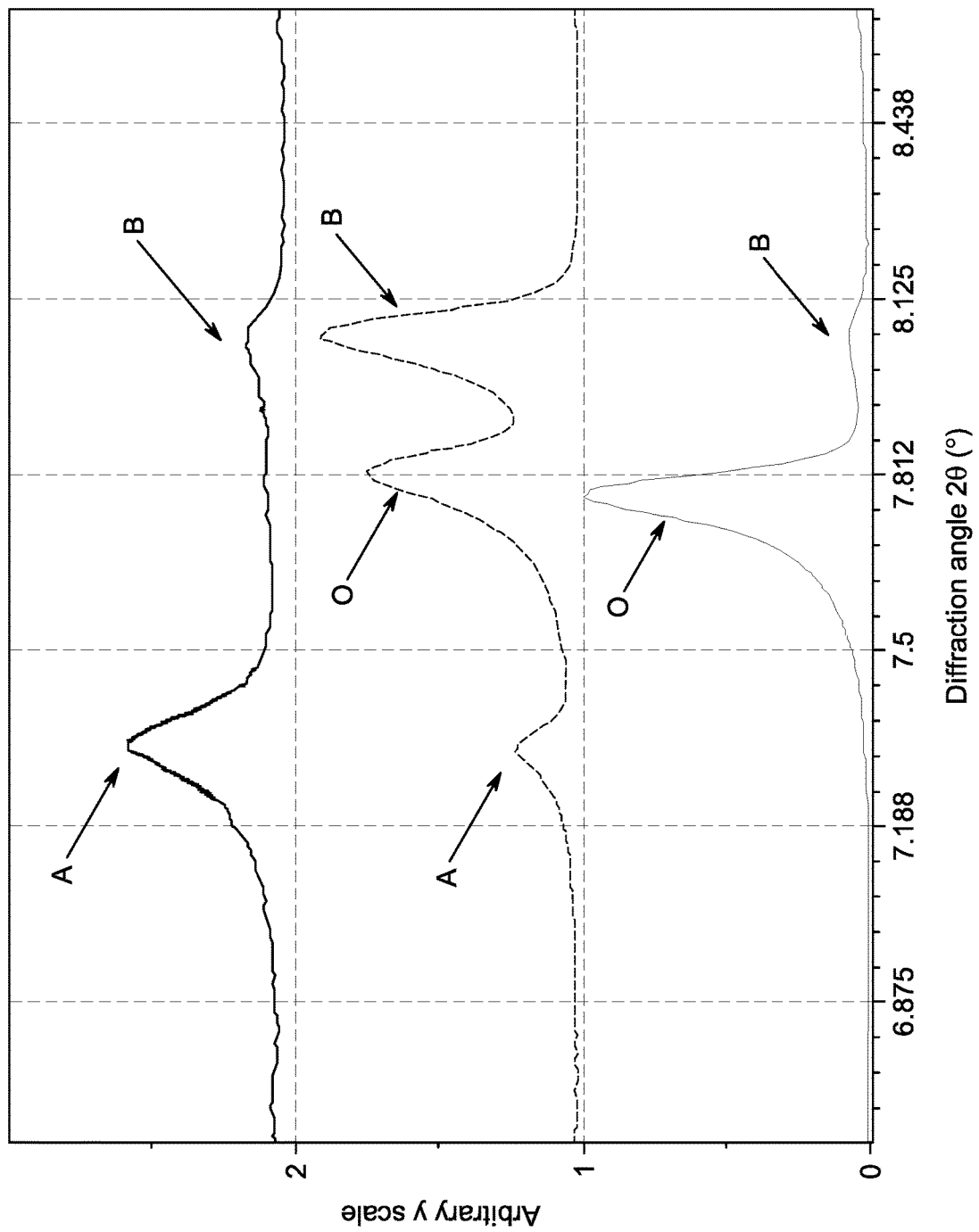
FIG. 14B provides a magnified view of the spectra from FIG. 14A between approx. 6.7 and 8.5 degrees 2-theta. Characteristic peak for each of Form A, Form B, and Form O of Compound 1 is labeled.

In certain embodiments, the X-ray powder diffraction pattern of Compound 1 Form O is substantially similar to the XRPD provided in FIG. 14A (bottom spectrum).

Methods for preparing Compound 1 Form O are described infra.

Compound 1 Form P

In certain embodiments, the present disclosure provides a solid form of Compound 1 referred to herein as Form P. In some embodiments, Compound 1 Form P is a mono- or bis-ethyl acetate solvate. In some embodiments, Compound 1 is provided as Form P, substantially free from other free base forms of Compound 1.

Figure 38:
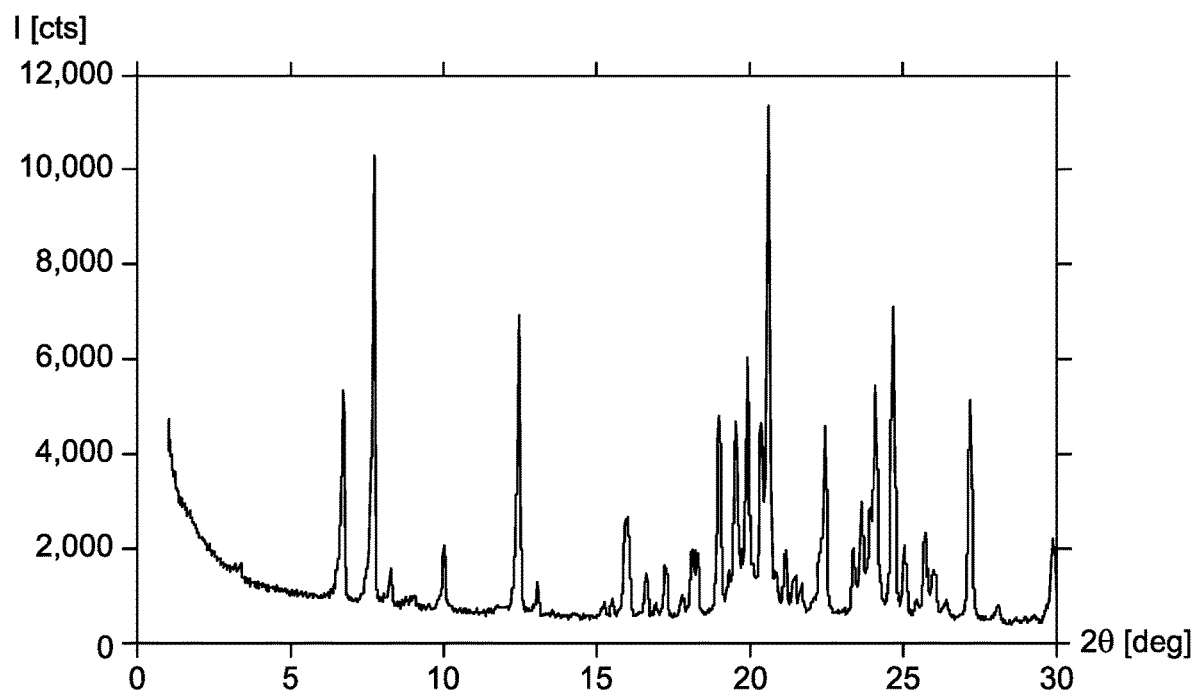
FIG. 38 provides a XRPD pattern of Compound 1 Form P.

In certain embodiments, the X-ray powder diffraction pattern of Compound 1 Form P is substantially similar to the XRPD provided in FIG. 38.

Methods for preparing Compound 1 Form P are described infra.

II. Combinations of Co-Formers with Compound 1

In some embodiments, Compound 1 and a co-former (e.g., an acid) are combined to provide a species where Compound 1 and the co-former are, e.g., ionically bonded or are hydrogen bonded to form a provided compound, as described herein. It is contemplated that provided compounds can exist in a variety of physical forms. For example, provided compounds can be in solution, suspension, or in solid form. In certain embodiments, a provided compound is in solid form. When provided compounds are in solid form, said compounds may be amorphous, crystalline, or a mixture thereof. Exemplary solid forms of Compounds 2 through 5 are described in more detail below.

2. Compound 2 (Hydrochloric Acid×Compound 1)

In some embodiments, the present disclosure provides a chemical species Compound 2 comprising Compound 1 and hydrochloric acid:

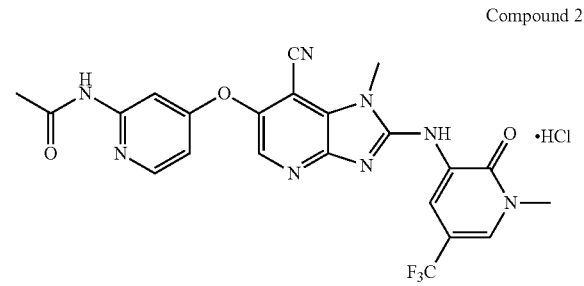 [SMILES: CC(=O)Nc1cc(Oc2cnc3nc(Nc4cc(C(F)(F)F)cn(C)c4=O)n(C)c3c2C#N)ccn1 ; Br]

Compound 2

It is contemplated that Compound 2 can exist in a variety of physical forms. For example, Compound 2 can be in solution, suspension, or in solid form. In certain embodiments, Compound 2 is in solid form. When Compound 2 is in solid form, said compound may be amorphous, crystalline, or a mixture thereof.

In some embodiments, a solid form of Compound 2 has a stoichiometry of (Compound 1):(hydrochloric acid) that is about 1:1. As used herein, the term "about", when used in reference to a stoichiometric ratio refers to 1:(1f0.25) ratio of (Compound 1):(co-former, e.g., an acid), e.g., a 1:(10.25) ratio, a 1:(10.2) ratio, a 1:(1f0.1) ratio, or a 1:(1±0.05) ratio.

In some embodiments, the present disclosure provides Compound 2 substantially free of impurities. As used herein, the term "substantially free of impurities" means that the compound contains no significant amount of extraneous matter. Such extraneous matter may include excess hydrochloric acid, excess Compound 1, residual solvents, or any other impurities that may result from the preparation of, and/or isolation of, Compound 2. In certain embodiments, at least about 95% by weight of Compound 2 is present. In certain embodiments, at least about 95%, about 96%, about 97%, about 98%, or about 99% by weight of Compound 2 is present. In still other embodiments of the disclosure, at least about 99% by weight of Compound 2 is present.

According to one embodiment, Compound 2 is present in an amount of at least about 97.0, 97.5, 98.0, 98.5, 99.0, 99.5, or 99.8 weight percent where the percentages are based on the total weight of the composition. According to another embodiment, Compound 2 contains no more than about 3.0 area percent HPLC of total organic impurities and, in certain embodiments, no more than about 1.5 area percent HPLC total organic impurities relative to the total area of the HPLC chromatogram. In some embodiments, Compound 2 contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 2 is also meant to include all tautomeric forms of Compound 2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this disclosure.

It has been found that Compound 2 can exist in a variety of solid forms. Exemplary such forms include polymorphs such as those described herein.

As used herein, the term "polymorph" refers to the different crystal structures into which a compound, or a salt or co-crystal or solvate thereof, can crystallize.

In some embodiments, Compound 2 is amorphous. In some embodiments, Compound 2 is amorphous, and is substantially free of crystalline Compound 2. As used herein, the term "substantially free of crystalline Compound 2" means that the compound contains no significant amount of crystalline Compound 2. In some embodiments, at least about 95%, about 96%, about 97%, about 98%, or about 99% by weight of amorphous Compound 2 is present. In some embodiments, at least about 99% by weight of amorphous Compound 2 is present.

In certain embodiments, Compound 2 is a crystalline solid. In other embodiments, Compound 2 is a crystalline solid substantially free of amorphous Compound 2. As used herein, the term "substantially free of amorphous Compound 2" means that the compound contains no significant amount of amorphous Compound 2. In certain embodiments, at least about 95% by weight of crystalline Compound 2 is present. In certain embodiments, at least about 95%, about 96%, about 97%, about 98%, or about 99% by weight of crystalline Compound 2 is present. In still other embodiments of the disclosure, at least about 99% by weight of crystalline Compound 2 is present.

When Compound 1 is in contact with one equivalent of HCl in various solvents, the resulting Compound 2 can exist in at least two polymorphic forms. In some embodiments, the present disclosure provides a polymorphic form of Compound 2 referred to herein as Form A. In some embodiments, the present disclosure provides a polymorphic form of Compound 2 referred to herein as Form B.

Compound 2 Form A

In some embodiments, Compound 2 Form A has at least 1, 2, 3, 4 or 5 X-ray Powder Diffraction (XRPD) peaks selected from the angles (degrees 2 theta±0.20) listed in Table 3 below.

TABLE 3

XRPD Peak Positions for Compound 2 Form A
Angle/° 2θ

| Angle/° 2θ |
|---|
| 7.38 |
| 8.17 |
| 10.01 |
| 11.29 |
| 11.98 |
| 12.3 |
| 12.75 |
| 14.83 |
| 15.63 |
| 16.6 |
| 17.41 |
| 17.59 |
| 18.15 |
| 19.21 |
| 20.12 |
| 20.71 |
| 21.64 |
| 22.11 |
| 22.38 |
| 23.29 |
| 23.60 |
| 23.83 |
| 24.16 |
| 24.54 |
| 24.77 |
| 25.40 |
| 26.24 |
| 27.23 |
| 28.2 |
| 28.61 |
| 29.85 |
| 30.14 |
| 30.40 |
| 30.63 |
| 31.25 |
| 32.05 |

In some embodiments, Compound 2 Form A is characterized by an X-ray powder diffraction (XRPD) pattern having diffractions at angles (degrees 2 theta±0.20) and corresponding d-spacing of:

TABLE 4

XRPD Peak Positions and d-Spacing for Compound 2 Form A

| Angle/° 2θ | d-spacing/Angstrom |
|---|---|
| 7.38 | 11.969 ± 0.324 |
| 8.17 | 10.813 ± 0.264 |
| 10.01 | 8.829 ± 0.176 |
| 11.29 | 7.831 ± 0.138 |
| 11.98 | 7.382 ± 0.123 |
| 12.30 | 7.190 ± 0.116 |
| 12.75 | 6.937 ± 0.108 |
| 14.83 | 5.969 ± 0.080 |
| 15.63 | 5.665 ± 0.072 |
| 16.60 | 5.336 ± 0.064 |
| 17.41 | 5.090 ± 0.058 |
| 17.59 | 5.038 ± 0.057 |
| 18.15 | 4.884 ± 0.053 |
| 19.21 | 4.617 ± 0.048 |
| 20.12 | 4.410 ± 0.043 |
| 20.71 | 4.285 ± 0.041 |
| 21.64 | 4.103 ± 0.037 |
| 22.11 | 4.017 ± 0.036 |
| 22.38 | 3.969 ± 0.035 |

TABLE 4-continued

XRPD Peak Positions and d-Spacing for Compound 2 Form A

| Angle/° 2θ | d-spacing/Angstrom |
|---|---|
| 23.29 | 3.816 ± 0.032 |
| 23.60 | 3.767 ± 0.031 |
| 23.83 | 3.731 ± 0.031 |
| 24.16 | 3.681 ± 0.030 |
| 24.54 | 3.625 ± 0.029 |
| 24.77 | 3.591 ± 0.029 |
| 25.40 | 3.504 ± 0.027 |
| 26.24 | 3.394 ± 0.025 |
| 27.23 | 3.272 ± 0.024 |
| 28.20 | 3.162 ± 0.022 |
| 28.61 | 3.118 ± 0.021 |
| 29.85 | 2.991 ± 0.020 |
| 30.14 | 2.963 ± 0.019 |
| 30.40 | 2.938 ± 0.019 |
| 30.63 | 2.916 ± 0.019 |
| 31.25 | 2.860 ± 0.018 |
| 32.05 | 2.790 ± 0.017 |

In some embodiments, Compound 2 Form A is characterized in that it has one or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has two or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has three or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has four or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has five or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has six or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has seven or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has eight or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has nine or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has ten or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has eleven or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has twelve or more peaks in its X-ray powder diffraction pattern selected from those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has peaks in its X-ray powder diffraction pattern comprising those at about 7.38, 8.17, 11.98, 12.30, 15.63, 19.21, 20.12, 20.71, 21.64, 22.11, 24.16, 25.40, and 27.23 degrees 2 theta. In some embodiments, Compound 2 Form A is characterized in that it has peaks in its X-ray powder diffraction pattern comprising those at about 7.38, 8.17, 11.98, 12.30, 15.63, 19.21, 20.12, 20.71, 21.64, 22.11, 24.16, 25.40, and 27.23 degrees 2 theta, corresponding to d-spacing shown in Table 4 above. As used herein, the term "about", when used in reference to a degree 2-theta value refers to the stated value±0.2 degree 2-theta.

Figure 4:
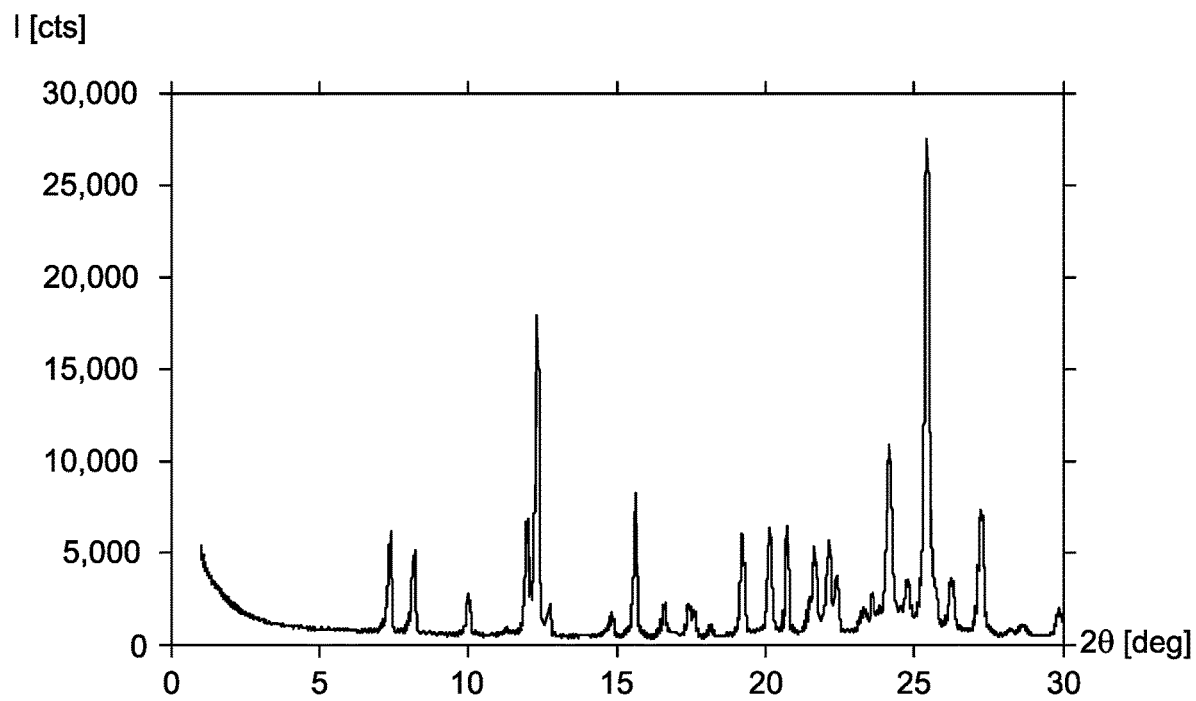
FIG. 4 provides a X-ray powder diffraction (XRPD) pattern of Compound 2 Form A.

In certain embodiments, the X-ray powder diffraction pattern of Compound 2 Form A is substantially similar to the XRPD provided in FIG. 4.

Methods for preparing Compound 2 Form A are described infra.

3. Compound 3 (Hydrobromic Acid×Compound 1)

In some embodiments, the present disclosure provides a chemical species Compound 3 comprising Compound 1 and hydrobromic acid:

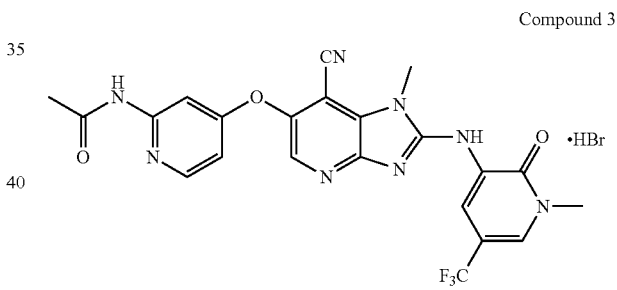

Compound 3

It is contemplated that Compound 3 can exist in a variety of physical forms. For example, Compound 3 can be in solution, suspension, or in solid form. In certain embodiments, Compound 3 is in solid form. When Compound 3 is in solid form, said compound may be amorphous, crystalline, or a mixture thereof.

In one embodiment, a solid form of Compound 3 has a stoichiometry of (Compound 1):(hydrobromic acid) that is about 1:1.

In some embodiments, the present disclosure provides Compound 3 substantially free of impurities. As used herein, the term "substantially free of impurities" means that the compound contains no significant amount of extraneous matter. Such extraneous matter may include excess hydrobromic acid, excess Compound 1, residual solvents, or any other impurities that may result from the preparation of, and/or isolation of, Compound 3. In certain embodiments, at least about 95% by weight of Compound 3 is present. In certain embodiments, at least about 95%, about 96%, about 97%, about 98%, or about 99% by weight of Compound 3 is present. In still other embodiments of the disclosure, at least about 99% by weight of Compound 3 is present.

According to one embodiment, Compound 3 is present in an amount of at least about 97.0, 97.5, 98.0, 98.5, 99.0, 99.5, or 99.8 weight percent where the percentages are based on the total weight of the composition. According to another embodiment, Compound 3 contains no more than about 3.0 area percent HPLC of total organic impurities and, in certain embodiments, no more than about 1.5 area percent HPLC total organic impurities relative to the total area of the HPLC chromatogram. In other embodiments, Compound 3 contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 3 is also meant to include all tautomeric forms of Compound 3. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this disclosure.

In some embodiments, Compound 3 is amorphous. In some embodiments, Compound 3 is amorphous, and is substantially free of crystalline Compound 3. As used herein, the term "substantially free of crystalline Compound 3" means that the compound contains no significant amount of crystalline Compound 3. In some embodiments, at least about 95%, about 96%, about 97%, about 98%, or about 99% by weight of amorphous Compound 3 is present. In some embodiments, at least about 99% by weight of amorphous Compound 3 is present.

In certain embodiments, Compound 3 is a crystalline solid. In other embodiments, Compound 3 is a crystalline solid substantially free of amorphous Compound 3. As used herein, the term "substantially free of amorphous Compound 3" means that the compound contains no significant amount of amorphous Compound 3. In certain embodiments, at least about 95% by weight of crystalline Compound 3 is present. In certain embodiments, at least about 95%, about 96%, about 97%, about 98%, or about 99% by weight of crystalline Compound 3 is present. In still other embodiments of the disclosure, at least about 99% by weight of crystalline Compound 3 is present.

It has been found that Compound 3 can exist in at least one solid form. In some embodiments, the present disclosure provides a solid form of Compound 3 referred to herein as Form A.

Compound 3 Form A

In some embodiments, Compound 3 Form A has at least 1, 2, 3, 4 or 5 X-ray Powder Diffraction (XRPD) peaks selected from the angles (degrees 2 theta±0.2) listed in Table 5 below.

TABLE 5

XRPD Peak Positions for Compound 3 Form A
Angle/° 2θ

| |
| --- |
| 7.10 |
| 8.72 |
| 9.82 |
| 10.45 |
| 10.68 |
| 12.14 |
| 12.40 |
| 13.33 |
| 13.87 |
| 14.25 |
| 14.53 |
| 15.19 |
| 15.99 |
| 16.38 |
| 17.18 |
| 17.35 |
| 17.51 |
| 18.10 |
| 18.61 |
| 19 27 |
| 19.62 |
| 20.13 |
| 20.42 |
| 20.76 |
| 21.01 |
| 21.48 |
| 22.40 |
| 22.93 |
| 24.43 |
| 24.98 |
| 25.14 |
| 25.95 |
| 26.27 |
| 26.76 |
| 27.23 |
| 27.91 |
| 28.09 |
| 28.57 |
| 28.77 |
| 29.32 |
| 29.86 |
| 30.84 |
| 31.09 |

In some embodiments, Compound 3 Form A is characterized by an X-ray powder diffraction (XRPD) pattern having diffractions at angles (degrees 2 theta±0.2) and corresponding d-spacing of:

TABLE 6

XRPD Peak Positions and d-Spacing for Compound 3 Form A

| Angle/° 2θ | d-spacing/Angstrom |
| --- | --- |
| 7.10 | 12.440 ± 0.350 |
| 8.72 | 10.132 ± 0.232 |
| 9.82 | 9.000 ± 0.183 |
| 10.45 | 8.459 ± 0.161 |
| 10.68 | 8.277 ± 0.155 |
| 12.14 | 7.285 ± 0.120 |
| 12.40 | 7.132 ± 0.115 |
| 13.33 | 6.637 ± 0.099 |
| 13.87 | 6.380 ± 0.092 |
| 14.25 | 6.210 ± 0.087 |
| 14.53 | 6.091 ± 0.083 |
| 15.19 | 5.828 ± 0.076 |
| 15.99 | 5.538 ± 0.069 |
| 16.38 | 5.407 ± 0.066 |
| 17.18 | 5.157 ± 0.060 |
| 17.35 | 5.107 ± 0.058 |
| 17.51 | 5.061 ± 0.057 |
| 18.10 | 4.897 ± 0.054 |
| 18.61 | 4.764 ± 0.051 |
| 19.27 | 4.602 ± 0.047 |
| 19.62 | 4.521 ± 0.046 |
| 20.13 | 4.408 ± 0.043 |
| 20.42 | 4.346 ± 0.042 |
| 20.76 | 4.275 ± 0.041 |
| 21.01 | 4.225 ± 0.040 |
| 21.48 | 4.134 ± 0.038 |
| 22.40 | 3.966 ± 0.035 |
| 22.93 | 3.875 ± 0.033 |

TABLE 6-continued

XRPD Peak Positions and d-Spacing for Compound 3 Form A

| Angle/° 2θ | d-spacing/Angstrom |
|---|---|
| 24.43 | 3.641 ± 0.029 |
| 24.98 | 3.562 ± 0.028 |
| 25.14 | 3.539 ± 0.028 |
| 25.95 | 3.431 ± 0.026 |
| 26.27 | 3.389 ± 0.025 |
| 26.76 | 3.329 ± 0.024 |
| 27.23 | 3.272 ± 0.024 |
| 27.91 | 3.194 ± 0.022 |
| 28.09 | 3.174 ± 0.022 |
| 28.57 | 3.122 ± 0.021 |
| 28.77 | 3.100 ± 0.021 |
| 29.32 | 3.044 ± 0.020 |
| 29.86 | 2.990 ± 0.020 |
| 30.84 | 2.897 ± 0.018 |
| 31.09 | 2.874 ± 0.018 |

In some embodiments, Compound 3 Form A is characterized in that it has one or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has two or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has three or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has four or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has five or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has six or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has seven or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has eight or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has nine or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has ten or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has eleven or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has twelve or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has thirteen or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has fourteen or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has fifteen or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has sixteen or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has seventeen or more peaks in its X-ray powder diffraction pattern selected from those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has peaks in its X-ray powder diffraction pattern comprising those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta. In some embodiments, Compound 3 Form A is characterized in that it has peaks in its X-ray powder diffraction pattern comprising those at about 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23 degrees 2 theta, corresponding to d-spacing shown in Table 6 above. As used herein, the term "about", when used in reference to a degree 2-theta value refers to the stated value±0.2 degree 2-theta.

Figure 8:
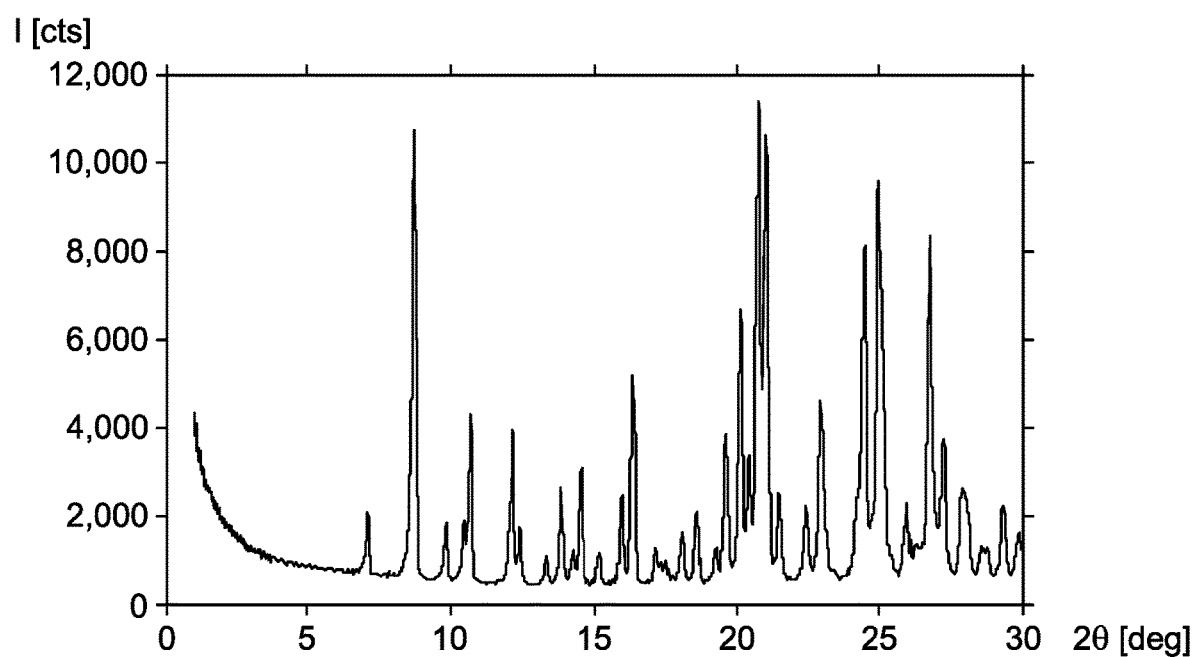
FIG. 8 provides a X-ray powder diffraction (XRPD) pattern of Compound 3 Form A.

In certain embodiments, the X-ray powder diffraction pattern of Compound 3 Form A is substantially similar to the XRPD provided in FIG. 8.

Methods for preparing Compound 3 Form A are described infra.

4. Compound 4 (Methanesulfonic Acid×Compound 1)

In some embodiments, the present disclosure provides a chemical species Compound 4 comprising Compound 1 and methanesulfonic acid:

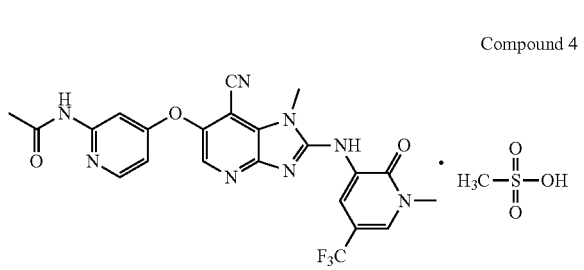

Compound 4

It is contemplated that Compound 4 can exist in a variety of physical forms. For example, Compound 4 can be in solution, suspension, or in solid form. In certain embodiments, Compound 4 is in solid form. When Compound 4 is in solid form, said compound may be amorphous, crystalline, or a mixture thereof.

In some embodiments, a solid form of Compound 4 has a stoichiometry of (Compound 1):(methanesulfonic acid) that is about 1:1.

In some embodiments, the present disclosure provides Compound 4 substantially free of impurities. As used herein, the term "substantially free of impurities" means that the compound contains no significant amount of extraneous matter. Such extraneous matter may include excess methanesulfonic acid, excess Compound 1, residual solvents, or any other impurities that may result from the preparation of, and/or isolation of, Compound 4. In certain embodiments, at least about 95% by weight of Compound 4 is present. In certain embodiments, at least about 95%, about 96%, about 97%, about 98%, or about 99% by weight of Compound 4 is present. In still other embodiments of the disclosure, at least about 99% by weight of Compound 4 is present.

According to one embodiment, Compound 4 is present in an amount of at least about 97.0, 97.5, 98.0, 98.5, 99.0, 99.5, or 99.8 weight percent where the percentages are based on the total weight of the composition. According to another embodiment, Compound 4 contains no more than about 3.0 area percent HPLC of total organic impurities and, in certain embodiments, no more than about 1.5 area percent HPLC total organic impurities relative to the total area of the HPLC chromatogram. In other embodiments, Compound 4 contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 4 is also meant to include all tautomeric forms of Compound 4. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this disclosure.

In some embodiments, Compound 4 is amorphous. In some embodiments, Compound 4 is amorphous, and is substantially free of crystalline Compound 4. As used herein, the term "substantially free of crystalline Compound 4" means that the compound contains no significant amount of crystalline Compound 4. In some embodiments, at least about 95%, about 96%, about 97%, about 98%, or about 99% by weight of amorphous Compound 4 is present. In some embodiments, at least about 99% by weight of amorphous Compound 4 is present.

In certain embodiments, Compound 4 is a crystalline solid. In other embodiments, Compound 4 is a crystalline solid substantially free of amorphous Compound 4. As used herein, the term "substantially free of amorphous Compound 4" means that the compound contains no significant amount of amorphous Compound 4. In certain embodiments, at least about 95% by weight of crystalline Compound 4 is present. In certain embodiments, at least about 95%, about 96%, about 97%, about 98%, or about 99% by weight of crystalline Compound 4 is present. In still other embodiments of the disclosure, at least about 99% by weight of crystalline Compound 4 is present.

It has been found that Compound 4 can exist in at least two polymorphic forms. In some embodiments, the present disclosure provides a polymorphic form of Compound 4 referred to herein as Form A. In some embodiments, the present disclosure provides a polymorphic form of Compound 4 referred to herein as Form B.

Compound 4 Form A

In some embodiments, Compound 4 Form A has at least 1, 2, 3, 4 or 5 X-ray Powder Diffraction (XRPD) peaks selected from the angles (degrees 2 theta±0.2) listed in Table 7 below.

TABLE 7

| XRPD Peak Positions for Compound 4 Form A Angle/° 2θ |
| --- |
| 7.35 |
| 8.52 |
| 9.31 |
| 10.03 |
| 10.65 |
| 11.89 |
| 13.19 |
| 13.68 |
| 14.48 |
| 15.45 |
| 15.89 |
| 16.84 |
| 17.49 |
| 17.66 |
| 18.80 |
| 19.19 |
| 19.48 |
| 20.14 |
| 20.57 |
| 21.43 |
| 21.79 |
| 22.23 |
| 22.52 |
| 22.82 |
| 23.58 |
| 23.94 |
| 24.60 |
| 25.43 |
| 25.83 |
| 26.45 |
| 27.06 |
| 27.62 |
| 28.31 |
| 29.22 |
| 29.83 |
| 30.73 |
| 32.08 |

In some embodiments, Compound 4 Form A is characterized by an X-ray powder diffraction (XRPD) pattern having diffractions at angles (degrees 2 theta±0.2) and corresponding d-spacing of:

TABLE 8

XRPD Peak Positions and d-Spacing for Compound 4 Form A

| Angle/° 2θ | d-spacing/Angstrom |
|---|---|
| 7.35 | 12.018 ± 0.327 |
| 8.52 | 10.370 ± 0.243 |
| 9.31 | 9.492 ± 0.203 |
| 10.03 | 8.812 ± 0.175 |
| 10.65 | 8.300 ± 0.155 |
| 11.89 | 7.437 ± 0.125 |
| 13.19 | 6.707 ± 0.101 |
| 13.68 | 6.468 ± 0.094 |
| 14.48 | 6.112 ± 0.084 |
| 15.45 | 5.731 ± 0.074 |
| 15.89 | 5.573 ± 0.070 |
| 16.84 | 5.261 ± 0.062 |
| 17.49 | 5.067 ± 0.057 |
| 17.66 | 5.018 ± 0.056 |
| 18.80 | 4.716 ± 0.050 |
| 19.19 | 4.621 ± 0.048 |
| 19.48 | 4.553 ± 0.046 |
| 20.14 | 4.405 ± 0.043 |
| 20.57 | 4.314 ± 0.041 |
| 21.43 | 4.143 ± 0.038 |
| 21.79 | 4.075 ± 0.037 |
| 22.23 | 3.996 ± 0.035 |
| 22.52 | 3.945 ± 0.035 |
| 22.82 | 3.894 ± 0.034 |
| 23.58 | 3.770 ± 0.032 |
| 23.94 | 3.714 ± 0.031 |
| 24.60 | 3.616 ± 0.029 |
| 25.43 | 3.500 ± 0.027 |
| 25.83 | 3.446 ± 0.026 |
| 26.45 | 3.367 ± 0.025 |
| 27.06 | 3.293 ± 0.024 |
| 27.62 | 3.227 ± 0.023 |
| 28.31 | 3.150 ± 0.022 |
| 29.22 | 3.054 ± 0.020 |
| 29.83 | 2.993 ± 0.020 |
| 30.73 | 2.907 ± 0.018 |
| 32.08 | 2.788 ± 0.017 |

In some embodiments, Compound 4 Form A is characterized in that it has one or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has two or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has three or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has four or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has five or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has six or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has seven or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has eight or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has nine or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has ten or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has eleven or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has twelve or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has thirteen or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has fourteen or more peaks in its X-ray powder diffraction pattern selected from those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has peaks in its X-ray powder diffraction pattern comprising those at about 8.52, 9.31, 11.89, 14.48, 15.45, 15.89, 18.80, 19.19, 20.14, 20.57, 23.94, 24.60, 25.83, 26.45, and 27.06 degrees 2 theta. In some embodiments, Compound 4 Form A is characterized in that it has peaks in its X-ray powder diffraction pattern comprising those at about 8.52, 9.31, 11.89, 14.48, 15.45, 15.89, 18.80, 19.19, 20.14, 20.57, 23.94, 24.60, 25.83, 26.45, and 27.06 degrees 2 theta, corresponding to d-spacing shown in Table 8 above. As used herein, the term "about", when used in reference to a degree 2-theta value refers to the stated value±0.2 degree 2-theta.

Figure 10:
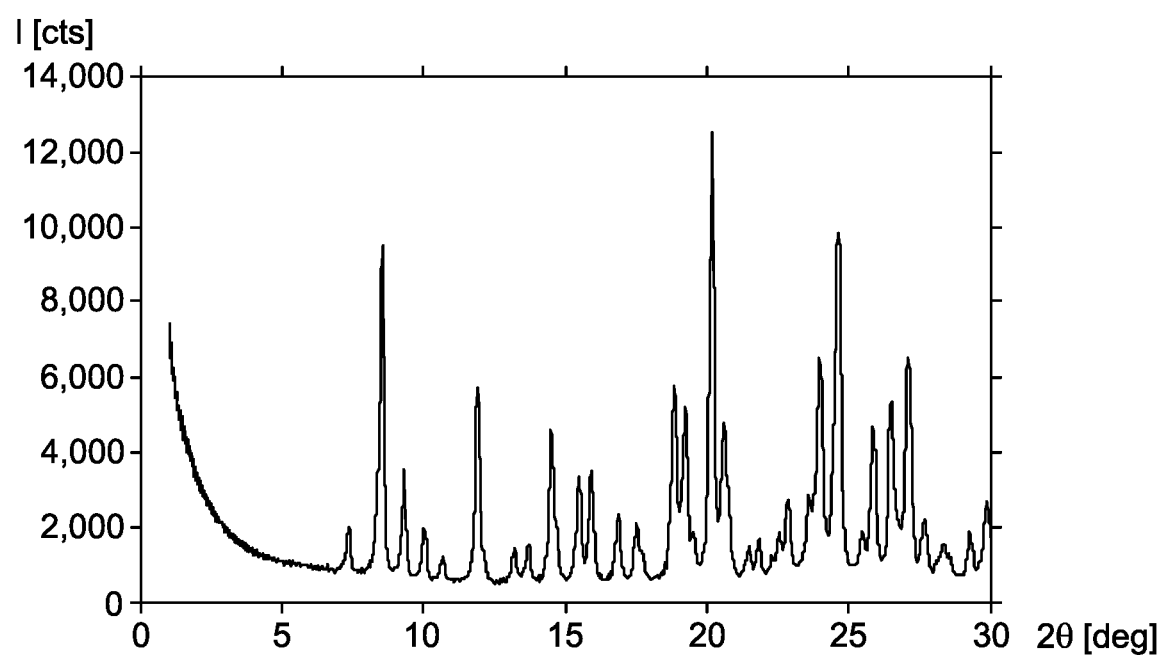
FIG. 10 provides a X-ray powder diffraction (XRPD) pattern of Compound 4 Form A.

In certain embodiments, the X-ray powder diffraction pattern of Compound 4 Form A is substantially similar to the XRPD provided in FIG. 10.

Methods for preparing Compound 4 Form A are described infra.

Compound 4 Form B

In some embodiments, Compound 4 Form B has at least 1, 2, 3, 4 or 5 X-ray Powder Diffraction (XRPD) peaks selected from the angles (degrees 2 theta 0.2) listed in Table 9 below.

TABLE 9

XRPD Peak Positions for Compound 4 Form B
Angle/° 2θ

| |
|---|
| 7.42 |
| 8.53 |
| 9.60 |
| 10.31 |
| 12.16 |
| 13.45 |
| 14.75 |
| 15.39 |
| 15.86 |
| 17.76 |
| 18.27 |
| 18.69 |
| 20.07 |
| 20.74 |
| 21.50 |
| 22.45 |
| 23.78 |
| 24.56 |
| 25.13 |
| 25.84 |
| 27.07 |
| 28.04 |
| 29.13 |
| 29.89 |
| 31.14 |
| 32.08 |
| 33.12 |

In some embodiments, Compound 4 Form B is characterized by an X-ray powder diffraction (XRPD) pattern having diffractions at angles (degrees 2 theta±0.2) and corresponding d-spacing of:

TABLE 10

XRPD Peak Positions and d-Spacing for Compound 4 Form B

| Angle/° 2θ | d-spacing/Angstrom |
|---|---|
| 7.42 | 11.904 ± 0.320 |
| 8.53 | 10.358 ± 0.242 |
| 9.60 | 9.206 ± 0.191 |
| 10.31 | 8.573 ± 0.166 |
| 12.16 | 7.273 ± 0.119 |
| 13.45 | 6.578 ± 0.097 |
| 14.75 | 6.001 ± 0.081 |
| 15.39 | 5.753 ± 0.074 |
| 15.86 | 5.583 ± 0.070 |
| 17.76 | 4.990 ± 0.056 |
| 18.27 | 4.852 ± 0.053 |
| 18.69 | 4.744 ± 0.050 |
| 20.07 | 4.421 ± 0.044 |
| 20.74 | 4.279 ± 0.041 |
| 21.50 | 4.130 ± 0.038 |
| 22.45 | 3.957 ± 0.035 |
| 23.78 | 3.739 ± 0.031 |
| 24.56 | 3.622 ± 0.029 |
| 25.13 | 3.541 ± 0.028 |
| 25.84 | 3.445 ± 0.026 |
| 27.07 | 3.291 ± 0.024 |
| 28.04 | 3.180 ± 0.022 |
| 29.13 | 3.063 ± 0.021 |
| 29.89 | 2.987 ± 0.020 |
| 31.14 | 2.870 ± 0.018 |
| 32.08 | 2.788 ± 0.017 |
| 33.12 | 2.703 ± 0.016 |

In some embodiments, Compound 4 Form B is characterized in that it has one or more peaks in its X-ray powder diffraction pattern selected from those at about 8.53, 9.60, 10.31, 12.16, 14.75, 15.86, 20.07, 20.74, 22.45, 24.56, and 27.07 degrees 2 theta. In some embodiments, Compound 4 Form B is characterized in that it has two or more peaks in its X-ray powder diffraction pattern selected from those at about 8.53, 9.60, 10.31, 12.16, 14.75, 15.86, 20.07, 20.74, 22.45, 24.56, and 27.07 degrees 2 theta. In some embodiments, Compound 4 Form B is characterized in that it has three or more peaks in its X-ray powder diffraction pattern selected from those at about 8.53, 9.60, 10.31, 12.16, 14.75, 15.86, 20.07, 20.74, 22.45, 24.56, and 27.07 degrees 2 theta. In some embodiments, Compound 4 Form B is characterized in that it has four or more peaks in its X-ray powder diffraction pattern selected from those at about 8.53, 9.60, 10.31, 12.16, 14.75, 15.86, 20.07, 20.74, 22.45, 24.56, and 27.07 degrees 2 theta. In some embodiments, Compound 4 Form B is characterized in that it has five or more peaks in its X-ray powder diffraction pattern selected from those at about 8.53, 9.60, 10.31, 12.16, 14.75, 15.86, 20.07, 20.74, 22.45, 24.56, and 27.07 degrees 2 theta. In same embodiments, Compound 4 Form B is characterized in that it has six or more peaks in its X-ray powder diffraction pattern selected from those at about 8.53, 9.60, 10.31, 12.16, 14.75, 15.86, 20.07, 20.74, 22.45, 24.56, and 27.07 degrees 2 theta. In same embodiments, Compound 4 Form B is characterized in that it has seven or more peaks in its X-ray powder diffraction pattern selected from those at about 8.53, 9.60, 10.31, 12.16, 14.75, 15.86, 20.07, 20.74, 22.45, 24.56, and 27.07 degrees 2 theta. In some embodiments, Compound 4 Form B is characterized in that it has eight or more peaks in its X-ray powder diffraction pattern selected from those at about 8.53, 9.60, 10.31, 12.16, 14.75, 15.86, 20.07, 20.74, 22.45, 24.56, and 27.07 degrees 2 theta. In some embodiments, Compound 4 Form B is characterized in that it has nine or more peaks in its X-ray powder diffraction pattern selected from those at about 8.53, 9.60, 10.31, 12.16, 14.75, 15.86, 20.07, 20.74, 22.45, 24.56, and 27.07 degrees 2 theta. In some embodiments, Compound 4 Form B is characterized in that it has ten or more peaks in its X-ray powder diffraction pattern selected from those at about 8.53, 9.60, 10.31, 12.16, 14.75, 15.86, 20.07, 20.74, 22.45, 24.56, and 27.07 degrees 2 theta. In some embodiments, Compound 4 Form B is characterized in that it has peaks in its X-ray powder diffraction pattern comprising those at about 8.53, 9.60, 10.31, 12.16, 14.75, 15.86, 20.07, 20.74, 22.45, 24.56, and 27.07 degrees 2 theta. In some embodiments, Compound 4 Form B is characterized in that it has peaks in its X-ray powder diffraction pattern comprising those at about 8.53, 9.60, 10.31, 12.16, 14.75, 15.86, 20.07, 20.74, 22.45, 24.56, and 27.07 degrees 2 theta, corresponding to d-spacing shown in Table 10 above. As used herein, the term "about", when used in reference to a degree 2-theta value refers to the stated value±0.2 degree 2-theta.

Figure 12:
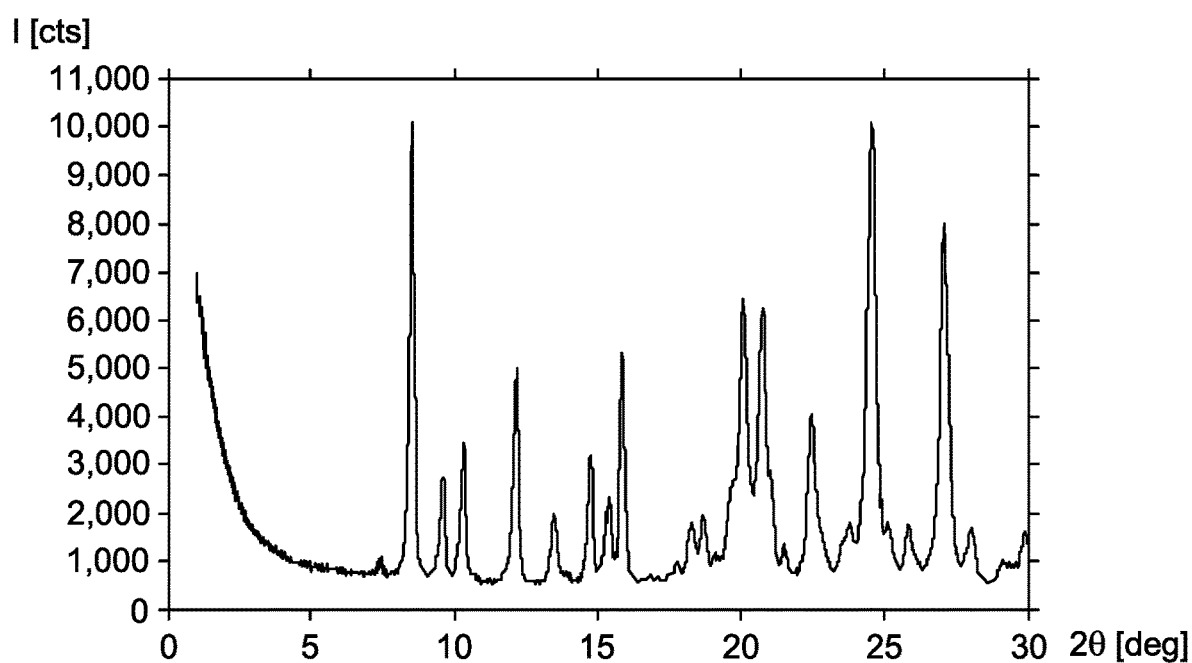
FIG. 12 provides a X-ray powder diffraction (XRPD) pattern of Compound 4 Form B.

In certain embodiments, the X-ray powder diffraction pattern of Compound 4 Form B is substantially similar to the XRPD provided in FIG. 12.

Methods for preparing Compound 4 Form B are described infra.

5. Compound 5 ((1R)-(−)-10-camphorsulfonic Acid×Compound 1)

In some embodiments, the present disclosure provides a chemical species Compound 5 comprising Compound 1 and (1R)-(−)-10-camphorsulfonic acid:

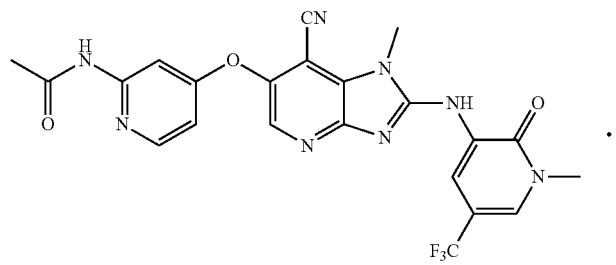
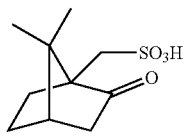

Compound 5

It is contemplated that Compound 5 can exist in a variety of physical forms. For example, Compound 5 can be in solution, suspension, or in solid form. In certain embodiments, Compound 5 is in solid form. When Compound 5 is in solid form, said compound may be amorphous, crystalline, or a mixture thereof.

In some embodiments, the solid form of Compound 5 has a stoichiometry of (Compound 1):((1R)-(−)-10-camphorsulfonic acid) that is about 1:1.

In some embodiments, the present disclosure provides Compound 5 substantially free of impurities. As used herein, the term "substantially free of impurities" means that the compound contains no significant amount of extraneous matter. Such extraneous matter may include excess (1R)-(−)-10-camphorsulfonic acid, excess Compound 1, residual solvents, or any other impurities that may result from the preparation of, and/or isolation of, Compound 5. In certain embodiments, at least about 95% by weight of Compound 5 is present. In certain embodiments, at least about 95%, about 96%, about 97%, about 98%, or about 99% by weight of Compound 5 is present. In still other embodiments of the disclosure, at least about 99% by weight of Compound 5 is present.

According to one embodiment, Compound 5 is present in an amount of at least about 97.0, 97.5, 98.0, 98.5, 99.0, 99.5, or 99.8 weight percent where the percentages are based on the total weight of the composition. According to another embodiment, Compound 5 contains no more than about 3.0 area percent HPLC of total organic impurities and, in certain embodiments, no more than about 1.5 area percent HPLC total organic impurities relative to the total area of the HPLC chromatogram. In other embodiments, Compound 5 contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 5 is also meant to include all tautomeric forms of Compound 5. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this disclosure.

In some embodiments, Compound 5 is amorphous. In some embodiments, Compound 5 is amorphous, and is substantially free of crystalline Compound 5. As used herein, the term "substantially free of crystalline Compound 5" means that the compound contains no significant amount of crystalline Compound 5. In some embodiments, at least about 95%, about 96%, about 97%, about 98%, or about 99% by weight of amorphous Compound 5 is present. In some embodiments, at least about 99% by weight of amorphous Compound 5 is present.

In certain embodiments, Compound 5 is a crystalline solid. In other embodiments, Compound 5 is a crystalline solid substantially free of amorphous Compound 5. As used herein, the term "substantially free of amorphous Compound 5" means that the compound contains no significant amount of amorphous Compound 5. In certain embodiments, at least about 95% by weight of crystalline Compound 5 is present. In certain embodiments, at least about 95%, about 96%, about 97%, about 98%, or about 99% by weight of crystalline Compound 5 is present. In still other embodiments of the disclosure, at least about 99% by weight of crystalline Compound 5 is present.

It has been found that Compound 5 can exist in at least one polymorphic form. In some embodiments, the present disclosure provides a polymorphic form of Compound 5 referred to herein as Form C.

Compound 5 Form C

In some embodiments, Compound 5 Form C has at least 1, 2, 3, 4 or 5 X-ray Powder Diffraction (XRPD) peaks selected from the angles (degrees 2 theta±0.2) listed in Table 11 below.

TABLE 11

XRPD Peak Positions for Compound 5 Form C
Angle /°2θ

| |
|---|
| 6.55 |
| 9.01 |
| 9.87 |
| 10.49 |
| 11.01 |
| 11.57 |
| 12.05 |
| 12.19 |
| 12.65 |
| 13.14 |
| 13.45 |
| 14.08 |
| 14.30 |
| 14.59 |
| 14.98 |
| 15.39 |
| 16.22 |
| 16.46 |
| 16.94 |
| 17.42 |
| 17.62 |
| 17.74 |
| 18.10 |
| 18.75 |
| 19.36 |
| 19.76 |
| 19.95 |
| 20.16 |

TABLE 11-continued

XRPD Peak Positions for Compound 5 Form C
Angle /°2θ

| Angle /°2θ |
|---|
| 20.50 |
| 20.81 |
| 20.91 |
| 21.10 |
| 21.57 |
| 21.99 |
| 22.16 |
| 22.45 |
| 22.87 |
| 23.59 |
| 24.39 |
| 24.66 |
| 25.47 |
| 25.95 |
| 26.48 |
| 26.70 |
| 27.04 |
| 27.30 |
| 27.70 |
| 28.08 |

In some embodiments, Compound 5 Form C is characterized by an X-ray powder diffraction (XRPD) pattern having diffractions at angles (degrees 2 theta±0.2) and corresponding d-spacing of:

TABLE 12

XRPD Peak Positions and d-Spacing for Compound 5 Form C

| Angle /°2θ | d-spacing/Angstrom |
|---|---|
| 6.55 | 13.484 ± 0.411 |
| 9.01 | 9.807 ± 0.217 |
| 9.87 | 8.954 ± 0.181 |
| 10.49 | 8.426 ± 0.160 |
| 11.01 | 8.030 ± 0.145 |
| 11.57 | 7.642 ± 0.132 |
| 12.05 | 7.339 ± 0.121 |
| 12.19 | 7.255 ± 0.119 |
| 12.65 | 6.992 ± 0.110 |
| 13.14 | 6.732 ± 0.102 |
| 13.45 | 6.578 ± 0.097 |
| 14.08 | 6.285 ± 0.089 |
| 14.30 | 6.189 ± 0.086 |
| 14.59 | 6.066 ± 0.083 |
| 14.98 | 5.909 ± 0.078 |
| 15.39 | 5.753 ± 0.074 |
| 16.22 | 5.460 ± 0.067 |
| 16.46 | 5.381 ± 0.065 |
| 16.94 | 5.230 ± 0.061 |
| 17.42 | 5.087 ± 0.058 |
| 17.62 | 5.029 ± 0.057 |
| 17.74 | 4.996 ± 0.056 |
| 18.10 | 4.897 ± 0.054 |
| 18.75 | 4.729 ± 0.050 |
| 19.36 | 4.581 ± 0.047 |
| 19.76 | 4.489 ± 0.045 |
| 19.95 | 4.447 ± 0.044 |
| 20.16 | 4.401 ± 0.043 |
| 20.50 | 4.329 ± 0.042 |
| 20.81 | 4.265 ± 0.041 |
| 20.91 | 4.245 ± 0.040 |
| 21.10 | 4.207 ± 0.039 |
| 21.57 | 4.116 ± 0.038 |
| 21.99 | 4.039 ± 0.036 |
| 22.16 | 4.008 ± 0.036 |
| 22.45 | 3.957 ± 0.035 |
| 22.87 | 3.885 ± 0.034 |
| 23.59 | 3.768 ± 0.031 |
| 24.39 | 3.647 ± 0.029 |
| 24.66 | 3.607 ± 0.029 |
| 25.47 | 3.494 ± 0.027 |
| 25.95 | 3.431 ± 0.026 |
| 26.48 | 3.363 ± 0.025 |
| 26.70 | 3.336 ± 0.025 |
| 27.04 | 3.295 ± 0.024 |
| 27.30 | 3.264 ± 0.023 |
| 27.70 | 3.218 ± 0.023 |
| 28.08 | 3.176 ± 0.022 |
| 28.41 | 3.140 ± 0.022 |
| 28.65 | 3.113 ± 0.021 |
| 29.06 | 3.071 ± 0.021 |
| 29 30 | 3.046 ± 0.020 |
| 29.74 | 3.001 ± 0.020 |
| 30.26 | 2.951 ± 0.019 |
| 31.41 | 2.846 ± 0.018 |
| 32.07 | 2.789 ± 0.017 |

In some embodiments, Compound 5 Form C is characterized in that it has one or more peaks in its X-ray powder diffraction pattern selected from those at about 6.55, 9.01, 12.05, 12.65, 14.08, 22.16, 22.45, and 25.47 degrees 2 theta. In some embodiments, Compound 5 Form C is characterized in that it has two or more peaks in its X-ray powder diffraction pattern selected from those at about 6.55, 9.01, 12.05, 12.65, 14.08, 22.16, 22.45, and 25.47 degrees 2 theta. In some embodiments, Compound 5 Form C is characterized in that it has three or more peaks in its X-ray powder diffraction pattern selected from those at about 6.55, 9.01, 12.05, 12.65, 14.08, 22.16, 22.45, and 25.47 degrees 2 theta. In some embodiments, Compound 5 Form C is characterized in that it has four or more peaks in its X-ray powder diffraction pattern selected from those at about 6.55, 9.01, 12.05, 12.65, 14.08, 22.16, 22.45, and 25.47 degrees 2 theta. In some embodiments, Compound 5 Form C is characterized in that it has five or more peaks in its X-ray powder diffraction pattern selected from those at about 6.55, 9.01, 12.05, 12.65, 14.08, 22.16, 22.45, and 25.47 degrees 2 theta. In some embodiments, Compound 5 Form C is characterized in that it has six or more peaks in its X-ray powder diffraction pattern selected from those at about 6.55, 9.01, 12.05, 12.65, 14.08, 22.16, 22.45, and 25.47 degrees 2 theta. In some embodiments, Compound 5 Form C is characterized in that it has seven or more peaks in its X-ray powder diffraction pattern selected from those at about 6.55, 9.01, 12.05, 12.65, 14.08, 22.16, 22.45, and 25.47 degrees 2 theta. In some embodiments, Compound 5 Form C is characterized in that it has peaks in its X-ray powder diffraction pattern comprising those at about 6.55, 9.01, 12.05, 12.65, 14.08, 22.16, 22.45, and 25.47 degrees 2 theta. In some embodiments, Compound 5 Form C is characterized in that it has peaks in its X-ray powder diffraction pattern comprising those at about 6.55, 9.01, 12.05, 12.65, 14.08, 22.16, 22.45, and 25.47 degrees 2 theta, corresponding to d-spacing shown in Table 12 above. As used herein, the term "about", when used in reference to a degree 2-theta value refers to the stated value±0.2 degree 2-theta.

Figure 13:
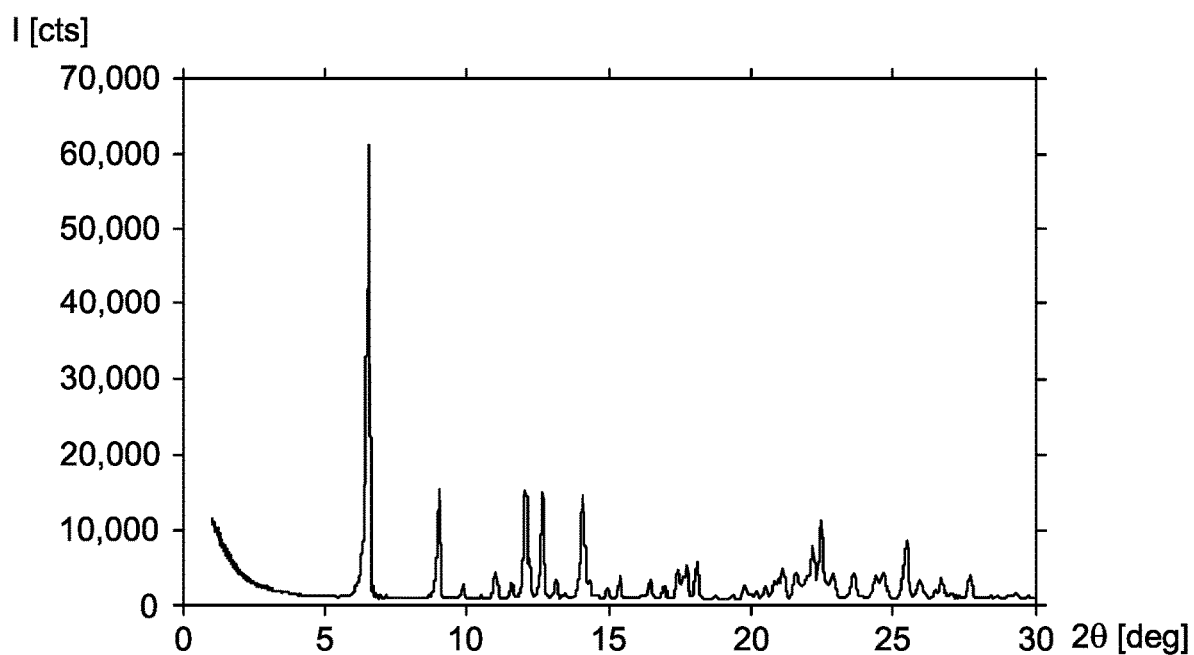
FIG. 13 provides X-ray powder diffraction (XRPD) pattern of Compound 5 Form C.

In certain embodiments, the X-ray powder diffraction pattern of Compound 5 Form C is substantially similar to the XRPD provided in FIG. 13.

Methods for preparing Compound 5 Form C are described infra.

General Methods of Providing the Compounds

Compound 1 is prepared according to the methods described in Example 1.

Acid addition compounds of general formula of Compound A, which formula encompasses, inter alia, Compounds 2 through 5, and/or particular forms thereof, are prepared from Compound 1, according to the general Scheme below.

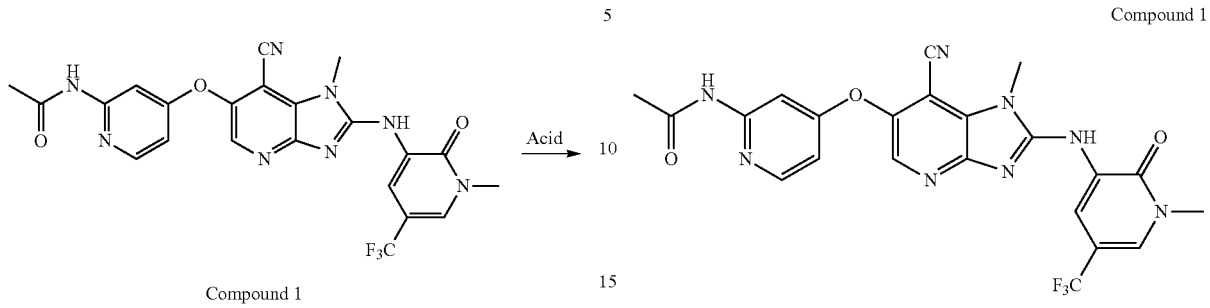

Compound 1

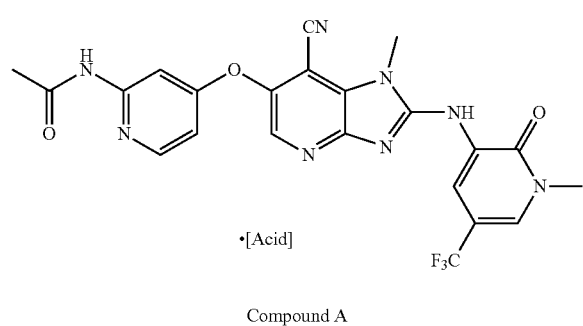

Compound A

In this scheme, "Acid" represents, e.g., any of the co-formers described herein. For instance, each of Compounds 2 through 5, and forms thereof, are prepared from Compound 1 by combining Compound 1 with an appropriate acid under suitable conditions to form the product Compound A. Thus, another aspect of the present disclosure provides a method for preparing Compounds 2 through 5, and forms thereof, by combining Compound 1 with an appropriate acid to form the product Compound A.

As described generally above, in some embodiments, the present disclosure provides a method for preparing Compound A:

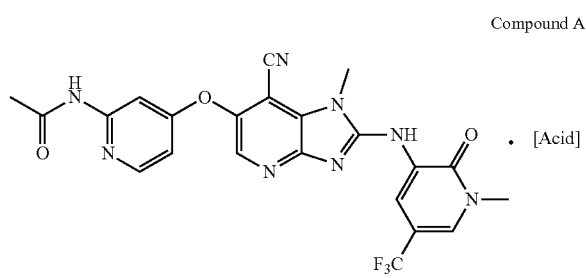

Compound A comprising steps of:
combining Compound 1:

Compound 1 with a suitable co-former (e.g., a suitable acid) and optionally a suitable solvent under conditions suitable for forming Compound A. In some embodiments, the present disclosure provides a solid form of Compound 1 obtained by a process comprising the step of contacting Compound 1 with a suitable acid under conditions and for a time effective to form a solid form (e.g., salt or co-crystal) of Compound 1.

In some embodiments, Compound 1 is treated with a co-former selected from: benzenesulfonic acid, camphorsulfonic acid (e.g., (1R)-(−)-10-camphorsulfonic acid), 1,2-ethanedisulfonic acid, ethansulfonic acid, hydrobromic acid, hydrochloric acid, methanesulfonic acid, phosphoric acid, and sulfuric acid.

In some embodiments, a suitable co-former is benzenesulfonic acid.

In some embodiments, a suitable co-former is (1R)-(−)-10-camphorsulfonic acid.

In some embodiments, a suitable co-former is 1,2-ethanedisulfonic acid.

In some embodiments, a suitable co-former is ethansulfonic acid.

In some embodiments, a suitable co-former is hydrobromic acid.

In some embodiments, a suitable co-former is hydrochloric acid.

In some embodiments, a suitable co-former is methanesulfonic acid.

In some embodiments, a suitable co-former is phosphoric acid.

In some embodiments, a suitable co-former is sulfuric acid.

A suitable solvent may be any solvent system (e.g., one solvent or a mixture of solvents) in which Compound 1 and/or an acid are soluble, or are at least partially soluble.

Examples of suitable solvents useful in the present disclosure include, but are not limited to protic solvents, aprotic solvents, polar aprotic solvent, or mixtures thereof. In certain embodiments, suitable solvents include an ether, an ester, an alcohol, a ketone, or a mixture thereof. In some embodiments, a solvent is one or more organic alcohols. In some embodiments, a solvent is chlorinated. In some embodiments, a solvent is an aromatic solvent.

In certain embodiments, a suitable solvent is tetrahydrofuran (THF), 2,2,2-trifluoroethanol, or acetone wherein said solvent is anhydrous or in combination with water. In some embodiments, a suitable solvent is 80:20 acetone/water. In some embodiments, a suitable solvent is THF. In some embodiments, a suitable solvent is 2,2,2-trifluoroethanol. In some embodiments, a suitable solvent is a combination of said solvents.

In some embodiments, a suitable solvent is acetic acid, cyclopentyl methyl ether (CPME), dimethylacetamide (DMA), dimethylformamide (DMF), dimethylsulfoxide (DMSO), ethyl acetate, hexafluoroisopropanol (HFIPA), isopropanol (IPA), isopropyl ether (IPE), methyl tert-butyl ether (MTBE), N-methyl-2-pyrrolidone (NMP), tert-amyl methyl ether (TAME), tetrahydrofuran (THF), or 2,2,2-trifluoroethanol (TFE), wherein said solvent is anhydrous or in combination with water. In some embodiments, a suitable solvent is acetic acid. In some embodiments, a suitable solvent is CPME. In some embodiments, a suitable solvent is DMA. In some embodiments, a suitable solvent is DMF. In some embodiments, a suitable solvent is DMSO. In some embodiments, a suitable solvent is ethyl acetate. In some embodiments, a suitable solvent is HFIPA. In some embodiments, a suitable solvent is IPA. In some embodiments, a suitable solvent is IPE. In some embodiments, a suitable solvent is MTBE. In some embodiments, a suitable solvent is NMP. In some embodiments, a suitable solvent is TAME. In some embodiments, a suitable solvent is THF. In some embodiments, a suitable solvent is 80:20 THF/water. In some embodiments, a suitable solvent is 99:1 THF/water. In some embodiments, a suitable solvent is 97:3 THF/water. In some embodiments, a suitable solvent is 93:7 THF/water. In some embodiments, a suitable solvent is TFE. In some embodiments, a suitable solvent is a combination of said solvents.

In some embodiments, the present disclosure provides a method for preparing (i) a free base form of Compound 1 or (ii) Compound A, comprising one or more steps of removing a solvent and adding a solvent. In some embodiments, an added solvent is the same as the solvent removed. In some embodiments, an added solvent is different from a solvent removed. Means of solvent removal are known in the synthetic and chemical arts and include, but are not limited to, any of those described herein and in the Exemplification.

In some embodiments, a method for preparing (i) a free base form of Compound 1 or (ii) Compound A comprises one or more steps of heating or cooling a preparation.

In some embodiments, a method for preparing (i) a free base form of Compound 1 or (ii) Compound A comprises one or more steps of agitating or stirring a preparation.

In some embodiments, a method for preparing (i) a free base form of Compound 1 or (ii) Compound A comprises a step of adding a suitable co-former to a solution or slurry of Compound 1.

In some embodiments, a method for preparing (i) a free base form of Compound 1 or (ii) Compound A comprises a step of adding a suitable acid to a solution or slurry of Compound 1.

In some embodiments, a method for preparing (i) a free base form of Compound 1 or (ii) Compound A comprises a step of heating.

In certain embodiments, a free base form of Compound 1 or Compound A precipitates from the mixture. In another embodiment, a free base form of Compound 1 or Compound A crystallizes from the mixture. In other embodiments, a free base form of Compound 1 or Compound A crystallizes from solution following seeding of the solution (i.e., adding crystals of a free base form of Compound 1 or Compound A to the solution).

A free base form of Compound 1 or Compound A can precipitate out of the reaction mixture, or be generated by removal of part or all of the solvent through methods such as evaporation, distillation, filtration (e.g., nanofiltration, ultrafiltration), reverse osmosis, absorption and reaction, by adding a suitable anti-solvent, by cooling or by different combinations of these methods.

As described generally above, a free base form of Compound 1 or Compound A is optionally isolated. It will be appreciated that a free base form of Compound 1 or Compound A may be isolated by any suitable physical means known to one of ordinary skill in the art. In certain embodiments, precipitated solid free base form of Compound 1 or Compound A is separated from the supernatant by filtration. In other embodiments, precipitated solid free base form of Compound 1 or Compound A is separated from the supernatant by decanting the supernatant.

In certain embodiments, a free base form of Compound 1 or Compound A is separated from the supernatant by filtration.

In certain embodiments, an isolated free base form of Compound 1 or Compound A is dried in air. In other embodiments isolated free base form of Compound 1 or Compound A is dried under reduced pressure, optionally at elevated temperature (e.g., a vacuum oven).

Methods of Use

The present disclosure provides uses for compounds and compositions described herein. In some embodiments, provided compounds and compositions are useful in medicine (e.g., as therapy). In some embodiments, provided compounds and compositions are useful in research as, for example, analytical tools and/or control compounds in biological assays.

In some embodiments, the present disclosure provides methods of administering provided compounds or compositions to a subject in need thereof. In some embodiments, the present disclosure provides methods of administering provided compounds or compositions to a subject suffering from or susceptible to a disease, disorder, or condition associated with JAK2.

In some embodiments, provided compounds are useful as JAK2 inhibitors. In some embodiments, provided compounds are useful as Type II JAK2 inhibitors. In some embodiments, the present disclosure provides methods of inhibiting JAK2 in a subject comprising administering a provided compound or composition. In some embodiments, the present disclosure provides methods of inhibiting JAK2 in a biological sample comprising contacting the sample with a provided compound or composition.

JAK (e.g., JAK2) has been implicated in various diseases, disorders, and conditions, such as myeloproliferative neoplasms (Vainchenker, W. et al., F1000Research 2018, 7 (F1000 Faculty Rev): 82), atopic dermatitis (Rodrigues, M. A. and Torres, T. J. Derm. Treat. 2019, 31(1), 33-40) and acute respiratory syndrome, hyperinflammation, and/or cytokine storm syndrome (*The Lancet*. doi:10.1016/S0140-6736(20)30628-0). Accordingly, in some embodiments, the present disclosure provides methods of treating a disease, disorder or condition associated with JAK2 in a subject in need thereof comprising administering to the subject a provided compound or composition. In some embodiments, a disease, disorder or condition is associated with overexpression of JAK2.

In some embodiments, the present disclosure provides methods of treating cancer, comprising administering a provided compound or composition to a subject in need thereof. In some embodiments, the present disclosure provides methods of treating proliferative diseases, comprising administering a provided compound or composition to a subject in need thereof.

In some embodiments, the present disclosure provides methods of treating a hematological malignancy, comprising administering a provided compound or composition to a subject in need thereof. In some embodiments, a hematological malignancy is leukemia (e.g., chronic lymphocytic leukemia, acute lymphoblastic leukemia, T-cell acute lymphoblastic leukemia, chronic myelogenous leukemia, acute myelogenous leukemia, or acute monocytic leukemia). In some embodiments, a hematological malignancy is lymphoma (e.g., Burkitt's lymphoma, Hodgkin's lymphoma, or non-Hodgkin's lymphoma). In some embodiments, a non-Hodgkin's lymphoma is a B-cell lymphoma. In some embodiments, a non-Hodgkin's lymphoma is a NK/T-cell lymphoma (e.g., cutaneous T-cell lymphoma). In some embodiments, a hematological malignancy is myeloma (e.g., multiple myeloma). In some embodiments, a hematological malignancy is myeloproliferative neoplasm (e.g., polycythemia vera, essential thrombocytopenia, or myelofibrosis). In some embodiments, a hematological malignancy is myelodysplastic syndrome.

In some embodiments, the present disclosure provides methods of treating an inflammatory disease, disorder, or condition (e.g., acute respiratory syndrome, hyperinflammation, and/or cytokine storm syndrome (including those associated with COVID-19) or atopic dermatitis), comprising administering a provided compound or composition to a subject in need thereof.

In some embodiments, a provided compound or composition is administered as part of a combination therapy. As used herein, the term "combination therapy" refers to those situations in which a subject is simultaneously exposed to two or more therapeutic or prophylactic regimens (e.g., two or more therapeutic or prophylactic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition.

For example, in some embodiments, a provided compound or composition is administered to a subject who is receiving or has received one or more additional therapies (e.g., an anti-cancer therapy and/or therapy to address one or more side effects of such anti-cancer therapy, or otherwise to provide palliative care). Exemplary additional therapies include BCL2 inhibitors (e.g., venetoclax), HDAC inhibitors (e.g., vorinostat), BET inhibitors (e.g., mivebresib), proteasome inhibitors (e.g., bortezomib), LSD1 inhibitors (e.g., IMG-7289), and CXCR2 inhibitors. Useful combinations of a JAK2 inhibitor with BCL2, HDAC, BET, and proteasome inhibitors have been demonstrated in cells derived from cutaneous T-cell lymphoma patients (Yumeen, S., et al., Blood Adv. 2020, 4(10), 2213-2226). A combination of a JAK2 inhibitor with a LSD1 inhibitor demonstrated good efficacy in a mouse model of myeloproliferative neoplasms (Jutzi, J. S., et al., HemaSphere 2018, 2(3), http://dx.doi.org/10.1097/HS9.00000000000054). CXCR2 activity has been shown to modulate signaling pathways involved in tumor growth, angiogenesis, and/or metastasis, including the JAK-STAT3 pathway (Jaffer, T., Ma, D. Transl. Cancer Res. 2016, 5 (Suppl. 4), S616-S628).

Pharmaceutical Compositions

In another aspect, the present disclosure provides pharmaceutical compositions comprising any of the compounds described herein (e.g., any of Compounds 1-5) or any of the compounds described herein (e.g., any of Compounds 1-5) in combination with a pharmaceutically acceptable excipient (e.g., carrier). In some embodiments, the present disclosure provides a pharmaceutical composition for oral administration, comprising a solid form of any of Compounds 1-5.

The pharmaceutical compositions include optical isomers, diastereomers, or pharmaceutically acceptable salts of the compounds disclosed herein.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water and one or more fillers, disintegrants, lubricants, glidants, anti-adherents, and/or anti-statics, etc. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure.

Provided pharmaceutical compositions can be in a variety of forms including oral dosage forms, topical creams, topical patches, iontophoresis forms, suppository, nasal spray and/or inhaler, eye drops, intraocular injection forms, depot forms, as well as injectable and infusible solutions. Methods of preparing pharmaceutical compositions are well known in the art.

In some embodiments, provided compounds are formulated in a unit dosage form for ease of administration and uniformity of dosage. The expression "unit dosage form" as used herein refers to a physically discrete unit of an active agent (e.g., a compound described herein) for administration to a subject. Typically, each such unit contains a predetermined quantity of active agent. In some embodiments, a unit dosage form contains an entire single dose of the agent. In some embodiments, more than one unit dosage form is administered to achieve a total single dose. In some embodiments, administration of multiple unit dosage forms is required, or expected to be required, in order to achieve an intended effect. A unit dosage form may be, for example, a liquid pharmaceutical composition containing a predetermined quantity of one or more active agents, a solid pharmaceutical composition (e.g., a tablet, a capsule, or the like) containing a predetermined amount of one or more active agents, a sustained release formulation containing a predetermined quantity of one or more active agents, or a drug delivery device containing a predetermined amount of one or more active agents, etc.

Provided compositions may be administered using any amount and any route of administration effective for treating or lessening the severity of any disease or disorder described herein.

EXEMPLARY EMBODIMENTS

The following numbered embodiments, while non-limiting, are exemplary of certain aspects of the present disclosure:

1. A solid form of Compound 1:

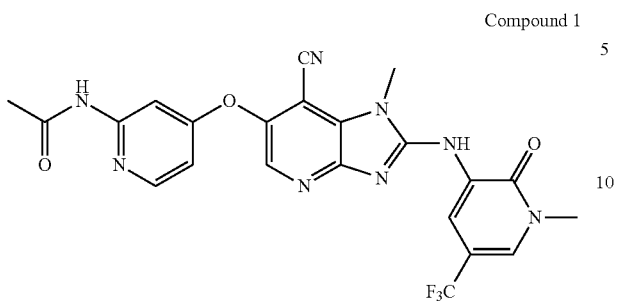

or a salt or co-crystal form thereof.
2. The solid form of embodiment 1, wherein the solid form is selected from the group consisting of a Compound 1 salt or co-crystal form of benzenesulfonic acid, camphorsulfonic acid (e.g., (1R)-(–)-10-camphorsulfonic acid), 1,2-ethanedisulfonic acid, ethansulfonic acid, hydrobromic acid, hydrochloric acid, methanesulfonic acid, phosphoric acid, and sulfuric acid.
3. The solid form of embodiment 1 or 2, wherein the solid form is a Compound 1 salt of hydrochloric acid.
4. The solid form of any one of the preceding embodiments, wherein the solid form is N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide hydrochloride.
5. The solid form of any one of the preceding embodiments, wherein the solid form is Compound 2 comprising Compound 1 and hydrochloric acid:

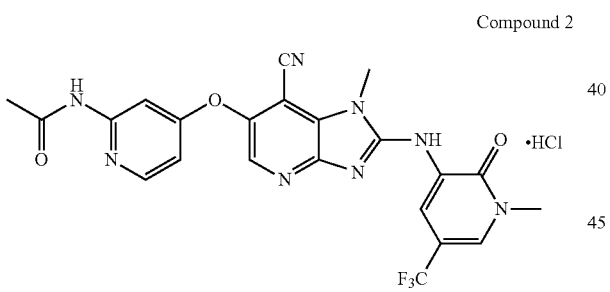

6. The solid form of any one of the preceding embodiments, where the solid form is characterized in that it has three or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.
7. The solid form of any one of the preceding embodiments, where the solid form is characterized in that it has four or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.
8. The solid form of any one of the preceding embodiments, where the solid form is characterized in that it has five or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.
9. The solid form of any one of the preceding embodiments, where the solid form is characterized in that it has six or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.
10. The solid form of any one of the preceding embodiments, where the solid form is characterized in that it has seven or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.
11. The solid form of any one of the preceding embodiments, where the solid form is characterized in that it has eight or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.
12. The solid form of any one of the preceding embodiments, where the solid form is characterized in that it has nine or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.
13. The solid form of any one of the preceding embodiments, where the solid form is characterized in that it has ten or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.
14. The solid form of any one of the preceding embodiments, where the solid form is characterized in that it has eleven or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.
15. The solid form of any one of the preceding embodiments, where the solid form is characterized in that it has twelve or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.
16. The solid form of any one of the preceding embodiments, where the solid form is characterized in that it has peaks in its X-ray powder diffraction (XRPD) pattern comprising those at angles (degrees 2 theta±0.2) of 7.38, 8.17, 11.98, 12.30, 15.63, 19.21, 20.12, 20.71, 21.64, 22.11, 24.16, 25.40, and 27.23.
17. The solid form of any one of the preceding embodiments, where the solid form is Compound 2 Form A and is characterized in that it has peaks in its X-ray powder diffraction (XRPD) pattern comprising those at angles (degrees 2 theta±0.2) of;

| Angle/°2θ |
| --- |
| 7.38 |
| 8.17 |
| 10.01 |
| 11.29 |
| 11.98 |
| 12.3 |
| 12.75 |
| 14.83 |
| 15.63 |

| Angle/°2θ |
|---|
| 16.6 |
| 17.41 |
| 17.59 |
| 18.15 |
| 19.21 |
| 20.12 |
| 20.71 |
| 21.64 |
| 22.11 |
| 22.38 |
| 23.29 |
| 23.60 |
| 23.83 |
| 24.16 |
| 24.54 |
| 24.77 |
| 25.40 |
| 26.24 |
| 27 23 |
| 28.2 |
| 28.61 |
| 29.85 |
| 30.14 |
| 30.40 |
| 30.63 |
| 31.25 |
| 32.05 |

18. The solid form of any one of embodiments 6-17, wherein the XRPD pattern is collected using Cu Kα radiation with a wavelength of 1.54059 Å, optionally wherein the XRPD pattern is collected according to the parameters in Table 13.

19. The solid form of any one of the preceding embodiments, characterized by a differential scanning calorimetry (DSC) endotherm having a minima at about 278.8° C.

20. The solid form of any one of the preceding embodiments, characterized by a thermogravimetric analysis (TGA) with a weight loss of about 0.3% between 42-165° C.

21. The solid form of any one of the preceding embodiments, characterized by an about 0.95% mass increase between 5 and 95% RH by dynamic vapor sorption (DVS) analysis.

22. The solid form of embodiment 1 or 2, wherein the solid form is a Compound 1 salt of hydrobromic acid.

23. The solid form of any one of embodiments 1, 2, or 22, wherein the solid form is N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide hydrobromide.

24. The solid form of any one of embodiments 1, 2, or 22-23, wherein the solid form is Compound 3 comprising Compound 1 and hydrobromic acid:

Compound 3

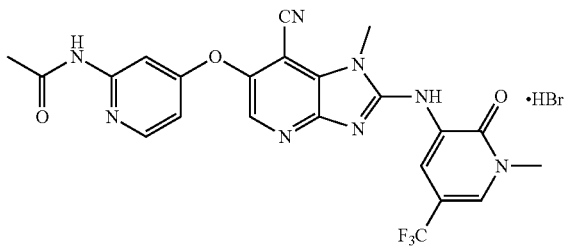

25. The solid form of any one of embodiments 1, 2, or 22-24, where the solid form is characterized in that it has three or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

26. The solid form of any one of embodiments 1, 2, or 22-25, where the solid form is characterized in that it has four or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

27. The solid form of any one of embodiments 1, 2, or 22-26, where the solid form is characterized in that it has five or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

28. The solid form of any one of embodiments 1, 2, or 22-27, where the solid form is characterized in that it has six or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

29. The solid form of any one of embodiments 1, 2, or 22-28, where the solid form is characterized in that it has seven or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

30. The solid form of any one of embodiments 1, 2, or 22-29, where the solid form is characterized in that it has eight or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

31. The solid form of any one of embodiments 1, 2, or 22-30, where the solid form is characterized in that it has nine or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

32. The solid form of any one of embodiments 1, 2, or 22-31, where the solid form is characterized in that it has ten or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

33. The solid form of any one of embodiments 1, 2, or 22-32, where the solid form is characterized in that it has eleven or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

34. The solid form of any one of embodiments 1, 2, or 22-33, where the solid form is characterized in that it has twelve or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

35. The solid form of any one of embodiments 1, 2, or 22-34, where the solid form is characterized in that it has thirteen or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

36. The solid form of any one of embodiments 1, 2, or 22-35, where the solid form is characterized in that it has fourteen or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

37. The solid form of any one of the embodiments 1, 2, or 22-36, where the solid form is characterized in that it has fifteen or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

38. The solid form of any one of embodiments 1, 2, or 22-37, where the solid form is characterized in that it has sixteen or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

39. The solid form of any one of embodiments 1, 2, or 22-38, where the solid form is characterized in that it has seventeen or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

40. The solid form of any one of embodiments 1, 2, or 22-39, where the solid form is characterized in that it has peaks in its X-ray powder diffraction (XRPD) pattern comprising those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

41. The solid form of any one of embodiments 1, 2, or 22-40, where the solid form is Compound 3 Form A and is characterized in that it has peaks in its X-ray powder diffraction (XRPD) pattern comprising those at angles (degrees 2 theta±0.2) of.

| Angle/°2θ |
| --- |
| 7.10 |
| 8.72 |
| 9.82 |
| 10.45 |
| 10.68 |
| 12.14 |
| 12.40 |
| 13.33 |
| 13.87 |
| 14.25 |
| 14.53 |
| 15.19 |
| 15.99 |
| 16.38 |
| 17.18 |
| 17.35 |
| 17.51 |
| 18.10 |
| 18.61 |
| 19.27 |
| 19.62 |
| 20.13 |
| 20.42 |
| 20.76 |
| 21.01 |
| 21.48 |
| 22.40 |
| 22.93 |
| 24.43 |
| 24.98 |
| 25.14 |
| 25.95 |
| 26.27 |
| 26.76 |
| 27.23 |
| 27.91 |
| 28.09 |
| 28.57 |
| 28.77 |
| 29 32 |
| 29.86 |
| 30.84 |
| 31.09 |

42. The solid form of any one of embodiments 25-41, wherein the XRPD pattern is collected using Cu Kα radiation with a wavelength of 1.54059 Å, optionally wherein the XRPD pattern is collected according to the parameters in Table 13.

43. The solid form of any one of embodiments 1, 2, or 22-42, characterized by a differential scanning calorimetry (DSC) endotherm having a minima at about 281.6° C.

44. The solid form of any one of embodiments 1, 2, or 22-43, characterized by a thermogravimetric analysis (TGA) with a weight loss of about 3.4% between 61-150° C.

45. The solid form of embodiment 1 or 2, wherein the solid form is a Compound 1 salt of methanesulfonic acid.

46. The solid form of any one of embodiments 1, 2, or 45, wherein the solid form is N-(4-((7-cyano-1-methyl-2-((1-methyl-2-oxo-5-(trifluoromethyl)-1,2-dihydropyridin-3-yl)amino)-1H-imidazo[4,5-h]pyridin-6-yl)oxy)pyridin-2-yl)acetamide mesylate.

47. The solid form of any one of embodiments 1, 2, or 45-46, wherein the solid form is Compound 4 comprising Compound 1 and methanesulfonic acid:

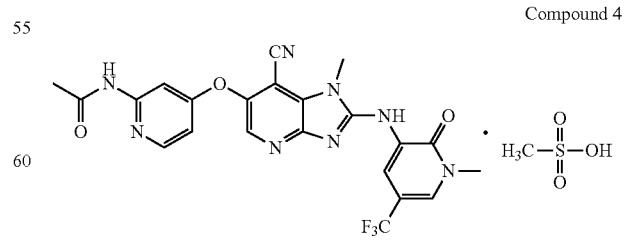

Compound 4

48. The solid form of any one of embodiments 1, 2, or 45-47, where the solid form is characterized in that it has three or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

49. The solid form of any one of embodiments 1, 2, or 45-48, where the solid form is characterized in that it has four or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

50. The solid form of any one of embodiments 1, 2, or 45-49, where the solid form is characterized in that it has five or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

51. The solid form of any one of embodiments 1, 2, or 45-50, where the solid form is characterized in that it has six or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

52. The solid form of any one of embodiments 1, 2, or 45-51, where the solid form is characterized in that it has seven or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

53. The solid form of any one of embodiments 1, 2, or 45-52, where the solid form is characterized in that it has eight or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

54. The solid form of any one of embodiments 1, 2, or 45-53, where the solid form is characterized in that it has nine or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

55. The solid form of any one of embodiments 1, 2, or 45-54, where the solid form is characterized in that it has ten or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

56. The solid form of any one of embodiments 1, 2, or 45-55, where the solid form is characterized in that it has eleven or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

57. The solid form of any one of embodiments 1, 2, or 45-56, where the solid form is characterized in that it has twelve or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

58. The solid form of any one of embodiments 1, 2, or 45-57, where the solid form is characterized in that it has thirteen or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

59. The solid form of any one of embodiments 1, 2, or 45-58, where the solid form is characterized in that it has fourteen or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

60. The solid form of any one of embodiments 1, 2, or 45-59, where the solid form is characterized in that it has peaks in its X-ray powder diffraction (XRPD) pattern comprising those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

61. The solid form of any one of embodiments 1, 2, or 45-60, where the solid form is Compound 4 Form A and is characterized in that it has peaks in its X-ray powder diffraction (XRPD) pattern comprising those at angles (degrees 2 theta±0.2) of:

| Angle/°2θ |
| --- |
| 7.35 |
| 8.52 |
| 9.31 |
| 10.03 |
| 10.65 |
| 11.89 |
| 13.19 |
| 13.68 |
| 14.48 |
| 15.45 |
| 15.89 |
| 16.84 |
| 17.49 |
| 17.66 |
| 18.80 |
| 19.19 |
| 19.48 |
| 20.14 |
| 20.57 |
| 21.43 |
| 21.79 |
| 22 23 |
| 99 50 |
| 22.82 |
| 23.58 |
| 23.94 |
| 24.60 |
| 25.43 |
| 25.83 |
| 26.45 |
| 27.06 |
| 27.62 |
| 28.31 |
| 29.22 |
| 29.83 |
| 30.73 |
| 32.08 |

62. The solid form of any one of embodiments 48-61, wherein the XRPD pattern is collected using Cu Kα radiation with a wavelength of 1.54059 Å, optionally wherein the XRPD pattern is collected according to the parameters in Table 13.

63. The solid form of any one of embodiments 1, 2, or 45-62, characterized by a differential scanning calorimetry (DSC) endotherm having a minima at about 295.5° C.

64. The solid form of any one of embodiments 1, 2, or 45-63, characterized by a thermogravimetric analysis (TGA) with a weight loss of about 3.3% between 44-114° C.

65. The solid form of any one of embodiments 1, 2, or 45-47, where the solid form is characterized in that it has three or more peaks in its X-ray powder diffraction (XRPD) pattern selected from those at angles (degrees 2 theta±0.2) of 8.53, 9.60, 10.31, 12.16, 14.75, 15.86, 20.07, 20.74, 22.45, 24.56, and 27.07.

66. The solid form of any one of embodiments 1, 2, 45-47, or 65 where the solid form is characterized in that it has four or more peaks in its X-ray powder diffraction (XRPD) pattern selected from those at angles (degrees 2 theta±0.2) of 8.53, 9.60, 10.31, 12.16, 14.75, 15.86, 20.07, 20.74, 22.45, 24.56, and 27.07.

67. The solid form of any one of embodiments 1, 2, 45-47, or 65-66 where the solid form is characterized in that it has five or more peaks in its X-ray powder diffraction (XRPD) pattern selected from those at angles (degrees 2 theta±0.2) of 8.53, 9.60, 10.31, 12.16, 14.75, 15.86, 20.07, 20.74, 22.45, 24.56, and 27.07.

68. The solid form of any one of embodiments 1, 2, 45-47, or 65-66 where the solid form is characterized in that it has six or more peaks in its X-ray powder diffraction (XRPD) pattern selected from those at angles (degrees 2 theta±0.2) of 8.53, 9.60, 10.31, 12.16, 14.75, 15.86, 20.07, 20.74, 22.45, 24.56, and 27.07.

69. The solid form of any one of embodiments 1, 2, 45-47, or 65-68 where the solid form is characterized in that it has seven or more peaks in its X-ray powder diffraction (XRPD) pattern selected from those at angles (degrees 2 theta±0.2) of 8.53, 9.60, 10.31, 12.16, 14.75, 15.86, 20.07, 20.74, 22.45, 24.56, and 27.07.

70. The solid form of any one of embodiments 1, 2, 45-47, or 65-69 where the solid form is characterized in that it has eight or more peaks in its X-ray powder diffraction (XRPD) pattern selected from those at angles (degrees 2 theta±0.2) of 8.53, 9.60, 10.31, 12.16, 14.75, 15.86, 20.07, 20.74, 22.45, 24.56, and 27.07.

71. The solid form of any one of embodiments 1, 2, 45-47, or 65-70 where the solid form is characterized in that it has nine or more peaks in its X-ray powder diffraction (XRPD) pattern selected from those at angles (degrees 2 theta±0.2) of 8.53, 9.60, 10.31, 12.16, 14.75, 15.86, 20.07, 20.74, 22.45, 24.56, and 27.07.

72. The solid form of any one of embodiments 1, 2, 45-47, or 65-71 where the solid form is characterized in that it has ten or more peaks in its X-ray powder diffraction (XRPD) pattern selected from those at angles (degrees 2 theta±0.2) of 8.53, 9.60, 10.31, 12.16, 14.75, 15.86, 20.07, 20.74, 22.45, 24.56, and 27.07.

73. The solid form of any one of embodiments 1, 2, 45-47, or 65-72 where the solid form is characterized in that it has more peaks in its X-ray powder diffraction (XRPD) pattern comprising those at angles (degrees 2 theta±0.2) of 8.53, 9.60, 10.31, 12.16, 14.75, 15.86, 20.07, 20.74, 22.45, 24.56, and 27.07.

74. The solid form of any one of embodiments 1, 2, 45-47, or 65-73 where the solid form is Compound 4 Form B and is characterized in that it has peaks in its X-ray powder diffraction (XRPD) pattern comprising those at angles (degrees 2 theta±0.2) of:

| Angle/°2θ |
| --- |
| 7.42 |
| 8.53 |
| 9.60 |
| 10.31 |
| 12.16 |
| 13.45 |
| 14.75 |
| 15.39 |
| 15.86 |
| 17.76 |
| 18.27 |
| 18.69 |
| 20.07 |
| 20.74 |
| 21.50 |
| 22.45 |
| 23.78 |
| 24.56 |
| 25.13 |
| 25.84 |
| 27.07 |
| 28.04 |
| 29.13 |
| 29.89 |
| 31.14 |
| 32.08 |
| 33.12 |

75. The solid form of any one of embodiments 65-74, wherein the XRPD pattern is collected using Cu Kα radiation with a wavelength of 1.5405929 Å, optionally wherein the XRPD pattern is collected according to the parameters in Table 13.

76. The solid form of any one of embodiments 1 or 2, wherein the solid form is N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide camsylate.

77. The solid form of embodiment 1, 2, or 76 wherein the solid form is a Compound 1 salt of (1R)-(−)-10-camphorsulfonic acid.

78. The solid form of any one of embodiments 1, 2, or 76-77, wherein the solid form is Compound 5 comprising Compound 1 and (1R)-(−)-10-camphorsulfonic acid.

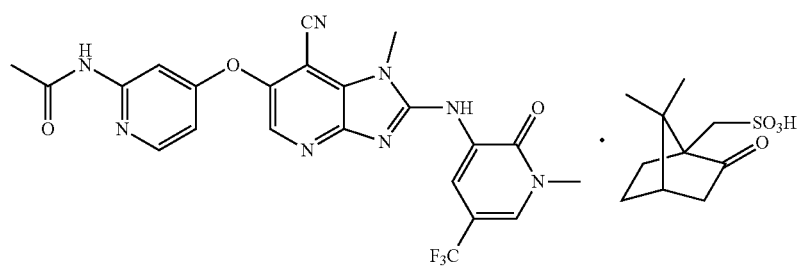

Compound 5

79. The solid form of any one of embodiments 1, 2, or 76-78, where the solid form is characterized in that it has three or more peaks in its X-ray powder diffraction (XRPD) pattern selected from those at angles (degrees 2 theta±0.2) of 6.55, 9.01, 12.05, 12.65, 14.08, 22.16, 22.45, and 25.47.

80. The solid form of any one of embodiments 1, 2, or 76-79, where the solid form is characterized in that it has four or more peaks in its X-ray powder diffraction (XRPD) pattern selected from those at angles (degrees 2 theta±0.2) of 6.55, 9.01, 12.05, 12.65, 14.08, 22.16, 22.45, and 25.47.

81. The solid form of any one of embodiments 1, 2, or 76-80, where the solid form is characterized in that it has five or more peaks in its X-ray powder diffraction (XRPD) pattern selected from those at angles (degrees 2 theta±0.2) of 6.55, 9.01, 12.05, 12.65, 14.08, 22.16, 22.45, and 25.47.

82. The solid form of any one of embodiments 1, 2, or 76-81, where the solid form is characterized in that it has six or more peaks in its X-ray powder diffraction (XRPD) pattern selected from those at angles (degrees 2 theta±0.2) of 6.55, 9.01, 12.05, 12.65, 14.08, 22.16, 22.45, and 25.47.

83. The solid form of any one of embodiments 1, 2, or 76-82, where the solid form is characterized in that it has seven or more peaks in its X-ray powder diffraction (XRPD) pattern selected from those at angles (degrees 2 theta±0.2) of 6.55, 9.01, 12.05, 12.65, 14.08, 22.16, 22.45, and 25.47.

84. The solid form of any one of embodiments 1, 2, or 76-83, where the solid form is characterized in that it has peaks in its X-ray powder diffraction (XRPD) pattern comprising those at angles (degrees 2 theta±0.2) of 6.55, 9.01, 12.05, 12.65, 14.08, 22.16, 22.45, and 25.47.

85. The solid form of any one of embodiments 1, 2, or 76-84, where the solid form is Compound 5 Form C and is characterized in that it has peaks in its X-ray powder diffraction (XRPD) pattern comprising those at angles (degrees 2 theta±0.2) of:

| Angle/°2θ |
| --- |
| 6.55 |
| 9.01 |
| 9.87 |
| 10.49 |
| 11.01 |
| 11.57 |
| 12.05 |
| 12.19 |
| 12.65 |

-continued

| Angle/°2θ |
| --- |
| 13.14 |
| 13.45 |
| 14.08 |
| 14.30 |
| 14.59 |
| 14.98 |
| 15.39 |
| 16.22 |
| 16.46 |
| 16.94 |
| 17.42 |
| 17.62 |
| 17.74 |
| 18.10 |
| 18.75 |
| 19.36 |
| 19.76 |
| 19.95 |
| 20.16 |
| 20.50 |
| 20.81 |
| 20.91 |
| 21.10 |
| 21.57 |
| 21.99 |
| 22.16 |
| 22.45 |
| 22.87 |
| 23.59 |
| 24.39 |
| 24.66 |
| 25.47 |
| 25.95 |
| 26.48 |
| 26.70 |
| 27.04 |
| 27.30 |
| 27.70 |
| 28.08 |

86. The solid form of any one of embodiments 79-85, wherein the XRPD pattern is collected using Cu Kα radiation with a wavelength of 1.5405929 Å, optionally wherein the XRPD pattern is collected according to the parameters in Table 13.

87. The solid form of embodiment 1, wherein the solid form is N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide.

88. The solid form of any one of embodiments 1 or 87, where the solid form is characterized in that it has three or more peaks in its X-ray powder diffraction (XRPD) pattern selected from those at angles (degrees 2 theta±0.2) of 7.33, 11.22, 11.46, 14.01, 16.89, 18.94, 19.70, 21.71, 23.31, 23.56, 25.22, 26.20, and 26.58.

89. The solid form of any one of embodiments 1 or 87-88, where the solid form is characterized in that it has four or more peaks in its X-ray powder diffraction (XRPD) pattern selected from those at angles (degrees 2 theta±0.2) of 7.33, 11.22, 11.46, 14.01, 16.89, 18.94, 19.70, 21.71, 23.31, 23.56, 25.22, 26.20, and 26.58.
90. The solid form of any one of embodiments 1 or 87-89, where the solid form is characterized in that it has five or more peaks in its X-ray powder diffraction (XRPD) pattern selected from those at angles (degrees 2 theta±0.2) of 7.33, 11.22, 11.46, 14.01, 16.89, 18.94, 19.70, 21.71, 23.31, 23.56, 25.22, 26.20, and 26.58.
91. The solid form of any one of embodiments 1 or 87-90, where the solid form is characterized in that it has six or more peaks in its X-ray powder diffraction (XRPD) pattern selected from those at angles (degrees 2 theta±0.2) of 7.33, 11.22, 11.46, 14.01, 16.89, 18.94, 19.70, 21.71, 23.31, 23.56, 25.22, 26.20, and 26.58.
92. The solid form of any one of embodiments 1 or 87-91, where the solid form is characterized in that it has seven or more peaks in its X-ray powder diffraction (XRPD) pattern selected from those at angles (degrees 2 theta±0.2) of 7.33, 11.22, 11.46, 14.01, 16.89, 18.94, 19.70, 21.71, 23.31, 23.56, 25.22, 26.20, and 26.58.
93. The solid form of any one of embodiments 1 or 87-92, where the solid form is characterized in that it has eight or more peaks in its X-ray powder diffraction (XRPD) pattern selected from those at angles (degrees 2 theta±0.2) of 7.33, 11.22, 11.46, 14.01, 16.89, 18.94, 19.70, 21.71, 23.31, 23.56, 25.22, 26.20, and 26.58.
94. The solid form of any one of embodiments 1 or 87-93, where the solid form is characterized in that it has nine or more peaks in its X-ray powder diffraction (XRPD) pattern selected from those at angles (degrees 2 theta±0.2) of 7.33, 11.22, 11.46, 14.01, 16.89, 18.94, 19.70, 21.71, 23.31, 23.56, 25.22, 26.20, and 26.58.
95. The solid form of any one of embodiments 1 or 87-94, where the solid form is characterized in that it has ten or more peaks in its X-ray powder diffraction (XRPD) pattern selected from those at angles (degrees 2 theta±0.2) of 7.33, 11.22, 11.46, 14.01, 16.89, 18.94, 19.70, 21.71, 23.31, 23.56, 25.22, 26.20, and 26.58.
96. The solid form of any one of embodiments 1 or 87-95, where the solid form is characterized in that it has eleven or more peaks in its X-ray powder diffraction (XRPD) pattern selected from those at angles (degrees 2 theta±0.2) of 7.33, 11.22, 11.46, 14.01, 16.89, 18.94, 19.70, 21.71, 23.31, 23.56, 25.22, 26.20, and 26.58.
97. The solid form of any one of embodiments 1 or 87-96, where the solid form is characterized in that it has twelve or more peaks in its X-ray powder diffraction (XRPD) pattern selected from those at angles (degrees 2 theta±0.2) of 7.33, 11.22, 11.46, 14.01, 16.89, 18.94, 19.70, 21.71, 23.31, 23.56, 25.22, 26.20, and 26.58.
98. The solid form of any one of embodiments 1 or 87-97, where the solid form is characterized in that it has peaks in its X-ray powder diffraction (XRPD) pattern comprising those at angles (degrees 2 theta±0.2) of 7.33, 11.22, 11.46, 14.01, 16.89, 18.94, 19.70, 21.71, 23.31, 23.56, 25.22, 26.20, and 26.58.
99. The solid form of any one of embodiments 88-98, wherein the XRPD pattern is collected using Cu Kα radiation with a wavelength of 1.5405929 Å, optionally wherein the XRPD pattern is collected according to the parameters in Table 13.
100. The solid form of any one of embodiments 1 or 87-99, characterized by an about 4.8% mass increase between 5 and 95% RH by dynamic vapor sorption (DVS) analysis.
101. The solid form of embodiment 1, wherein the solid form is N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide besylate.
102. The solid form of embodiment 1, wherein the solid form is N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide edisylate.
103. The solid form of embodiment 1, wherein the solid form is N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide esylate.
104. The solid form of embodiment 1, wherein the solid form is N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide phosphate.
105. The solid form of embodiment 1, wherein the solid form is N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide sulfate.
106. A solid form of Compound 1:

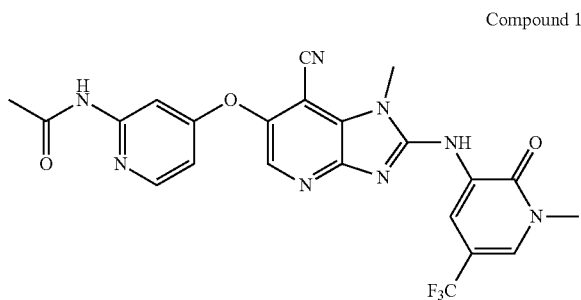 [SMILES: CC(=O)Nc1cc(Oc2cnc3nc(Nc4cc(C(F)(F)F)cn(C)c4=O)n(C)c3c2C#N)ccn1]

Compound 1 prepared by the method of Example 1.
107. A solid form of Compound 2;

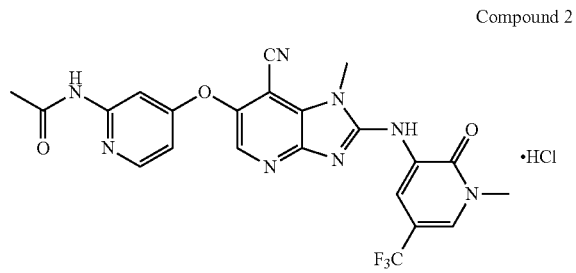 [SMILES: CC(=O)Nc1cc(Oc2cnc3nc(Nc4cc(C(F)(F)F)cn(C)c4=O)n(C)c3c2C#N)ccn1 ; Cl]

Compound 2 prepared by a method comprising the steps of adding hydrochloric acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, and then removing the solvent to provide the solid form of Compound 2.

108. A solid form of Compound 2:

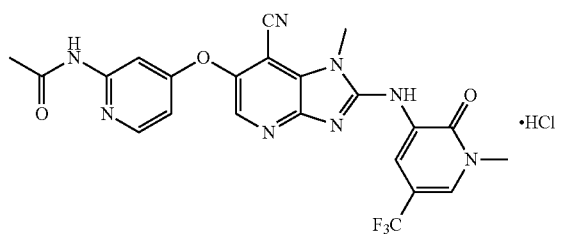

Compound 2

·HCl prepared by a method comprising the steps of adding hydrochloric acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in 2,2,2-trifluoroethanol, cooling the resulting solution to −20° C., and then removing the solvent to provide the solid form of Compound 2.

109. A solid form of Compound 3:

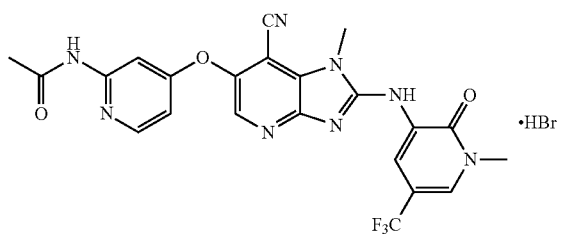

Compound 3

·HBr prepared by a method comprising the steps of adding hydrobromic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, and then removing the solvent to provide the solid form of Compound 3.

110. A solid form of Compound 3:

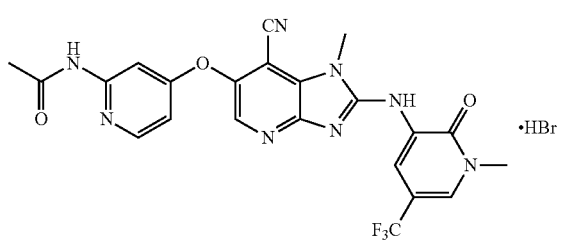

Compound 3

·HBr prepared by a method comprising the steps of adding hydrobromic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in 2,2,2-trifluoroethanol, cooling the resulting solution to −20° C., and then removing the solvent to provide the solid form of Compound 3.

111. A solid form of Compound 4:

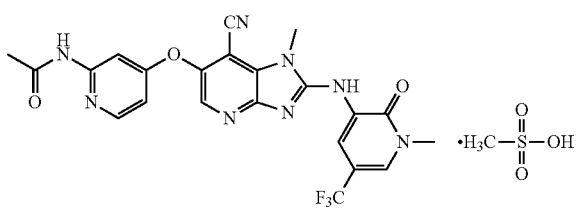

Compound 4

·H₃C—S(=O)₂—OH prepared by a method comprising the steps of adding methanesulfonic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, and then removing the solvent to provide the solid form of Compound 4.

112. A solid form of Compound 4:

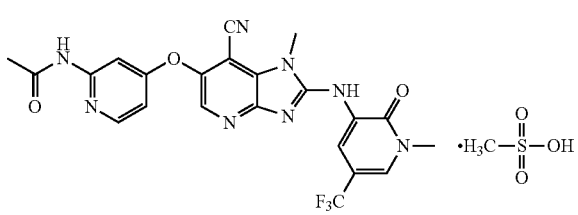

Compound 4

·H₃C—S(=O)₂—OH prepared by a method comprising the steps of adding methanesulfonic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, removing the solvent, and drying in a vacuum oven at 45° C. to provide the solid form of Compound 4.

113. A solid form of Compound 5:

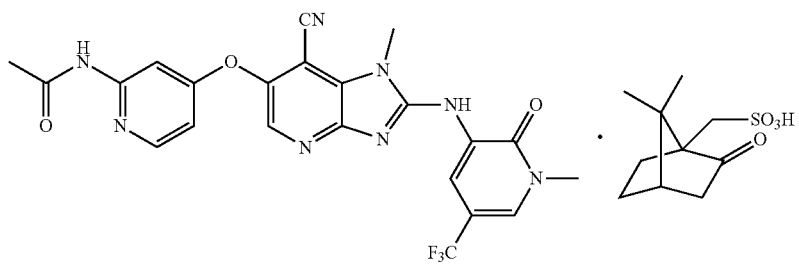

Compound 5

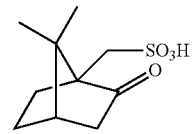

prepared by a method comprising the steps of adding a solution of (1R)-(−)-10-camphorsulfonic acid in tetrahydrofuran to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, isolating the solids, and drying in a vacuum oven at ambient temperature to provide the solid form of Compound 5.

114. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide besylate, prepared by a method comprising the steps of adding a solution of benzenesulfonic acid in tetrahydrofuran to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, and then removing the solvent to provide the solid form.

115. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide besylate, prepared by a method comprising the steps of adding a solution of benzenesulfonic acid in tetrahydrofuran to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, removing the solvent, and drying in a vacuum oven at ambient temperature to provide the solid form.

116. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide besylate, prepared by a method comprising the steps of adding a solution of benzenesulfonic acid in 2,2,2-trifluoroethanol to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, cooling the resulting solution to −20° C., and then removing the solvent to provide the solid form.

117. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide edisylate, prepared by a method comprising the steps of adding a solution of 1,2-ethanedisulfonic acid in tetrahydrofuran to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, and then removing the solvent to provide the solid form.

118. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide edisylate, prepared by a method comprising the steps of adding a solution of 1,2-ethanedisulfonic acid in tetrahydrofuran to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, removing the solvent, and drying in a vacuum oven at ambient temperature to provide the solid form.

119. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide edisylate, prepared by a method comprising the steps of adding a slurry of 1,2-ethanedisulfonic acid in 2,2,2-trifluoroethanol to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, cooling the resulting solution to −20° C., and then removing the solvent to provide the solid form.

120. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide esylate, prepared by a method comprising the steps of adding ethanesulfonic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, and then removing the solvent to provide the solid form.

121. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide esylate, prepared by a method comprising the steps of adding ethanesulfonic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in 2,2,2-trifluoroethanol, cooling the resulting solution to −20° C., and then removing the solvent to provide the solid form.

122. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide phosphate, prepared by a method comprising the steps of adding phosphoric acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2- yl)acetamide in tetrahydrofuran, and then removing the solvent to provide the solid form.

123. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide phosphate, prepared by a method comprising the steps of adding phosphoric acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in 2,2,2-trifluoroethanol, and then removing the solvent to provide the solid form.

124. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide sulfate, prepared by a method comprising the steps of adding sulfuric acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, and then removing the solvent to provide the solid form.

125. A solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide sulfate, prepared by a method comprising the steps of adding sulfuric acid to a slurry of N-(4-((7-cyano-1-methyl-2-((1-methyl-2-oxo-5-(trifluoromethyl)-1,2-dihydropyidin-3-yl)amino)-1H-imidazo[4,5-b]pyridin-6-yl)oxy)pyridin-2-yl)acetamide in 2,2,2-trifluoroethanol, and then removing the solvent to provide the solid form.

126. The solid form according to any one of embodiments 1-125, wherein the solid form of the compound has a ratio of about 1:1 of Compound 1 to co-former.

127. The solid form according to any one of embodiments 1-126, wherein said solid form is crystalline.

128. The solid form according to any one of embodiments 1-127, wherein said solid form is substantially free of the amorphous form of the compound.

129. The solid form according to any one of embodiments 1-126, wherein said solid form is amorphous.

130. The solid form according to any one of embodiments 1-129, wherein said solid form is substantially free of impurities.

131. A pharmaceutical composition comprising the solid form according to any one of embodiments 1-130 and a pharmaceutical acceptable carrier or excipient.

132. A process for preparing a solid form of Compound 2:

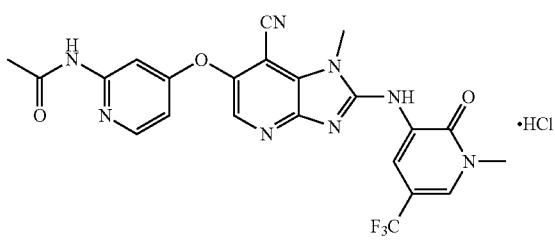

Compound 2 the process comprising the steps of adding hydrochloric acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, and then removing the solvent to provide the solid form of Compound 2.

133. A process for preparing a solid form of Compound 2;

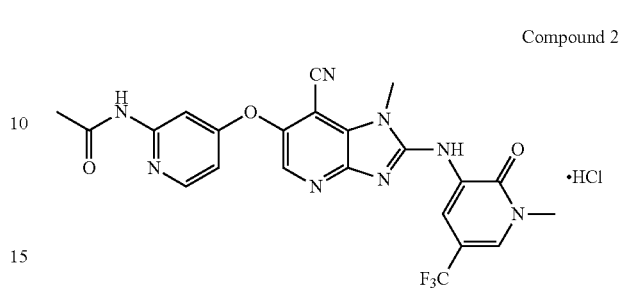

Compound 2 the process comprising the steps of adding hydrochloric acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in 2,2,2-trifluoroethanol, cooling the resulting solution to −20° C., and then removing the solvent to provide the solid form of Compound 2.

134. A process for preparing a solid form of Compound 3:

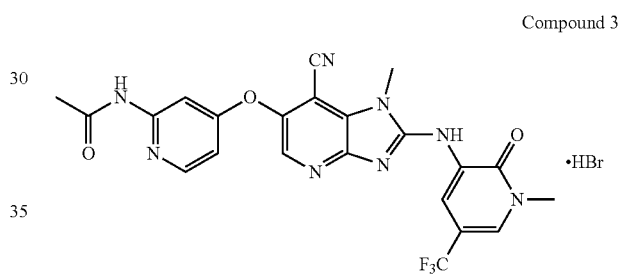

Compound 3 the process comprising the steps of adding hydrobromic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, and then removing the solvent to provide the solid form of Compound 3.

135. A process for preparing a solid form of Compound 3:

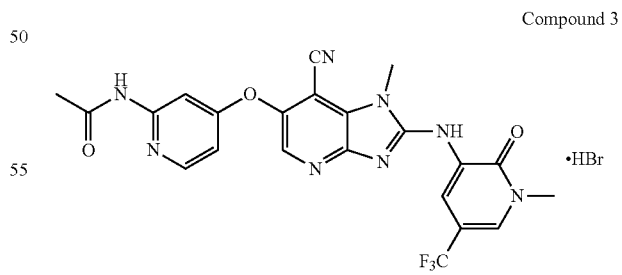

Compound 3 the process comprising the steps of adding hydrobromic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in 2,2,2-trifluoroethanol, cooling the resulting solution to −20° C., and then removing the solvent to provide the solid form of Compound 3.

136. A process for preparing a solid form of Compound 4:

Compound 4

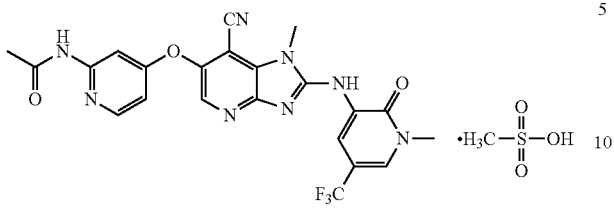

the process comprising the steps of adding methanesulfonic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, and then removing the solvent to provide the solid form of Compound 4.

137. A process for preparing a solid form of Compound 4:

Compound 4

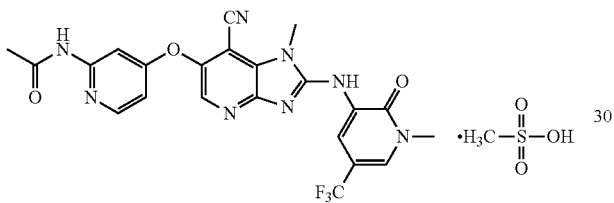

the process comprising the steps of adding methanesulfonic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, removing the solvent, and drying in a vacuum oven at 45° C. to provide the solid form of Compound 4.

138. A process for preparing a solid form of Compound 5:

Compound 5

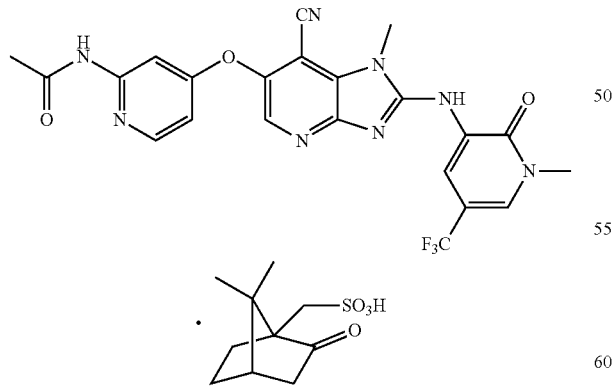

the process comprising the steps of adding a solution of (1R)-(−)-10-camphorsulfonic acid in tetrahydrofuran to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, isolating the solids, and drying in a vacuum oven at ambient temperature to provide the solid form of Compound 5.

139. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide besylate, the process comprising the steps of adding a solution of benzenesulfonic acid in tetrahydrofuran to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, and then removing the solvent to provide the solid form.

140. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide besylate, the process comprising the steps of adding a solution of benzenesulfonic acid in tetrahydrofuran to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, removing the solvent, and drying in a vacuum oven at ambient temperature to provide the solid form.

141. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide besylate, the process comprising the steps of adding a solution of benzenesulfonic acid in 2,2,2-trifluoroethanol to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, cooling the resulting solution to −20° C., and then removing the solvent to provide the solid form.

142. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide edisylate, the process comprising the steps of adding a solution of 1,2-ethanedisulfonic acid in tetrahydrofuran to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, and then removing the solvent to provide the solid form.

143. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide edisylate, the process comprising the steps of adding a solution of 1,2-ethanedisulfonic acid in tetrahydrofuran to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, removing the solvent, and drying in a vacuum oven at ambient temperature to provide the solid form.

144. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide edisylate, the process comprising the steps of adding a slurry of 1,2-ethanedisulfonic acid in 2,2,2-trifluoroethanol to N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide, cooling the resulting solution to −20° C., and then removing the solvent to provide the solid form.

145. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide esylate, the process comprising the steps of adding ethanesulfonic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, and then removing the solvent to provide the solid form.

146. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide esylate, the process comprising the steps of adding ethanesulfonic acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in 2,2,2-trifluoroethanol, cooling the resulting solution to −20° C., and then removing the solvent to provide the solid form.

147. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide phosphate, the process comprising the steps of adding phosphoric acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in tetrahydrofuran, and then removing the solvent to provide the solid form.

148. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide phosphate, the process comprising the steps of adding phosphoric acid to a slurry of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide in 2,2,2-trifluoroethanol, and then removing the solvent to provide the solid form.

149. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide sulfate, the process comprising the steps of adding sulfuric acid to a slurry of N-(4-((7-cyano-1-methyl-2-((1-methyl-2-oxo-5-(trifluoromethyl)-1,2-dihydropyridin-3-yl)amino)-11H-imidazo[4,5-b]pyridin-6-yl)oxy)pyridin-2-yl)acetamide in tetrahydrofuran, and then removing the solvent to provide the solid form.

150. A process for preparing a solid form of N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide sulfate, the process comprising the steps of adding sulfuric acid to a slurry of N-(4-((7-cyano-1-methyl-2-((1-methyl-2-oxo-5-(trifluoromethyl)-1,2-dihydropyridin-3-yl)amino)-11H-imidazo[4,5-b]pyridin-6-yl)oxy)pyridin-2-yl)acetamide in 2,2,2-trifluoroethanol, and then removing the solvent to provide the solid form.

151. A method of inhibiting JAK2 in a subject comprising administering the compound of any one of embodiments 1-130 or the composition of embodiment 131.

152. A method of treating a disease, disorder, or condition associated with JAK2, comprising administering to a subject in need thereof the compound of any one of embodiments 1-130 or the composition of embodiment 131.

153. A method of treating cancer, comprising administering to a subject in need thereof the compound of any one of embodiments 1-130 or the composition of embodiment 131.

154. A method of treating a hematological malignancy, comprising administering to a subject in need thereof the compound of any one of embodiments 1-130 or the composition of embodiment 131.

155. The method of embodiment 154, wherein the hematological malignancy is leukemia or lymphoma.

156. A method of treating a myeloproliferative neoplasm, comprising administering to a subject in need thereof the compound of any one of embodiments 1-130 or the composition of embodiment 131.

157. The method of embodiment 156, wherein the myeloproliferative neoplasm is polycythemia vera, essential thrombocytopenia or myelofibrosis.

158. A solid form of Compound 1:

Compound 1

159. The solid form of embodiment 158, wherein the solid form is a hydrate.

160. The solid form of embodiment 158 or 159, wherein the solid form is characterized in that it has three or more peaks in its X-ray powder diffraction (XRPD) pattern selected from those at angles (degrees 2 theta±0.2) of 7.32, 11.15, 13.99, 16.58, 18.95, 21.68, 23.56, 25.23, and 26.60.

161. The solid form of embodiment 158 or 159, wherein the solid form is characterized in that it has four or more peaks in its X-ray powder diffraction (XRPD) pattern selected from those at angles (degrees 2 theta±0.2) of 7.32, 11.15, 13.99, 16.58, 18.95, 21.68, 23.56, 25.23, and 26.60.

162. The solid form of embodiment 158 or 159, wherein the solid form is characterized in that it has five or more peaks in its X-ray powder diffraction (XRPD) pattern selected from those at angles (degrees 2 theta±0.2) of 7.32, 11.15, 13.99, 16.58, 18.95, 21.68, 23.56, 25.23, and 26.60.

163. The solid form of embodiment 158 or 159, wherein the solid form is characterized in that it has six or more peaks in its X-ray powder diffraction (XRPD) pattern selected from those at angles (degrees 2 theta±0.2) of 7.32, 11.15, 13.99, 16.58, 18.95, 21.68, 23.56, 25.23, and 26.60.

164. The solid form of embodiment 158 or 159, wherein the solid form is characterized in that it has seven or more peaks in its X-ray powder diffraction (XRPD)

pattern selected from those at angles (degrees 2 theta±0.2) of 7.32, 11.15, 13.99, 16.58, 18.95, 21.68, 23.56, 25.23, and 26.60.

165. The solid form of embodiment 158 or 159, wherein the solid form is characterized in that it has eight or more peaks in its X-ray powder diffraction (XRPD) pattern selected from those at angles (degrees 2 theta±0.2) of 7.32, 11.15, 13.99, 16.58, 18.95, 21.68, 23.56, 25.23, and 26.60.

166. The solid form of embodiment 158 or 159, wherein the solid form is characterized in that it has peaks in its X-ray powder diffraction (XRPD) pattern selected from those at angles (degrees 2 theta±0.2) of 7.32, 11.15, 13.99, 16.58, 18.95, 21.68, 23.56, 25.23, and 26.60.

167. The solid form of any of embodiments 158-166, wherein the solid form is Compound 1 Form A and is characterized in that it has peaks in its X-ray powder diffraction (XRPD) pattern comprising those at angles (degrees 2 theta±0.2) of:

| Angle/°2θ |
|---|
| 7.32 |
| 9.57 |
| 9.77 |
| 11.15 |
| 11.45 |
| 12.90 |
| 13.20 |
| 13.99 |
| 14.41 |
| 14.69 |
| 16.39 |
| 16.58 |
| 16.85 |
| 17.24 |
| 17.98 |
| 18.60 |
| 18.95 |
| 19.23 |
| 19.68 |
| 20.23 |
| 20.75 |
| 21.29 |
| 21.68 |
| 22.19 |
| 22.40 |
| 22.93 |
| 23.56 |
| 23.98 |
| 24.51 |
| 25.23 |
| 25.97 |
| 26.60 |
| 27.25 |
| 27.80 |
| 28.78 |
| 29.07 |
| 29.78 |
| 30.70 |

168. The solid form of any one of embodiments 160-167, wherein the XRPD pattern is collected using Cu Kα radiation with a wavelength of 1.54059 Å, optionally wherein the XRPD pattern is collected according to the parameters in Table 13.

169. The solid form of any one of embodiments 158-168, characterized by a differential scanning calorimetry (DSC) endotherm having a minima at about 117.9° C. and/or about 307.8° C.

170. The solid form of any one of embodiments 158-169, characterized by a thermogravimetric analysis (TGA) with a weight loss of about 9.3% between 41-136° C.

171. The solid form of embodiment 158, wherein the solid form is anhydrous.

172. The solid form of embodiment 158 or 171, wherein the solid form is characterized in that it has a X-ray powder diffraction pattern substantially similar to FIG. 22.

173. The solid form of any one of embodiments 158, 171, and 172, characterized by a differential scanning calorimetry (DSC) endotherm having a minima at about 307.8° C.

174. The solid form of any one of embodiments 158 and 171-173, characterized by a thermogravimetric analysis (TGA) with a weight loss of about 0.1% between 50-121° C. and/or a weight loss of about 0.2% between 229-267° C.

175. The solid form of embodiment 158, wherein the solid form is an acetic acid solvate.

176. The solid form of embodiment 158 or 175, wherein the solid form is characterized in that it has a X-ray powder diffraction pattern substantially similar to FIG. 23.

177. The solid form of any one of embodiments 158, 175, and 176, characterized by a differential scanning calorimetry (DSC) endotherm having a minima at about 102.8° C. and/or about 190.1° C. and/or about 308.4° C.

178. The solid form of any one of embodiments 158 and 175-177, characterized by a thermogravimetric analysis (TGA) with a weight loss of about 16.6% between 71-137° C. and/or a weight loss of about 8% between 171-203° C.

179. The solid form of embodiment 158, wherein the solid form is a dimethylacetamide solvate.

180. The solid form of embodiment 158 or 179, wherein the solid form is characterized in that it has a X-ray powder diffraction pattern substantially similar to FIG. 25.

181. The solid form of any one of embodiments 158, 179, and 180, characterized by a differential scanning calorimetry (DSC) endotherm having a minima at about 117.7° C. and/or about 305.4° C.

182. The solid form of any one of embodiments 158 and 179-181, characterized by a thermogravimetric analysis (TGA) with a weight loss of about 25.5% between 101-186° C.

183. The solid form of embodiment 158, wherein the solid form is a dimethylsulfoxide solvate.

184. The solid form of embodiment 158 or 183, wherein the solid form is characterized in that it has a X-ray powder diffraction pattern substantially similar to FIG. 27.

185. The solid form of embodiment 158, wherein the solid form is a N-methyl-2-pyrrolidone solvate.

186. The solid form of embodiment 158 or 185, wherein the solid form is characterized in that it has a X-ray powder diffraction pattern substantially similar to FIG. 29.

187. The solid form of any one of embodiments 158, 185, and 186, characterized by a differential scanning calorimetry (DSC) endotherm having a minima at about 126.5° C. and/or about 305.4° C.

188. The solid form of any one of embodiments 158 and 185-187, characterized by a thermogravimetric analysis (TGA) with a weight loss of about 27.5% between 104-233° C.

189. The solid form of embodiment 158, wherein the solid form is a dimethylformamide solvate.

190. The solid form of embodiment 158 or 189, wherein the solid form is characterized in that it has a X-ray powder diffraction pattern substantially similar to FIG. 31.
191. The solid form of embodiment 158, wherein the solid form is characterized in that it has a X-ray powder diffraction pattern substantially similar to FIG. 28.
192. The solid form of embodiment 158, wherein the solid form is characterized in that it has a X-ray powder diffraction pattern substantially similar to FIG. 32.
193. The solid form of embodiment 158, wherein the solid form is characterized in that it has a X-ray powder diffraction pattern substantially similar to FIG. 33.
194. The solid form of embodiment 158, wherein the solid form is a tetrahydrofuran solvate.
195. The solid form of embodiment 158 or 194, wherein the solid form is characterized in that it has a X-ray powder diffraction pattern substantially similar to FIG. 34.
196. The solid form of embodiment 158 or 194, wherein the solid form is characterized in that it has a X-ray powder diffraction pattern substantially similar to FIG. 35.
197. The solid form of embodiment 158 or 171, wherein the solid form is characterized in that it has three or more peaks in its X-ray powder diffraction (XRPD) pattern selected from those at angles (degrees 2 theta 0.2) of 8.08, 11.76, 15.73, 17.31, 19.32, 19.54, 23.13, 25.90, and 27.31.
198. The solid form of embodiment 158 or 171, wherein the solid form is characterized in that it has four or more peaks in its X-ray powder diffraction (XRPD) pattern selected from those at angles (degrees 2 theta±0.2) of 8.08, 11.76, 15.73, 17.31, 19.32, 19.54, 23.13, 25.90, and 27.31.
199. The solid form of embodiment 158 or 171, wherein the solid form is characterized in that it has five or more peaks in its X-ray powder diffraction (XRPD) pattern selected from those at angles (degrees 2 theta±0.2) of 8.08, 11.76, 15.73, 17.31, 19.32, 19.54, 23.13, 25.90, and 27.31.
200. The solid form of embodiment 158 or 171, wherein the solid form is characterized in that it has six or more peaks in its X-ray powder diffraction (XRPD) pattern selected from those at angles (degrees 2 theta 0.2) of 8.08, 11.76, 15.73, 17.31, 19.32, 19.54, 23.13, 25.90, and 27.31.
201. The solid form of embodiment 158 or 171, wherein the solid form is characterized in that it has seven or more peaks in its X-ray powder diffraction (XRPD) pattern selected from those at angles (degrees 2 theta±0.2) of 8.08, 11.76, 15.73, 17.31, 19.32, 19.54, 23.13, 25.90, and 27.31.
202. The solid form of embodiment 158 or 171, wherein the solid form is characterized in that it has eight or more peaks in its X-ray powder diffraction (XRPD) pattern selected from those at angles (degrees 2 theta±0.2) of 8.08, 11.76, 15.73, 17.31, 19.32, 19.54, 23.13, 25.90, and 27.31.
203. The solid form of embodiment 158 or 171, wherein the solid form is characterized in that it has peaks in its X-ray powder diffraction (XRPD) pattern selected from those at angles (degrees 2 theta±0.2) of 8.08, 11.76, 15.73, 17.31, 19.32, 19.54, 23.13, 25.90, and 27.31.
204. The solid form of any one of embodiments 158 and 197-203, wherein the solid form is Compound 1 Form N and is characterized in that it has peaks in its X-ray powder diffraction (XRPD) pattern comprising those at angles (degrees 2 theta±0.2) of:

| Angle/°2θ |
|---|
| 8.08 |
| 8.62 |
| 9.75 |
| 9.81 |
| 11.76 |
| 12.62 |
| 13.44 |
| 13.56 |
| 15.73 |
| 16.21 |
| 17.31 |
| 17.59 |
| 17.87 |
| 19.32 |
| 19.54 |
| 19.74 |
| 20.21 |
| 20.74 |
| 21.00 |
| 21.39 |
| 21.62 |
| 22.15 |
| 22.52 |
| 23.13 |
| 23.86 |
| 24.34 |
| 24.66 |
| 25.02 |
| 25.57 |
| 25.90 |
| 26.38 |
| 27.06 |
| 27.31 |
| 27.85 |
| 28.49 |
| 28.77 |
| 29.55 |
| 29.81 |
| 30.47 |
| 31.04 |
| 31.79 |
| 32.46 |
| 33.27 |
| 34.45 |
| 34.83 |

205. The solid form of any one of embodiments 197-204, wherein the XRPD pattern is collected using Cu Kα radiation with a wavelength of 1.5405929 Å, optionally wherein the XRPD pattern is collected according to the parameters in Table 13.
206. The solid form of any one of embodiments 158 and 197-205, characterized by a differential scanning calorimetry (DSC) endotherm having a minima at about 307.2° C.
207. The solid form of any one of embodiments 158 and 197-206, characterized by a thermogravimetric analysis (TGA) with a weight loss of about 0.1% between 50-120° C. and/or a weight loss of about 0.2% between 209-252° C.
208. The solid form of embodiment 158, wherein the solid form is an ethyl acetate solvate.
209. The solid form of embodiment 158 or 208, wherein the solid form is characterized in that it has a X-ray powder diffraction pattern substantially similar to FIG. 38.
210. A solid form of Compound 1 prepared by a method comprising steps of stirring Compound 2 in water, and then removing the solvent to provide the solid form of Compound 1.

211. The solid form of embodiment 210, wherein the method further comprises steps of adding hydrochloric acid to a slurry of Compound 1 in tetrahydrofuran, and then removing the solvent to provide the Compound 2.

212. A solid form of Compound 1 prepared by a method comprising steps of stirring Compound 1 in tert-amyl methyl ether, and then removing the solvent to provide the solid form of Compound 1.

213. A solid form of Compound 1 prepared by a method comprising steps of stirring Compound 1 in acetic acid, and then removing the solvent to provide the solid form of Compound 1.

214. A solid form of Compound 1 prepared by a method comprising steps of stirring Compound 1 in dimethylacetamide, and then removing the solvent to provide the solid form of Compound 1.

215. A solid form of Compound 1 prepared by a method comprising steps of stirring Compound 1 in dimethylsulfoxide, and then removing the solvent to provide the solid form of Compound 1.

216. A solid form of Compound 1 prepared by a method comprising steps of stirring Compound 1 in N-methyl-2-pyrrolidone, and then removing the solvent to provide the solid form of Compound 1.

217. A solid form of Compound 1 prepared by a method comprising steps of stirring Compound 1 in dimethylformamide, and then removing the solvent to provide the solid form of Compound 1.

218. A solid form of Compound 1 prepared by a method comprising steps of stirring Compound 1 in dimethylsulfoxide, removing the solvent, and drying the resulting solids in an oven to provide the solid form of Compound 1.

219. A solid form of Compound 1 prepared by a method comprising steps of providing a solution of Compound 1 in hexafluoroisopropanol, and then removing the solvent to provide the solid form of Compound 1.

220. A solid form of Compound 1 prepared by a method comprising steps of providing a solution of Compound 1 in 2,2,2-trifluoroethanol, and then removing the solvent to provide the solid form of Compound 1.

221. A solid form of Compound 1 prepared by a method comprising steps of stirring Compound 1 in 99:1 tetrahydrofuran:water, and then removing the solvent to provide the solid form of Compound 1.

222. A solid form of Compound 1 prepared by a method comprising steps of stirring Compound 1 in 97:3 tetrahydrofuran:water, and then removing the solvent to provide the solid form of Compound 1.

223. A solid form of Compound 1 prepared by a method comprising steps of stirring Compound 1 in cyclopentyl methyl ether, and then removing the solvent to provide the solid form of Compound 1.

224. A solid form of Compound 1 prepared by a method comprising steps of stirring Compound 1 in ethyl acetate, and then removing the solvent to provide the solid form of Compound 1.

225. The solid form of any one of embodiments 158-224, wherein the solid form is crystalline.

226. The solid form of any one of embodiments 158-225, wherein the solid form is substantially free of an amorphous form of Compound 1.

227. The solid form of any one of embodiments 158-226, wherein the solid form is substantially free of impurities.

228. The solid form of any one of embodiments 158-227, wherein the solid form is substantially free of other free base solid forms of Compound 1.

229. The solid form of any one of embodiments 159-170, wherein the solid form is substantially free of Compound 1 Form B.

230. A pharmaceutical composition comprising the solid form of any one of embodiments 158-229 and a pharmaceutically acceptable carrier or excipient.

231. A process for preparing a solid form of Compound 1, wherein the process comprises steps of stirring Compound 2 in water, and then removing the solvent to provide the solid form of Compound 1.

232. The process of embodiment 231, wherein the process further comprises steps of adding hydrochloric acid to a slurry of Compound 1 in tetrahydrofuran, and then removing the solvent to provide Compound 2.

233. A process for preparing a solid form of Compound 1, wherein the process comprises steps of stirring Compound 1 in a suitable solvent, and then removing the solvent to provide the solid form of Compound 1.

234. The process of embodiment 233, wherein the suitable solvent is tert-amyl methyl ether.

235. The process of embodiment 233, wherein the suitable solvent is acetic acid.

236. The process of embodiment 233, wherein the suitable solvent is dimethylacetamide.

237. The process of embodiment 233, wherein the suitable solvent is dimethylsulfoxide.

238. The process of embodiment 233, wherein the suitable solvent is N-methyl-2-pyrrolidone.

239. The process of embodiment 233, wherein the suitable solvent is dimethylformamide.

240. The process of embodiment 237, wherein the process further comprises a step of drying the resulting solids in an oven to provide the solid form of Compound 1.

241. The process of embodiment 233, wherein the suitable solvent is 99:1 tetrahydrofuran:water.

242. The process of embodiment 233, wherein the suitable solvent is 97:3 tetrahydrofuran:water.

243. The process of embodiment 233, wherein the suitable solvent is cyclopentyl methyl ether.

244. The process of embodiment 233, wherein the suitable solvent is ethyl acetate.

245. A process for preparing a solid form of Compound 1, wherein the process comprises steps of providing a solution of Compound 1 in a suitable solvent, and then removing the solvent to provide the solid form of Compound 1.

246. The process of embodiment 245, wherein the suitable solvent is hexafluoroisopropanol.

247. The process of embodiment 245, wherein the suitable solvent is 2,2,2-trifluoroethanol.

248. A method of inhibiting JAK2 in a subject comprising administering the compound of any one of embodiments 158-229 or the composition of embodiment 230.

249. A method of treating a disease, disorder, or condition associated with JAK2, comprising administering to a subject in need thereof the compound of any one of embodiments 158-229 or the composition of embodiment 230.

250. A method of treating cancer, comprising administering to a subject in need thereof the compound of any one of embodiments 158-229 or the composition of embodiment 230.

251. A method of treating a hematological malignancy, comprising administering to a subject in need thereof the compound of any one of embodiments 158-229 or the composition of embodiment 230.

252. The method of embodiment 251, wherein the hematological malignancy is leukemia or lymphoma.
253. A method of treating a myeloproliferative neoplasm, comprising administering to a subject in need thereof the compound of any one of embodiments 158-229 or the composition of embodiment 230.
254. The method of embodiment 253, wherein the myeloproliferative neoplasm is polycythemia vera, essential thrombocytopenia or myelofibrosis.

EXAMPLES

The examples below are meant to illustrate certain embodiments of the disclosure, and not to limit the scope of the disclosure.

General Experimental

Abbreviations

ACN Acetonitrile
API Active pharmaceutical ingredient
B/E Birefringence and extinction
BR Birefringence
CPME Cyclopentylmethyl ether
DCM Dichloromethane
DMA Dimethylacetamide
DMF Dimethylformamide
DMSO Dimethylsulfoxide
DSC Differential scanning calorimetry
DVS Dynamic (water) vapor sorption
Endo/endo Endotherm or endothermic
Exo/exo Exotherm or exothermic
FB Free base
FE Fast evaporation
FF Free form
HFIPA Hexafluoroisopropanol
IPA Isopropyl alcohol
IPE Isopropyl ether
IS Insufficient solids/sample
LIMS Laboratory Information Management System
Max/max Maximum or maxima
MeOH Methanol
MTBE Methyl tert-butyl ether
NMP N-methyl-2-pyrrolidone
NMR Nuclear magnetic resonance spectroscopy
Obs Observation
PO Preferred orientation
ppt Precipitate or precipitation
RH Relative humidity
RT Room temperature
Soln/soln Solution
TAME Tert-amyl methyl ether
TFE 2,2,2-trifluoroethanol
TG/TGA Thermogravimetry/Thermogravimetric analysis
THF Tetrahydrofuran
vac Vacuum
VRH-XRPD Variable relative humidity X-ray powder diffraction
XRF X-ray fluorescence
XRPD X-ray powder diffraction
Instruments and Methods
A. X-Ray Powder Diffraction (XRPD)
Transmission XRPD pattern was collected with a PANalytical X'Pert PRO MPD or PANalytical Empyrean diffractometer using an incident beam of Cu radiation produced using a long, fine-focus source. An elliptically graded multilayer mirror was used to focus Cu Kα X-rays through the specimen and onto the detector. Prior to the analysis, a silicon specimen (NIST SRM 640f) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening and asymmetry from axial divergence. Diffraction patterns were collected using a scanning position-sensitive detector (X'Celerator) located 240 mm from the specimen and Data Collector software v. 5.5.

TABLE 13

| Compound | X-ray wavelength | Scan range | Step size | Speed | Collection time |
|---|---|---|---|---|---|
| Compound 1 Form 1[a] | Cu (1.5405929 Å) | 1.0000-40.0041° 2θ | 0.0167° 2θ | 3.2°/min. | 723 s |
| Compound 5 Form C[a] | Cu (1.5405929 Å) | 1.0000-40.0041° 2θ | 0.0167° 2θ | 3.2°/min. | 721 s |
| Compound 3 Form A[b] | Cu (1.54059 Å) | 1.00-39.99° 2θ | 0.017° 2θ | 3.3°/min | 718 s |
| Compound 2 Form A[b] | Cu (1.54059 Å) | 1.00-3999° 2θ | 0.017° 2θ | 3.3°/min. | 718 s |
| Compound 4 Form A[b] | Cu (1.54059 Å) | 1.00-39.99° 2θ | 0.017° 2θ | 3.2°/min. | 720 s |
| Compound 4 Form B[a] | Cu (15405929 Å) | 1.0000-40.0041° 2θ | 0.0167° 2θ | 3.3°/min | 719 s |
| Compound 1 Form A[b] | Cu (1.54059 Å) | 1.00-39.99° 2θ | 0.017° 2θ | 3.2°/min. | 724 s |
| Compound 1 Form N[a] | Cu (1.5405929 Å) | 1.0000-40.0041° 2θ | 0.0167° 2θ | 3.2°/min | 722 s |

[a] A PANalytical Empyrean X-ray Powder Diffractometer was used.
[b] A PANalytical X'Pert PRO MPD X-ray Powder Diffractometer was used.

B. Thermogravimetric (TGA) and Differential Scanning Calorimetry (DSC)

TG analysis was performed using a Mettler-Toledo TGA/DSC3+ analyzer. Temperature and enthalpy adjustments were performed using indium, tin, and zinc, and then verified with indium. The balance was verified with calcium oxalate. The sample was placed in an open aluminum pan. The pan was then inserted into the TG furnace. A weighed aluminum pan configured as the sample pan was placed on the reference platform. The furnace was heated under nitrogen. The sample was analyzed from 25° C. to 350° C. at 10° C./min.

DSC was performed using a Mettler-Toledo DSC3+ differential scanning calorimeter. A tau lag adjustment was performed with indium, tin, and zinc. The temperature and enthalpy were adjusted with octane, phenyl salicylate, indium, tin and zinc. The adjustment was then verified with octane, phenyl salicylate, indium, tin, and zinc. The sample was placed into a hermetically sealed aluminum DSC pan, the weight was accurately recorded, the lid was pierced, and the sample was inserted into the DSC cell. A weighed aluminum pan configured as the sample pan was placed on the reference side of the cell. The pan lid was pierced prior to sample analysis. The sample was analyzed from −30° C. to 250° C. or 350° C. at 10° C./min.

C. Dynamic Vapor Sorption (DVS)

Automated vapor sorption (VS) data were collected on a Surface Measurement System DVS Intrinsic instrument. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

D. Solution NMR

NMR spectra for Compound 1 were recorded on a Bruker 400 MHz Avance III HD instrument with 5 mm PABBO BB/19F-1H/D Z-GRD Z108618 probe, or on an Avance 600 MHz NMR Spectrometer, using DMSO-d6 as a solvent.

NMR spectra for Compounds 2-5 were acquired with an Avance 600 MHz NMR spectrometer. The samples were prepared by dissolving given amount of sample in DMSO-d6 containing TMS.

E. X-Ray Fluorescence (XRF)

Microbeam energy dispersive X-ray fluorescence (μEDXRF) spectra were collected with a Horiba XGT-9000 equipped with a microfocus Rh X-ray source powered at 50 kV and automatically controlled current. A vacuum atmosphere was used during data collection. The silicon-strip detector (SSD) was used in the high-resolution mode, P5.

A monocapillary optic with a nominal focal spot of 1.2 mm was used for analysis of two areas on the sample. The analysis of one of these areas was repeated once. Quantitative analysis of chlorine was completed using fundamental parameters model in the Horiba X-ray Lab software application using a one-point calibration from a measured standard material with known chlorine content. The results were an average from the three spectra collected.

F. Variable Relative Humidity X-Ray Powder Diffraction (VRH-XRPD)

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Data were collected and analyzed using Data Collector software v. 5.5. Prior to the analysis, a silicon specimen (NIST SRM 640f) was analyzed to verify the observed position of the Si 111 peak is consistent with the NIST-certified position. A specimen of the sample was packed in a nickel-coated copper well. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 5.5.

An Anton Paar temperature-humidity chamber (THC) was used while collecting in-situ XRPD patterns as a function of humidity. The temperature of the specimen was changed with a Peltier thermoelectric device located directly under the specimen holder and monitored with a platinum-100 resistance sensor located in the specimen holder. The thermoelectric device was powered and controlled by an Anton Paar TCU 50 interfaced with Data Collector. The humidity was generated with an RH-200 manufactured by VTI Inc. and carried by a flow of nitrogen gas. The humidity was monitored by a HygroClip sensor manufactured by Rotronic located next to the specimen inside the THC.

Example 1: N-(4-((7-cyano-1-methyl-2-((1-methyl-2-oxo-5-(trifluoromethyl)-1,2-dihydropyridin-3-yl)amino)-1H-imidazo[4,5-b]pyridin-6-yl)oxy)pyridin-2-yl)acetamide (Compound 1)

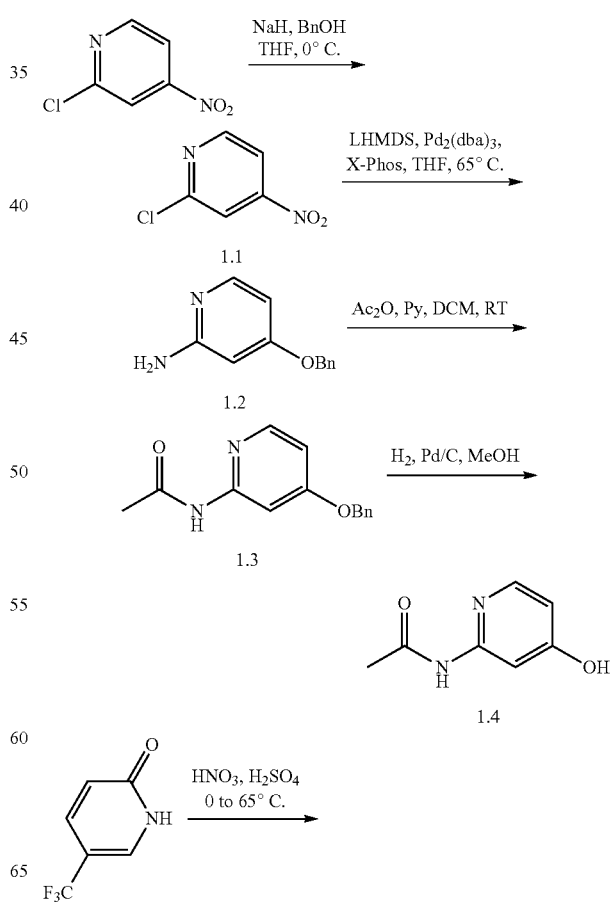

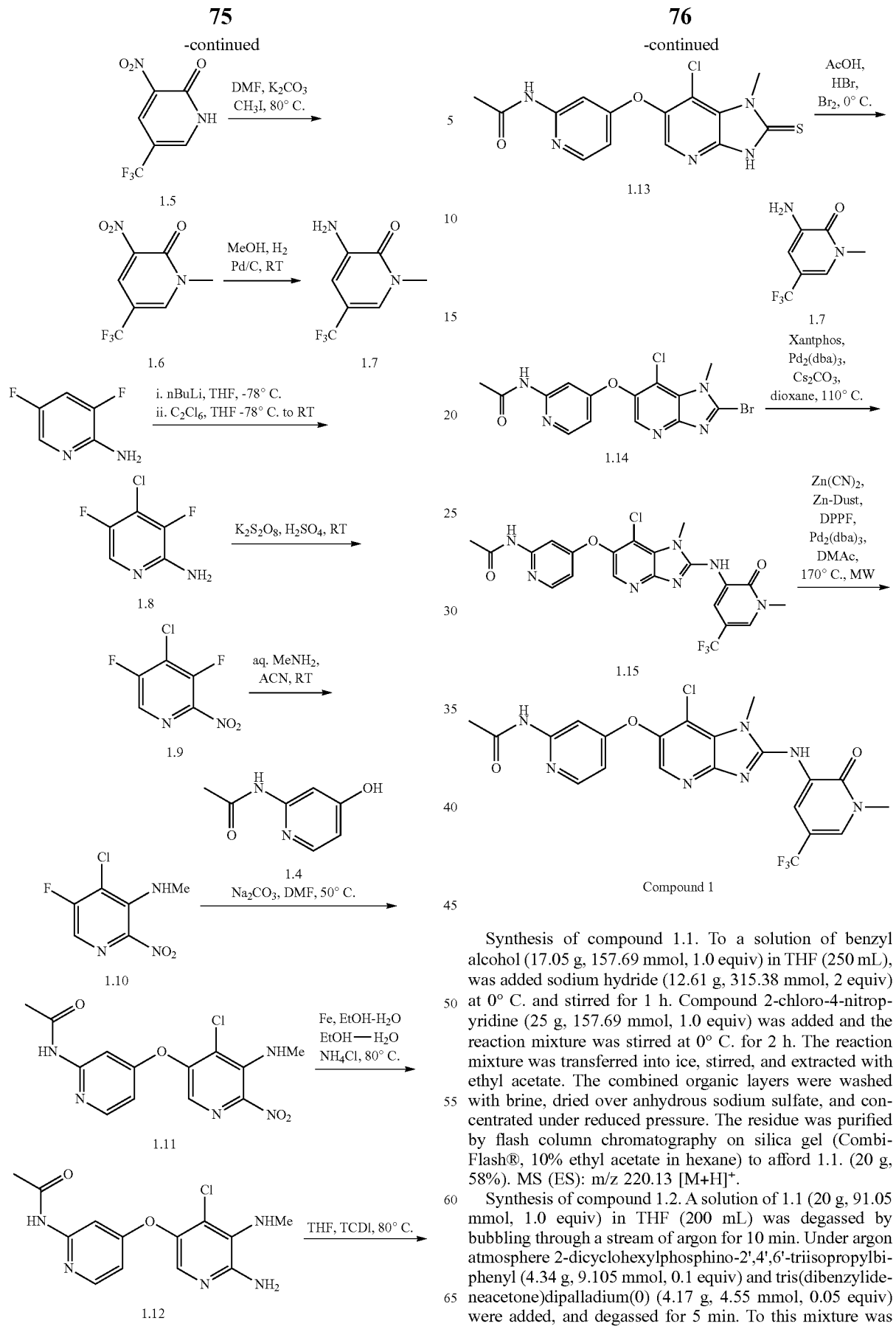

Synthesis of compound 1.1. To a solution of benzyl alcohol (17.05 g, 157.69 mmol, 1.0 equiv) in THF (250 mL), was added sodium hydride (12.61 g, 315.38 mmol, 2 equiv) at 0° C. and stirred for 1 h. Compound 2-chloro-4-nitropyridine (25 g, 157.69 mmol, 1.0 equiv) was added and the reaction mixture was stirred at 0° C. for 2 h. The reaction mixture was transferred into ice, stirred, and extracted with ethyl acetate. The combined organic layers were washed with brine, dried over anhydrous sodium sulfate, and concentrated under reduced pressure. The residue was purified by flash column chromatography on silica gel (Combi-Flash®, 10% ethyl acetate in hexane) to afford 1.1. (20 g, 58%). MS (ES): m/z 220.13 [M+H]+.

Synthesis of compound 1.2. A solution of 1.1 (20 g, 91.05 mmol, 1.0 equiv) in THF (200 mL) was degassed by bubbling through a stream of argon for 10 min. Under argon atmosphere 2-dicyclohexylphosphino-2',4',6'-triisopropylbiphenyl (4.34 g, 9.105 mmol, 0.1 equiv) and tris(dibenzylideneacetone)dipalladium(0) (4.17 g, 4.55 mmol, 0.05 equiv) were added, and degassed for 5 min. To this mixture was added lithium bis(trimethylsilyl)amide solution (1 M in THF, 182 mL, 182.1 mmol, 2.0 equiv) and the reaction mixture was stirred at 65° C. for 1 h. It was cooled to room temperature, transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3% methanol in DCM) to afford 1.2 (11.2 g, 61%). MS (ES): m/z 201.2 [M+H]$^+$.

Synthesis of compound 1.3. To a solution of 1.2 (11.2 g, 55.93 mmol, 1.0 equiv) and pyridine (6.3 mL, 78.30 mmol, 1.4 equiv) in DCM (110 mL) was added acetic anhydride (6.34 mL, 67.11 mmol, 1.2 equiv) at room temperature and stirred for 1 h. The reaction mixture was transferred into ice, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 1% methanol in DCM) to afford 1.3 (6.1 g, 45%). MS (ES): m/z 243.21 [M+H]$^+$.

Synthesis of compound 1.4. A mixture of compound 1.3 (6.1 g, 25.18 mmol, 1.0 equiv) and 10%/o palladium on carbon (2 g) in methanol (60 mL) was stirred under hydrogen (1 atm) for 2 h. It was filtered through a pad of Celite® and rinsed with methanol. The filtrate was concentrated under reduced pressure. The residue was purified by flash column chromatography on silica gel (CombiFlash®, 5% methanol in DCM) to afford 1.4 (3.3 g, 86%). MS (ES): m/z 153.2 [M+H]$^+$.

Synthesis of compound 1.5. To a solution of 5-(trifluoromethyl)pyridin-2(1H)-one (5.0 g, 30.66 mmol, 1.0 equiv) in conc. sulfuric acid (25 mL) was added fuming nitric acid (8 mL) at 0° C. The reaction mixture was stirred at 65° C. for 6 h. It was pour over crushed ice, stirred and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford 1.5 (2.0 g, 31%). MS (ES): m/z 209.10 [M+H]$^+$.

Synthesis of compound 1.6. To a mixture of 1.5 (1.0 g, 4.81 mmol, 1.0 equiv) and potassium carbonate (1.3 g, 9.62 mmol, 2.0 equiv) in DMF (15 mL) was stirred for 15 min before the addition of methyl iodide (1.0 g, 7.21 mmol, 1.5 equiv). The reaction mixture was stirred at 80° C. for 2 h. The reaction mixture was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 40% ethyl acetate in hexane) to afford 1.6 (0.57 g, 53%). MS (ES): m/z 223.12 [M+H]$^+$.

Synthesis of compound 1.7. A mixture of compound 1.6 (0.57 g, 2.57 mmol, 1.0 equiv) and 10% palladium on carbon (0.3 g) in methanol (18 mL) was stirred under hydrogen (1 atm) for 1 h. It was filtered through a pad of Celite® and rinsed with methanol. The filtrate was concentrated under reduced pressure to obtain 1.7 (0.34 g, 68.96%). MS (ES): m/z 193.14 [M+H]$^+$. It was used without purification.

Synthesis of compound 1.8. To a solution of 3,5-difluoropyridin-2-amine (10 g, 76.87 mmol, 1.0 equiv) in THF (200 mL), was added n-butyl lithium (2.5 M in hexane, 61.4 mL, 153.7 mmol, 2.0 equiv) at −78° C. and stirred for 40 min. Hexachloroethane (36.3 g, 153.7 mmol, 2.0 equiv) was added and the reaction mixture was stirred at −78° C. for 30 min. After completion of reaction, a saturated aqueous ammonium chloride solution was added carefully and stirred. The mixture was allowed to warm to room temperature and extracted with ethyl acetate. The combined organic layers were washed with brine, dried over anhydrous sodium sulfate, filtered, and concentrated under reduced pressure. The residue was purified by flash column chromatography on silica gel (CombiFlash®, 12% ethyl acetate in hexane) to afford 1.8 (8.0 g, 63%). $^1$H NMR (DMSO-d6, 400 MHz): δ 7.98-7.94 (m, 1H), 6.48 (bs, 2H).

Synthesis of compound 1.9. Concentrated sulfuric acid (3 mL) was added dropwise to potassium persulfate (2.05 g, 7.6 mmol, 2.5 equiv) at room temperature and stirred for 15 min. To the mixture was added 1.8 (0.5 g, 3.04 mmol, 1.0 equiv) in portions to maintain the temperature between 30-40° C. After the addition, the reaction mixture was stirred at room temperature for 3 h. It was poured over crushed ice, stirred, basified with saturated sodium bicarbonate, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2-3% ethyl acetate in hexane) to afford 1.9 (0.970 g, 16.41%). $^1$H NMR (DMSO-d6, 400 MHz): δ 8.78 (s, 1H).

Synthesis of compound 1.10. To a solution of 1.9 (0.970 g, 4.99 mmol, 1.0 equiv) in acetonitrile (10 mL) was added aqueous methylamine solution (40%, 0.8 mL, 9.98 mmol, 2.0 equiv) dropwise at 0° C. The reaction mixture was stirred at room temperature for 20 min. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 10% ethyl acetate in hexane) to afford 1.10 (0.930 g, 91%). $^1$H NMR (DMSO-d6, 400 MHz). S 7.98 (s, 1H), 7.05 (bs, 1H), 2.79 (d, 3H).

Synthesis of compound 1.11. To a solution of 1.10 (0.930 g, 4.52 mmol, 1.0 equiv) in DMF (10 mL) was added 1.4 (0.895 g, 5.88 mmol, 1.3 equiv) followed by sodium carbonate (0.958 g, 9.04 mmol, 2.0 equiv). The reaction mixture was stirred at 50° C. for 6 h. It was cooled to room temperature, poured into ice-water. The precipitated solids were collected by filtration, washed with water and dried under vacuum to obtain 1.11 (0.850 g, 56%). MS (ES): m/z 338.7 [M+H]$^+$.

Synthesis of compound 1.12. A mixture of compound 1.11 (0.850 g, 2.52 mmol, 1.0 equiv), iron powder (0.705 g, 12.6 mmol, 5.0 equiv) and ammonium chloride (0.673 g, 12.6 mmol, 5.0 equiv) in ethanol-water (8:2, 10 mL) was stirred at 80° C. for 2 h. It was cooled to room temperature, filtered through a pad of Celite® and rinsed with ethanol. The filtrate was concentrated under reduced pressure. The residue was purified by flash column chromatography on silica gel (CombiFlash®, 2.4% methanol in DCM) to afford 1.12 (0.710 g, 92%). MS (ES): m/z 308.5 [M+H]$^+$.

Synthesis of compound 1.13. To a solution of 1.12 (0.150 g, 0.487 mmol, 1.0 equiv) in THF (2 mL) was added 1,1'-thiocarbonyldiimidazole (0.433 g, 2.43 mmol, 5.0 equiv). The reaction mixture was stirred at 80° C. for 1 h. It was cooled to room temperature and poured into ice-water. The precipitated solids were collected by filtration and triturated with hexane to obtain 1.13 (0.110 g, 65%). MS (ES): m/z: 350.7 [M+H]$^+$.

Synthesis of compound 1.14. To a solution of 1.13 (0.110 g, 0.314 mmol, 1.0 equiv) in acetic acid (5 mL) was added aqueous hydrobromic acid (0.037 g, 0.471 mmol, 1.5 equiv) at 0° C. followed by bromine (0.200 g, 1.25 mmol, 4.0 equiv). The reaction mixture was stirred for 10 min. It was transferred into a saturated aqueous sodium bicarbonate solution, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford 1.14 (0.063 g, 51%). MS (ES): m/z 397.6 [M+H]$^+$.

Synthesis of compound 1.15 A mixture of 1.14 (0.220 g, 0.554 mmol, 1.0 equiv), 1.7 (0.127 g, 0.665 mmol, 1.2 equiv) and cesium carbonate (0.450 g, 1.385 mmol, 2.5 equiv) in 1,4-dioxane (12 mL) was degassed by bubbling through a stream of argon for 10 min. Under argon atmosphere 4,5-bis(diphenylphosphino)-9,9-dimethylxanthene (0.064 g, 0.110 mmol, 0.2 equiv) and tris(dibenzylideneacetone)dipalladium(0) (0.051 g, 0.055 mmol, 0.1 equiv) were added, and degassed for 5 min. The reaction mixture was stirred at 110° C. for 2 h. It was cooled to room temperature, transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.3% methanol in DCM) to afford 1.15 (0.050 g, 26%). MS (ES): m/z: 508.2 [M]$^+$.

Synthesis of Compound 1. A mixture of 1.15 (0.077 g, 0.151 mmol, 1.0 equiv), zinc dust (0.0019 g, 0.030 mmol, 0.2 equiv) and zinc cyanide (0.088 g, 0.755 mmol, 5.0 equiv) in dimethylacetamide (5 mL) was degassed by bubbling through a stream of Celite® for 10 min. Under argon atmosphere were added 1,1'-ferrocenediyl-bis(diphenylphosphine) (0.025 g, 0.045 mmol, 0.3 equiv) and tris (dibenzylideneacetone)dipalladium(0)(0.020 g, 0.022 mmol, 0.15 equiv), and degassed for 5 min. The reaction mixture was stirred at 170° C. in a microwave reactor for 2 h. It was cooled to room temperature, transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford Compound 1 (0.025 g, 33%). MS (ES): m/z: 499.0 [M]$^+$, LCMS purity: 99.34%, HPLC purity: 96.76%, $^1$H NMR (DMSO-d6, 400 MHz): δ 10.67 (s, 1H), 9.06 (s, 1H), 8.65 (s, 1H), 8.32 (s, 1H), 8.25-8.23 (d, J=5.6 Hz, 1H), 8.19 (s, 1H), 7.75 (s, 1H), 6.76-6.75 (m, 1H), 3.96 (s, 3H), 3.66 (s, 3H), 2.06 (s, 3H).

Example 2: Characterization of Compound 1

Compound 1 was prepared generally as described in Example 1. A lot of Compound 1 (Lot I) prepared as described in Example 9 was characterized as described below and denoted Compound 1 Form 1.

FIG. 1 provides the XRPD pattern of Compound 1 Form 1.

Figure 2:
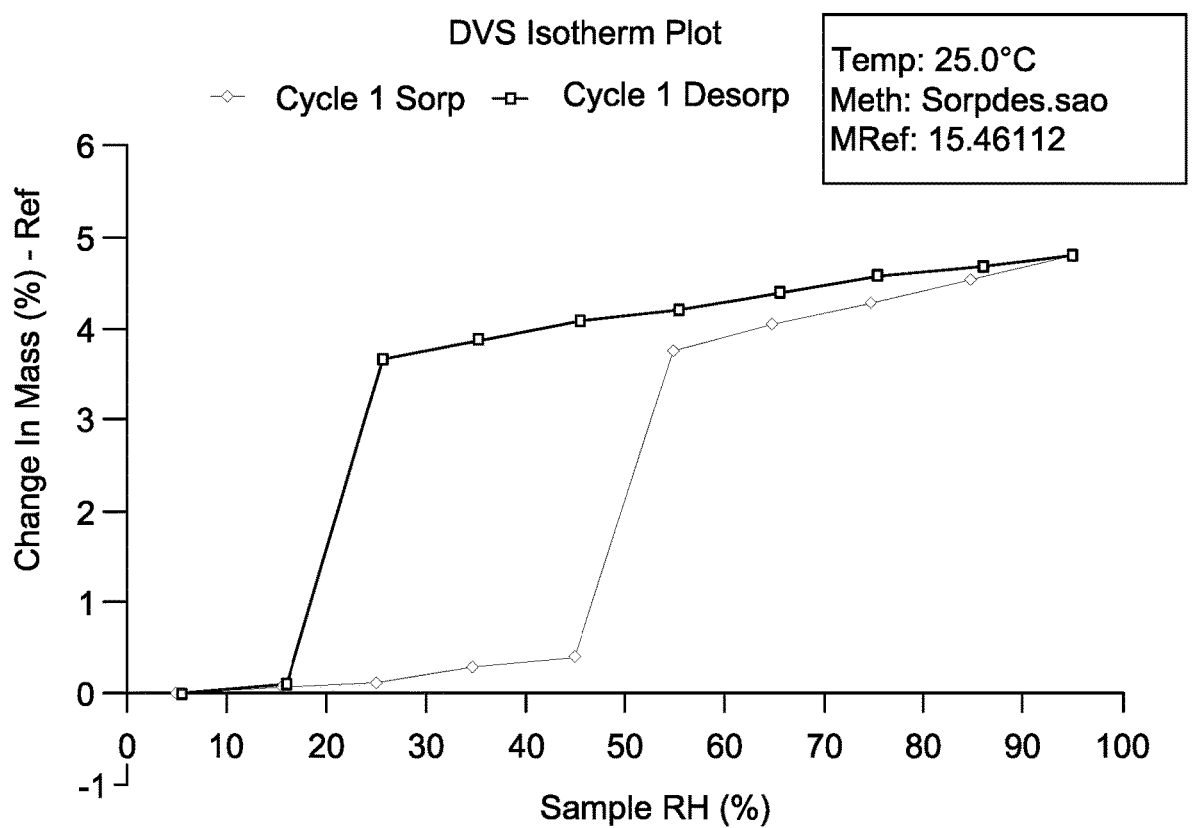
FIG. 2 provides a DVS isotherm plot of Compound 1 Form 1 (free base).

Hygroscopicity of Compound 1 Form 1 was analyzed by dynamic vapor sorption (DVS) from 5% to 95% relative humidity (FIG. 2 and Table 14). A total of 4.80% weight gain was observed from 5% to 95% RH, equal to 1.4 mol/mol $H_2O$, with 3.36% (1.0 mol/mol $H_2O$) of that weight being picked up from 45% to 55% RH. Upon desorption to 5% RH, 4.82% (1.4 mol/mol $H_2O$) was lost with hysteresis evident. 3.55% (1.0 mol/mol $H_2O$) of the weight loss occurred from 25% to 15% RH. The XRPD pattern of the post-DVS material was very similar to the XRPD pattern of material prepared via Example 1, but with a few missing peaks (FIG. 3).

TABLE 14

| | Target RH (%) | Sample RH (%) | Sorp Mass Change (%) | Sample RH (%) | Desorp Mass Change (%) | Hysteresis |
|---|---|---|---|---|---|---|
| Cycle 1 | 5.0 | 5.0 | 0.001 | 5.5 | −0.011 | |
| | 15.0 | 15.5 | 0.068 | 16.0 | 0.103 | 0.036 |
| | 25.0 | 25.0 | 0.118 | 25.6 | 3.654 | 3.536 |
| | 35.0 | 34.7 | 0.292 | 35.3 | 3.877 | 3.585 |
| | 45.0 | 44.9 | 0.396 | 45.5 | 4.084 | 3.687 |
| | 55.0 | 54.9 | 3.757 | 55.4 | 4.203 | 0.446 |
| | 65.0 | 64.8 | 4.049 | 65.6 | 4.403 | 0.354 |
| | 75.0 | 74.8 | 4.282 | 75.4 | 4.578 | 0.296 |
| | 85.0 | 84.8 | 4.534 | 86.1 | 4.677 | 0.142 |
| | 95.0 | 95.0 | 4.804 | 95.0 | 4.804 | |

Figure 3:
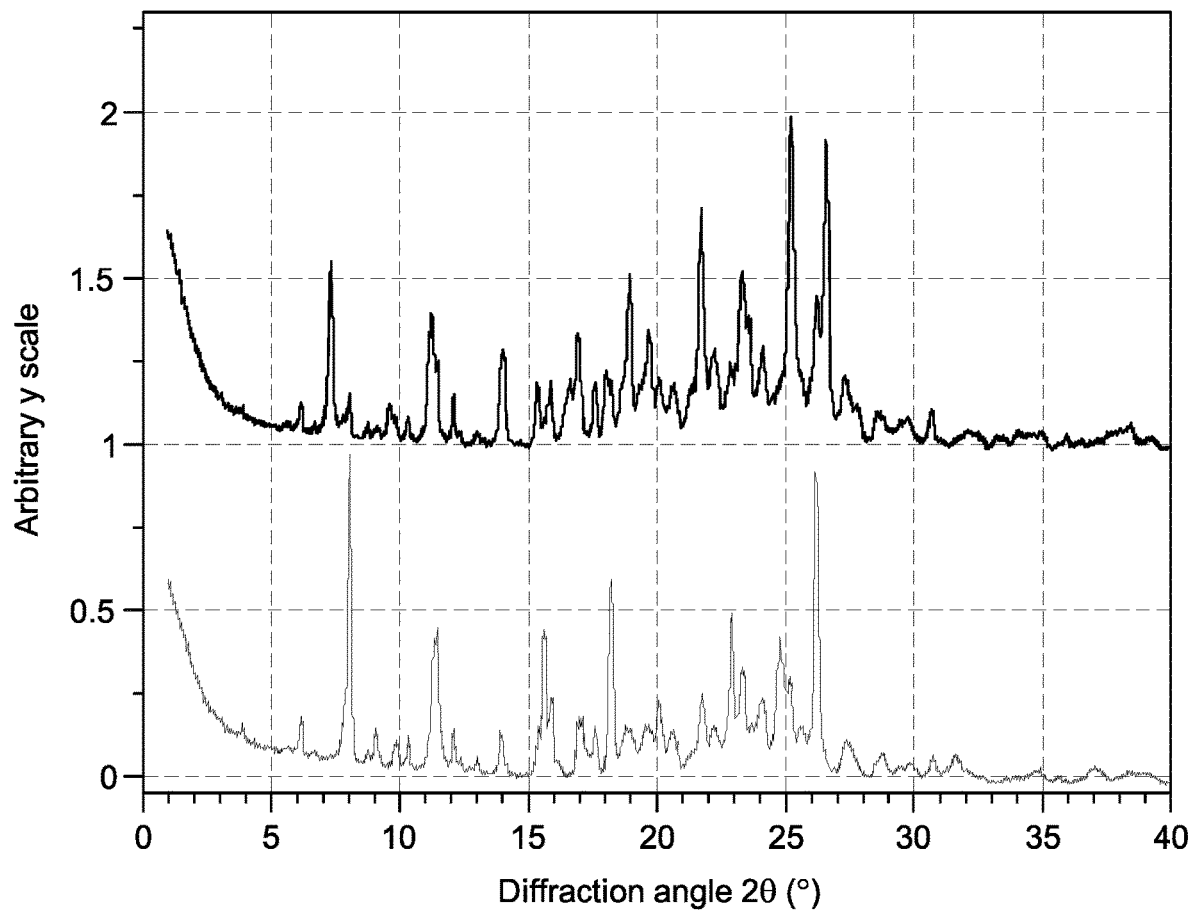
FIG. 3 depicts a XRPD overlay of Compound 1 Form 1 post-DVS material (lower) with pre-DVS material (upper).

FIG. 3 provides an overlay XRPD pattern of Compound 1 Form 1 post-DVS material (lower) with pre-DVS material (upper).

Solubility Study

Aliquots of various solvents were added to measured amounts of Compound 1 Form 1 with agitation at ambient temperature until complete dissolution was achieved, as judged by visual observation. Compound 1 Form 1 obtained from the synthetic procedure described in Example 1 was found to show limited solubility in most of the organic solvents assessed. See Table 15 below, where A is 5-20 mg/mL; B is 1-4.9 mg/mL; and C is <1 mg/mL.

TABLE 15

Solubility of Compound 1 Form 1 in Various Solvents

| Solvent | Solubility at ambient temperature (mg/mL)$^a$ |
|---|---|
| acetone | C |
| ACN | C |
| DCM | C |
| DMA | A |
| $H_2O$ | C |
| MeOH | C |
| TFE | A |
| THF | B |

$^a$Solubilities were calculated based on the total solvent used to give a solution; actual solubilities may be greater because of the volume of the solvent portions used or a slow rate of dissolution. If dissolution did not occur as determined by visual assessment, the value was reported as Example 3: Salt Screening of Compound 1

In an effort to find salts of Compound 1, a salt/co-crystal screen was conducted under different conditions with various salt/co-crystal co-formers and solvent systems.

Compound obtained from the synthetic procedure described in Example 1 was used as the starting material for salt and cocrystal experiments.

For each condition, about 50-100 mg of Compound 1 was used. The results are summarized in Table 16, below:

TABLE 16

| Coformer[a] | Conditions | Observations | XRPD Result |
|---|---|---|---|
| aspartic acid | 1) coformer shiny in THF/$H_2O$ (10:1 THF/$H_2O$) was added to API<br>2) stirred, RT, 4 d<br>3) positive pressure filtration | 1) pale yellow slurry<br>2) pale yellow slurry<br>3) off-white solids; fines & aggregates, B/E | FB + aspartic acid |
| | 1) coformer slurry in 80:20 acetone/$H_2O$ was added to API<br>2) stirred, RT, 2 d<br>3) positive pressure filtration | 1) off-white slurry<br>2) yellowish slurry<br>3) off-white solids; fines & aggregates, B/E | FB + aspartic acid |
| benzene sulfonic acid | 1) THF soln of coformer was added to API<br>2) stirred, RT, 4 d<br>3) positive pressure filtration | 1) yellow slurry<br>2) yellow slurry<br>3) yellow solids; fines & aggregates, B/E | Besylate Form A |
| | 1) acid soln in TFE was added to API<br>2) stirred, RT, 1 d<br>3) stirred, −20° C., 1 d<br>4) FE | 1) clear yellow soln<br>2) clear soln<br>3) clear soln<br>4) some yellow gel and yellow solids; fine needles & aggregates, B/E | Besylate Form B |
| (1R)-(−)-10-camphorsulfonic acid | 1) THF soln of coformer was added to API<br>2) stirred, RT, 4 d<br>3) positive pressure filtration | 1) yellow slurry<br>2) yellow slurry<br>3) yellow solids; fines & aggregates, B/E | Compound 5 Fotin A |
| | 1) acid soln in TFE was added to API<br>2) stirred, RT, 1 d<br>3) stirred, −20° C., 1 d<br>4) FE | 1) clear yellow soln<br>2) clear soln<br>3) clear soln<br>4) yellow solids in some yellow gel; long needles & aggregates, B/E | Compound 5 Form B |
| 1,2-ethanedisulfonic acid | 1) THF soln of coformer was added to API<br>2) stirred, RT, 4 d<br>3) positive pressure filtration | 1) dark yellow slurry<br>2) dark yellow slurry<br>3) dark yellow solids; fines & aggregates, B/E | Edisylate Form A |
| | 1) acid slurry in TFE was added to API<br>2) stirred, RT, 1 d<br>3) stirred, −20° C., 1 d<br>4) FE | 1) clear orange soln<br>2) clear soln<br>3) clear soln<br>4) yellow & off-white solids: fines & aggregates, B/E | Edisylate Form B |
| ethanesulfonic acid | 1) acid was added to API slurry in THF<br>2) stirred, RT, 4 d<br>3) positive pressure filtration | 1) thick yellow slurry<br>2) yellow slurry<br>3) yellow solids; fines & aggregates, partial B/E | Esylate Form A |
| | 1) acid added to API slurry in TFE<br>2) stirred, RT, 1 d<br>3) stirred, −20° C., 1 d<br>4) FE | 1) clear yellow soln<br>2) clear soln<br>3) clear soln<br>4) yellow & off-white solids; fines, rosettes, & aggregates, B/E | Esylate Form B |
| hydrobromic acid | 1) acid was added to API slurry in THF<br>2) stirred, RT, 4 d<br>3) positive pressure filtration | 1) dark yellow slurry<br>2) pale pink slurry<br>3) off-white solids: fines & aggregates, B/E | Compound 3 Form A |
| | 1) acid added to API slurry in TFE<br>2) stirred, RT, 1 d<br>3) stirred, −20° C., 1 d<br>4) FE | 1) clear yellow soln<br>2) clear soln<br>3) clear soln<br>4) yellow & off-white solids; fines, rosettes, & aggregates, B/E | Compound 3 Form A |
| hydrochloric acid | 1) acid was added to API slurry in THF<br>2) stirred, RT, 4 d<br>3) positive pressure filtration | 1) dark yellow shiny<br>2) pale yellow slurry<br>3) pale yellow solids; fines & aggregates, B/E | Compound 2 Form A + minor FB |
| | 1) acid was added to API slurry in THF<br>2) stirred, RT, 4 d<br>3) positive pressure filtration | 1) dark yellow slurry<br>2) pale yellow slurry<br>3) pale yellow solids; fines & aggregates, B/E | Compound 2 Form A + minor peak at 8.54° 2θ |
| | 1) acid added to API slurry in TFE<br>2) stirred, RT, 1 d<br>3) stirred, −20° C., 1 d<br>4) FE | 1) clear yellow soln<br>2) clear soln<br>3) clear soln<br>4) dark yellow solids; fines & aggregates, B/E | Compound 2 Form B |
| maleic acid | 1) THF soln of coformer was added to API<br>2) stirred, RT, 4 d<br>3) positive pressure filtration | 1) pale yellow slurry<br>2) pale pink slurry<br>3) off-white solids; fines & aggregates, B/E | FB + peaks |
| methane sulfonic acid | 1) acid was added to API slurry in THF<br>2) stirred, RT, 4 d<br>3) positive pressure filtration | 1) yellow slurry<br>2) yellow slurry<br>3) yellow solids; fines & aggregates, partial B/E | Compound 4 Form A |

TABLE 16-continued

| Coformer[a] | Conditions | Observations | XRPD Result |
|---|---|---|---|
| oxalic acid | 1) THF soln of coformer was added to API 2) stirred, RT, 4 d 3) positive pressure filtration | 1) pale yellow slurry 2) pale yellow slurry 3) off-white solids; fines & aggregates, B/E | FB + peaks |
| | 1) coformer slurry in 80:20 acetone/H$_2$O was added to API 2) stirred, RT, 2 d 3) positive pressure filtration | 1) off-white slurry 2) yellowish slurry 3) off-white solids; fines & aggregates, B/E | FB + peaks |
| phosphoric acid | 1) acid was added to API slurry in THF 2) stirred, RT, 4 d 3) positive pressure filtration | 1) pale yellow slurry 2) thick pale yellow slurry 3) sticky yellow solids; fines & aggregates, B/E | Phosphate Form A |
| | 1) acid added to API slurry in TFE 2) stirred, RT, 2 d 3) positive pressure filtration | 1) off-white slurry 2) yellowish slurry 3) some yellow solids (some deliquesced); fines & aggregates, partial B/E | Phosphate Form A (slight disorder) |
| sulfuric acid | 1) acid added to API slurry in TFE 2) stirred, RT, 1 d 3) stirred, –20° C., 1 d 4) FE | 1) clear yellow soln 2) clear soln 3) clear soln 4) dark yellow solids; fines & aggregates, B/E | Sulfate Form A |
| | 1) acid was added to API slurry in THF 2) stirred, RT, 4 d 3) positive pressure filtration | 1) dark yellow slurry 2) pale yellow slurry 3) pale yellow solids; fines & aggregates, B/E | Sulfate Form B |

[a]mol Compound 1/mol conformer for each experiment was 1:1

TABLE 17

Characterization Data of Solid Forms

| Material/Form | Technique | Results |
|---|---|---|
| Compound 5 Form C | XRPD | successfully indexed as 1:1 with some excess volume in the unit cell |
| Esylate Form A | $^1$H NMR | 1:1 Compound 1/ethanesulfonic acid with slight peak shifting; 0.1 mol/mol THF |
| Compound 3 Form A | XRPD | successfully indexed as 1:1 HBr salt with a small amount of excess volume in unit cell. |
| | $^1$H NMR | consistent w/ chemical structure-some peak shifting indicative of salt formation; negligible amount of THF |
| | DSC[a] | large broad endo at 109.7° C.; followed by potential melt/decomp. w/onset at 278.1° C. |
| | TGA[b] | 3.4% wt loss over 61 to 150° C.; 1.1 mol/mol H$_2$O |
| Compound 2 Form A | XRPD | successfully indexed as unsolvated 1:1 HCl salt |
| | $^1$H NMR | consistent w/ chemical structure—some peak shifting indicative of salt formation; negligible amount of THF |
| | XRF | 0.83 mol Cl–/mol API |
| | DSC[a] | very shallow, broad endo at 47.0° C.; followed by potential melt/decomp. w/onset at 271.8° C. |
| | TGA[b] | 0.3% wt loss over 42 to 165° C.; <0.1 mol/mol H$_2$O |
| | DVS | wt gain 5% to 95%: 0.9468% (0.3 mol/mol H$_2$O) wt loss 95% to 5%: 1.0059% (0.3 mol/mol H$_2$O) |
| | post-DVS XRPD | Compound 2 Form A |
| Compound 4 Form A | XRPD | successfully indexed as unsolvated 1:1 mesylate salt |
| | $^1$H NMR | consistent w/ 1.1:1 mol MSA/mol API— some peak shifting indicative of salt formation; 0.1 mol/mol THF |
| | DSC[a] | large broad endo at 77.7° C. then small endo at 254.4° C.; potential melt/decomp, w/ onset at 289.8° C. |
| | TGA[b] | 3.3% wt loss over 44 to 114° C.; 1.1 mol/mol H$_2$O |
| Compound 4 Form B | XRPD | successfully indexed as unsolvated 1:1 mesylate saltslightly smaller unit cell than Compound 4 Form A |
| Phosphate Form A | $^1$H NMR | consistent w/ chemical structure—no peak shifting; negligible amount of THF |

[a]Temperatures (° C.) reported were transition maxima unless otherwise stated. Temperatures were rounded to the nearest tenth of a degree.
[b]Weight loss (%) at a certain temperature; weight changes (%) were rounded to 1 decimal place; temperatures were rounded to the nearest degree.

Approximate Aqueous Solubility of Selected Solid Forms

Aliquots of various solvents were added to measured amounts of provided compounds with agitation at ambient temperature until complete dissolution was achieved, as judged by visual observation. If dissolution occurred after the addition of the first aliquot, values were reported as ">". Results are shown in Table 18, where A is <2 mg/mL; B is <1 mg/mL.

TABLE 18

| Source Form/Material | Estimated Aqueous Solubility (mg/mL) |
|---|---|
| Compound 2 Form A | A |
| Besylate Form A | B |
| Edisylate Form A | B |
| Esylate Form A | B |
| Phosphate Form A | B |

TABLE 19

Physical Stability of Selected Solid Forms

| Source Form | Condition | XRPD Result |
|---|---|---|
| Besylate Form A | vac. oven, RT, 5 d | Besylate Form C |
| Compound 5 Form A | vac. oven, RT, 5 d | Compound 5 Form C |
| Edisylate Form A | vac. oven, RT, 5 d | Edisylate Form C |
| Esylate Form A | vac. oven, RT, 5 d | Esylate Form A |
| Compound 3 Form A | vac. oven, 45° C., 2 d | Compound 3 Form A + minor FB |
| Compound 4 Form A | vac. oven, 45° C., 2 d | Compound 4 Form B |
| Phosphate Form A | vac. oven, RT, 5 d | Phosphate Form A |

Example 4: Compound 2 (Hydrochloric Acid×Compound 1)

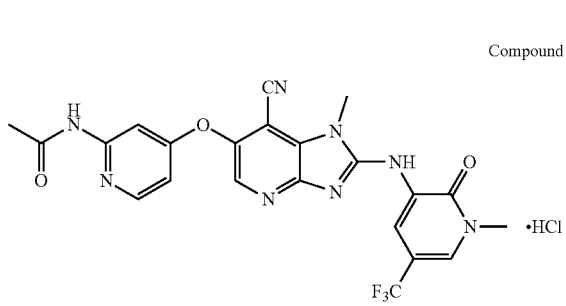
Compound 2

Compound 2 Form A

Compound 1 (93.0 mg) was slurried in THF (2 mL). Concentrated HCl (16.0 μL) was added to the slurry. The slurry was stirred at ambient temperature for 4 days. Solids were isolated by filtration to provide Compound 2 Form A.

X-ray fluorescence was used to determine the approximate stoichiometry of Cl⁻ in Compound 2 Form A. This was determined to be approximately 0.83 mol Cl⁻/mol Compound 1.

Figure 6:
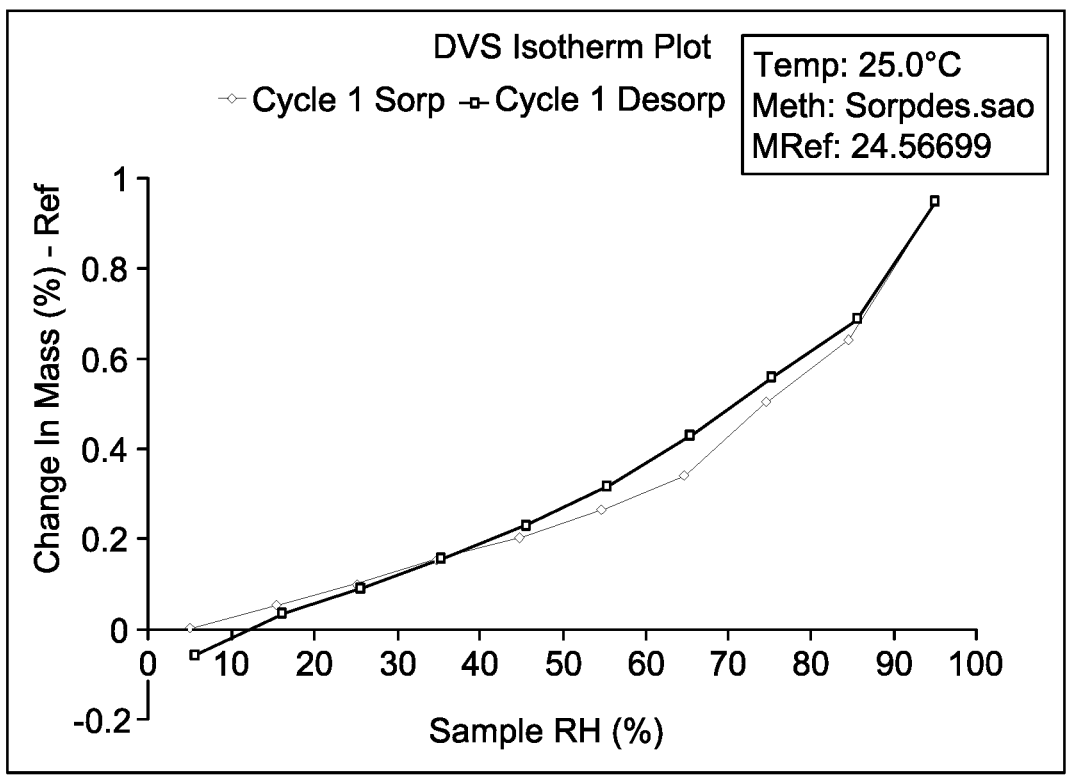
FIG. 6 provides a DVS isotherm plot of Compound 2 Form A.

DVS was also obtained for Compound 2 Form A, displaying a weight gain of only 0.95%, or 0.3 mol/mol $H_2O$, up to 95% RH and a weight loss of 1.01% upon desorption to 5% RH (FIG. 6 and Table 20). No hysteresis was observed. Aqueous solubility of Compound 2 Form A was visually approximated to be less than 2 mg/mL. The remaining solids were stirred for 1 day and collected.

TABLE 20

| | Target RH (%) | Sample RH (%) | Sorp Mass Change (%) | Sample RH (%) | Desorp Mass Change (%) | Hysteresis |
|---|---|---|---|---|---|---|
| Cycle 1 | 5.0 | 5.0 | 0.0009 | 5.6 | −0.0582 | |
| | 15.0 | 15.5 | 0.0521 | 16.1 | 0.0326 | −0.0195 |
| | 25.0 | 24.9 | 0.0998 | 25.6 | 0.0900 | −0.0098 |
| | 35.0 | 34.6 | 0.1539 | 35.4 | 0.1559 | 0.0020 |
| | 45.0 | 44.8 | 0.2007 | 45.6 | 0.2304 | 0.0297 |
| | 55.0 | 54.7 | 0.2634 | 55.4 | 0.3159 | 0.0525 |
| | 65.0 | 64.7 | 0.3387 | 65.5 | 0.4283 | 0.0896 |
| | 75.0 | 74.7 | 0.5032 | 75.3 | 0.5577 | 0.0545 |
| | 85.0 | 84.6 | 0.6403 | 85.6 | 0.6871 | 0.0468 |
| | 95.0 | 95.0 | 0.9477 | 95.0 | 0.9477 | |

FIG. 4 provides the XRPD pattern of the Compound 2 Form A.

Figure 5:
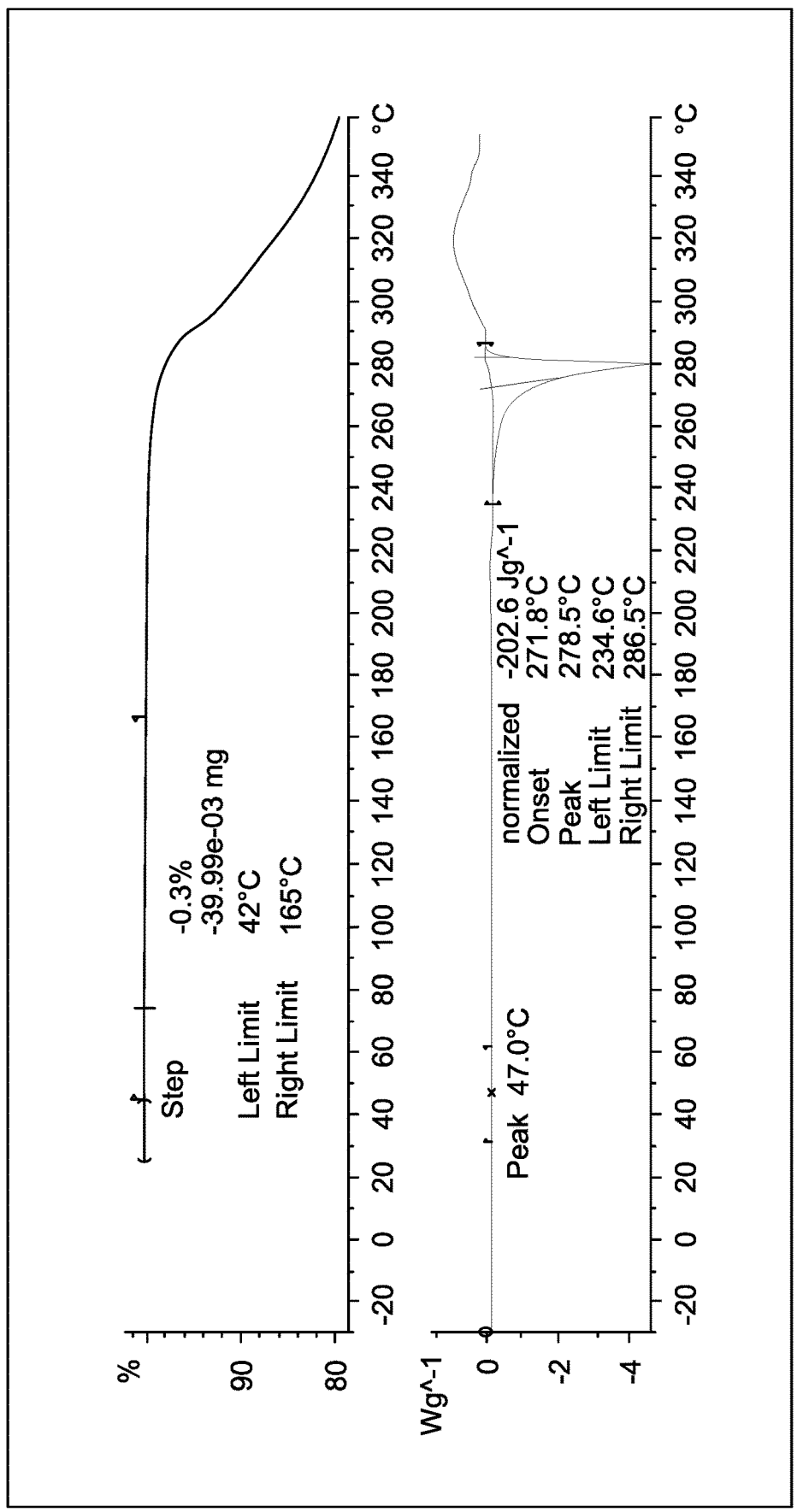
FIG. 5 provides TGA (top)/DSC (bottom) curves for Compound 2 Form A.

FIG. 5 provides the TGA/DSC curves of Compound 2 Form A.

Figure 7:
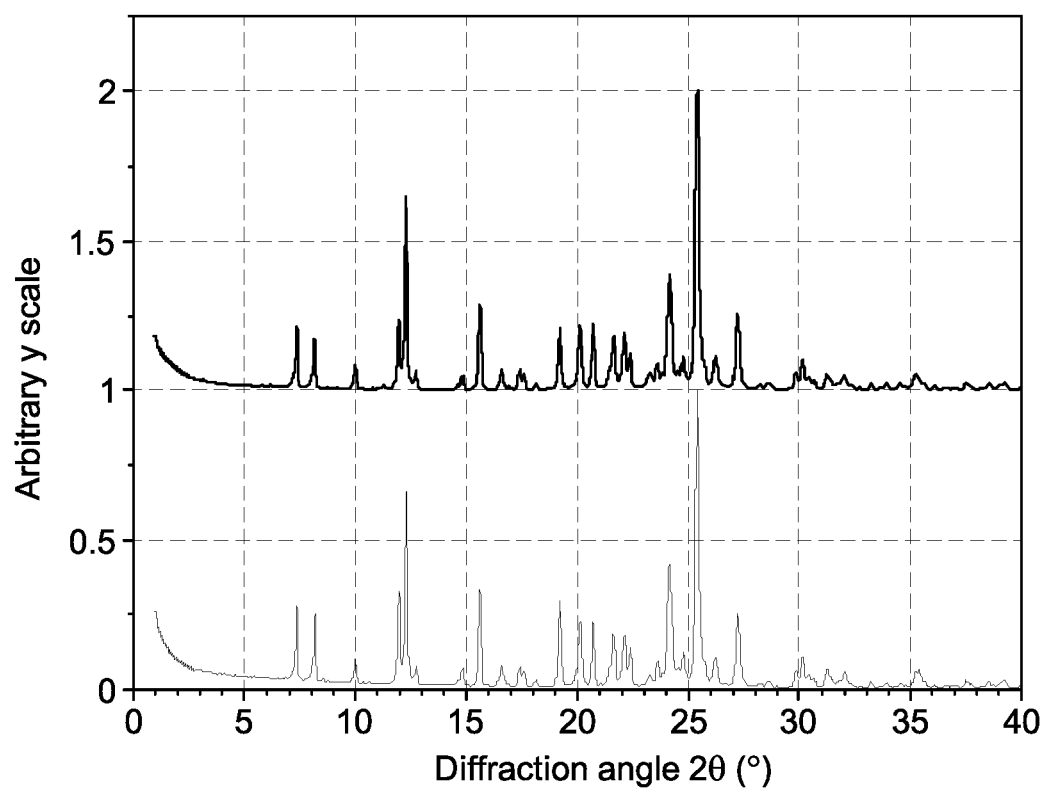
FIG. 7 depicts a XRPD overlay of Compound 2 Form A post-DVS material (lower) with pre-DVS material (upper).

FIG. 7 depicts a XRPD overlay of Compound 2 Form A post-DVS material (lower) with pre-DVS material (upper).

Example 5: Compound 3 (Hydrobromic Acid×Compound 1)

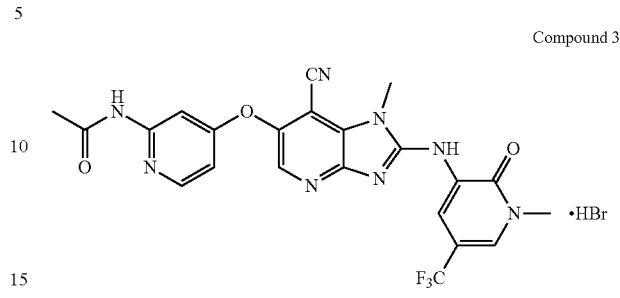
Compound 3

Compound 3 Form A

Compound 1 (83.8 mg) was slurried in THF (2 mL). Concentrated HBr (19.5 μL) was added to the slurry. The slurry was stirred at ambient temperature for 4 days. Solids were isolated by filtration to provide Compound 3 Form A.

FIG. 8 provides the XRPD pattern of the Compound 3 Form A.

Figure 9:
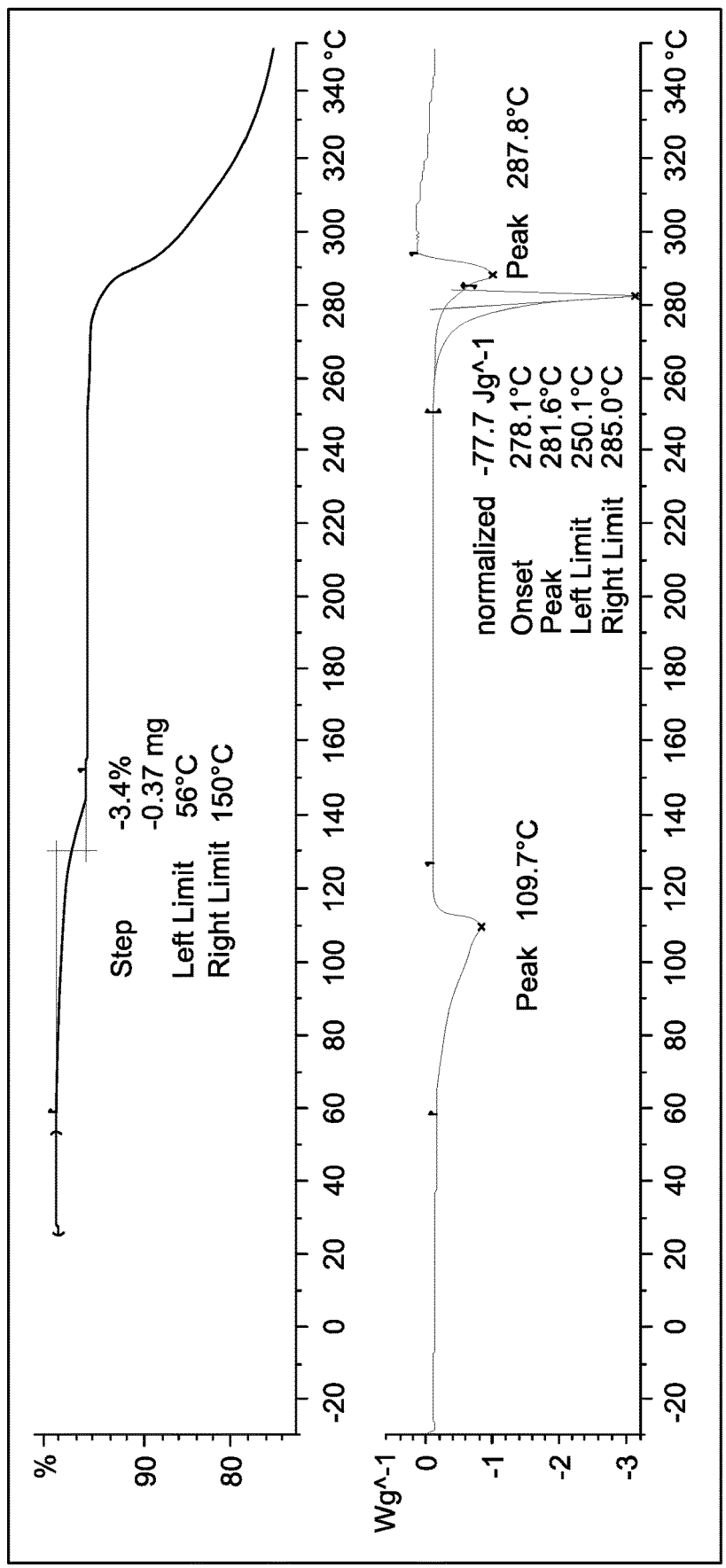
FIG. 9 provides TGA (top)/DSC (bottom) curves for Compound 3 Form A.

FIG. 9 provides the TGA/DSC curves of Compound 3 Form A.

Example 6: Compound 4 (Methanesulfonic Acid×Compound 1)

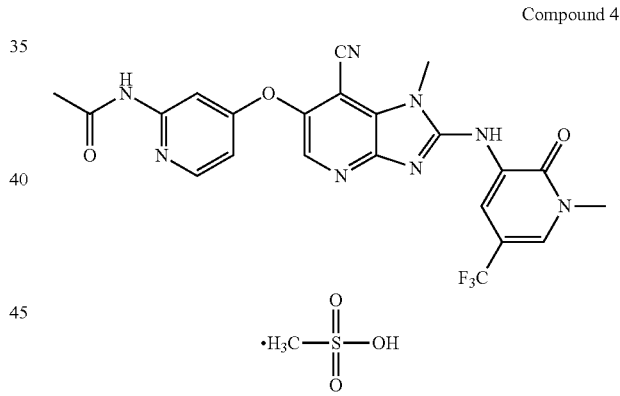
Compound 4

Compound 4 Form A

Compound 1 (81.0 mg) was slurried in THF (2 mL). Methanesulfonic acid (11.0 μL) was added to the slurry. The slurry was stirred at ambient temperature for 4 days. Solids were isolated by filtration to provide Compound 4 Form A.

FIG. 10 provides the XRPD pattern of Compound 4 Form A.

Figure 11:
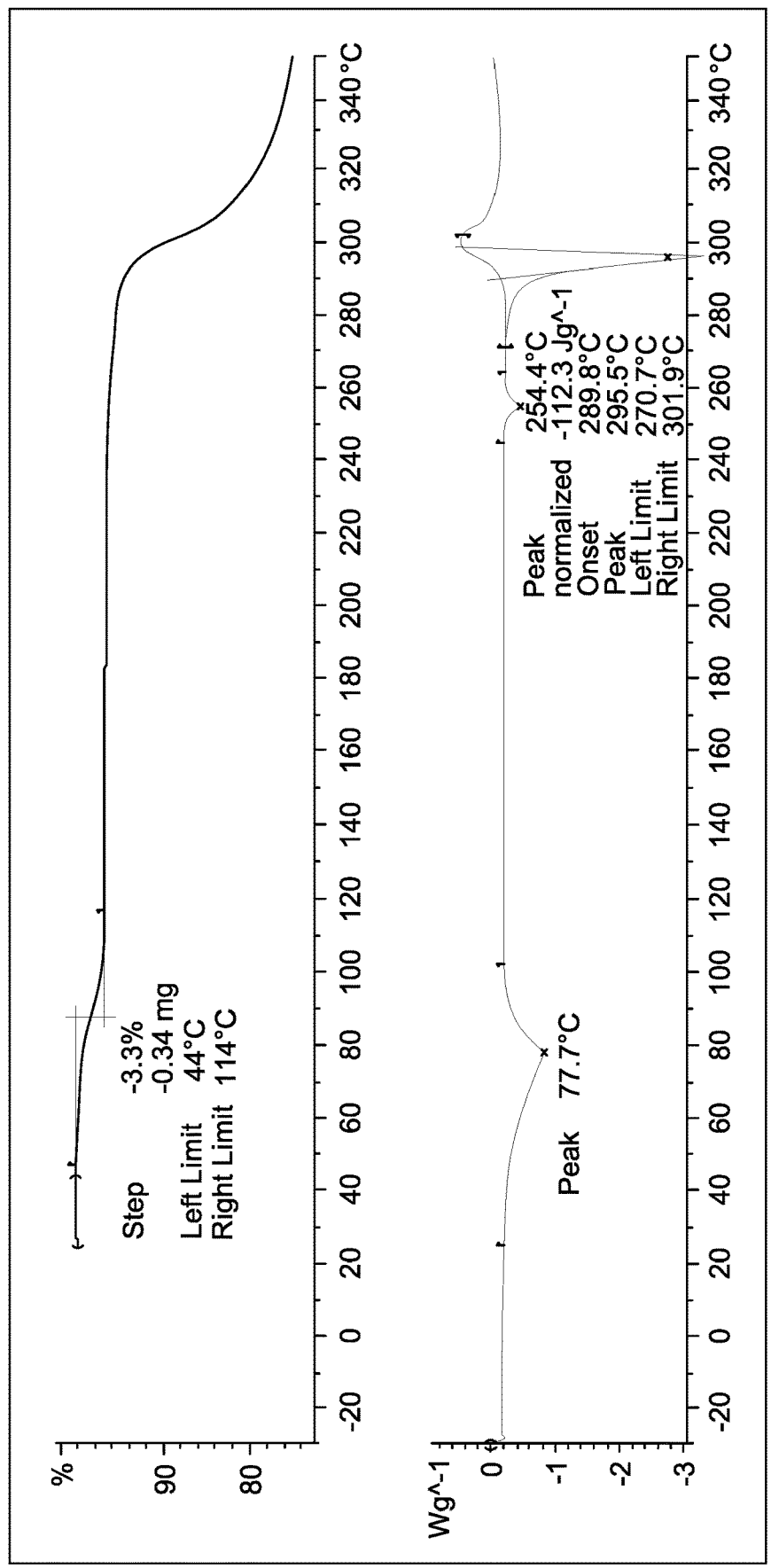
FIG. 11 provides TGA (top)/DSC (bottom) curves for Compound 4 Form A.

FIG. 11 provides the TGA/DSC curves of Compound 4 Form A.

Compound 4 Form B

Compound 4 Form A material was placed in a 45° C. vacuum oven in a loosely capped vial for 2 days. The vial was capped and cooled to ambient temperature over desiccant to provide Compound 4 Form B.

FIG. 12 provides the XRPD pattern of Compound 4 Form B.

Example 7: Compound 5
((1R)-(−)-10-camphorsulfonic Acid×Compound 1)

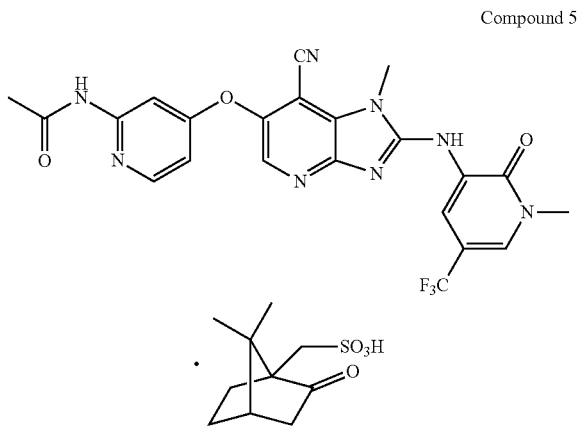

Compound 5

Compound 5 Form C (1R)-(−)-10-camphorsulfonic acid (39.2 mg) was dissolved in THF (2 mL) with sonication. The coformer solution was added to Compound 1 (77.7 mg). The slurry was stirred at ambient temperature for 4 days. Solids were isolated by filtration and further dried in a vacuum oven at ambient temperature for 5 days to provide Compound 5 Form C.

FIG. 13 provides the XRPD pattern of Compound 5 Form C.

Example 8: Biological Characterization of Provided Compounds

JAK2 Binding Assay

JAK2 (JH1domain-catalytic, Y1007F,Y1008F) kinase was expressed as N-terminal fusion to the DNA binding domain of NFkB in transiently transfected HEK293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mmol/L DTT) to remove unbound ligand and to reduce nonspecific phage binding. Binding reactions were assembled by combining kinases, liganded affinity beads, and test compounds in 1× binding buffer (1×PBS, 0.05% Tween 20, 0.1% BSA, 1 mmol/L DTT). Test compound was prepared as 111× stocks in 100% DMSO and directly diluted into the assay wells. All reactions were performed in polypropylene 384-well plates in a final volume of 0.02 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µmol/L non-biotinylated affinity ligand) and incubated at room temperature with shaking for 30 minutes. The kinase concentration in the eluate was measured by qPCR. Compound 1 as prepared by Example 1 was found to have a $K_d<10$ nM.

JAK Family Selectivity Assays

Provided compounds are evaluated for selectivity by comparing their JAK2 binding affinity ($K_d$) in the above JAK2 Binding Assay with their binding affinity ($K_d$) for one or more other kinases. Binding affinity for other kinases is determined as follows: Kinase-tagged T7 phage strains are prepared in an E. coli host derived from the BL21 strain. E. coli are grown to log-phase and infected with T7 phage and incubated with shaking at 32° C. until lysis. The lysates are centrifuged and filtered to remove cell debris. The remaining kinases are produced in HEK-293 cells and subsequently tagged with DNA for qPCR detection. Streptavidin-coated magnetic beads are treated with biotinylated small molecule ligands for 30 minutes at room temperature to generate affinity resins for kinase assays. The liganded beads are blocked with excess biotin and washed with blocking buffer (SeaBlock (Pierce), 1% BSA, 0.05% Tween 20, 1 mM DTT) to remove unbound ligand and to reduce non-specific binding. Binding reactions are assembled by combining kinases, liganded affinity beads, and test compounds in 1× binding buffer (20% SeaBlock, 0.17×PBS, 0.05% Tween 20, 6 mM DTT). Test compounds are prepared as 111× stocks in 100% DMSO. Kds are determined using an 11-point 3-fold compound dilution series with three DMSO control points. All compounds for Kd measurements are distributed by acoustic transfer (non-contact dispensing) in 100/6 DMSO. The compounds are then diluted directly into the assays such that the final concentration of DMSO is 0.9%. All reactions are performed in polypropylene 384-well plate. Each has a final volume of 0.02 ml. The assay plates are incubated at room temperature with shaking for 1 hour and the affinity beads are washed with wash buffer (1×PBS, 0.05% Tween 20). The beads are then re-suspended in elution buffer (1×PBS, 0.05% Tween 20, 0.5 µM non-biotinylated affinity ligand) and incubated at room temperature with shaking for 30 minutes. The kinase concentration in the eluates is measured by qPCR. Compounds that exhibit a better binding affinity for JAK2 compared to one or more other kinases are considered to be JAK2-selective compounds. In some embodiments, provided compounds may be JAK2-selective over one or more of the following kinases: JAK1, JAK3, and Tyk2.

SET2-pSTAT5 Cellular Assay

This assay measures inhibition of JAK2-mediated pSTAT5 signaling in constitutively active essential thrombocytopenia cells carrying the V617F mutation. Cells are harvested from a flask into cell culture medium, and the number of cells is counted. The cells are diluted with culture medium and 100 µL of cell suspension (50000/well) is added into each well of a 96-well cell culture plate. A solution of test compound is added to the assay plate. The plates are covered with a lid and placed in a 37° C. 5% $CO_2$ incubator for 4 hours. After 4 hours, the cells are spun, and the cell pellets are re-suspended with 100 µL cold PBS. Then, the cells are spun again at 4° C. and 4000 rpm for 5 min. PBS is aspirated, and 25 µL lysis buffer (with protease and phosphatase inhibitor cocktail) is added to each cell pellet. The cell lysate is shaken at 4° C. for 20 min to fully lyse the cells. The cell lysate is spun at 4° C. and 4000 rpm for 15 min, and then the supernatant is transferred into a new plate and stored at −80° C. Meso-scale discovery (MSD) is used to analyze plates as follows: a standard MSD plate is coated with capture antibody in PBS (40 µL/well) and is incubated at 4° C. overnight with shaking. The MSD plate is washed three times with 150 µL/well of 1×MSD Wash Buffer (Tris-buffered saline with 0.1% Tween® 20 detergent, TBST). The MSD plates are then blocked with 150 µL of blocking buffer (5% BSA in TBST) and shaken for 1 h at room temperature and 600 rpm. The MSD plate is washed three times with 150 µL/well of 1×MSD Wash Buffer (TBST). Sample lysates are then added to MSD plates (25 μL/well) and shaken for 1 h at room temperature and 600 rpm. The MSD plate is washed three times with 150 μL/well of 1×MSD Wash Buffer (TBST). Detection antibody (prepared in Antibody Detection buffer, 1% BSA in 1×TBST) is then added to the MSD plates, and they are shaken for 1 h at room temperature and 600 rpm. The MSD plate is washed three times with 150 μL/well of 1×MSD Wash Buffer (TBST). A secondary detection antibody (prepared in Antibody Detection buffer, 1% BSA in 1×TBST) is then added to the MSD plates, and they are shaken for 1 h at room temperature and 600 rpm. The MSD plate is washed three times with 150 μL/well of 1×MSD Wash Buffer (TBST). MSD reading buffer (1×) is added to the plates (150 μL/well), and they are diluted from 4× with water. The plates are imaged using an MSD imaging instrument according to the manufacturer's instructions.

Caco2 Permeability Assay

Preparation of Caco-2 Cells: 50 μL and 25 mL of cell culture medium are added to each well of a Transwell® insert and reservoir, respectively. Then, the HTS Transwell® plates are incubated at 37° C., 5% $CO_2$ for 1 hour before cell seeding. Caco-2 cell cells are diluted to 6.86×105 cells/mL with culture medium, and 50 μL of cell suspension are dispensed into the filter well of the 96-well HTS Transwell® plate. Cells are cultivated for 14-18 days in a cell culture incubator at 37° C., 5% $CO_2$, 95% relative humidity. Cell culture medium is replaced every other day, beginning no later than 24 hours after initial plating.

Preparation of Stock Solutions: 10 mM stock solutions of test compounds are prepared in DMSO. The stock solutions of positive controls are prepared in DMSO at the concentration of 10 mM. Digoxin and propranolol are used as control compounds in this assay.

Assessment of Cell Monolayer Integrity: Medium is removed from the reservoir and each Transwell® insert and is replaced with prewarmed fresh culture medium. Transepithelial electrical resistance (TEER) across the monolayer is measured using Millicell Epithelial Volt-Ohm measuring system (Millipore, USA). The Plate is returned to the incubator once the measurement is done. The TEER value is calculated according to the following equation: TEER measurement (ohms)×Area of membrane ($cm^2$)=TEER value (ohm·$cm^2$). A TEER value greater than 230 ohm·$cm^2$ indicates a well-qualified Caco-2 monolayer.

Assay Procedure: The Caco-2 plate is removed from the incubator and washed twice with pre-warmed HBSS (10 mM HEPES, pH 7.4), and then incubated at 37° C. for 30 minutes. The stock solutions of control compounds are diluted in DMSO to get 1 mM solutions and then diluted with HBSS (10 mM HEPES, pH 7.4) to get 5 μM working solutions. The stock solutions of the test compounds are diluted in DMSO to get 1 mM solutions and then diluted with HBSS (10 mM HEPES and 4% BSA, pH 7.4) to get 5 μM working solutions. The final concentration of DMSO in the incubation system is 0.5%. To determine the rate of drug transport in the apical to basolateral direction. 75 μL of 5 μM working solutions of test compounds are added to the Transwell® insert (apical compartment) and the wells in the receiver plate (basolateral compartment) are filled with 235 μL of HBSS (10 mM HEPES and 4% BSA, pH 7.4). To determine the rate of drug transport in the basolateral to apical direction, 235 μL of 5 μM working solutions of test compounds are added to the receiver plate wells (basolateral compartment) and then the Transwell® inserts (apical compartment) are filled with 75 μL of HBSS (10 mM HEPES and 4% BSA, pH 7.4). Time 0 samples are prepared by transferring 50 μL of 5 μM working solution to wells of the 96-deepwell plate, followed by the addition of 200 μL cold methanol containing appropriate internal standards (IS). The plates are incubated at 37° C. for 2 hours. At the end of the incubation, 50 μL samples from donor sides (apical compartment for Ap→Bl flux, and basolateral compartment for Bl→Ap) and receiver sides (basolateral compartment for Ap→Bl flux, and apical compartment for Bl→Ap) are transferred to wells of a new 96-well plate, followed by the addition of 4 volume of cold acetonitrile or methanol containing appropriate internal standards (IS). Samples are vortexed for 5 minutes and then centrifuged at 3,220 g for 40 minutes. An aliquot of 100 μL of the supernatant is mixed with an appropriate volume of ultra-pure water before LC-MS/MS analysis. To determine the Lucifer Yellow leakage after 2 hour transport period, stock solution of Lucifer yellow is prepared in ultra-pure water and diluted with HBSS (10 mM HEPES, pH 7.4) to reach the final concentration of 100 μM. 100 μL of the Lucifer yellow solution is added to each Transwell® insert (apical compartment), followed by filling the wells in the receiver plate (basolateral compartment) with 300 μL of HBSS (10 mM HEPES, pH 7.4). The plates are incubated at 37° C. for 30 minutes. 80 μL samples are removed directly from the apical and basolateral wells (using the basolateral access holes) and transferred to wells of new 96 wells plates. The Lucifer Yellow fluorescence (to monitor monolayer integrity) signal is measured in a fluorescence plate reader at 485 nM excitation and 530 nM emission.

Cytotoxicity Assay

HEK293T cells are harvested from flask into cell culture medium, and then the cells are counted. The cells are diluted with culture medium to the desired density, and 40 μL of cell suspension is added into each well of a 384-well cell culture plate. The plates are covered with a lid and spun at room temperature at 1,000 RPM for 1 minute and then transferred into 37° C. 5% $CO_2$ incubator overnight. Test compounds are dissolved at 10 mM DMSO stock solution. 45 μL of stock solution is then transferred to a 384 PP-plate. A 3-fold, 10-point dilution is performed via transferring 15 μL compound into 30 μL DMSO by using TECAN (EVO200) liquid handler. The plates are spun at room temperature at 1,000 RPM for 1 minute and shaken on a plate shaker for 2 minutes. 40 nL of diluted compound is transferred from compound source plate into the cell plate by using liquid handler Echo550. After compound treatment for 48 hours, CTG detection is performed for compound treatment plates: the plates are removed from incubators and equilibrated at room temperature for 15 minutes. 30 μL of CellTiter-Glo reagent is added into each well to be detected. The plates are then placed at room temperature for 30 min followed by reading on EnVision. Inhibition activity is calculated with the following formula: % Inhibition=100× (LumHC−LumSample)/(LumHC−LumLC), wherein HC is reading obtained from cells treated with 0.1% DMSO only and LC is reading from cells treated with 10 μL staurosporine. $IC_{50}$ values are calculated using XLFit (equation 201).

Hepatocyte Stability Assay 10 mM stock solutions of test compound and positive control are prepared in DMSO. Stock solutions are diluted to 100 μM by combining 198 μL of 50% acetonitrile/50% water and 2 μL of 10 mM stock solution. Verapamil is used as positive control in the assay. Vials of cryopreserved hepatocytes are thawed in a 37° C. water bath with gently shaking. The contents are poured into the 50 mL thawing medium conical tube. Vials are centrifuged at 100 g for 10 minutes at room temperature. Thawing medium is aspirated and hepatocytes are re-suspended with serum-free incubation medium to yield ~1.5×106 cells/mL. Cell viability and density are counted using a Trypan Blue exclusion, and then cells are diluted with serum-free incubation medium to a working cell density of 0.5×106 viable cells/mL. A portion of the hepatocytes at 0.5×106 viable cells/mL are boiled for 5 min prior to adding to the plate as negative control to eliminate the enzymatic activity so that little or no substrate turnover should be observed. Aliquots of 198 µL hepatocytes are dispensed into each well of a 96-well non-coated plate. The plate is placed in the incubator for approximately 10 minutes. Aliquots of 2 µL of the 100 µM test compound and 2 µL positive control are added into respective wells of a non-coated 96-well plate to start the reaction. The final concentration of test compound is 1 µM. This assay is performed in duplicate. The plate is incubated in the incubator for the designed time points. 25 µL of contents are transferred and mixed with 6 volumes (150 µL) of cold acetonitrile with internal standard (100 nM alprazolam, 200 nM labetalol, 200 nM caffeine and 200 nM diclofenac) to terminate the reaction at time points of 0, 15, 30, 60, 90 and 120 minutes. Samples are centrifuged for 25 minutes at 3,220 g and aliquots of 150 µL of the supernatants are used for LC-MS/MS analysis.

Kinetic Solubility Assay

Stock solutions of test compounds are prepared in DMSO at the concentration of 10 mM, and a stock solution of control compound is prepared in DMSO at the concentration of 30 mM. Diclofenac is used as positive control in the assay. 30 µL stock solution of each compound is placed into their a 96-well rack, followed by adding 970 µL of PBS at pH 4.0 and pH 7.4 into each vial of the cap-less solubility sample plate. This study is performed in duplicate. One stir stick is added to each vial and then vials are sealed using a molded PTDE/SIL 96-Well Plate Cover. The solubility sample plate is transferred to the Thermomixer comfort plate shaker and incubated at RT for 2 hours with shaking at 1100 rpm. After 2 hours incubation, stir sticks are removed using a big magnet and all samples from the solubility sample plate are transferred into the filter plate. All the samples are filtered by vacuum manifold. The filtered samples are diluted with methanol. Samples are analyzed by LC-MS/MS and quantified against a standard of known concentration in DMSO using LC coupled with Mass spectral peak identification and quantitation. The solubility values of the test compounds are calculated as follows, wherein INJ VOL is injection volume, DF is dilution factor, and STD is standard:

$$[Sample] = \frac{AREA_{Sample} \times INJ\ VOL_{Std} \times DF_{Sample} \times [STD]}{AREA_{Std} \times INJ\ VOL_{Sample}}$$

Plasma Protein Binding Assay

Working solutions of test compounds and control compound are prepared in DMSO at the concentration of 200 µM, and then the working solutions are spiked into plasma. The final concentration of compound is 1 µM. The final concentration of DMSO is 0.5%. Ketoconazole is used as positive control in the assay. Dialysis membranes are soaked in ultrapure water for 60 minutes to separate strips, then in 20% ethanol for 20 minutes, finally in dialysis buffer for 20 minutes. The dialysis set up is assembled according to the manufacturer's instruction. Each Cell is with 150 µL of plasma sample and dialyzed against equal volume of dialysis buffer (PBS). The assay is performed in duplicate. The dialysis plate is sealed and incubated in an incubator at 37° C. with 5% $CO_2$ at 100 rpm for 6 hours. At the end of incubation, 50 µL of samples from both buffer and plasma chambers are transferred to wells of a 96-well plate. 50 µL of plasma is added to each buffer samples and an equal volume of PBS is supplemented to the collected plasma sample. 400 µL of precipitation buffer acetonitrile containing internal standards (IS, 100 nM alprazolam, 200 nM labetalol, 200 nM imipramine and 2 µM ketoplofen) is added to precipitate protein and release compounds. Samples are vortexed for 2 minutes and centrifuged for 30 minutes at 3,220 g. Aliquot of 50 µL of the supernatant is diluted by 150 µL acetonitrile containing internal standards: ultra-pure $H_2O$=1:1, and the mixture is used for LC-MS/MS analysis.

Example 9: Preparation and Characterization of Additional Lots of Compound 1

Three lots of Compound 1 were prepared and used for salt and polymorph screening (e.g., as described in the Examples herein).

Lot I

Lot I was prepared generally according to Example 1, with the last step as follows. To a solution of 1.15 (12.5 g, 24.6 mmol, 1.0 equiv) in dimethylacetamide (60 mL) were added zinc dust (0.368 g, 5.67 mmol, 0.23 equiv), zinc cyanide (1.69 g, 14.5 mmol, 0.59 equiv), 1,1'-ferrocenediyl-bis(diphenylphosphine) (3.4 g, 6.15 mmol, 0.25 equiv), and tris(dibenzylideneacetone)dipalladium(0) (2.8 g, 3.07 mmol, 0.125 equiv). The mixture was degassed for 10 min. The reaction mixture was stirred in a sealed tube at 205-210° C. for 4-5 h. After completion of reaction, the reaction mixture was transferred into ice-cold water and extracted with dichloromethane. The organic layers were combined, washed with brine solution, dried over sodium sulfate, and concentrated under reduced pressure. The crude material was purified by column chromatography using 2.0% methanol in dichloromethane as eluent to obtain Compound 1 (5 g, 40.76% yield).

Based on XRPD analysis, Lot I was a mixture of hydrate Form A with a minor amount of anhydrous Form B (FIG. 14A, top).

Additional characterization of Lot I is described in Example 2 above.

Lot II

Lot II was prepared generally according to Example 1, with the last step as follows: To a solution of 1.15 (23 g, 45.36 mmol, 1.0 equiv) in N-methyl-2-pyrrolidone (115 mL) was added zinc dust (0.678 g, 10.4 mmol, 0.23 equiv), zinc cyanide (3.13 g, 26.7 mmol, 0.59 equiv), 1,1'-ferrocenediyl-bis(diphenylphosphine) (6.28 g, 11.3 mmol, 0.25 equiv) and tris(dibenzylideneacetone)dipalladium(0) (5.18 g, 5.67 mmol, 0.125 equiv). The mixture was degassed for 10 min. The reaction mixture was stirred in a sealed tube at 140° C. for 4-5 h. After completion of reaction, the reaction mixture transferred into ice-cold water and extracted with dichloromethane. The organic layers were combined, washed with brine solution, dried over sodium sulfate, and concentrated under reduced pressure. The crude material was purified by column chromatography using 2.0% methanol in dichloromethane as eluent to obtain Compound 1 (10 g, 44.30% yield).

Based on XRPD analysis, Lot 11 was a mixture of Form B and Form O with a minor amount of Form A (FIG. 14A, middle). By solution $^1$H NMR, a sample of Lot II was consistent with the chemical structure of Compound 1 and showed no organic solvents.

Figure 15:
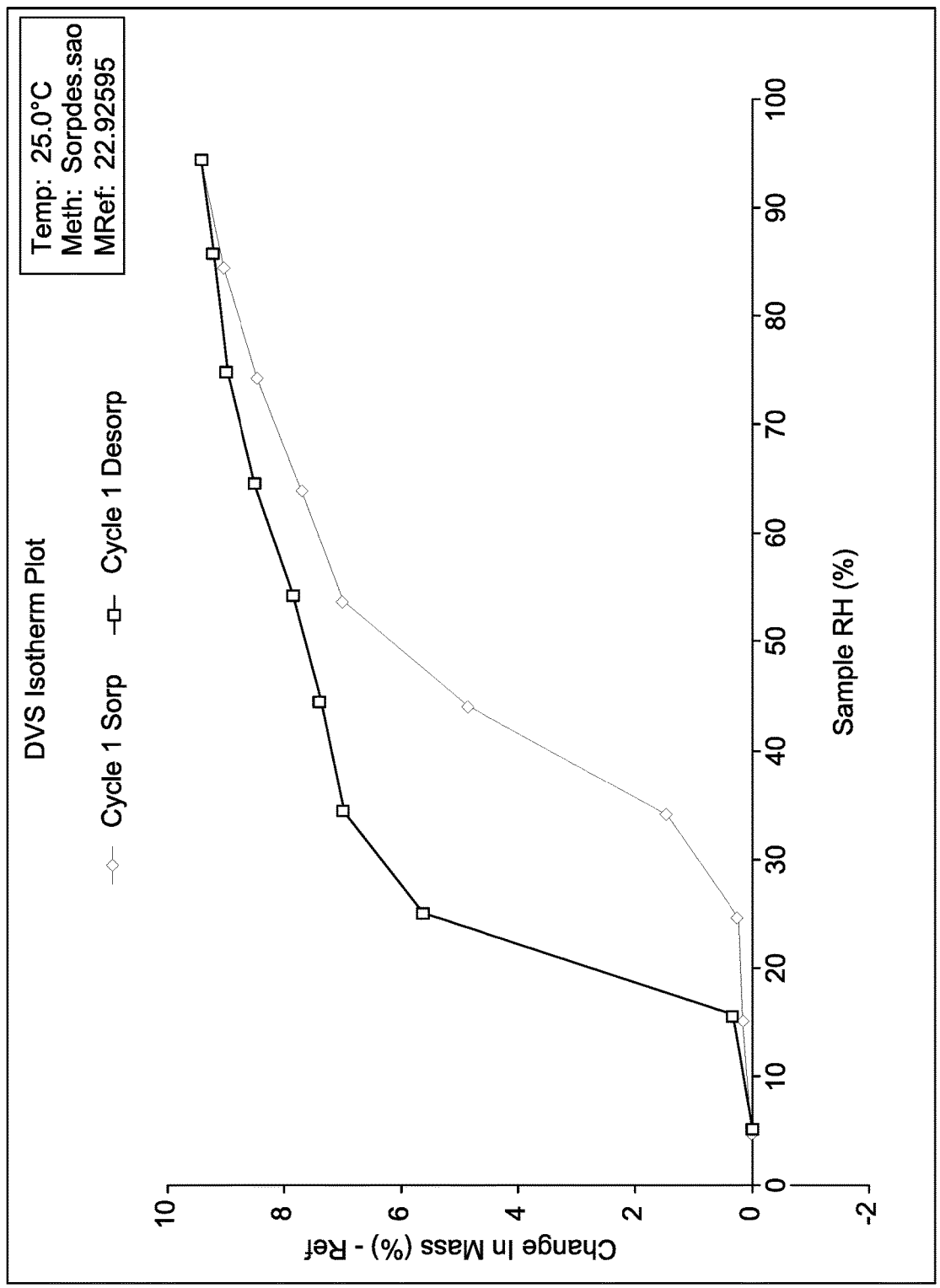
FIG. 15 provides a DVS isotherm plot of a sample from Compound 1 Lot II.
Figure 16:
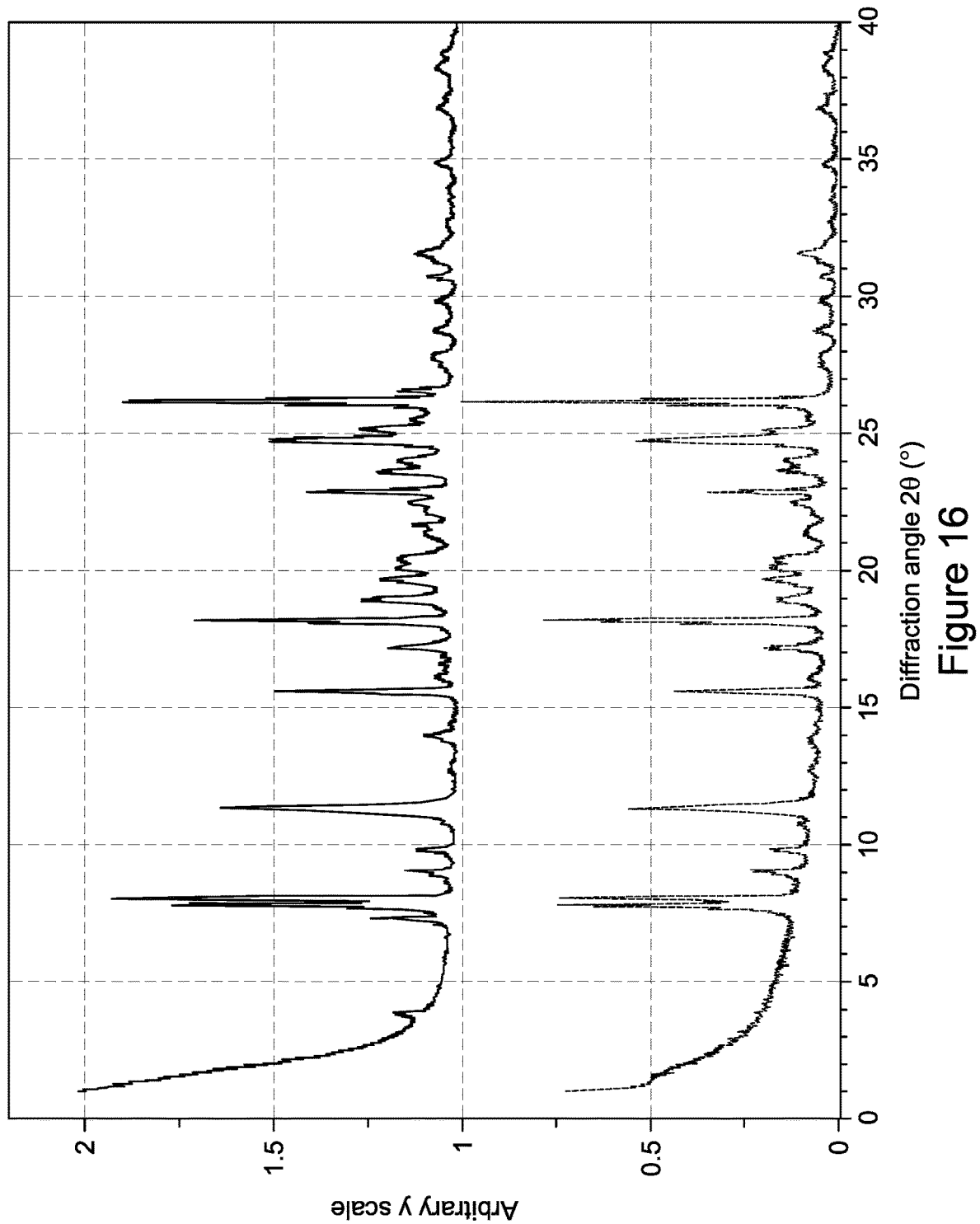
FIG. 16 depicts a XRPD overlay of Compound 1 Lot II post-DVS material (lower) with pre-DVS material (upper).

DVS analysis of Lot II was performed (FIG. 15 and Table 21). Lot II displayed a much larger weight gain compared to Lot I. From 5% to 95% RH, a 9.4% weight gain was observed which was calculated to be approximately 2.9 mol/mol $H_2O$. The sharpest increase in water uptake occurred from 25% to 55% which accounted for 6.7% (~2.0 mol/mol $H_2O$) of the total weight gain. Upon desorption from 95% to 5% RH, 9.4% weight was lost which is equivalent to ~2.9 mol/mol $H_2O$. Hysteresis was observed with desorption, and the sharpest decrease in weight occurring from 35% RH to 15% RH. The XRPD pattern of the post-DVS material removed at low RH conditions was shown to be mostly Form B with some peaks attributed to Form O present (FIG. 16).

TABLE 21

| Target RH (%) | Sample RH (%) | Sorp Mass Change (%) | Sample RH (%) | Desorp Mass Change (%) | Hysteresis |
|---|---|---|---|---|---|
| Cycle 1 | 5.0 | 4.7 | 0.000 | 5.1 | −0.019 | |
| | 15.0 | 15.2 | 0.152 | 15.6 | 0.332 | 0.180 |
| | 25.0 | 24.7 | 0.250 | 25.0 | 5.623 | 5.373 |
| | 35.0 | 34.2 | 1.468 | 34.5 | 6.984 | 5.516 |
| | 45.0 | 44.1 | 4.861 | 44.6 | 7.374 | 2.513 |
| | 55.0 | 53.8 | 6.994 | 54.3 | 7.842 | 0.848 |
| | 65.0 | 64.0 | 7.697 | 64.7 | 8.505 | 0.808 |
| | 75.0 | 74.3 | 8.454 | 74.9 | 8.972 | 0.518 |
| | 85.0 | 84.5 | 9.042 | 85.9 | 9.206 | 0.164 |
| | 95.0 | 94.5 | 9.408 | 94.5 | 9.408 | |

Kinetic solubility of Compound 1 Lot II was visually estimated at ambient temperature (Table 22). Aliquots of various solvents were added to weighed samples of Compound 1 Lot II with agitation at ambient temperature until complete dissolution was achieved, as judged by visual observation. If dissolution occurred after the addition of the first aliquot, values were reported as ">". If dissolution did not occur, values were reported as "<".

At ambient temperature, limited solubility values (1-20 mg/mL) were observed for AcOH, DMF, DMSO, 50:50 MeOH/DCM, 50:50 MeOH/CHCl$_3$, NMP, TFE, and 50:50 TFE/H$_2$O. In THF, initially sample did not appear to completely dissolve at a concentration of 1 mg/mL. However, solids appeared to be almost completely dissolved when left at ambient temperature overnight indicating a solubility of at least 1 mg/mL. The only solvent that displayed a solubility of greater than 20 mg/mL was HFIPA (84 mg/mL). See Table 22, where A is 5-20 mg/mL; B is 1-4.9 mg/mL; and C is <1 mg/mL.

TABLE 22

| Solvent[a] | Solubility (mg/mL)[b] |
|---|---|
| Acetone | C |
| 50:50 acetone/water | B |
| ACN | C |
| AcOH | A |
| CHCl$_3$ | C |
| DCM | C |
| DMA | A |
| DMF | B |
| DMSO | A |
| Ethylene glycol | C |
| HFIPA | A |
| H$_2$O | C |
| MeOH | C |
| 50:50 MeOH/DCM | A |
| 50:50 MeOH/CHCl$_3$ | A |
| 50:50 MeOH/H$_2$O | C |

TABLE 22-continued

| Solvent[a] | Solubility (mg/mL)[b] |
|---|---|
| NMP | A |
| TFE | A |
| THF | B[c] |
| 50:50 DMA/H$_2$O | C |
| 5:95 HFIPA/H$_2$O | C |
| 50:50 TFE/H$_2$O | B |
| 50:50 THF/H$_2$O | B |

[a]Solvent ratios are v/v.
[b]Solubilities are calculated based on the total solvent used to give a solution. Actual solubilities may be greater because of the volume of solvent portions used or a slow rate of dissolution.
[c]Solution was almost completely clear after 24 h.

Lot III

Lot III was prepared using a different synthetic route than that described in Example 1. The last step was performed as follows:

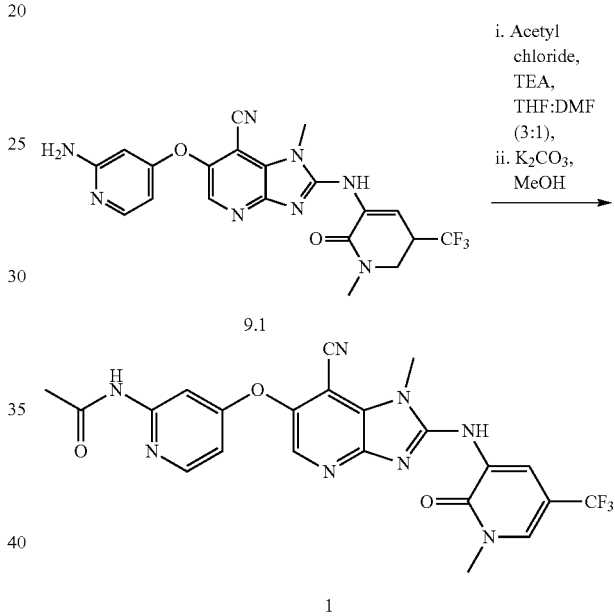

Synthesis of Compound 1. To solution of 9.1 (15 g, 32.87 mmol, 1.0 equiv) in tetrahydrofuran (350 mL) and N,N-dimethylformamide (150 mL) was added triethylamine (13.7 mL, 98.61 mmol, 3.0 equiv), cooled to 0° C., followed by addition of acetyl chloride (3.51 mL, 49.30 mmol, 1.5 equiv), and stirred at room temperature for 1 h. After completion of reaction, the reaction mixture was transferred into water and extracted with ethyl acetate. The organic layers were combined, washed with brine solution, dried over sodium sulfate and concentrated under reduced pressure. The residue was taken up in methanol (200 mL), and potassium carbonate (13.6 g, 98.61 mmol, 3.0 equiv) was added. The reaction mixture was stirred at room temperature for 1 h. The reaction mixture was filtered and washed with 20% methanol in dichloromethane. The filtrate was concentrated under reduced pressure. The crude material was purified by column chromatography using 3.5% methanol in dichloromethane as eluent to give Compound 1 (10 g, 61.04% yield). MS (ES): m/z: 499.2 [M+H]$^+$, $^1$H NMR (DMSO-d6, 400 MHz): δ 10.66 (s, 1H), 9.04 (s, 1H), 8.66 (s, 1H), 8.32 (s, 1H), 8.26-8.24 (d, J=5.6 Hz, 1H), 8.19 (s, 1H), 7.76 (s, 1H), 6.77-6.76 (m, 1H), 3.97 (s, 3H), 3.67 (s, 3H), 2.07 (s, 3H).

Figure 17:
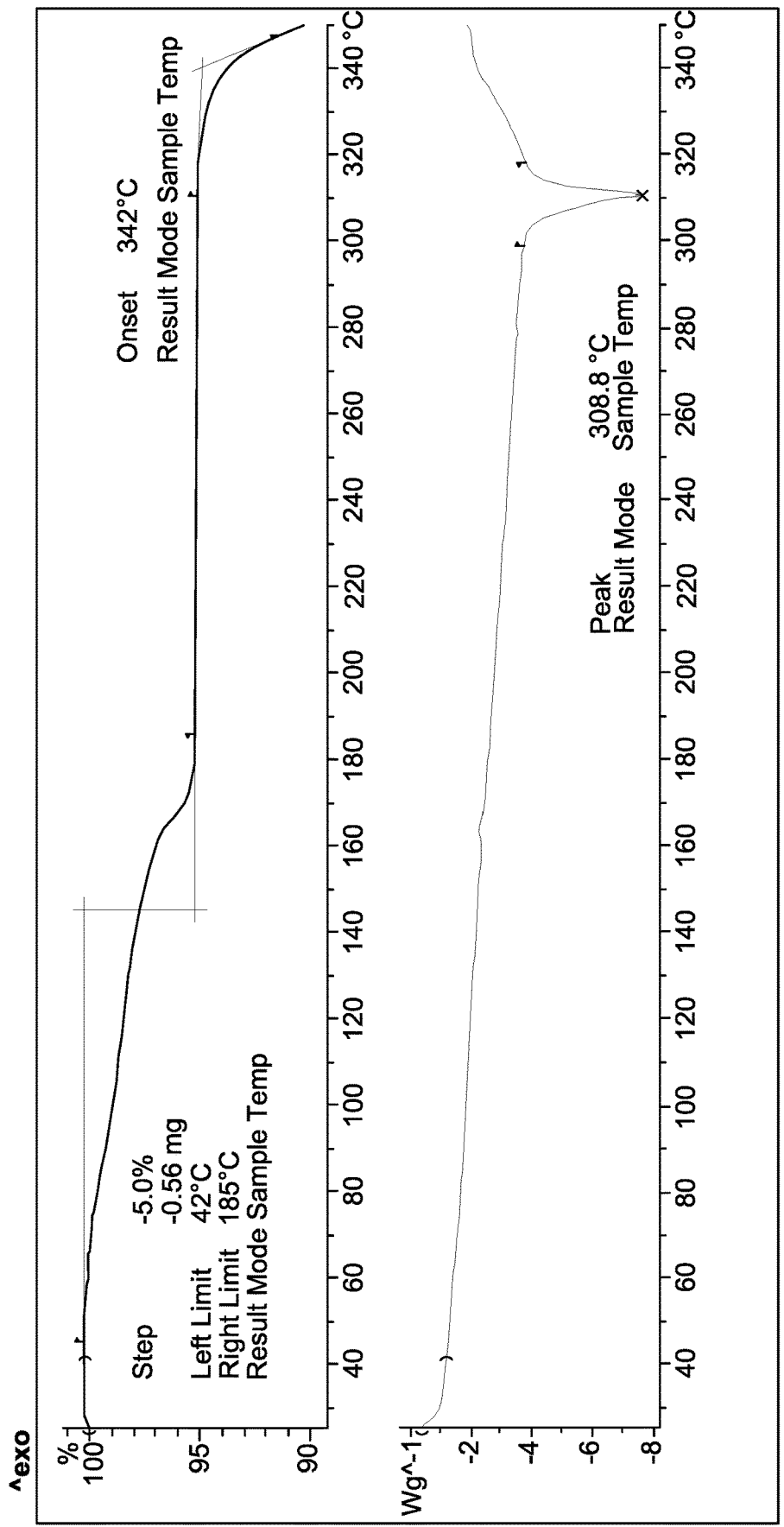
FIG. 17 provides TGA (top)/DSC (bottom) curves for Compound 1 Lot III.

Based on XRPD analysis, Lot III was a mixture of Form O with a minor amount of Form B (FIG. 14A, bottom). Approximately 0.24 mol/mol EtOAc and negligible amounts of $Et_2O$ and DCM were present in Lot III, as judged by NMR, suggesting that its primary component Form O could be solvated. Lot III was analyzed on a combination thermogravimetric analysis and differential scanning calorimetry instrument (FIG. 17). A 5% weight loss over 42° C. to 185° C. was observed by TGA. A sharp endotherm was also shown in the DSC at 308.8° C.

Example 10: Polymorph Screening of Compound 1

Compound 1 Lots I and II were used for stable form and polymorph screening experiments. Sixteen slurry experiments were done at ambient temperature and 50° C. to target a stable form. The polymorph landscape was evaluated primarily using kinetic techniques such as vapor stressing, evaporation, and cooling. Generated solids were observed by polarized light microscopy (PLM) and/or analyzed by X-ray powder diffraction (XRPD). In some instances, solids were analyzed wet to increase the likelihood of identifying labile hydrated or solvated forms. To investigate the physical stability of these solvated/hydrated materials, samples were placed under vacuum at ambient and elevated temperature (Table 25). Water activity slurries and relative humidity stressing were also utilized to further evaluate the propensity of Compound 1 to form hydrates. Fifteen forms were identified from these studies. Most identified forms were solvates, evidencing Compound 1's propensity toward polymorphism and solvation. Polymorph screening experiments were typically performed on a scale of about 50 mg of Compound 1.

The following techniques were used:

Fast evaporation: Solutions of Compound 1 were prepared in dry HFIPA and dry TFE. Solutions were filtered with 0.2 μm PTFE syringe filters and left open at ambient conditions until there was no apparent solvent. Dry solids were analyzed by XRPD.

Drying experiments: Damp and solvated Compound 1 materials were placed in vacuum ovens set to ambient temperature or 80° C. for 1 day. Dried solids were analyzed by XRPD.

Relative humidify jar experiments: Solid Compound 1 was placed in relative humidity jars containing saturated solutions of various salts to maintain a desired relative humidity level at 25° C. One sample of Compound 1 was placed in a jar containing P2O5 in an effort to maintain 0% RH.

Slow cooling: A solution of Compound 1 was prepared in THC at 55° C. The solution was filtered, hot, with a 0.2 μm nylon filter into a wart vial. The vial was capped and returned to the heat block with the heat turned off to slowly cool to ambient temperature. Clear solution was decanted and solids were analyzed by XRPD.

Slurrying experiments: Saturated solutions of Compound 1 were prepared in various solvents and aqueous solvent mixtures. Mixtures were stirred at elevated and ambient temperatures for the given length of time. Solids were collected by the stated technique.

The results of these experiments are summarized in Table 23, Table 24, Table 25, and Table 26.

TABLE 23

| Solvent[a] | Conditions[b] | Observations | XRPD Results |
|---|---|---|---|
| AcOH | 1) slurry, RT, 10 d 2) positive pressure filtration | 1) off-white slurry 2) white solids, fine & aggregates, partial B/E | C |
| Dry CPME | 1) slurry, 50° C., 7 d 2) positive pressure filtration | 1) pale yellow slurry 2) off-white solids | N |
| Dry DMA | 1) slurry, RT, 10 d 2) positive pressure filtration | 1) orange slurry 2) off-white solids; fine & aggregates, B/E | D (analyzed damp)[c] |
| Dry DMF | 1) slurry, RT, 10 d 2) positive pressure filtration | 1) pink slurry 2) off-white solids; fine & aggregates, B/E | G (analyzed damp)[f] |
| Dry DMSO | 1) slurry, RT, 10 d 2) positive pressure filtration | 1) orange slurry 2) off-white solids; fine & aggregates, B/E | E (analyzed damp)[d] |
| EtOAc | 1) slurry, RT, 3 d 2) positive pressure filtration | 1) off-white slurry 2) off-white solids; fine & aggregates, B/E | P |
| EtOH | 1) slurry, 50° C., 7 d 2) positive pressure filtration | 1) pale yellow slurry 2) off-white solids | Disordered mixture of peaks |
| Dry IPA | 1) slurry, RT, 14 d 2) positive pressure filtration | 1) off-white slurry 2) off-white solids, fine & aggregates, B/E | B + peaks |
| Dry IPE | 1) slurry, 50° C., 7 d 2) positive pressure filtration | 1) pale yellow slurry 2) off-white solids | B + peaks |
| MTBE | 1) slurry, 50° C., 7 d 2) positive pressure filtration | 1) pale yellow slurry 2) off-white solids | B + peaks |
| Dry NMP | 1) slurry, RT, 10 d 2) positive pressure filtration | 1) orange slurry 2) off-white solids; fine & aggregates, B/E | F (analyzed damp)[e] |
| TAME | 1) slurry, 50° C., 7 d 2) positive pressure filtration | 1) pale yellow slurry 2) off-white solids | B + minor peaks |
| 80:20 TFE/H2O ($a_w$ = 1.00) | 1) slurry, RT, 10 d 2) positive pressure filtration | 1) off-white slurry 2) off-white solids; fine & aggregates, partial B/E | A + peaks (disordered) |
| 99:1 THF/H2O ($a_w$ = 0.21) | 1) slurry, RT, 11 d 2) centrifuge & decant | 1) pale orange slurry 2) damp off-white solids; fines, B/E | L (analyzed damp) |
| 97:3 THF/H2O ($a_w$ = 0.53) | 1) slurry, RT, 11 d 2) centrifuge & decant | 1) yellow slurry 2) damp off-white solids; fines, B/E | M (analyzed damp) |
| 93:7 THF/H2O ($a_w$ = 0.91) | 1) slurry, RT, 11 d 2) centrifuge & decant | 1) yellow slurry 2) damp off-white solids; fines, B/E | L + peaks (analyzed damp) |

[a]Solvent ratios are v/v.
[b]Temperatures and times are approximate.
[c]Sample 1 in Table 25.
[d]Sample 3 in Table 25.
[e]Sample 4 in Table 25.
[f]Sample 5 in Table 25.

TABLE 24

| Solvent[a] | Conditions[b] | Observations | XRPD Results |
|---|---|---|---|
| — | P2O5 jar, 0% RH RT, 12 d | White solids | B + peaks (slight disorder) |

TABLE 24-continued

| Solvent[a] | Conditions[b] | Observations | XRPD Results |
|---|---|---|---|
| — | 23% RH, RT, 6 d | White solids | B + minor A |
| — | 43% RH, RT, 6 d | White solids | A + B |
| — | 54% RH, RT, 6 d | White solids | A + B |
| Dry CPME | 1) slurry, 50° C., 7 d<br>2) positive pressure filtration<br>3) 90% RH, RT, 10 d | 1) pale yellow slurry<br>2) off-white solids<br>3) off-white solids | A + minor N |
| EtOH | 1) slurry, 50° C., 7 d<br>2) positive pressure filtration<br>3) 90% RH, RT, 10 d | 1) pale yellow slurry<br>2) off-white solids<br>3) off-white solids | Disordered mixture of peaks |
| Dry IPE | 1) slurry, 50° C., 7 d<br>2) positive pressure filtration<br>3) 90% RH, RT, 10 d | 1) pale yellow slurry<br>2) off-white solids<br>3) off-white solids | A (shifted) + minor B + peaks |
| MTBE | 1) slurry, 50° C., 7 d<br>2) positive pressure filtration<br>3) 90% RH, RT, 10 d | 1) pale yellow slurry<br>2) off-white solids<br>3) off-white solids | A (shifted) + minor B + peaks |
| Dry HFIPA | FE | Orange solids; long, dendritic needles & aggregates, B/E | J |
| TAME | 1) slurry, 50° C., 7 d<br>2) positive pressure filtration<br>3) 90% RH, RT, 10 d | 1) pale yellow slurry<br>2) off-white solids<br>3) off-white solids | A + minor B + minor peaks |
| Dry TFE | FE | Pale orange solids; dendritic needles & aggregates, B/E | K |
| Dry THF | SC (55° C. to RT) | Tablets in clear soln; B/E- potential singles | L + minor B |

[a]Solvent ratios are v/v.
[b]Temperatures and times are approximate.

TABLE 25

| Starting Material | Condition | XRPD Result |
|---|---|---|
| Form D (Sample 1) | vac., RT, 1 d | Form D[a] |
| Form D (Sample 2) | vac., 80° C., 1 d | Form D + peaks (some disorder) |
| Form E (Sample 3) | vac., RT, 1 d | Form H (some disorder) |
| Form F (Sample 4) | vac., RT, 1 d | Form F |
| Form G (Sample 5) | vac., RT, 1 d | Form B + peaks (some disorder) |

[a]Sample 2.

TABLE 26

| Form | Analytical Technique | Results |
|---|---|---|
| A | XRPD | Consistent w/indexing solution; has slight solvent halo |
| | $^1$H NMR | Consistent w/chemical structure; no apparent organic solvent |
| | TGA/DSC[a] | 9.3% wt loss over 41 to 136° C. (equivalent to 2.8 mol/mol H$_2$O) (TGA); large broad endo at 117.9° C. and sharper endo at 307.8° C. (DSC) |
| | VRH-XRPD | Form A-initial scan; equilibrated ~45 min at ~30% RH variable RH patterns (10 min. scans)<br>Form B-initial scan after equilibrating under N2 stream (~0% RH) 17 h variable RH patterns (10 min. scans) |
| B | XRPD | consistent w/indexing solution from VRH-XRPD experiments, with additional minor peaks |
| | $^1$H NMR | Consistent w/chemical structure; negligible amount of TAME |
| | TGA/DSC[a] | 0.1% wt loss over 50 to 121° C. and 0.2% wt loss over 229 to 267° C.; decomp, onset at 334° C. (TGA); 2 overlapping endos w/peak at 307.8° C. (DSC) |
| C | XRPD | successfully indexed; unit cell capable of containing up to 3 acetic acid molecules |
| | $^1$H NMR | consistent w/chemical structure, 2.9 mol/mol AcOH |
| | TGA/DSC[a] | 16.6% wt loss over 71 to 137° C. (equivalent to 1.7 mol/mol AcOH) and 8.0% wt loss over 171 to 203° C. (equivalent to 0.7 mol/mol AcOH) (TGA); Endotherms at 102.8° C., 190.1° C., & 308.4° C. (DSC) |
| D | XRPD | successfully indexed as di-DMA solvate; isostructural with Form F |
| | $^1$H NMR | consistent with chemical structure; 1.7 mol/mol DMA & 0.2 mol/mol NMP[b] |
| | TGA/DSC[a] | 25.5% wt loss over 101 to 186° C. (equivalent to 1.9 mol/mol DMA) (TGA); sharp endotherms at 117.7° C. and 305.4° C. (DSC) |
| E | XRPD | successfully indexed; unit cell capable of containing 2-3 DMSO molecules |
| F | XRPD | successfully indexed as di-NMP solvate; isostructural with Form D |
| | $^1$H NMR | consistent with chemical structure; equivalent to 1.7 mol/mol NMP & 0.2 mol/mol DMA[b] |
| | TGA/DSCA | 27.5% wt loss over 104 to 233° C. (equivalent to 1.9 mol/mol NMP) (TGA); sharp endotherms at 126.5° C. and 305.4° C. (DSC) |
| G | XRPD | successfully indexed; unit cell capable of containing up to 2 DMF molecules |
| H | XRPD | Not indexable |
| J | XRPD | Not indexable |
| K | XRPD | Not indexable |
| L | XRPD | successfully indexed; unit cell capable of containing up to 2 THF molecules |
| M | XRPD | successfully indexed; unit cell capable of containing 2-3 THF molecules |
| N | XRPD | successfully indexed as anhydrous material |
| | $^1$H NMR | consistent w/chemical structure; negligible amount of CPME |
| | TGA/DSC[a] | 0.1% wt loss over 50 to 120° C. and 0.2% wt loss over 209 to 252° C.; decomp, onset at 336° C. (TGA); two overlapping endotherms with peak at 307.2° C. (DSC) |
| P | XRPD | successfully indexed with a few minor peaks that are not included in indexing solution, space for 1-2 EtOAc molecules |

[a]Weight changes (%) in TGA are rounded to 1 decimal place; temperatures are rounded to nearest degree. Temperatures in DSC are rounded to 1 decimal place.
[b]Samples were under vacuum in same oven as each other, allowing solvent to swap between isostructural solvates.

Figure 18A:
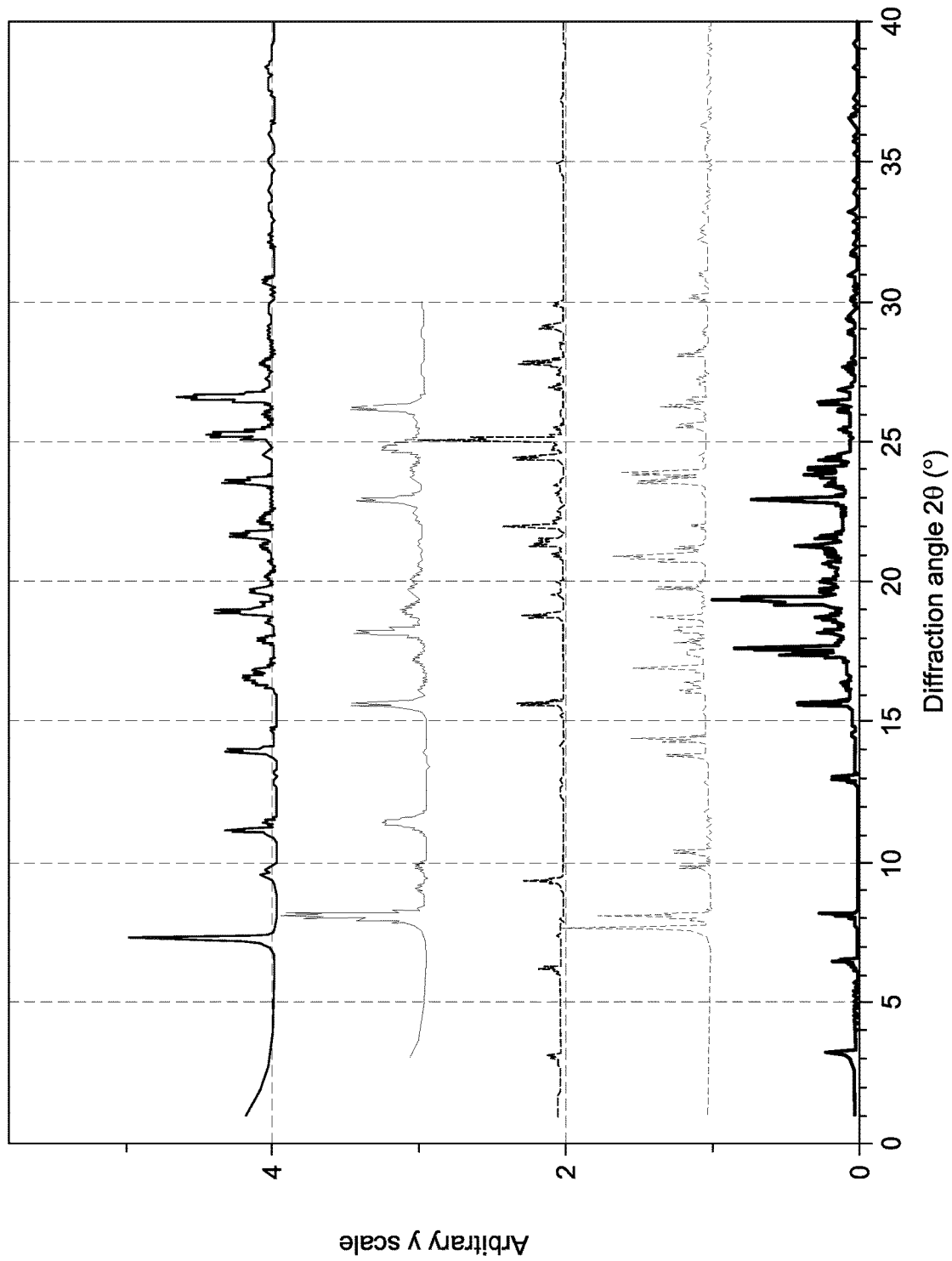
FIG. 18A depicts an XRPD overlay of Compound 1 Forms. From top to bottom; Form A, Form B, Form C, Form D, Form E.
Figure 18B:
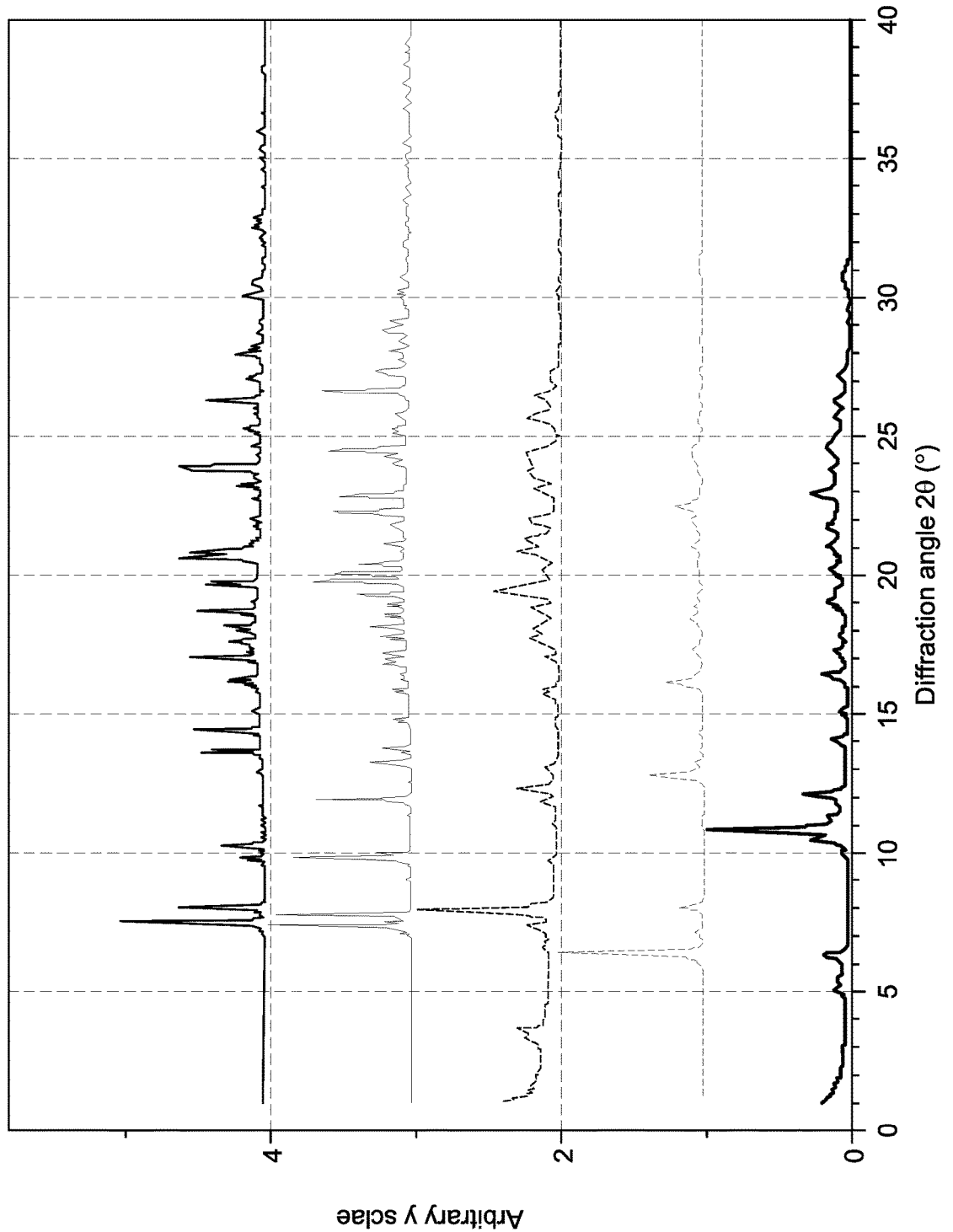
FIG. 18B depicts an XRPD overlay of Compound 1 Forms. From top to bottom: Form F, Form G, Form H, Form J, Form K.
Figure 18C:
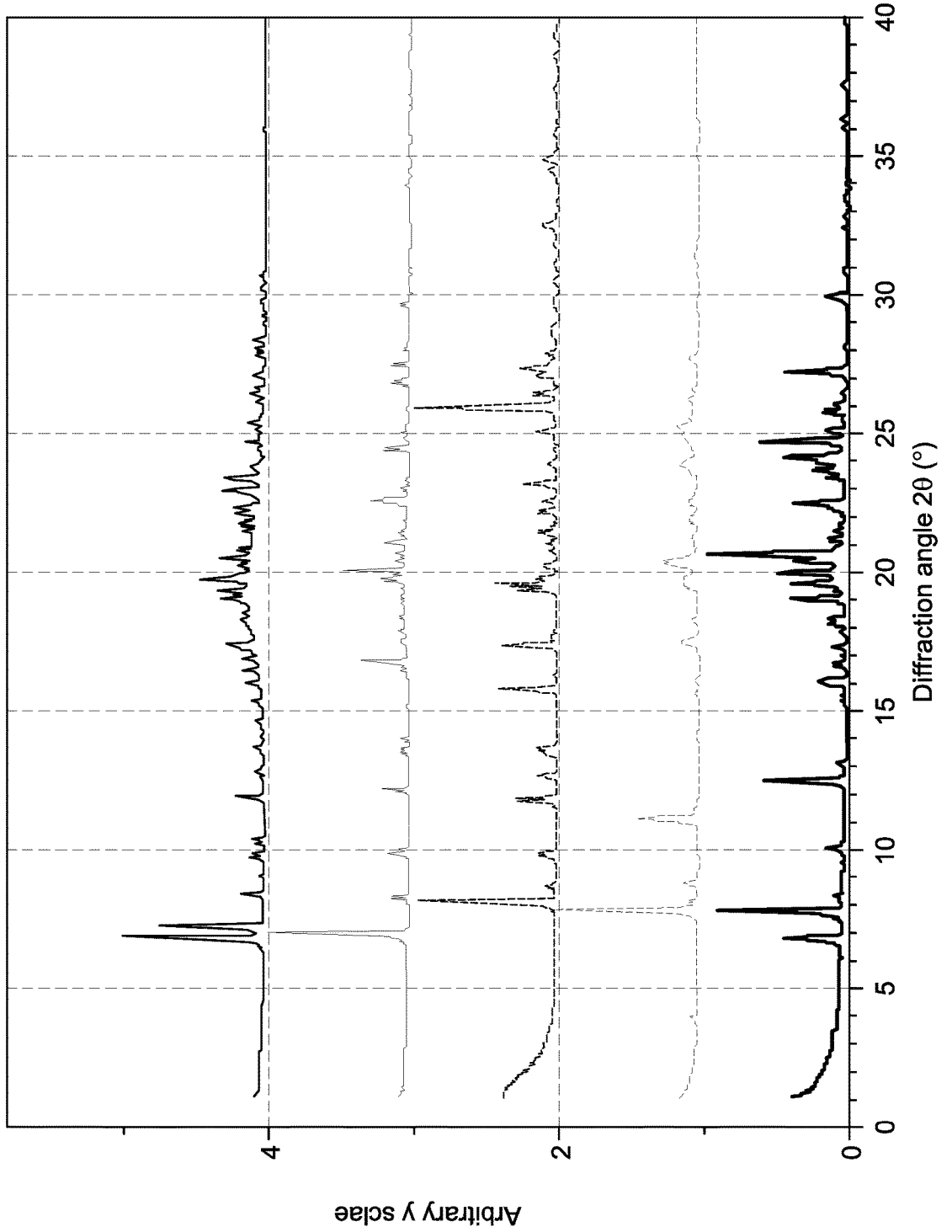
FIG. 18C depicts an XRPD overlay of Compound 1 Forms. From top to bottom: Form L, Form M, Form N, Form O+minor Form B, Form P.

FIG. 18A, FIG. 18B, and FIG. 18C provide a summary of the XRPD spectra for various Forms identified.

Figure 43:
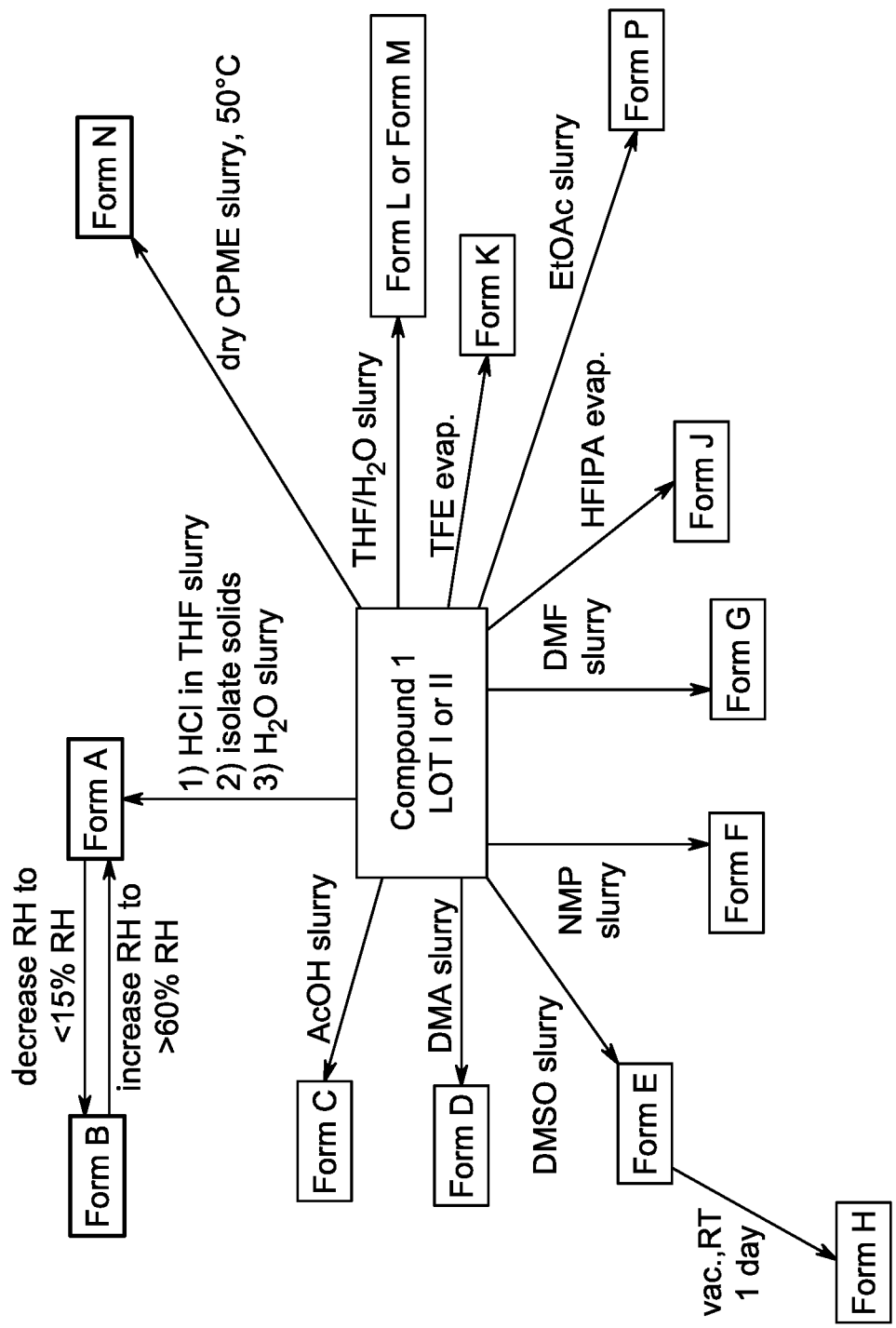
FIG. 43 is a schematic presentation of the results from certain polymorph screening experiments described herein.

FIG. 43 provides a schematic representation of certain results obtained from these polymorph screening experiments.

Example 11: Compound 1 Form A

An exemplary procedure for preparing Compound 1 Form A is as follows: Compound 1 Lot II (459.1 mg) was slurried in THF (4 mL). Concentrated HCl (154 µL, 2 equiv.) was added to the slurry. The off-white slurry rapidly changed to a yellow slurry. The slurry was stirred at ambient temperature for 1 day. Solids were collected by vacuum filtration and briefly dried under vacuum. The yellow material, assumed to be an HCl salt, was collected by vacuum filtration. The material (543.2 mg) was then suspended in $H_2O$ (5 mL) and stirred at ambient temperature for 2 days. Pale yellow solids were collected by vacuum filtration but appeared to still contain some HCl salt by XRPD. Solids were re-slurried in $H_2O$ (1 mL) at ambient temperature for additional 3 days. The off-white solids were collected by vacuum filtration and dried on filter until solids were no longer visibly damp.

Solution $^1H$ NMR for Form A was consistent with the chemical structure and contained no apparent organic solvent.

FIG. 19 provides an XRPD spectrum of Compound 1 Form A.

Figure 20:
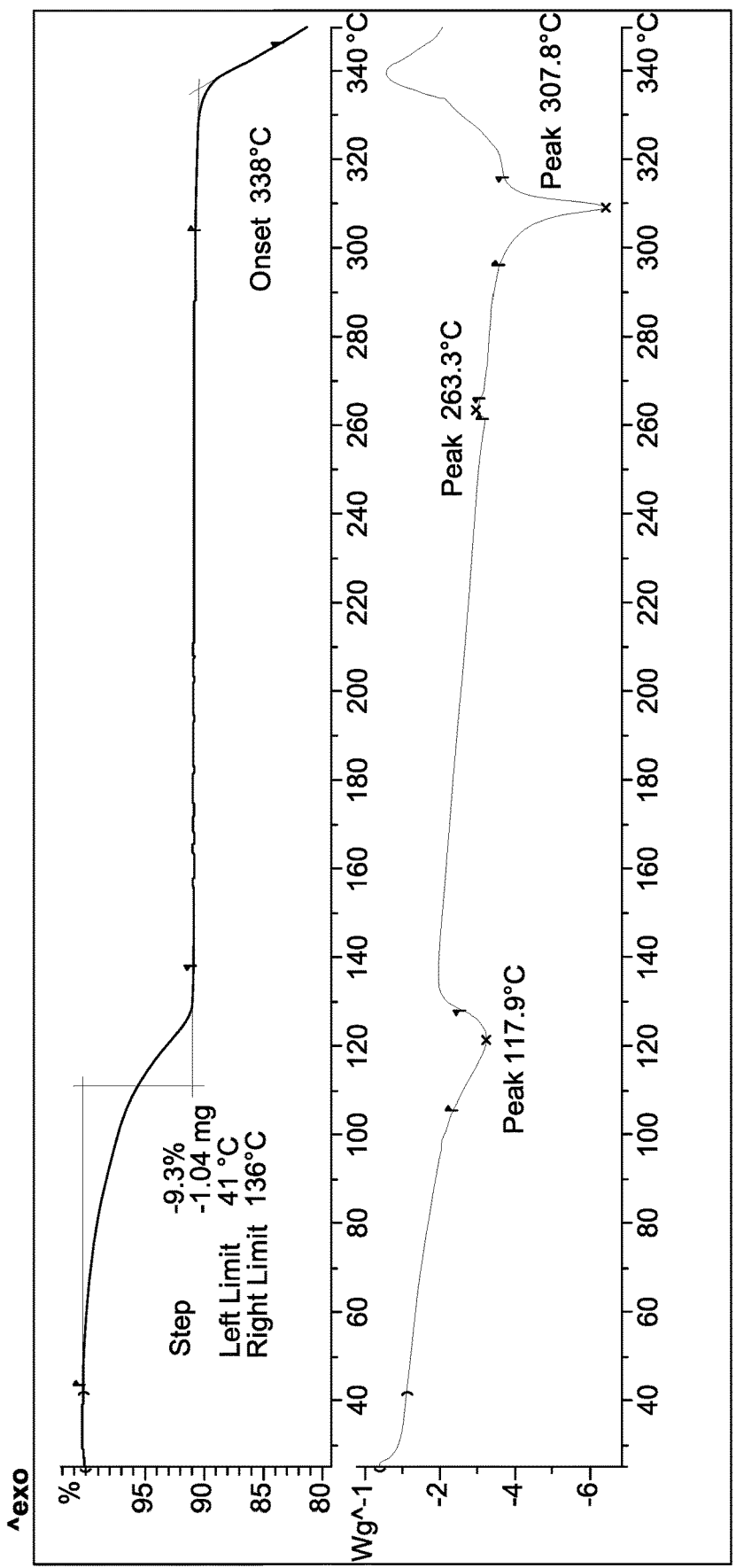
FIG. 20 provides TGA (top)/DSC (bottom) curves for Compound 1 Form A.

FIG. 20 provides a TGA/DSC curve of Compound 1 Form A. Thermal characterization by TGA provided a 9.3% weight loss from 41 to 136° C. which was calculated to be equivalent to ~2.8 mol/mol $H_2O$. DSC displayed a large broad endotherm at 117.9° C. and a slightly sharper endotherm at 307.8° C.

Example 12: Compound 1 Form B

Form B was observed in Compound 1 Lots I, II, and III. Additionally, Form B was prepared by slurrying Compound 1 (approx. 50 mg) in tert-amyl methyl ether (TAME) at 50° C. for 7 days. The solids were isolated by filtration and analyzed. An XRPD spectrum of the sample contained a few additional minor peaks, and $^1H$ NMR was consistent with the chemical structure of Compound 1. A negligible amount of TAME was also present in the sample.

Figure 21:
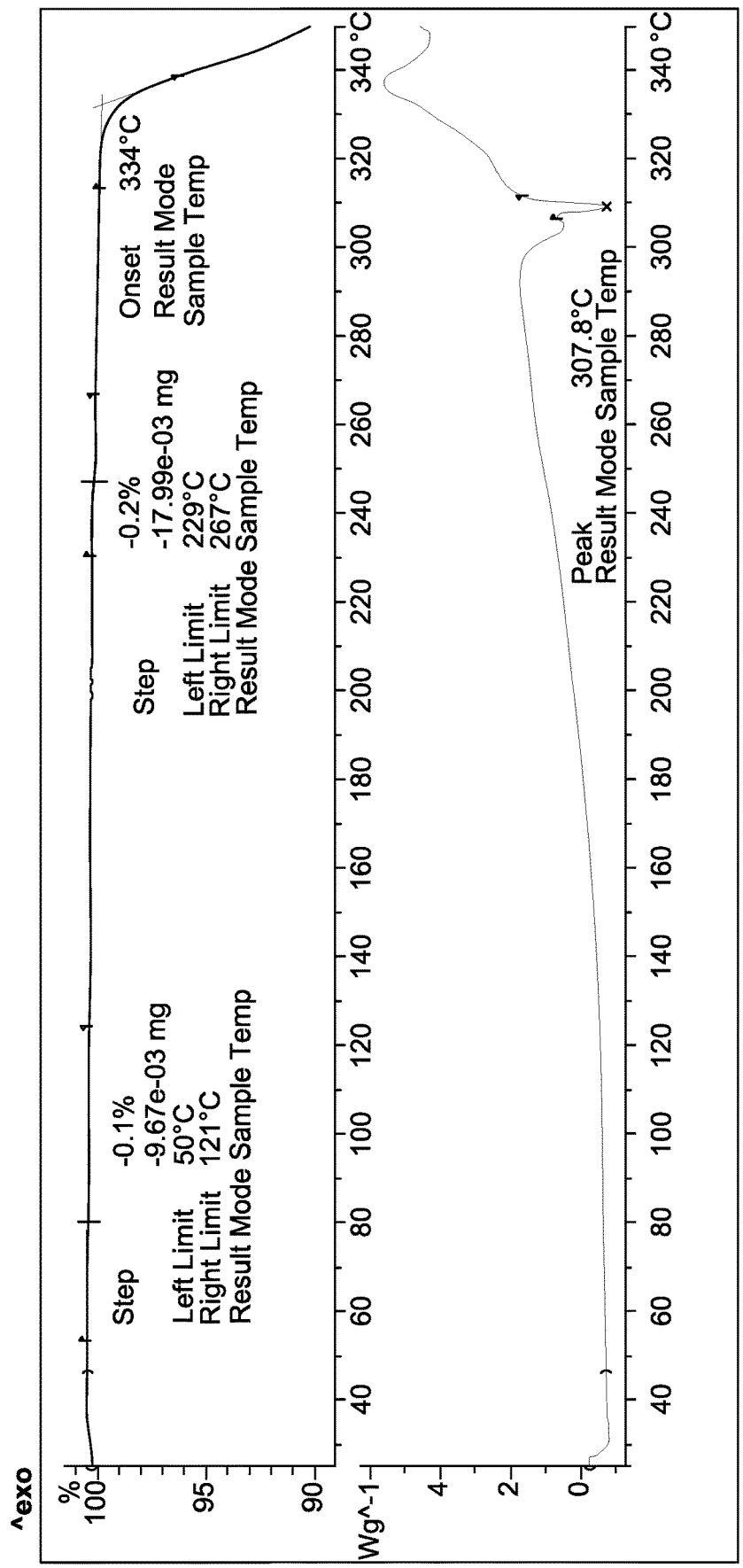
FIG. 21 provides TGA (top)/DSC (bottom) curves for Compound 1 Form B.

Thermal characterization by TGA and DSC was also obtained (FIG. 21). Only a 0.1% weight loss was observed from 50° C. to 121° C. with an additional 0.2% weight loss over 229-267° C. range. The onset of decomposition appeared to occur at approximately 334° C. The DSC thermogram displayed two overlapping endotherms with the sharpest peak at 307.8° C.

FIG. 22 provides an XRPD spectrum of Compound 1 Form B, obtained at low relative humidity (RH) during a variable relative humidity experiment of Example 24. Indexing of this spectrum suggested a unit cell volume consistent with an anhydrous form.

Example 13: Compound 1 Form C

Form C was prepared by slurring Compound 1 (approx. 50 mg) in acetic acid at ambient temperature for 10 days. The solids were isolated by filtration and analyzed.

XRPD analysis indicated a unit cell capable of containing up to 3 acetic acid molecules (FIG. 23). The proton NMR spectrum obtained for this sample was consistent with Compound 1 containing ~2.9 mol/mol AcOH.

Figure 24:
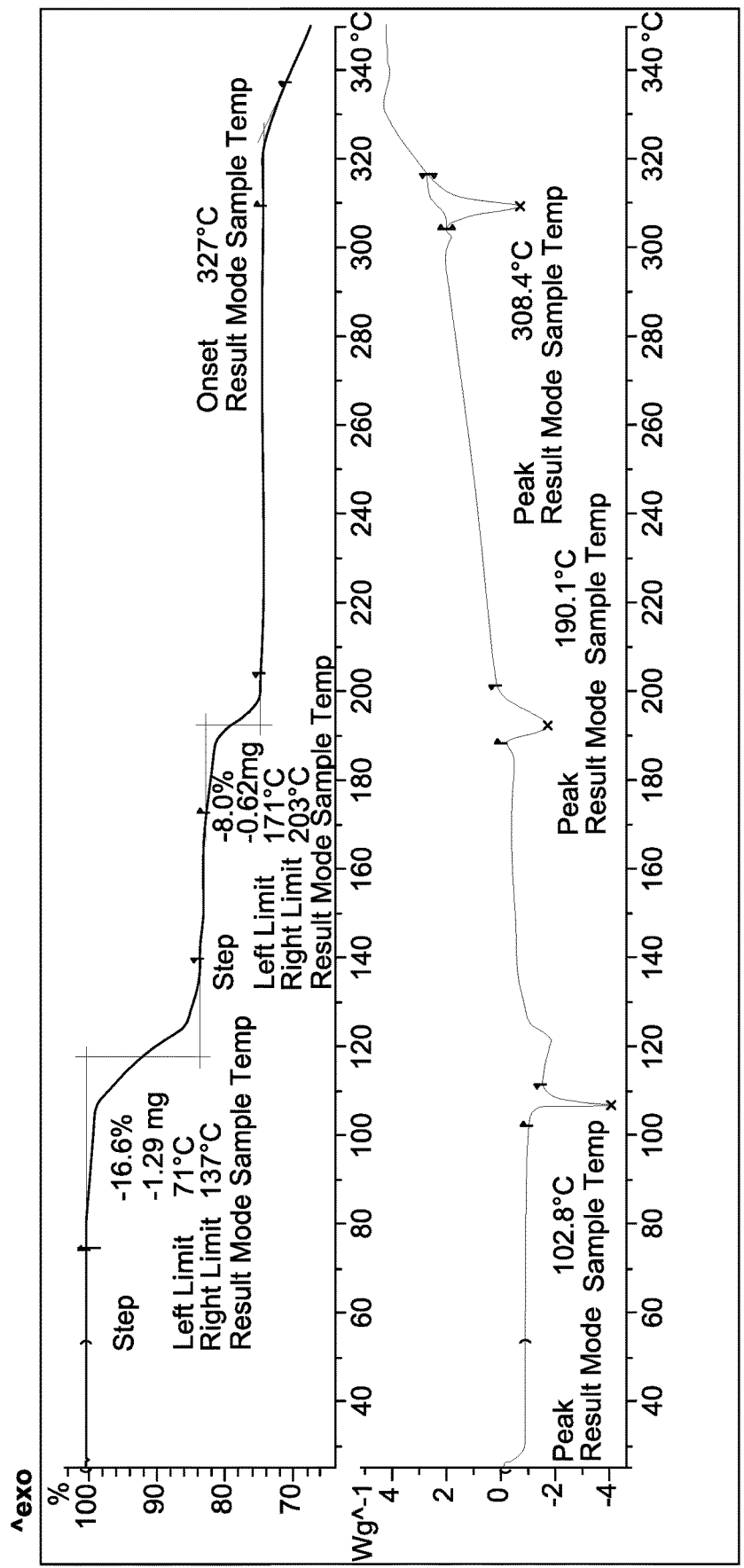
FIG. 24 provides TGA (top)/DSC (bottom) curves for Compound 1 Form C.

Thermal characterization by TGA provided a thermogram with a two-step weight loss (FIG. 24). A 16.6% weight loss, equivalent to ~1.7 mol/mol AcOH, was observed from 71° C. to 137° C. followed by an 8% weight loss, equivalent to ~0.7 mol/mol AcOH, from 171° C. to 203° C. The DSC thermogram displayed endotherms that coincided with the TGA events with peaks at 102.8° C., 190.1° C. and 308.4° C.

Form C was assigned as a tri-acetic acid cocrystal.

Example 14: Compound 1 Form D

Form D was prepared by slurrying Compound 1 (approx. 50 mg) in DMA at ambient temperature for 10 days. The solids were isolated by filtration and analyzed.

XRPD analysis of the slightly damp material indicated a unit cell consistent with a di-DMA solvate (FIG. 25). This XRPD pattern also appeared to be isostructural with NMP-solvated material, Form F.

Before further characterization was completed, the damp solids were dried in a vacuum oven with other damp materials, including Form F produced in NMP. Proton NMR spectroscopy data was consistent with chemical structure of Compound 1 and showed ~1.7 mol/mol DMA. In addition, a small amount of NMP appeared to be present (0.2 mol/mol NMP). This was likely due to a solvent exchange that occurred during vacuum drying.

Figure 26:
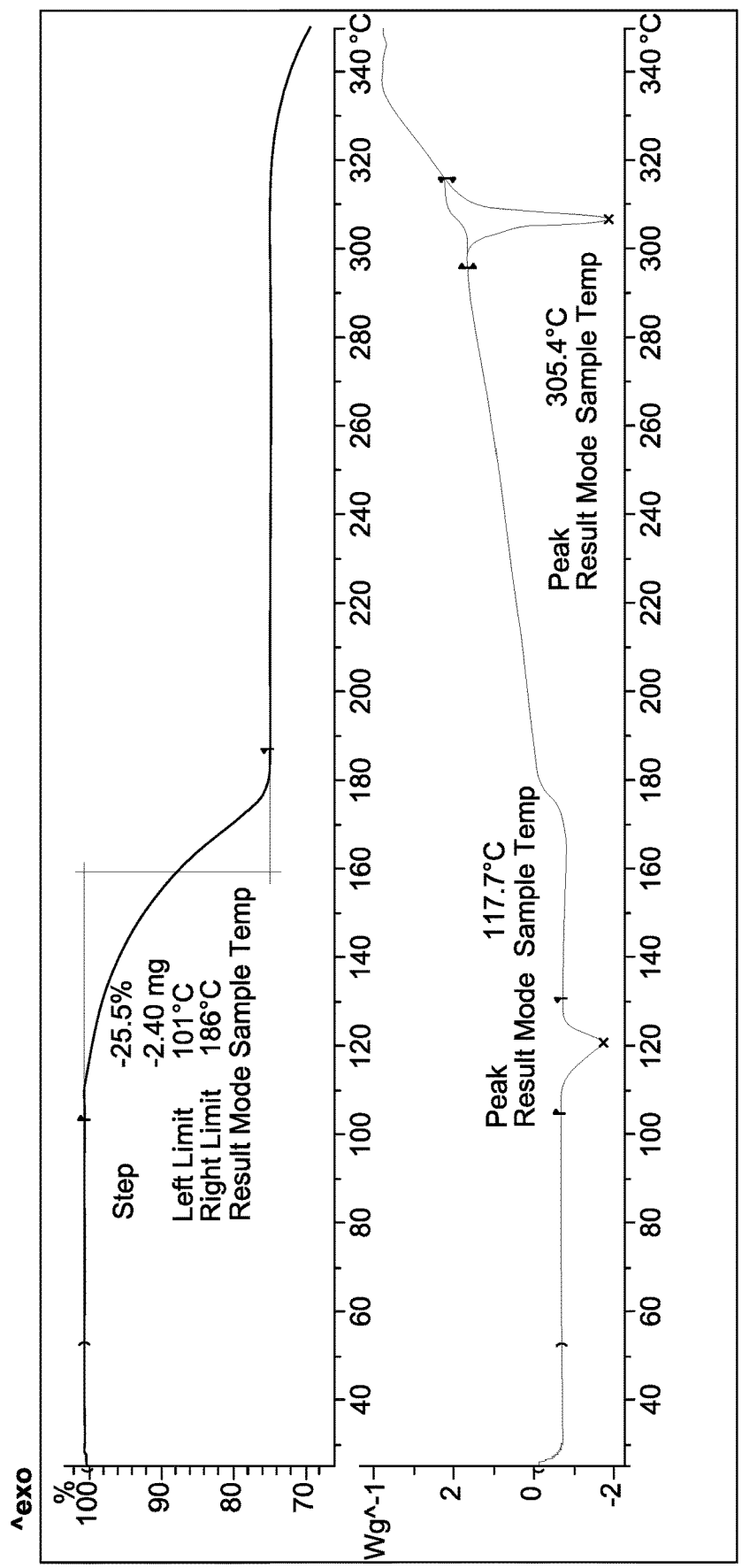
FIG. 26 provides TGA (top)/DSC (bottom) curves for Compound 1 Form D.

The TGA thermogram displayed a 25.5% weight loss over 101° C. to 186° C. (FIG. 26), equivalent to ~1.9 mol/mol DMA. The weight loss coincided with an endotherm at 117.7° C. in the DSC thermogram. A sharp endotherm was also observed at 305.4° C.

Example 15: Compound 1 Form E and Compound 1 Form H

Form E was prepared by slurrying Compound 1 (approx. 50 mg) in DMSO at ambient temperature for 10 days. The solids were isolated by filtration and analyzed.

XRPD analysis of the damp solids indicated a unit cell capable of containing up to 3 DMSO molecules (FIG. 27).

The sample was then dried in an ambient temperature vacuum oven. After 1 day, a new XRPD pattern was observed and designated Form H (FIG. 28).

Example 16: Compound 1 Form F

Form F was prepared by slurrying Compound 1 (approx. 50 mg) in NMP at ambient temperature for 10 days. The solids were isolated by filtration and analyzed.

XRPD analysis of the slightly damp material indicated a unit cell consistent with a di-NMP solvate of Compound 1 (FIG. 29). This XRPD pattern was similar to the pattern of Form D, which suggested that the two forms are isostructural.

Before further characterization was conducted, the damp solids were dried in a vacuum oven with other damp materials, including Form D. Proton NMR spectroscopy was consistent with chemical structure of Compound 1 and contained ~1.7 mol/mol NMP. In addition, a small amount of DMA appeared to be present (~0.2 mol/mol DMA). This was likely due to a solvent exchange that occurred during vacuum drying.

Figure 30:
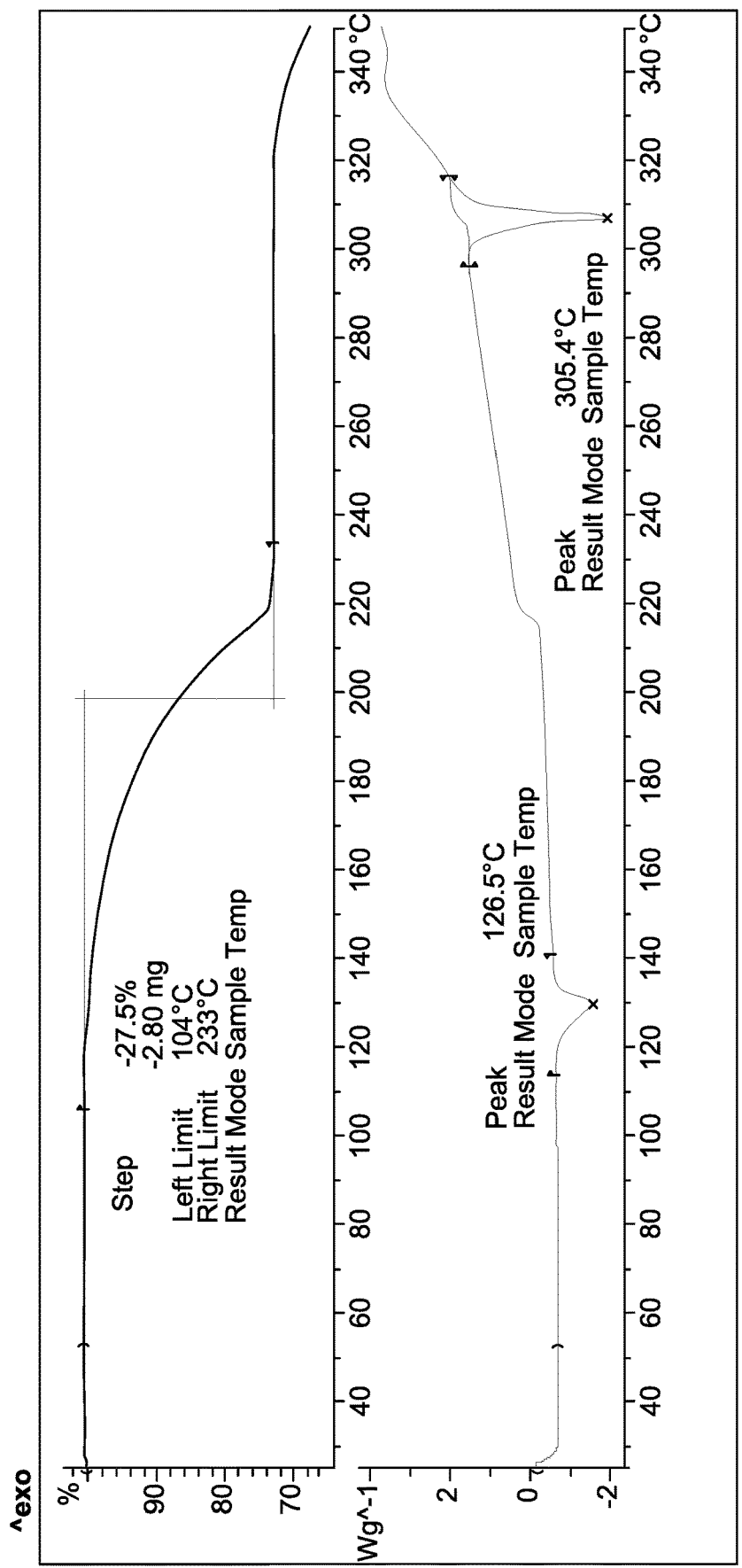
FIG. 30 provides TGA (top)/DSC (bottom) curves for Compound 1 Form F.

Thermal characterization by TGA displayed a 27.5% weight loss over 104° C. to 233° C., which is consistent with a loss of ~1.9 mol/mol NMP (FIG. 30). The DSC thermogram displayed an endotherm at 126.5° C., which is consistent with the weight loss in the TGA. An additional sharp endotherm was observed at 305.4° C.

Example 17: Compound 1 Form G

Form G was prepared by slurrying Compound 1 (approx. 50 mg) in DMF at ambient temperature for 10 days. The solids were isolated by filtration and analyzed.

XRPD analysis of the slightly damp material indicated a unit cell capable of containing up to 2 molecules of DMF (FIG. 31). Upon vacuum drying, the sample desolvated to give Form B.

Example 18: Compound 1 Form J and Compound 1 Form K

Form J and Form K were prepared by fast evaporation from hexafluoroisopropanol (HFIPA) and trifluoroethanol (TFE), respectively: A solution of Compound 1 was prepared in dry HFIPA or dry TFE. The solution was filtered with a 0.2 μm PTFE syringe filter and left open at ambient conditions until there was no apparent solvent. Dry solids were analyzed by XRPD.

FIG. 32 provides an XRPD pattern of Form J, and FIG. 33 provides an XRPD pattern of Form K, obtained from these experiments.

Example 19: Compound 1 Form L

Form L was prepared by slurrying Compound 1 (approx. 50 mg) in THF/$H_2O$ (99:1) at ambient temperature for 11 days. The solids were isolated by centrifugation and decantation, then analyzed.

XRPD analysis indicated a unit cell capable of containing up to 2 molecules of THF (FIG. 34).

Example 20: Compound 1 Form M

Form M was prepared by slurrying Compound 1 (approx. 50 mg) in THF/$H_2O$ (97:3) at ambient temperature for 11 days. The solids were isolated by centrifugation and decantation, then analyzed.

Figure 35:
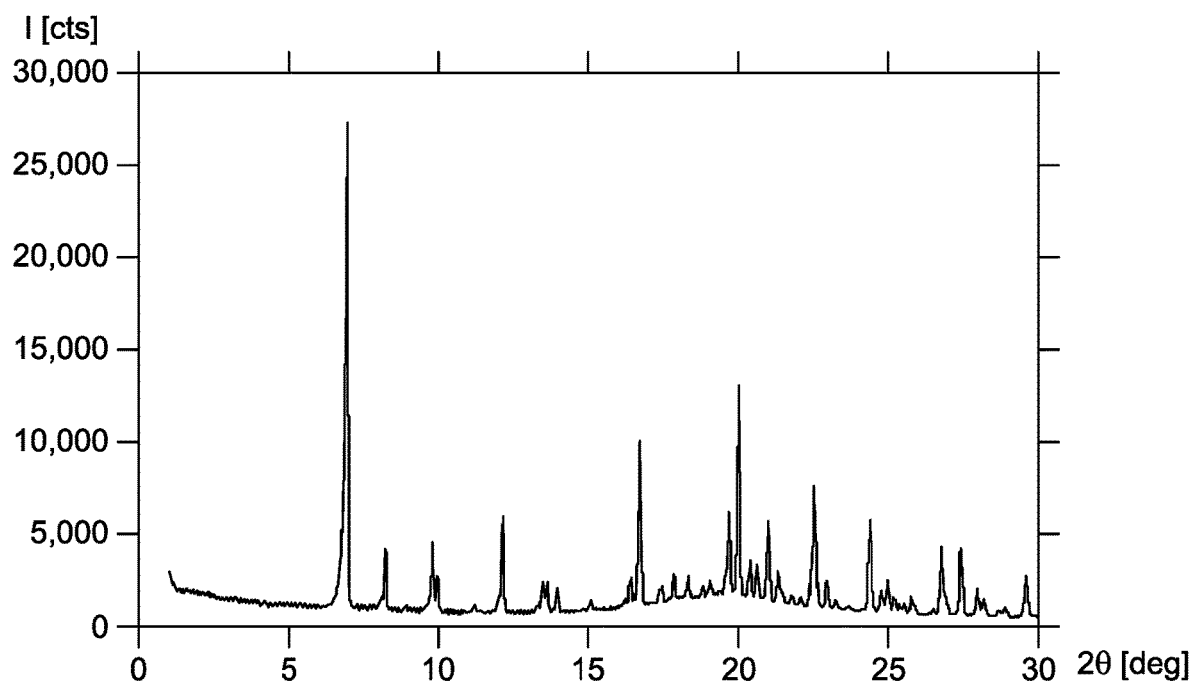
FIG. 35 provides a XRPD pattern of Compound 1 Form M.

XRPD analysis indicated a unit cell capable of containing 2-3 molecules of THE (FIG. 35).

Example 21: Compound 1 Form N

An exemplary procedure for preparing Compound 1 Form N is as follows: Compound 1 Lot II (61.0 mg) was slurried in dry cyclopentyl methyl ether (CPME) (2 mL) at 50° C. for 7 days. Pale yellow solids were collected by positive pressure filtration on a 0.2 μm nylon filter. The solids were stored in a clean vial over Drierite until XRPD analysis was performed.

Solution $^1$H NMR of Form N was consistent with the chemical structure of Compound 1 and contained less than ~0.1 mol/mol CPME.

FIG. 36 provides an XRPD spectrum of Compound 1 Form N. XRPD analysis indicated a unit cell smaller than that observed for Form B.

Figure 37:
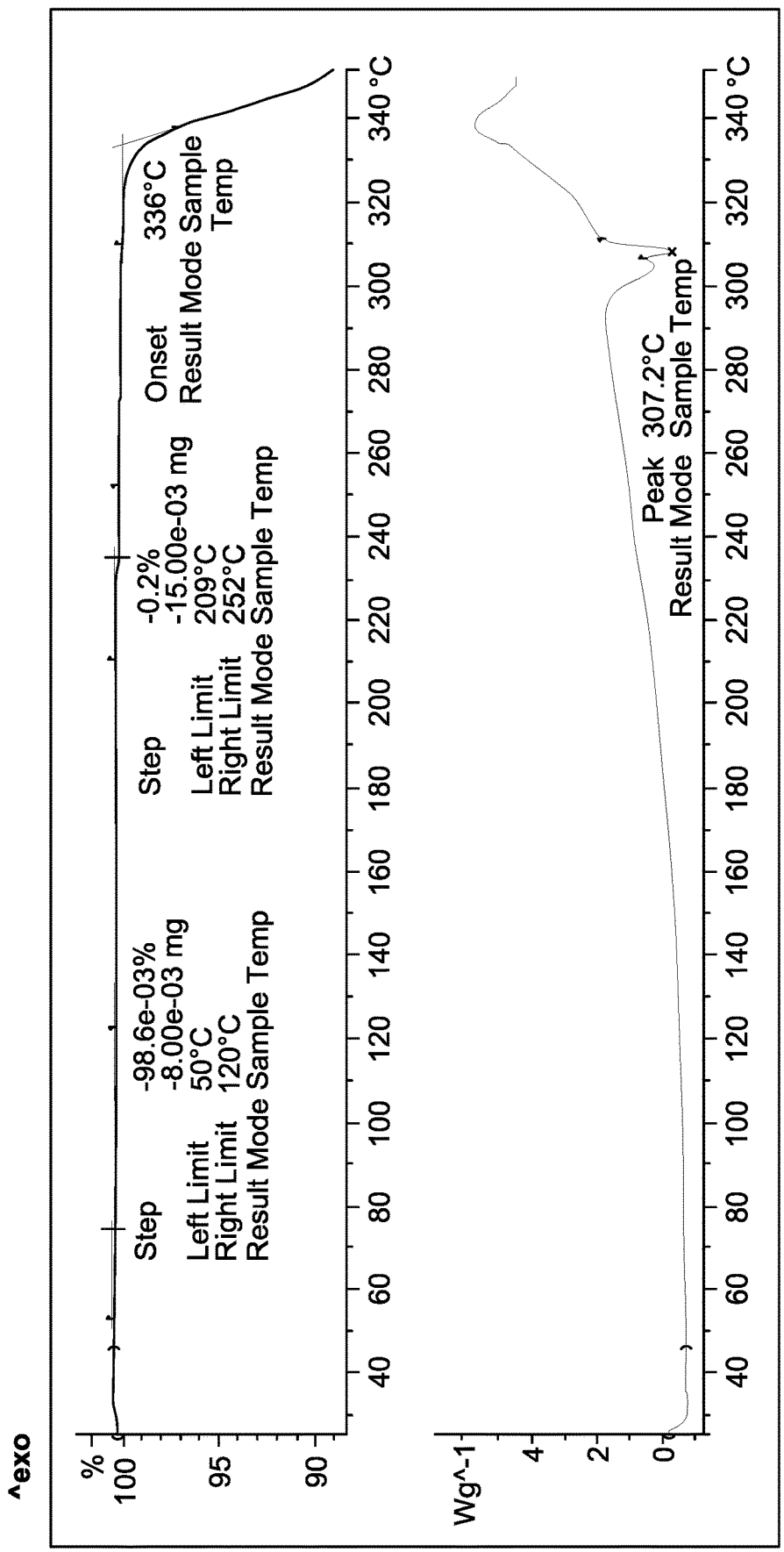
FIG. 37 provides TGA (top)/DSC (bottom) curves for Compound 1 Form N.

The TGA thermogram displayed a 0.1% weight loss over 50° C. to 120° C. and a 0.2% weight loss over 209° C. to 252° C. (FIG. 37). Decomposition appears to have an onset at 336° C. The DSC thermogram displayed two overlapping endotherms with a peak at 307.2° C.

Form N was assigned as an anhydrous form.

Example 22: Compound 1 Form P

Form P was prepared by slurrying Compound 1 (approx. 50 mg) in ethyl acetate at ambient temperature for 3 days. The solids were isolated by filtration and analyzed.

XRPD analysis indicated a unit cell capable of containing 1-2 ethyl acetate molecules (FIG. 38).

Example 23: Variable Relative Humidity (VRH) Experiments

VRH-XRPD analysis was conducted to help determine water activity boundary for the solid-state conversion between hydrated Form A and anhydrous Form B. This method was utilized due the observed high tendency of Compound 1 to form solvates, which precluded the use of solvent-mediated approach.

Overall, two VRH-XRPD experiments were conducted to qualitatively evaluate RH conditions leading to predominance of Form A over Form B and vice versa. The kinetic component was not assessed.

Experiment 1

Figure 39:
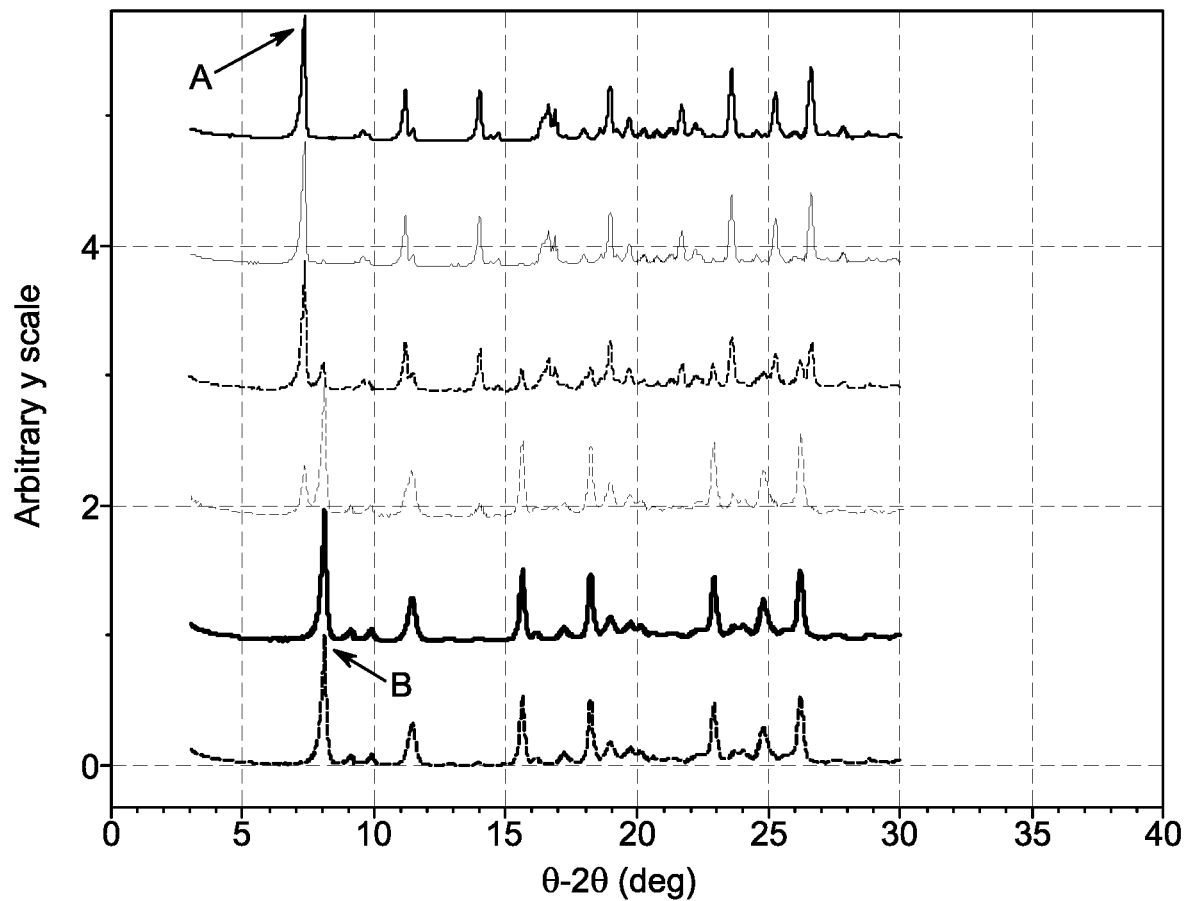
FIG. 39 depicts a series of XRPD spectra obtained in a variable relative humidity (VRH)-XRPD experiment of Form A. From top to bottom: ambient RH (~30%); ~21% RH; ~15% RH; ~11% RH; ~7% RH; ~5% RH. Characteristic peak for each of Form A and Form B of Compound 1 is labeled.

The first VRH-XRPD experiment was conducted with a goal of observing dehydration of hydrated Form A. An initial XRPD scan was, therefore, acquired on Form A equilibrated in-situ at ambient RH for 45 minutes, which at the time of the analysis was ~30%. The XRPD pattern from this scan was consistent with Form A (FIG. 39, top).

The RH level was increased to ~85% RH over 2.5 hours and after that, incrementally decreased while holding at each RH level for 1-2 hours. XRPD patterns were collected throughout the course of the experiment, each with a 10 minute scan.

Only Form A and Form B were observed in the experiment. The XRPD patterns were consistently Form A throughout the increase and decrease of the RH until the RH was lowered to approximately 21% RH, at which point a small amount of Form B became visible (FIG. 39, second from top). The amount of Form B remained unchanged until the RH was lowered to ~15% RH, where more Form B was observed. At 11% RH, Form B became the predominant phase in the mixture. As the RH level continued to drop, more Form B and less Form A was present from 15% to 7% RH (FIG. 39, middle two spectra). By the time the RH reached ~5% RH, Form A was no longer visible in the patterns (FIG. 39, bottom two spectra).

Experiment 2

Figure 40:
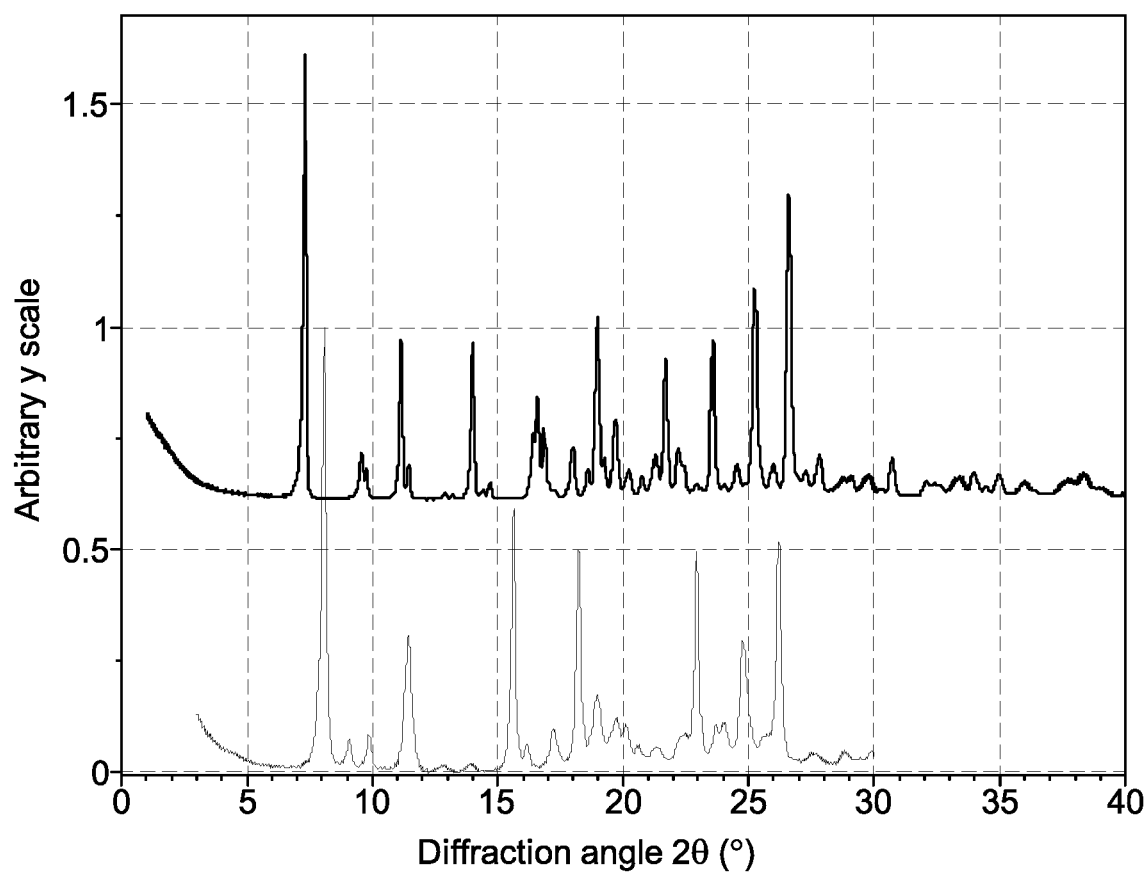
FIG. 40 provides an overlay of XRPD spectra of Form A before (top) and after exposure to a nitrogen stream for 17 h (bottom), whereby it has converted to Form B.

The focus of the second VRH-XRPD experiment was to observe transformation of anhydrous Form B. For this purpose, the starting Form A was converted to Form B in-situ by an overnight hold under nitrogen stream (~0% RH) (FIG. 40).

Figure 41:
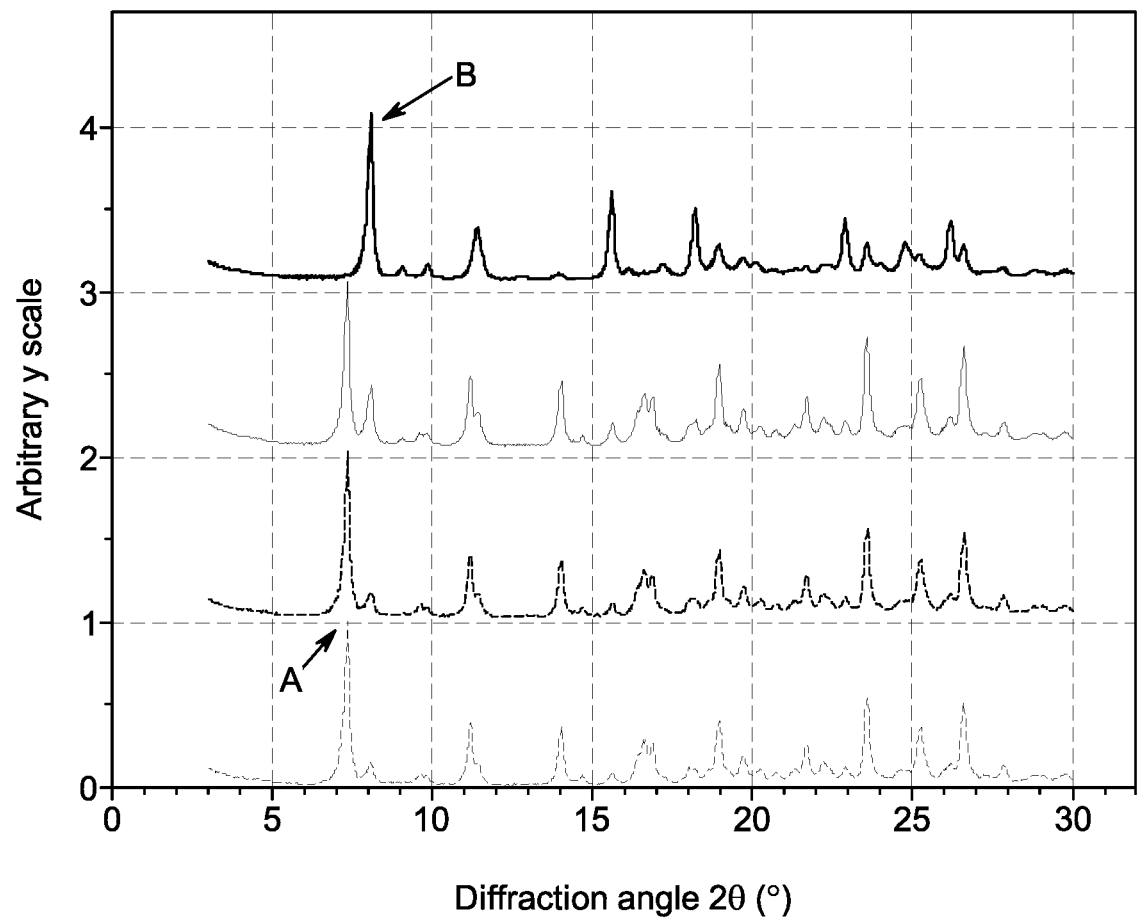
FIG. 41 provides a series of XRPD spectra obtained in a VRH-XRPD experiment of Form B. From top to bottom: ~53% RH; ~62% RH; ~61% RH; ~61% RH.

The RH was then incrementally increased with long holds at each step (15% up to ~60%). XRPD patterns were collected throughout the course of the experiment, each with a 10 minute scan. The XRPD patterns remained Form B until the RH reached approximately 60% RH, where Form A became the primary phase with some Form B remaining (FIG. 41, top two spectra). Further decrease of Form B was observed through the remainder of the 60% RH hold at which point the experiment ended (FIG. 41, bottom two spectra). Complete conversion to Form A from Form B was not observed under these conditions.

Figure 42:
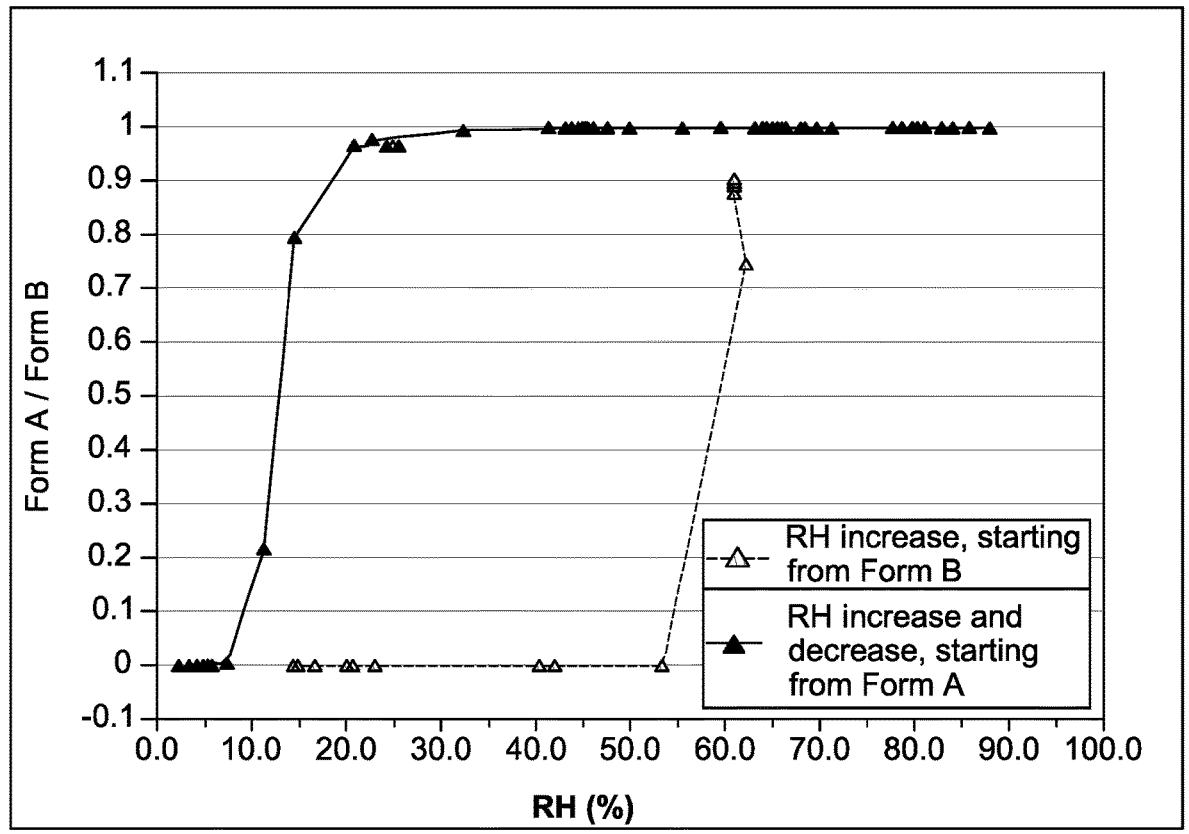
FIG. 42 is a schematic presentation of both VRH-XRPD experiments, plotting Form A/Form B ratios versus average RH values.

A schematic presentation of both VRH-XRPD experiments is provided in FIG. 42 where Form A/Form B ratios were plotted versus average RH values. The ratios were estimated for illustration purposes only and do not provide quantitative assessment of Form A and Form B contents. Intensities of selected XRPD peaks were used for ratios estimations and specificity, preferred orientation, etc. were not evaluated.

The plotted VRH-XRPD data were compared with water uptakes seen for Compound 1 Lot I during its DVS analysis (FIG. 2).

Overall, VRH-XRPD and DVS data were in good agreement, indicating that anhydrous Form B likely exists below 20% RH but may be kinetically stable at up to 40-60% RH. Hydrated Form A will expect to begin dehydration at 20% RH and fully convert to anhydrous Form B at zero RH.

While we have described a number of embodiments of this disclosure, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

We claim:

1. A solid form of Compound 1:

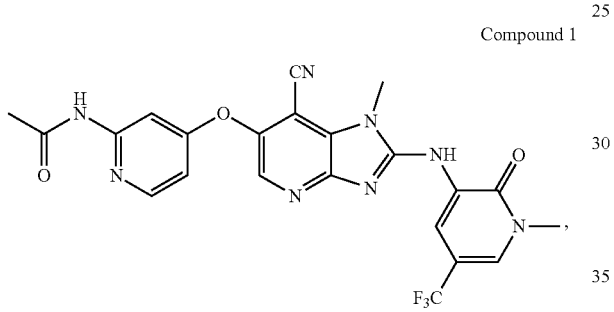

Compound 1 wherein the solid form is a hydrate and is characterized in that it has three or more peaks in its X-ray powder diffraction (XRPD) pattern selected from those at angles (degrees 2 theta±0.2) of 7.32, 11.15, 13.99, 16.58, 18.95, 21.68, 23.56, 25.23, and 26.60.

2. The solid form of claim 1, wherein the solid form is characterized in that it has peaks in its X-ray powder diffraction (XRPD) pattern comprising those at angles (degrees 2 theta±0.2) of:

| Angle/°2θ |
|---|
| 7.32 |
| 9.57 |
| 9.77 |
| 11.15 |
| 11.45 |
| 12.90 |
| 13.20 |
| 13.99 |
| 14.41 |
| 14.69 |
| 16.39 |
| 16.58 |
| 16.85 |
| 17.24 |
| 17.98 |
| 18.60 |
| 18.95 |
| 19.23 |
| 19.68 |
| 20.23 |

-continued

| Angle/°2θ |
|---|
| 20.75 |
| 21.29 |
| 21.68 |
| 22.19 |
| 22.40 |
| 22.93 |
| 23.56 |
| 23.98 |
| 24.51 |
| 25.23 |
| 25.97 |
| 26.60 |
| 27.25 |
| 27.80 |
| 28.78 |
| 29.07 |
| 29.78 |
| 30.70. |

3. A solid form of Compound 1:

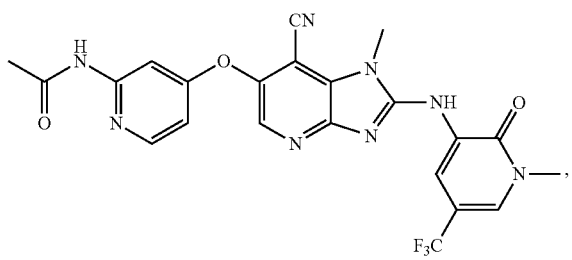

Compound 1 wherein the solid form is anhydrous and is characterized in that it has three or more peaks in its X-ray powder diffraction (XRPD) pattern selected from those at angles (degrees 2 theta±0.2) of 8.08, 11.76, 15.73, 17.31, 19.32, 19.54, 23.13, 25.90, and 27.31.

4. The solid form of claim 3, wherein the solid form is characterized in that it has peaks in its X-ray powder diffraction (XRPD) pattern comprising those at angles (degrees 2 theta±0.2) of:

| Angle/°2θ |
|---|
| 8.08 |
| 8.62 |
| 9.75 |
| 9.81 |
| 11.76 |
| 12.62 |
| 13.44 |
| 13.56 |
| 15.73 |
| 16.21 |
| 17.31 |
| 17.59 |
| 17.87 |
| 19.32 |
| 19.54 |
| 19.74 |
| 20.21 |
| 20.74 |
| 21.00 |
| 21.39 |
| 21.62 |
| 22.15 |
| 22.52 |

| Angle/°2θ |
|---|
| 23.13 |
| 23.86 |
| 24.34 |
| 24.66 |
| 25.02 |
| 25.57 |
| 25.90 |
| 26.38 |
| 27.06 |
| 27.31 |
| 27.85 |
| 28.49 |
| 28.77 |
| 29.55 |
| 29.81 |
| 30.47 |
| 31.04 |
| 31.79 |
| 32.46 |
| 33.27 |
| 34.45 |
| 34.83. |

5. A solid form of Compound 1:

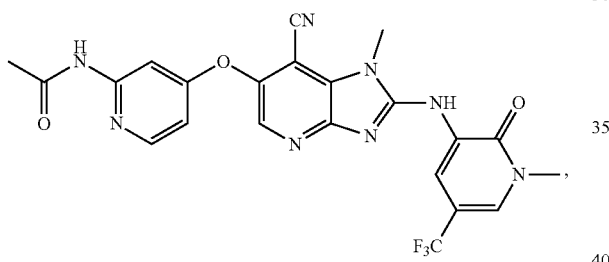

Compound 1 wherein the solid form is a Compound 1 salt or co-crystal form of hydrochloric acid ("Compound 2"):

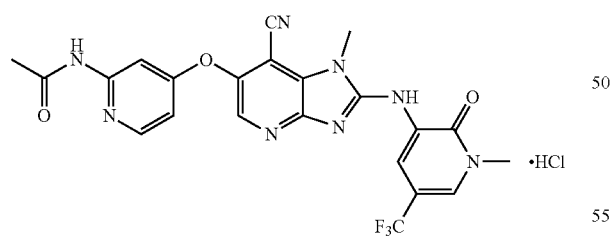

Compound 2

·HCl wherein the solid form is characterized in that it has three or more peaks in its X-ray powder diffraction (XRPD) pattern selected from those at angles (degrees 2 theta±0.2) of 7.38, 8.17, 11.98, 12.30, 15.63, 19.21, 20.12, 20.71, 21.64, 22.11, 24.16, 25.40, and 27.23.

6. The solid form of claim 5, wherein the solid form is characterized in that it has peaks in its X-ray powder diffraction (XRPD) pattern comprising those at angles (degrees 2 theta±0.2) of:

| Angle/°2θ |
|---|
| 7.38 |
| 8.17 |
| 10.01 |
| 11.29 |
| 11.98 |
| 12.3 |
| 12.75 |
| 14.83 |
| 15.63 |
| 16.6 |
| 17.41 |
| 17.59 |
| 18.15 |
| 19.21 |
| 20.12 |
| 20.71 |
| 21.64 |
| 22.11 |
| 22.38 |
| 23.29 |
| 23.60 |
| 23.83 |
| 24.16 |
| 24.54 |
| 24.77 |
| 25.40 |
| 26.24 |
| 27.23 |
| 28.2 |
| 28.61 |
| 29.85 |
| 30.14 |
| 30.40 |
| 30.63 |
| 31.25 |
| 32.05. |

7. A solid form of Compound 1:

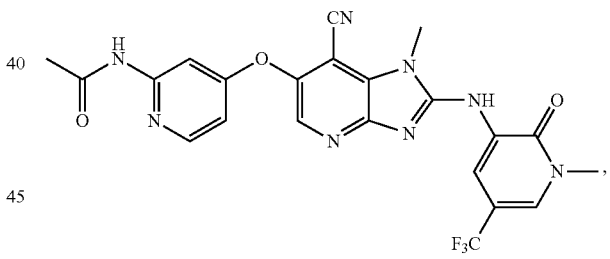

Compound 1 wherein the solid form is a Compound 1 salt or co-crystal form of hydrobromic acid ("Compound 3"):

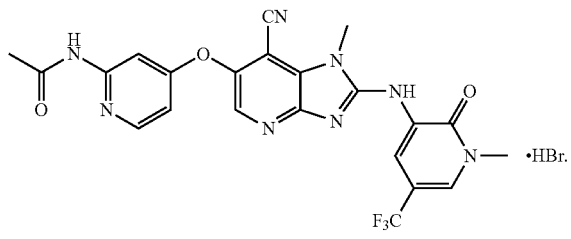

Compound 3

·HBr.

wherein the solid form is characterized in that it has three or more peaks in its X-ray powder diffraction (XRPD) pattern selected from those at angles (degrees 2 theta±0.2) of 8.72, 10.68, 12.14, 13.87, 14.53, 15.99, 16.38, 19.62, 20.13, 20.42, 20.76, 21.01, 22.93, 24.43, 24.98, 25.14, 26.76, and 27.23.

8. The solid form of claim 7, wherein the solid form is characterized in that it has peaks in its X-ray powder diffraction (XRPD) pattern comprising those at angles (degrees 2 theta±0.2) of:

| Angle/°2θ |
| --- |
| 7.10 |
| 8.72 |
| 9.82 |
| 10.45 |
| 10.68 |
| 12.14 |
| 12.40 |
| 13.33 |
| 13.87 |
| 14.25 |
| 14.53 |
| 15.19 |
| 15.99 |
| 16.38 |
| 17.18 |
| 17.35 |
| 17.51 |
| 18.10 |
| 18.61 |
| 19.27 |
| 19.62 |
| 20.13 |
| 20.42 |
| 20.76 |
| 21.01 |
| 21.48 |
| 22.40 |
| 22.93 |
| 24.43 |
| 24.98 |
| 25.14 |
| 25.95 |
| 26.27 |
| 26.76 |
| 27.23 |
| 27.91 |
| 28.09 |
| 28.57 |
| 28.77 |
| 29.32 |
| 29.86 |
| 30.84 |
| 31.09. |

9. A solid form of Compound 1:

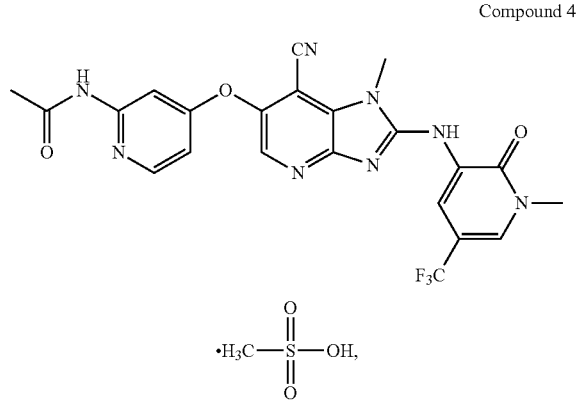

Compound 1 wherein the solid form is a Compound 1 salt or co-crystal form of methanesulfonic acid ("Compound 4"):

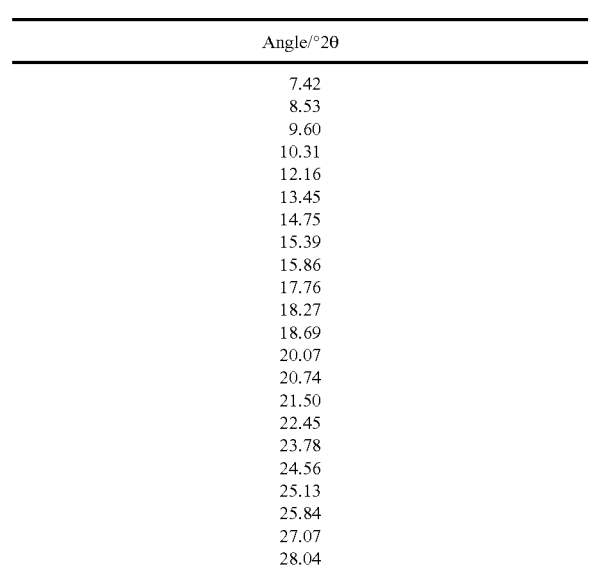

Compound 4 wherein the solid form is characterized in that it
(i) has three or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06; or
(ii) has three or more peaks in its X-ray powder diffraction (XRPD) pattern selected from those at angles (degrees 2 theta±0.2) of 8.53, 9.60, 10.31, 12.16, 14.75, 15.86, 20.07, 20.74, 22.45, 24.56, and 27.07.

10. The solid form of claim 9, wherein the solid form is characterized in that it has three or more peaks in its X-ray powder diffraction (XRPD) pattern selected from those at angles (degrees 2 theta±0.2) of 8.53, 9.60, 10.31, 12.16, 14.75, 15.86, 20.07, 20.74, 22.45, 24.56, and 27.07.

11. The solid form of claim 10, wherein the solid form is characterized in that it has peaks in its X-ray powder diffraction (XRPD) pattern comprising those at angles (degrees 2 theta±0.2) of:

| Angle/°2θ |
| --- |
| 7.42 |
| 8.53 |
| 9.60 |
| 10.31 |
| 12.16 |
| 13.45 |
| 14.75 |
| 15.39 |
| 15.86 |
| 17.76 |
| 18.27 |
| 18.69 |
| 20.07 |
| 20.74 |
| 21.50 |
| 22.45 |
| 23.78 |
| 24.56 |
| 25.13 |
| 25.84 |
| 27.07 |
| 28.04 |

-continued

| Angle/°2θ |
|---|
| 29.13 |
| 29.89 |
| 31.14 |
| 32.08 |
| 33.12. |

12. The solid form of claim 9, wherein the solid form is characterized in that it has three or more peaks in its X-ray powder diffraction (XRPD) pattern selected from those at angles (degrees 2 theta±0.2) of 8.52, 9.31, 11.89, 14.48, 15.45, 15.89, 18.80, 19.19, 20.14, 20.57, 23.94, 24.60, 25.83, 26.45, and 27.06.

13. The solid form of claim 12, wherein the solid form is characterized in that it has peaks in its X-ray powder diffraction (XRPD) pattern comprising those at angles (degrees 2 theta±0.2) of:

| Angle/°2θ |
|---|
| 7.35 |
| 8.52 |
| 9.31 |
| 10.03 |
| 10.65 |
| 11.89 |
| 13.19 |
| 13.68 |
| 14.48 |
| 15.45 |
| 15.89 |
| 16.84 |
| 17.49 |
| 17.66 |
| 18.80 |
| 19.19 |
| 19.48 |
| 20.14 |
| 20.57 |
| 21.43 |
| 21.79 |
| 22.23 |
| 22.52 |
| 22.82 |
| 23.58 |
| 23.94 |
| 24.60 |
| 25.43 |
| 25.83 |
| 26.45 |
| 27.06 |
| 27.62 |
| 28.31 |
| 29.22 |

-continued

| Angle/°2θ |
|---|
| 29.83 |
| 30.73 |
| 32.08. |

14. A solid form of Compound 1:

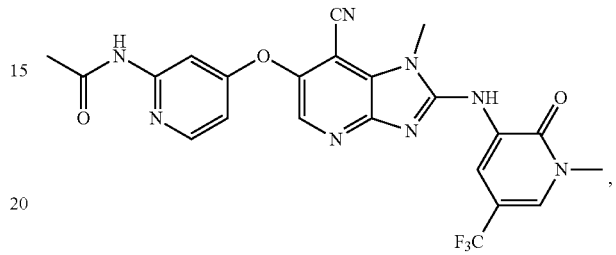

Compound 1 wherein the solid form is a Compound 1 salt or co-crystal form of (1R)-(−)-10-camphorsulfonic acid ("Compound 5"):

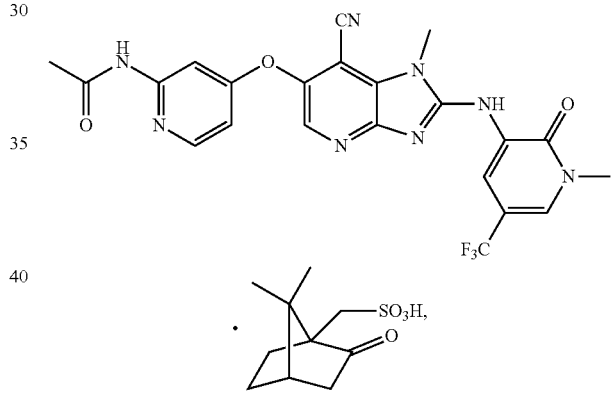

Compound 5 wherein the solid form is characterized in that it has three or more peaks in its X-ray powder diffraction (XRPD) pattern selected from those at angles (degrees 2 theta±0.2) of 6.55, 9.01, 12.05, 12.65, 14.08, 22.16, 22.45, and 25.47.

15. The solid form of claim 14, wherein the solid form is characterized in that it has peaks in its X-ray powder diffraction (XRPD) pattern comprising those at angles (degrees 2 theta±0.2) of:

| Angle/°2θ |
|---|
| 6.55 |
| 9.01 |
| 9.87 |
| 10.49 |
| 11.01 |
| 11.57 |
| 12.05 |
| 12.19 |
| 12.65 |
| 13.14 |

-continued

| Angle/°2θ |
|---|
| 13.45 |
| 14.08 |
| 14.30 |
| 14.59 |
| 14.98 |
| 15.39 |
| 16.22 |
| 16.46 |
| 16.94 |
| 17.42 |
| 17.62 |
| 17.74 |
| 18.10 |
| 18.75 |
| 19.36 |
| 19.76 |
| 19.95 |
| 20.16 |
| 20.50 |
| 20.81 |
| 20.91 |
| 21.10 |
| 21.57 |
| 21.99 |
| 22.16 |
| 22.45 |
| 22.87 |
| 23.59 |
| 24.39 |
| 24.66 |

-continued

| Angle/°2θ |
|---|
| 25.47 |
| 25.95 |
| 26.48 |
| 26.70 |
| 27.04 |
| 27.30 |
| 27.70 |
| 28.08. |

16. The solid form according to claim 5, wherein the solid form of the compound has a ratio of about 1:1 of Compound 1 to co-former hydrochloric acid.

17. The solid form according to claim 7, wherein the solid form of the compound has a ratio of about 1:1 of Compound 1 to co-former hydrobromic acid.

18. The solid form according to claim 9, wherein the solid form of the compound has a ratio of about 1:1 of Compound 1 to co-former methanesulfonic acid.

19. The solid form according to claim 14, wherein the solid form of the compound has a ratio of about 1:1 of Compound 1 to co-former (1R)-(−)-10-camphorsulfonic acid.

20. A pharmaceutical composition comprising the solid form according to claim 1 and a pharmaceutically acceptable carrier or excipient.

* * * * *